(12) United States Patent
Tkachenko

(10) Patent No.: US 11,744,838 B2
(45) Date of Patent: *Sep. 5, 2023

(54) METHODS OF TREATING HYPOGONADISM WITH TRANSNASAL TESTOSTERONE BIO-ADHESIVE GEL FORMULATIONS IN MALE WITH ALLERGIC RHINITIS, AND METHODS FOR PREVENTING AN ALLERGIC RHINITIS EVENT

(71) Applicant: Acerus Biopharma Inc., Mississauga (CA)

(72) Inventor: Natalia Tkachenko, Georgetown (CA)

(73) Assignee: ACERUS BIOPHARMA INC., Ontario (CA)

( * ) Notice: Subject to any disclaimer, the term of this patent is extended or adjusted under 35 U.S.C. 154(b) by 0 days.

This patent is subject to a terminal disclaimer.

(21) Appl. No.: 16/532,776

(22) Filed: Aug. 6, 2019

(65) Prior Publication Data

US 2021/0100815 A1 Apr. 8, 2021

Related U.S. Application Data

(63) Continuation of application No. 16/275,633, filed on Feb. 14, 2019, now abandoned, which is a continuation of application No. 16/044,903, filed on Jul. 25, 2018, now abandoned, which is a continuation of application No. 15/856,156, filed on Dec. 28, 2017, now abandoned, which is a continuation of application No. 15/599,316, filed on May 18, 2017, now abandoned, which is a continuation of application No. 15/284,479, filed on Oct. 3, 2016, now abandoned, which is a continuation of application No. 15/045,208, filed on Feb. 16, 2016, now abandoned, which is a continuation of application No. 14/753,552, filed on Jun. 29, 2015, now abandoned, which is a continuation of application No. 14/536,130, filed on Nov. 7, 2014, now abandoned, which is a continuation of application No. 14/215,882, filed on Mar. 17, 2014, now abandoned.

(60) Provisional application No. 61/802,297, filed on Mar. 15, 2013.

(51) Int. Cl.
*A61K 31/568* (2006.01)
*A61P 15/00* (2006.01)
*A61K 31/4174* (2006.01)
*A61P 37/08* (2006.01)
*A61K 9/00* (2006.01)

(52) U.S. Cl.
CPC .......... *A61K 31/568* (2013.01); *A61K 9/0043* (2013.01); *A61K 31/4174* (2013.01); *A61P 15/00* (2018.01); *A61P 37/08* (2018.01)

(58) Field of Classification Search
CPC .............. A61K 31/568; A61K 31/4174; A61K 9/0043; A61P 15/00
See application file for complete search history.

(56) References Cited

U.S. PATENT DOCUMENTS

| | | |
|---|---|---|
| 3,923,190 A | 12/1975 | Roth |
| 4,051,265 A | 9/1977 | Kirshenbaum et al. |
| 4,071,623 A | 1/1978 | van der Vies |
| 4,083,973 A | 4/1978 | van der Vies |
| 4,123,417 A | 10/1978 | Finberg |
| 4,315,925 A | 2/1982 | Hussain et al. |
| 4,546,882 A | 10/1985 | Hsu et al. |
| 4,581,225 A | 4/1986 | Su et al. |
| 4,752,425 A | 6/1988 | Martin et al. |
| 4,786,678 A | 11/1988 | Dobreski et al. |
| 4,812,448 A | 3/1989 | Knepper |
| 4,826,852 A | 5/1989 | Haffer et al. |
| 5,049,387 A | 9/1991 | Amkraut |

(Continued)

FOREIGN PATENT DOCUMENTS

| | | |
|---|---|---|
| CA | 2135203 A1 | 12/1993 |
| CA | 2463384 A1 | 4/2003 |

(Continued)

OTHER PUBLICATIONS

Highlights of Prescribing Information for NATESTO (testosterone) nasal gel GIII; Initial U.S. Approval: 1953; Proposed Draft Labeling Text; Reference ID 3514261; Approved: May 2014.

(Continued)

*Primary Examiner* — Shobha Kantamneni

(74) *Attorney, Agent, or Firm* — Howard M. Gitten, Esq.; Lewis Brisbois Bisgaard & Smith LLP

(57) ABSTRACT

The present invention relates to methods of treating hypogonadism in a male subject through administering intranasally to the male subject an intranasal testosterone bio-adhesive gel formulation to deliver a therapeutically effective amount of testosterone. In particular, the testosterone therapy of the invention remains effective if an allergic rhinitis event occurs in the male during the treatment or when the male subject uses a topical nasal vasoconstrictor or a topical intranasal decongestant during the hypogonadism treatment. Further, the present invention relates to a method of preventing the occurrence of an allergic rhinitis event in a male, who is undergoing a hypogonadism treatment with an intranasal testosterone bio-adhesive gel. In certain embodiments, the intranasal testosterone bio-adhesive gel formulation according to the invention comprises 4.0% and 4.5% testosterone.

2 Claims, 45 Drawing Sheets

(56) References Cited

U.S. PATENT DOCUMENTS

| | | | |
|---|---|---|---|
| 5,130,137 A | 7/1992 | Crowley, Jr. | |
| 5,248,501 A | 9/1993 | Parnell | |
| 5,397,771 A | 3/1995 | Bechgaard et al. | |
| 5,455,286 A | 10/1995 | Amidon et al. | |
| 5,500,261 A | 3/1996 | Takei et al. | |
| 5,514,673 A | 5/1996 | Heckenmuller et al. | |
| 5,554,378 A | 9/1996 | Uda et al. | |
| 5,624,960 A | 4/1997 | Wenzel et al. | |
| 5,635,203 A | 6/1997 | Gale et al. | |
| 5,645,856 A | 7/1997 | Lacy et al. | |
| 5,739,176 A | 4/1998 | Dunn et al. | |
| 5,747,058 A | 5/1998 | Tipton et al. | |
| 5,756,071 A | 5/1998 | Mattern et al. | |
| 5,855,905 A | 1/1999 | Oettel et al. | |
| 5,863,554 A | 1/1999 | Illum | |
| 5,877,216 A | 3/1999 | Place et al. | |
| 5,891,462 A | 4/1999 | Carrara | |
| 5,891,920 A | 4/1999 | Hirano et al. | |
| 5,897,894 A | 4/1999 | Glass | |
| 5,908,638 A | 6/1999 | Huber et al. | |
| 5,948,492 A | 9/1999 | Cargile | |
| 6,096,733 A | 8/2000 | Lubkin | |
| 6,187,323 B1 | 2/2001 | Aiache | |
| 6,231,662 B1 | 5/2001 | Atkinson | |
| 6,248,363 B1 | 6/2001 | Patel | |
| 6,262,021 B1 | 7/2001 | Uvnas-Moberg et al. | |
| 6,287,588 B1 | 9/2001 | Shih et al. | |
| 6,306,841 B1 | 10/2001 | Place et al. | |
| 6,309,663 B1 | 10/2001 | Patei et al. | |
| 6,310,089 B1 | 10/2001 | Watts et al. | |
| 6,319,905 B1 | 11/2001 | Mandel et al. | |
| 6,319,913 B1 | 11/2001 | Mak et al. | |
| 6,333,313 B1 | 12/2001 | Copland, III et al. | |
| 6,423,701 B1 | 7/2002 | Hussain | |
| 6,432,440 B1 | 8/2002 | Watts et al. | |
| 6,451,339 B2 | 9/2002 | Patel et al. | |
| 6,503,894 B1 | 1/2003 | Dudley et al. | |
| 6,562,790 B2 | 5/2003 | Chein | |
| 6,583,129 B1 | 6/2003 | Mazer et al. | |
| 6,589,549 B2 | 7/2003 | Shin et al. | |
| 6,610,670 B2 | 8/2003 | Backensfeld et al. | |
| 6,669,879 B1 | 12/2003 | Spengler et al. | |
| 6,712,803 B1 * | 3/2004 | Paritsky | A61K 9/0043 128/200.22 |
| 6,720,001 B2 | 4/2004 | Chen et al. | |
| 6,737,084 B2 | 5/2004 | Crosby et al. | |
| 6,761,903 B2 | 7/2004 | Chen et al. | |
| 6,800,363 B2 | 10/2004 | Su et al. | |
| 6,815,506 B2 | 11/2004 | Takashima et al. | |
| 6,833,478 B2 | 12/2004 | Bottaro et al. | |
| 6,838,091 B2 | 1/2005 | Lipari et al. | |
| 6,881,423 B2 | 4/2005 | Dohi et al. | |
| 6,958,142 B2 | 10/2005 | Daniels et al. | |
| 6,982,281 B1 | 1/2006 | Chen et al. | |
| 7,029,657 B2 | 4/2006 | Pike et al. | |
| 7,186,706 B2 | 3/2007 | Rosario-Jansen et al. | |
| 7,198,801 B2 | 4/2007 | Carrara et al. | |
| 7,404,965 B2 | 7/2008 | Carrara et al. | |
| 7,459,445 B2 | 12/2008 | Hill et al. | |
| 7,470,433 B2 | 12/2008 | Carrara et al. | |
| 7,479,478 B2 | 1/2009 | Bringhurst et al. | |
| 7,731,990 B2 | 6/2010 | Dohi et al. | |
| 7,749,989 B2 | 7/2010 | Hill et al. | |
| 7,799,337 B2 | 9/2010 | Levin | |
| 7,799,769 B2 | 9/2010 | White et al. | |
| 8,067,399 B2 | 11/2011 | Lehman et al. | |
| 2001/0055569 A1 | 12/2001 | Davis et al. | |
| 2002/0032171 A1 | 3/2002 | Chen | |
| 2002/0114933 A1 | 8/2002 | Gould | |
| 2002/0136752 A1 | 9/2002 | Whittle et al. | |
| 2002/0198136 A1 | 12/2002 | Mak et al. | |
| 2002/3002287 | 1/2003 | Dudley | |
| 2003/1393841 | 7/2003 | Dudley | |
| 2003/1535401 | 8/2003 | Rosario-Jansen et al. | |
| 2004/0005275 A1 | 1/2004 | Gizurarson et al. | |
| 2004/0022738 A1 | 2/2004 | Pike et al. | |
| 2004/0022739 A1 | 2/2004 | Daniels et al. | |
| 2004/0028613 A1 | 2/2004 | Quay | |
| 2004/0044086 A1 | 3/2004 | Schulze et al. | |
| 2004/0115226 A1 | 6/2004 | Li et al. | |
| 2005/0020552 A1 | 1/2005 | Aschkenasy et al. | |
| 2005/0042268 A1 | 2/2005 | Aschkenasy et al. | |
| 2005/0049233 A1 | 3/2005 | Dudley | |
| 2005/0070516 A1 | 3/2005 | Wilson et al. | |
| 2005/0112181 A1 | 5/2005 | Dudley et al. | |
| 2005/0113353 A1 | 5/2005 | Dudley et al. | |
| 2005/0129756 A1 | 6/2005 | Podhaisky et al. | |
| 2005/0142173 A1 | 6/2005 | Dudley et al. | |
| 2005/0152956 A1 | 7/2005 | Dudley | |
| 2005/0153946 A1 | 7/2005 | Hirsh et al. | |
| 2005/0187188 A1 | 8/2005 | Stein et al. | |
| 2005/0245494 A1 | 11/2005 | Thompson et al. | |
| 2006/0008420 A1 | 1/2006 | Daniels et al. | |
| 2006/0147385 A1 | 7/2006 | Pike et al. | |
| 2006/0153905 A1 | 7/2006 | Carrara et al. | |
| 2006/0210622 A1 | 9/2006 | Pace et al. | |
| 2006/0211664 A1 | 9/2006 | Dudley | |
| 2007/0134332 A1 | 6/2007 | Turnell et al. | |
| 2007/0190120 A1 | 8/2007 | Rosario-Jansen et al. | |
| 2007/0264312 A1 | 11/2007 | Skaggs et al. | |
| 2009/0062244 A1 | 3/2009 | Schwarz et al. | |
| 2009/0299156 A1 | 12/2009 | Simpson et al. | |
| 2009/0318398 A1 | 12/2009 | Dudley et al. | |
| 2010/0136105 A1 | 6/2010 | Chen et al. | |
| 2010/0173882 A1 | 7/2010 | Gillyar et al. | |
| 2010/0273838 A1 | 10/2010 | Cui et al. | |
| 2011/0009318 A1 | 1/2011 | White et al. | |
| 2011/0172196 A1 | 7/2011 | Dudley et al. | |
| 2011/0195114 A1 | 8/2011 | Carrara et al. | |
| 2011/0245215 A1 | 10/2011 | Carrara et al. | |
| 2011/0284579 A1 | 11/2011 | Pardes et al. | |
| 2011/0306582 A1 | 12/2011 | Dudley et al. | |
| 2011/0306583 A1 | 12/2011 | Malladi | |
| 2012/0058981 A1 | 3/2012 | Dudley et al. | |
| 2013/0040922 A1 | 2/2013 | Kreppner et al. | |
| 2013/0040923 A1 | 2/2013 | Kreppner et al. | |
| 2013/0045958 A1 | 2/2013 | Kreppner et al. | |
| 2013/0059827 A1 | 3/2013 | Kreppner et al. | |

FOREIGN PATENT DOCUMENTS

| | | |
|---|---|---|
| CN | 101801388 A | 8/2010 |
| DE | 943792 C | 6/1956 |
| DE | 1569286 A1 | 7/1969 |
| EP | 0084922 A2 | 8/1983 |
| EP | 0160501 A2 | 11/1985 |
| EP | 0349091 A1 | 1/1990 |
| EP | 1530965 A1 | 5/2005 |
| EP | 2068825 A1 | 6/2009 |
| EP | 2191833 A1 | 6/2010 |
| GB | 761618 A | 11/1956 |
| GB | 2237510 A | 5/1991 |
| JP | 50144579 | 11/1975 |
| JP | 54072192 | 6/1979 |
| JP | 01016716 | 1/1989 |
| JP | 01160916 | 6/1989 |
| JP | 2002541111 A | 12/2002 |
| JP | 2003509453 A | 3/2003 |
| JP | 2003519085 A | 6/2003 |
| JP | 2007524589 A | 8/2007 |
| JP | 2007530446 A | 11/2007 |
| JP | 2008522997 A | 7/2008 |
| JP | 2008536851 A | 9/2008 |
| KR | 200282242 | 7/2002 |
| TW | 175318 | 12/1991 |
| WO | 9520945 A | 8/1995 |
| WO | 9740823 A1 | 11/1997 |
| WO | 9809166 A1 | 3/1998 |
| WO | 9834621 A1 | 8/1998 |
| WO | 9847535 A1 | 10/1998 |
| WO | 0059512 A1 | 10/2000 |
| WO | 0141732 A1 | 6/2001 |
| WO | 0195888 A1 | 12/2001 |
| WO | 02051452 A1 | 7/2002 |

(56) References Cited

FOREIGN PATENT DOCUMENTS

| WO | 03011301 A1 | 2/2003 |
|---|---|---|
| WO | 03063833 A1 | 8/2003 |
| WO | 03088974 A1 | 10/2003 |
| WO | 2008040488 A1 | 4/2008 |
| WO | 2009133352 A2 | 11/2009 |
| WO | 2012022446 A1 | 2/2012 |
| WO | 2012156821 A1 | 11/2012 |

OTHER PUBLICATIONS

Ahmed et al. "Transdermal Testosterone Therapy in the Treatment of Male Hypogonadism," J. Clin Endocrinol Metab, 1988; 66(3):546-551.
Aleman et al. "A single administration of testosterone improces visuospatial ability in young women," Psychoneuroendocrinology; 2004; 29, 612-617.
Alexander et al., "Testosterone and libido in surgically and naturally menopausal women," Women's Health 2006;2(3): 459-77.
Alexander et al. "The effeccts of postmenopausal hormone therapies on female sexual functioning: a review of double-blindm randomized controlled trials," Menopause, 2004; 11(6) 749-765.
Amaral et al. "Topographic organization of projections from the amygdala to the visual cortex in the macaque monkey," Neuroscience, 2003; 118:1099-1120.
Amiaz et al. "Testosterone gel replacement improves sexual function in depressed men taking serotonergic antidepressants: a randomized placebo-controlled clinical trial," J. of Sex and Marital Therapy, 2011; 37:243-254.
Anderson et al. "The associationof testosterone, sleep, and sexual function in men and women," Brain Res. 2011; 1416:80-104.
Anonymous "Advisory Committee Briefing Document: Intrinsac (testosterome transdermal system); NDA No. 21-769" Procter & Gamble Pharmaceuticals, Inc. 2004.
Araujo et al. "Prevalence of symptomatic androgen deficiency in men," J Clin Endocrinol Metab. 2007; 92 (11):4241-7.
Arnow et al. "Women with hypoactive sexual desire disorder compared to normal females: a functional magnetic resonance Imaging study," Neuroscience 2009, 158:484-502.
Arora et al. "Permeability issues in nasal drug delivery," Drug Discov Today. 2002; 7(18):967-975.
Aspide et al. "Non-selective attention and nitric oxide in putative animal models of Attention-Deficit Hyperactivity Disorder," Behaf. Brain Res. 1998;95, 123-133.
Aspide et al. "Non-selecctive attention in a rat model of hyperactivity and attention deficit: subchronic methylphenydate and nitric oxide synthesis inhibitor treatment," Neurosci. Biobehav. Rev. 2000; 24, 59-71.
Bachmann et al. "Female androgen insufficiency: the Princeton consensus statement on definition, classification, and assessment," Fertility & Sterility 2002; 77(4): 660-665.
Bagger et al. "The potential of nasal application for delivery to the central brain—a microdialysis study of fluorescein in rats," Eur J Pharm Sci. 2004; 21: 235-242.
Baird et al. "The amygdala and sexual drive: insights from temporal lobe epilepsy surgery," Ann Neurol. 2004; 55(1):87-96.
Bals-Pratsch et al. "Substitution Therapy of Hypogonadal Men with Transdermal Testosterone Over One Year," Accta Endocrinologica (Copenh) 1988; 118: 7-13.
Bals-Pratsch et al. "Transdermal testosterone substitution therapy for male hypogonadism," Lancet 1986; 943-946.
Banks et al, "Brain uptake of glucagon-like peptide-1 antagonist exendin(9-39) after intranasal administration," J Pharmacol Exp Ther. 2004; 309(2): 469-475.
Banks et al. "Delivery of testosterone to the brain by intranasal administration: Comparison to intravenous testosterone," Journal of Drug Targeting 2008;17(2): 91-7.
Behre et al. "Intramuscular injection of testosterone undecancate for the treatment of male hypogonadism: phase I studies," Eur J Endocrinol 1999; 140(5): 414-419.

Benedict et al. "Intranasal insulin improves memory in humans," Psychoneuroendocrinology 2004: 29(10) 1326-1334.
Beral et al. "Evidence from randomised trials on the long-term effects of hormone replacement therapy," Lancet 2002; 60(9337): 942-4.
Berman et al. "Female sexual dysfunction," Urol Clin North Am 2001: 28(2) 405-416.
Berner et al. "Pharmacokinetic Characterisation of Transdermal Delivery System," Clin Pharmacokinet 1994; 26(2):121-134.
Bhasin et al. "Androgens in Men Guideline Task Force. Testosterone therapy in adult men with androgen deficiency syndromes: An Endocrine Society clinical practice guideline," J Clin Endocrinol Metab 2010; 95(6): 2536-2559.
Bhasin et al. "Clinical Review 34—Androgen Treatment of Hypogonadal Men," J. Colinical Endocrinology and Metabolism, 1992; 74(6): 1221-1225.
Bhowmick et al. "Sexual precocity in a 16-Month-Old Boy Induced by Indirect Topical Exposure to Testosterone," Clinical Pediatrics 2007; 46(6): 540-543.
Bjork et al. "Degradable starch microspheres as a nasal delivery system for insulin," Int. J. Pharm. 1988; 47, 233-238.
Born et al. "Sniffing neuropeptides: a transnasal approach to the human brain," Nat Neurosci 2002; 5(6): 514-516.
Boulous "Testim 1% testosterone gel for the treatment of male hypogonadism," Clin Ther 2005; 27(3): 286-98.
Bracket et al. "Children's Virilization and the Use of a Testosterone Gel by Their Fathers," Eur. J. Pediatr. 2005; 164:646-647.
Braunstein et al. "Safety and efficacy of a testosterone patch for the treatment of hypoactive sexual desire disorder in surgically menopausal women: A randomized, placebo-controlled trial," Archives of Internal Medicine 2005; 165, 1582-1589.
Braunstein "Androgen insufficiency in women," Growth Horm ME Res. 2006; 16:Supp1:109-17.
Brittebo et al. "Metabolism of Xenobiotics and Steroid Hormones in the Nsala Mucosa," Toxicology of the Nasal Passages, C.S. Barrow Editor. 1986. Washington.
Brittebo et al. "Steroid Metabolism by Rat Nasal Mucosa: Studies on Progesterone and Testosterone," J. Steroid Biochem. 1984; 20(5): 1147-1151.
Brittebo et al. Taurine in the olfactory system: effects of the olfactory toxicant dihlobenil, Neurotoxicology, 1995; 16(2) 271-280.
Brittebo et al. "N-demethylation of aminopyrine by the nasal mucosa in mice and rats," Acta Pharmacol. Toxicol. 1982; 51:227-232.
Brocks et al. "Pharmacokinetics of testosterone in hypogonadal men after transdermal delivery: influence of dose," J. Clin Pharmacol. 1996; 36(8): 732-739.
Buddengerg et al. "Behavioral actions of intranasal application of dopamine: effects on forced swimming, elevated plus-maze and open field parameters," Neuropsychobiology 2008; 57(1-2): 70-9.
Burger et al. "Effect of combined implants of oestradiol and testosterone on libido in post-menopausal women," Br Med J (Ciin Res Ed) 1987; 294(6577):1417-8.
Buster et al. "Testosterone patch far low sexual desire in surgically menopausal women: a randomized trial," Obstet. GynecoL 2005; 105 (5 Pt. 1): 944-952.
Cahill "Why sex matters for neuroscience" Nat Rev Neurosci 2006; 7:477-484.
Cameron et al., "Androgen replacement therapy in women" FertilSteriL 2004; 82(2)273-289.
Cardozo et al., "The effects of subcutaneous hormone implants during the climacteric" Maturitas 1984; 5(3) 177-84.
Carey et al., "Transdermal Testosterone Treatment of Hypogonadal Men" J of Urology 1988: (140):76-79.
Center for Drug Evaluation & Research Application No. 21-015. Medical Review. Feb. 15, 2000.
Center for Drug Evaluation & Research Application No. 021463Orig1s000. Medical Review. Jun. 30, 2000.
Center for Drug Evaluation & Research Application No. 022504Orig1s000. Medical Review. Nov. 19, 2010.

(56) References Cited

OTHER PUBLICATIONS

Char et al., "Nasal delivery of [14c] dextromethorphan hydrochloride in rats: levels in plasma and brain" J Pharm Sci 1992; 81(8) 750-752.
Chen et al., Delivery of nerve growth factor to the brain via the offactory pathway, J Alzheimer's Dis. 1998: 1:35-44.
Cherrier et al., "Cognitive changes associated with supplementation of testosterone or dihydrotestosterone in mildly hypogonadal men: a preliminary report," J AndroL 2003: 24(4): 568-76.
Chiang et al., "Testosterone gel monotherapy improves sexual function of hypogonadal men mainly through restoring erection," Evaluation by IIEF Score Urology. 2009; 73(4): 762-766.
Chien et al. [editors] "Nasal systemic drug delivery." Drugs and the pharmaceutical sciences, vol. 39 New Vork Marcel Dekker Inc. 1989 pp. 1-9; 27-32; 39-78 and 200-219.
Chou et al., "Lidocaine distribution into the CNS following nasal and arterial delivery: a comparison of local sampling and microdialysis techniques," Int. J. Pharm. 1998; 171, 53-61.
Chow et al., "Direct nose-brain transport of benzoylecgonine following intranasal administration in rats," J Pharm Sci. 2001; 90:1729-1735.
Chow et al., "Direct transport of cocaine from the nasal cavity to the brain following intranasal cocaine administration in rats," J. Pharm Scci. 1999; 88(8) 754-758.
Chu et al., "Formulations and use of androgens in women," Mayo Clin Proc. 2004; 79(Suppl.);S3-7.
Cicinelli et al., "Administration of unmodified progesterone by nasal spray in fertile women," Gynecol. Endocrinol. vol. 9, pp. 289-293, 1995.
Cicinelli et al., "Nasal spray administration of unmodified progesterone: evaluation of progesterone serum levels with three different radioimmunoassay techniques," Maturitas Journal of the Climacteric & Posimenopause, 19(1994), pp. 43-52.
Cicinelli et al., "Progesterone administration by nasal spray in menopausal women: comparison between two different spray formulations," Gynecol. Endocrinol. 6(1992) pp. 247-251.
Cicinelli et al., "Progesterone administration by nasal spray," Fertility and Sterility, vol. 56, No. 1, Jul. 1991, pp. 139-141.
Cicinelli et al., "Nasally-administered progesterone: comparison of ointment and spry formulations," Maturitas vol. 13 pp. 313-317, 1991.
Cicinelli et al., "Effects of the repetitive administration of progesterone by nasal spray in postmenopausal women," FertiL SteriL 1993; 60(6): 1020-1024.
Clayton et al.. "Validation of the Sexual Interest and Desire Inventory-Finale in Hypoactive Sexual Desire Disorder," J. Sex. Med. 2010; 7(12): 3918-3928.
Clayton,"Epidemiology and neurobiology of female sexual dysfunction," J Sex Med. 2007; 4:260-8.
Cofrancesco et al., "Transdermal testosterone delivery systems," The Endocrinologist 1996; 6:207-213.
Corbo et al., "Drug absorption through mucosal membranes: effect of mucosal route and penetrant hydrophilicity." Pharm. Res. 1989; 6(10): 848-852.
Corbo et al. "Nasal delivery of progestational steroids in ovariectomized rabbits. II. Effect of penetrant hydrophilicity," International Journal of Pharmaceutics vol. 50 pp. 253-260 1989.
Corbo et al., "Nasal delivery of progestational steroids in ovariectomized rabbits: I. progesterone—comparison of pharmacokinetics with intravenous and oral administration" International Journal of Pharmaceutics 1988 vol. 46 issues 1-2 pp. 133-140.
Corona et al., "Six-month administration of 1% testosterone gel is able to restore erectile function in hypogonadal patients with erectile dysfunction," Arch It Ural Androl. 2003; 80(3): 103-8.
Corona et al., "Update in testosterone therapy for men," The Journal of Sexual Medicine. 2011; 8(3) 639-54.
Cunningham et al., "Testosterone Replacement Therapy and Sleep-Related Erections in Hypogonadal Men," J. Clinical Endocrinology and Metabolism1990; 70(3) 792-797.

Cutter, "Compounded-Percutaneous testosterone gel: use and effects in Hypogonadal men," J Am Board Fam Pract 2001 14(1):22-32.
Czerniawska, "Experimental Investigations on the penetration of Au from nasal mucous membrane into cerebrospinal fluid," Acta Otolaryng 1970; 70, 58-61.
Dabbs et al., "Salivary testosterone measurements among women: relative magnitude of Circadian and menstrual cycles," Hormone Research 1991 35:182-184.
Dahlin et al., "Transfer of Dopamine in the Olfactory Pathway Following Nasal Administration in Mice," Pharmaceutical Research vol. 17 No. 6 pp. 737-742 2000.
Dahlin et al. "Levels of dopamine in blood and brain following nasal administration to rats," Eur J Pharm Sci. Aug. 14, 2001(1):75-80.
Dahlin, "Nasal Administration of Compounds Active in the Central Nervous System—Exploring the Olfactory Pathway," Acta Universitatis Upsaliensis, Comprehensive Summaries of Uppsala Dissertations from the Faculty of Pharmacy 240, 48 pp. 2000.
Danner et al., "Androgen Substitution with Testosterone Containing Nasal Drops," International Journal of Andrology vol. 3 No. 4 pp. 429-435 1980.
David et al., "Bioavailability of progesterone enhanced by intranasal spraying," Experientia, vol. 37 pp. 533-534 1981.
Davis et al., "Androgen replacement in women: a commentary," J Clin Endrocrinol. Metab 1999 84(8) 1886-1891.
Davis et al., "Circulating androgen levels and self-reported sexual function in women," JAMA 2005 294(1) 91-96.
Davis et al., "Effects of aromatase inhibition on sexual function and well-being in postmenopausal women treated with testosterone: a randomized, placebo-controlled trial," Menopause 2006 13(1) 37-45.
Davis et al., "Efficacy and safety of a testosterone patch for the treatment of hypoactive sexual desire disorder in surgically menopausal women: a randomized, placebo-controlled trial, "Menopause 2006 13(3) 387-396.
Davis et al., "Perceived effects of testosterone replacement therapy in perimenopausal and postmenopausal women: an internet pilot study," Health Care Women Int. 2003 24(9) 831-848.
Davis et al., "The Incidence of invasive breast cancer among women prescribed testosterone for low libido," .J Sex Med 2009; 6:1850-1856.
Davis et al., "What are 'normal' testosterone levels for women?" J Clinical Endocrinology and Metabolism 2001 vol. 86 No. 4 p. 1842-1843.
Davis et al., "Testosterone for Low Libido in Postmenopausal Women not Taking Estrogen," N ENgl J Med 2008: 359: 2005-2017.
Davis, "The effects of tibolone on mood and libido," Menopause 2002. 9(3): 162-170.
Davison et al., "Androgen levels in adult females: changes with age, menopause, and oophorectomy," J Clin Endocrinol Metab 2005: 90(7): 3847-3853.
Dazzi et al., "Progesterone enhances ethanol-enduced modulation of mesocortical dopamine neurons: antagonism by finasteride," J Neurochem 2002; 83:1103-1109.
De Souza et al., "Dopaminegic and serotonergic activity in neostriatum and nucleus accumbens enhanced by intranasal administration of testosterone," European Neuropsychopharmacology 2009: 19, 53-63.
De Souza Silva et al., "Increased neostriatal dopamine activity after intraperitoneal or intranasal administration of L-DOPA: on the role of benserazide pretreatment," Synapse. 1997; 27: 294-302.
De Souza Silva et al., "Intranasal administration of the dopaminergic agonists L-DOPA, amphetamine, and cocaine increases dopamine activity in the neostriatum: a microdialysis study in the rat," J Neurochem 1997; 68(1) 233-9.
De Souza Silva et al., "Intranasal dopamine application increases dopaminergic activity in the neostriatum and nucleus accumbens and enhances motor activity in the open field," Synapse. 2008; 62(3): 176-84.
Derad et al., "Intranasal angiotensin II directly influences central nervous regulation of blood pressure," American Journal of Hypertension 1998; 11, 971-977.

(56) References Cited

OTHER PUBLICATIONS

Derogatis et al., "The Female Sexual Distress Scale (FSDS): Initial validation of a standardized scale for assessment of sexually related personal distress in women," Journal of Sex and Marital Therapy, 2002: 28, 317-330.
Derogatis et al., "Validation of the Female Sexual Distress Scale-Revised for Assessing Distress in Women with Hypoactive Sexual Desire Disorder," J Sex Med 2008: 5(2): 357-364.
Dluzen et al., "The effects of intranasal infusion of 1-methyl-4-phenyl-1,2,3,6-tetrahydropyridine (MPTP) upon catecholamine concentrations within olfactory bulbs and corpus striatum of male mice," Brain Res. 1996; 741, 215-219.
Dobs et al., "Pharmacokinetic characteristics, efficacy, and safety of bucccal testosterone in hypogonadal males: a pilot study," J Clin Endocrinol. Metab. 1998: 63(1) 33-39.
Dobs et al., "Pharmacokinetics, efficacy, and safety of a permeation-enhanced testosterone transdermal system in comparison with bi-weekly injections of testosterone enanthate for the treatment of hypogonadal men," J Clin EndocrinolLMetab 1999; 84(10): 3469-3478.
Dondeti et al., "Bioadhesive and formulation parameters affecting nasal absorption," International Journal of Pharmaceutics 127 (1996) 115-133.
Draghia et al., "Gene delivery into the central nervous system by nasal instillation in rats," Gene Therapy 1995: 2, 418-423.
Ducharme et al., "Brain distribution and behavioral effects of progesterone and pregnenolone after intranasal or intravenous administration," Eur J Pharmacol Sep. 1, 2010: 641(203): 128-34.
During et al., "Glucagon-like peptide-1 receptor is involved in learning and neuroprotection," Nature Med 2003: 9(9) 1173-1179.
Eden, "A pilot study of andro-feme cream (1% testosterone)," In Proceedings of the 4th Annual Congress of the Australasian Menopause Society, 2000, Adelaide SA Australia Abstract.
Eli Lilly and Company, "Highlights of Prescribing Information for Axiron," 2010.
Eriksson et al., "Transfer of some carboxylic acids in the olfactory system following intranasal administration," Drug Target 1999; 7(2): 131-142.
Ernesti et al., "Absorption and Metabolism of Topically Applied Testosterone in an Organotypic Skin Culture," Skin Pharmmacol 1992; 5(3) 146-153.
Fabbri et al., "Testosterone treatment to mimic hormone physiology in androgen replacement therapy. A view on testosterone gel and other preparations available." Expert Opin Biol Ther, 2007 7(7) 1093-1106.
Faber, "The nasal mucosa and the subarachnoid space," Am J Anat 1937; 62, 121-148.
Ferguson, "Clinical trial development in female sexual dysfunction," J Sex Marital Ther 2002; 28(s): 77-83.
Findlay et al., "Treatment of primary hypogonadism in men by the transdermal administration of testosterone," EndocrinoL Metab 1989; 68(2): 369-373.
Fisher et al., "Di-iodo-L-tyrosine-labelled dextrans as molecular size markers of nasal absorption in the rat," J Pharm PharmacoL 1992; 44:550-554.
Fisher et al., "The effect of molecular size on the nasal absorption of water-soluble compounds in the albino rat," J. Pharm. PharmacoL 1987; 9, 357-362.
Floter et al., "Addition of testosterone to estrogen replacement therapy in oophorectomized women: effects on sexuality and well-being," Climacteric 2002; 5:357-365.
Floter et al., "Administration of testosterone undecanoate in postmenopausal women: effects on androgens, estradiol, and gonadotrophins," Menopause 2000 7(4) 251-256.
Frey et al., "Delivery of 125I-NGF to the brain via the olfactory route," Drug Deliv. 1997; 4, 87-92.
Frey, "Bypassing the blood-brain barrier to deliver therapeutic agents to the brain and spinal cord," Drug Development & Delivery 2002 2(5) 46-49.
Gelfand et al., "Androgen and estrogen-androgen hormone replacement therapy: a review of the safety literature, 1941 to 1995," Clin Ther 1997; 19(3) 383-404 discussion 367-8.
Giagulli et al., "Evidence-based medicine update on testosterone replacement therapy (TRT) in male hypogonadism: focus on new formulations," Curr Pharm Des 2011 17:1500-11.
Gizurarson, "Animal models for intranasal drug delivery studies," Acta Pharm Nord 1990; 2(2) 105-122.
Goldstat et al., "Transdermal testosterone therapy improves well-being, mood, and sexual function in premenopausal women," Menopause. 2003; 10(5):390-398.
Goldstein et al., "Hormonal cycle modulates arousal circuitry in women using functional magnetic resonance imaging," J Neurosci 2005; 25(40) 9309-9316.
Goldstein et al., "National Differences in Patient-Clinician Communication Regarding Hypoactive Sexual Desire Disorder," J Sex Med 2009 6(5) 1349-1357.
Goudsmit et al., "Testosterone fails to reverse spatial memory decline in aged rats and impairs retention in young and middle-aged animals," Behay. Neural Biol 1990:53-6-20.
Goudsmit et al., "Testosterone locally increases vasopressin content but fails to restore choline acetyltransferase activity in other regions in the senescent male rat brain," Neurosci. Lett. 1990; 112, 290-296.
Goudsmit et al., "Testosterone supplementation restores vasopressin innervation in the senescent rat brain," Brain Res. 1988; 473:306-313.
Gracia et al., "Predictors of decreased libido in women during the late reproductive years," Menopause 2004; 11(2) 144-150.
Graham et al., "The Sexual Excitation/Sexual Inhibition Inventory for Women: Psychometric Properties," Archives of Sexual Behavior 2006: 35: 397-409.
Graham, "The DSM Diagnostic Criteria for Female Orgasmic Disorder," Archives of Sexual Behavior 2010; 39: 256-270.
Gray et al., "Dose-dependent effects of testosterone on sexual function, mood, and visuospatial cognition in older men," J Clinical Endocrinology and Metabolism 2005; 90(7) 3838-3846.
Greenblatt, "Androgenic therapy in women," The Journal of Clinical Endocrinology 1942; 2:665-6.
Grober et al., "Efficacy of changing testosterone gel preparations (Androgel or Testim) among suboptimally responsive hypogonadal men," Int J Impot Res 2008; 20:213-7.
Gu et al., "Cytochrome P450 and steroid hydroxylase activity in mouse olfactory and vomeronasal mucosa," Biochem. Biophys. Res Comm. 1999; 266(1) 262-267.
Guay et al., "Serum androgen levels in healthy premenopausal wommen with and without sexual dysfunction: Part A. Serum androgen levels in women aged 20-49 years with no complaints of sexual dysfunction," Int J Impot.Res 2004; 16(2) 112-120.
Guay et al., "Serum androgen levels in healthy premenopausal women with and without sexual dysfunction: Part B: Reduced serum androgen levels in healthy premenopausal women with complaints of sexual dysfunction," Int.J Impot. Res 2004 16(2) 121-129.
Guay, "Commentary on androgen deficiency in women and the FDA advisory board's recent decision to request more safety data," International Journal of Impotence Research 2005 1, 375-376.
Guay, "Decreased testosterone in regularly menstruating women with decreased libido: a clinical observation," J Sex Marital Ther 2001; 27(5) 513-519.
Hacker et al., "Androgenic substitution for the aging male by nasal administration of a precursor of testosterone," First World Congress on Aging Male, Geneva, Switzerland 1998, Abstract.
Harris, et al., "Intranasal administration of peptides: nasal deposition, biological response, and absorption of 50 desmopressin," J Pharm Sci 19861 75(11) 1085-1088.
Hayes et al., "The impact of aging on sexual function and sexual dysfunction in women: a review of population-based studies," J Sex Med. 2005; 2(3):317-330.
Heard-Davison et al., "Genital and Subjective Measurement of Time Course Effects of an Acute Dose of Testosterone vs. Placebo in Postmenopausal Women," J. Sexual Medicine 2007; 4:209-217.

(56) References Cited

OTHER PUBLICATIONS

Heiman, "A Psychophysiological Exploration of Sexual Arousal Patterns in Females and Males," Psychophysiology 1977; 14(3):266-274.
Henriksson et al., "Uptake of inorganic mercury in the olfactory bulbs via olfactory pathways in rats," Environ. Res. 1988; 77, 130-140.
Henry et al., "A pharmacokinetic study of midazolam in dogs: nasal drop vs. atomizer administration," Pediatr. Dent. 1988; 20(5), 321-326.
Hirai et al., "Absorption of drugs from the nasal mucosa of rat," J. Pharm. 1981; 7, 317-325.
Hubayter et al., "Testosterone therapy for sexual dysfunction in postmenopausal women," Climacteric. 2008; 11:181-91.
Hussain et al., "Intranasal absorption of physostigmine and aercoline," J. Pharm. Sci. 1991; 80(8), 750-751.
Hussain et al., "Intranasal Drug Delivery," Advanced Drug Delivery Reviews, vol. 29, pp. 39-49, 1998.
Hussain et al., "Nasal Absorption of Propranolol from Different Dosage Forms by Rats and Dogs," Journal of Pharmaceutical Sciences, vol. 69, No. 12, pp. 1411-1413, Dec. 1980.
Hussain et al., "Nasal Absorption of Testosterone in Rats," Journal of Pharmaceutical Sciences, vol. 73, No. 9, pp. 1300-1301, Sep. 1984.
Hussain et al., "Nasal administration of a cognition enhancer provides improved bioavailability but not enhanced brain delivery," J. Pharm. Sci. 1990; 79(9), 771-772.
Hussain et al., "Physiochemical considerations in intranasal drug administrations," In: Chien, Y.W. (Ed) Transnasal systemic medications. Fundamentals, developmental concepts and biomedical assessments. Elsevier, Amsterdam. 1985; 121-137.
Hussain et al., "Testosterone 178-N, N-Dimethylglycinate Hydrochloride: A Prodrug with a Potential for Nasal Delivery of Testosterone," Journal of Pharmaceutical Sciences, vol. 91, No. 3 Mar. 2002, pp. 785-789.
Huston et al., "Intranasal administration of testosterone increases dopaminergic and serotonergic activities in the neostriatum and nucleus accumbens of the male rat," International Journal of Neuropsychopharmacology. 2008, 11:210 (P-05.08).
Ikeda et al., "Enhancement of bioavailability of dopamine via nasal route in beagle dogs." Chem Pharm Bull (Tokyo) Aug. 1992 40*8) 2155-8.
Illum, "Is nose-to-brain transport of drugs in man a reality?" J. Pharm. Pharmacol 2004: 56m 3-17.
Illum, "Transport of drugs from the nasal cavity to the central nervous system,"European Journal of Pharmaceutical Sciences, vol. 11 pp. 1-18, 2000.
North American Menopause Society, The Role of Testosterone Therapy in Postmenopausal Women: Position Statement of the North American Menopause Society, Menopause 2005; 12:497-511.
Edwards et al., (Science vol. 276, Jun. 20, 1997)(Year: 1997).
Aurora, J., "Development of Nasal Delivery Systems: A Review." Drug Development & Delivery. 2002. http://drug-dev.com/main/back-issues/developement-of-nasal-delivery-sstems-a-review-489.aspx.
Javanbakht et al., "Pharmacokinetics of a Novel Testosterone Matrix Transdermal System in Healthy, Premenopausal Women and Women Infected with the Human Immunodeficiency Virus," J. Clin. EndocrinoL. Metab. 2000; 85(7): 2395-2401.
Jockenhovel, "Testosterone Therapy—What, When and to Whom?" Aging Male. 2004; 7:319-24.
Jones et al., "Testosterone replacement in hypogonadal men with type 2 diabetes and/or metabolic syndrome (the TIMES2 Study)," Diabetes Care 2011; 34: 828-837.
Jung et al., "Prolonged delivery of nicotine in rats via nasal administration of proliposomes," Journal of Controlled Release, vol. 66, pp. 73-79 2000.
Junginger et al., "Mucoadhesivev Hydrogels in Drug Delivery," in Encyclopedia Pharm. Technol Swarbrick and Boylan editors. 2002; New York pp. 1848-1863.

Kaufman et al., "Efficacy and safety study of 1.62% testosterone gel for the treatment of hypogonadal men," J Sex Med. 2011; 8:2079-89.
Kaufman, "Efficacy and Safety of a New, Topical Testosterone Gel (T-gel) for Male Hormonal Supplementation," International Journal of Impotence Research 2000; 12(Supplement 3):S75(B9).
Kern et al., "Central nervous system of intranasally administered insulin duringeuglycemia in men," Diabetes. 1999; 48:557-563.
Khera et al., "Improved sexual function with testosterone replacement therapy in hypogonadal men: real-world data from the Testim Registry in the United States (TRIUS)," J Sex Med. 2011; 8:3204-13.
Kim et al., "Effects of Ovariectomy and Steroid Hormones on Vaginal Smooth Muscle Contractility," Int. J. Impot. Res. 2004; 16(1):43-50.
Kimura et al., "Relationship between nasal absorption and physiocochemical properties of quaternary ammonium compounds," rch Int Pharmacodyn Ther, 1991; 310:13-21.
Kingsberg et al., "Female Sexual Disorders: Assessment, Diagnosis, and Treatment," CNS Spectr. 2011, 16:2 pp. 49-62.
Kingsberg, "Testosterone treatment for hypoactive sexual desire disorder in postmenopausal women," J Sex Med. 2007; 4 Suppl 3:227-34.
Klugo et al., "Response of Micropenis to Topical Testosterone and Gonadotropin," J. Urology, 1978; 119:667-668.
Ko et al., "Emulsion formulations of testosterone for nasal administration," Journal of Microencapsulation, 1998, vol. 15, No. 2 pp. 197-205.
Korenman et al., "Androgen Therapy of Hypogonadal Men with Transscrotal Testosterone Systems," Am. J. Med., 1987; 83(3): 471-478.
Kuhnert et al., Testisteribe substitution with a new transdermal, hydroalcoholic gel applied of scrotal or non-scrotal skin: a multicentre trial,: Eur J.Endocrinol.Aug. 2005 153(2):317-26.
Kuile et al., "The Female Sexual Function Index (FSFI) and the Female Sexual Distress Scale (FSDS): Psychometric properties within a Dutch population," Journal of Sex and Marital Therapy 2006:32, 289-304.
Kumar et al., "A New Approach to Fertility Regulation by Interfering with Neuroendocrine Pathways," Neuroendocrine Regulation of Fertility, Int. Symp. Simla, pp. 314-322, 1974.
Kumar et al., "Pharmacokinetics of progesterone after its administration to ovariectomized rhesus monkeys by injection, infusion, or nasal spraying," Proc. Natl. Acad. Sci. USA, vol. 79, pp. 4185-4189 Jul. 1982.
Kumar et al., "Uptake of radioactivity by body fluids and tissues in rhesus monkeys after intravenous injection or intranasal spray of tritium-labeled oestradiol and progesterone," Curr. Sci. 1974a; 43, 435-439.
Kunz et al., "Virilization of Young Children fter Topical Androgen Use by Their Parents," Pediatrics 2004; 114: 282-284.
Laan et al., "Assessment of female sexual arousal: response specificity and construct validity," Psychophysiology 1995; 32:476-485.
Laan et al., "Genital responsiveness in healthy women with and without sexual arousal disorder," Journal of Sexual Medicine, 2008; 5, 1494-1435.
Laan et al., "Standard Operating Procedures for Female Orgasmic Disorder: Consensus of the International Society for Sexual Medicine," Journal of Sexual Medicine, 2013; 10:74-82.
Laan et al., "Women's sexual and emotional responses to male- and female-produced erotics," Archives of Sexual Behavior, 1994; 23, 153-169.
Laughlin et al., "Hysterectomy, oophorectomy, and endogenous sex hormone levels in older women: the Rancho Bernado Study," J Clin Endocrinal Metab. 2000; 85(2): 645-651.
Laughlin et al., "Postmenopausal Testosterone," J. Clinical Endocrinology and Metabolism, 2001; vol. 86 No. 4 pp. 1843-1844.
Laumann et al., Sexual dysfunction in the United States: prevalence and predictors,: JAMA Feb. 10, 1999; 281(6) 537-44.
Lewis et al., "Definitions/epidemiology/high risk factors for sexual dysfunction," Journal of Sexual Medicine, 2010; 7, 1598-1607.

(56) References Cited

OTHER PUBLICATIONS

Liu et al., "Intranasal administration of insulin-like growth factor-I bypasses the blood-brain barrier and protects against focal cerebral ischemic damage," J Neurol Sci. 2001; 187:91-97.

Liu et al., "Treatment of Naturally Menopausal Women with Hypoactive Sexual Desire Disorder: Effect of Transdermal Testosterone Patch in the NM2 Trial," abstract presented at the ISSWSH Meeting 2008.

Lobo et al., "Comparative effects of oral esterified estrogens with and without methyltestosterone on endocrine profiles and dimensions of sexual function in postmenopausal women with hypoactive sexual desire," Fertil Steril 2003; 79(6) 1341-52.

Lobo, "Androgens in postmenopausal women: production, possible role, and replacement options," Obstet Gynecol Surv 2001; 56(6) 361-376.

Longo et al., "Comparison of drug metabolizing system in nasal mucosa and liver of Sprague Dawley rats," Ital. J. Biochem. (Meeting) 1988; 37(1) 31A-32A.

Longo et al., "Drug-metabolizing enzymes in liver, olfactory, and respiratory epi-thelium of cattle," J Biochem Toxicot 1991 6(2) 123-128.

Lowhagen et al., "The nasal route of cerebrospinal fluid drainage in man. A light-microscope study," Neuropathol Appl Neurobiol 1994 20:543-550.

Lupo et al., "Testosterone metabolism in the olfactory epithelium of intact and castrated male rats," Neurosci Lett 1986 69(3) 259-262.

Luthold et al., "Serum testosterone tractions in women: normal and abnormal clinical states," Metabolism 1993 42(5) 638-643.

Madrid et al., "Intranasal drug delivery to the central nervous system," In 18th Int. Symp. Control. Rel. Bioact. Mater. 1991; 283-284.

Marbury et al., "Evaluation of the pharmacokinetic profiles of the new testosterone topical gel formulation, Testim, compared to AndroGel," Biopharm Drug Dispos 2003 24: 115-20.

Marynick et al., "Studies of the Transfer of Steroid Hormones cross the Blood-Cerebrospinal Fluid Barrier in the Rhesus Monkey," Endo vol. 99 No. 2 pp. 400-405, 1976.

Mathiowitz et al. [editors], "Bioadhesive Drug Delivery Systems: Fundamentals, Novel Approaches, and Development," Marcel Dekker, Inc. NYC USA 1999 523-525.

Mathison et al., "Nasal Route for Direct Delivery of Solutes to the Central Nervous System: Fact or Fiction?" Journal of Drug Targeting 1998 5(6) 415-441.

Mattern et al., "Development of a drug formulation for nasal administration of a testosterone precursor and test of its bioavailability," First World Congress on Aging Male, Geneva, Switzerland 1998 abstract.

Mattern et al., "Testosterone supplementation for hypogonadal men by the nasal route," The Aging Male vol. 11 No. 4 pp. 171-178, Dec. 2008.

Mattsson et al., "Clinical equivalence of intranasal and oral 17beta-estradiol for postmenopausal syptoms," Am J Obstet Gynecol 2000 182:545-552.

Mazer et al., "Comparison of the steady-state pharmocokinetics, metabolism, and variability of a transdermal testosterone patch versus a transdermal testosterone gel in hypogonadal men," J Sex Med Mar. 2005; 2(2) 213-26.

Mazer et al., "Enhanced transdermal delivery of testosterone: a new physiological approach for androgen replacement in hypogonadal men," J Controlled Release 1992 19(1-3) 347-361.

Mazer, "New Clinical Applications of Transdermal Testosterone Delivery in Men and Women," J Controlled Rlease 2000 65(1-2) 303-315.

Mazer, "Testosterone deficiency in women: etiologies, diagnosis, and emerging treatments," Int J Ter-til Women Med. 2002 47(2) 77-86. .

McClellan et al., "Transdermal Testosterone, ADIS New Drug Profile," Drugs, 1998 55(2) 253-258.

McClure et al, "Hypogonadal Impotence Treated by Transdermal Testosterone," Urology 1991 37(3) 224-228.

McMartin et al., "Analysis of structural requirements for the absorption of drugs and macromolecules from the nasal cavity," J Pharm Sci 1987 76(7) 535-540.

McNichols et al., "A novel testosterone gel formulation normalizes androgen levels in hypogonadal men, with improvements in body composition and sexual function," BJU Int. 2003 91:69-74.

McNichols et al., "Review of Testim gel," Expert Opin Pharmacother. 2006 7(4) 477-84.

Meikle et al., "Enhanced transdermal delivery of testosterone across non-scrotal skin produces physiological concentrations of testosterone and its metabolites in hypogonadal men," J Clin Endocrinol Metab 1992 74(3) 623-628.

Meikle et al., "Pharmacokinetics and Metabolism of a Permeation-Enhanced Testosterone Transdermal System in Hypogonadal Men: Influence of Application Site—a Clinical Research Center Study," J Clin Endocrinol Metab 1996 81 (5)1832-1840.

Meikle et al, "Transdermal testosterone gel: pharmacokinetics, efficacy of dosing and application site in hypogonadal men," BJU Int 2004 93:789-95.

Meston et al., "Disorders of Orgasm in Women," J Sex Med 2004 1(1) 66-68.

Meston et al., "Update on female sexual function," Curt Opin Urol 2001; 11(6):603-609.

Meston, "Validation of the Female Sexual Function Index (FSFI) in women with female orgasmic disorder and in women with hypoactive sexual desire disorder," J Sex Marital Ther. 2003 29(1) 39-46.

Miller et al., "Transdermal testosterone administration in women with acquired immunodeficiency syndrome wasting: a pilot study," J Clin Endocrinol Metab 1998 83(8) 2717-25.

Miller et al., "Pharmacokinetics and relative bioavailability of absorbed testosterone after administration of a 1.62% testosterone gel to different application sites in men with hypogonadism," Endocr Pract 2011 17(4) 574-83.

Miller et al., "Female Sexual Dysfunction: Review of the Disorder and evidencec for vailable Treatment alternatives," Journal of Pharmacy Practice 2003 16(3) 200-208.

Min et al., "Effects of ovariectomy and estrogen and androgen treatment on sildenafil-mediated changes in female genital blood flow and vaginal lubrication in the animal model," Ant J Obstet Gynecol 2002 187(5) 1370-1376.

Minn et al., "Drug transport into the mammalian brain: the nasal pathway and its specific metabolic barrier," J Drug Target 2002 10(4) 285-296.

Misra et al., "Biphasic testosterone delivery profile observed with two different transdermal formulations," Pharm Res 1997 14(9) 1264-8.

Misra et al., "Formulation of a tranasdermal system for biphasic delivery of testosterone," J. Congrolled Relea 1996 39 1-7.

Modelska et al., "Female sexual dysfunction in postmenopausal women: systematic review of placebo-controlled rats," Am J Obstet Gynecol 2003 188(1) 286-293.

Morales et al., "Testosterone supplementation for hypogonadal impotence: assessment of biochemical measures and therapeutic outcomes," J Urol 1997 157:849-54.

Muller et al., "Androgenic deficiencies of the aging male and psychophysiological performance-test system for clinical diagnosis" First World Congress on Aging Male, Geneva, Switzerland 1998 abstract.

Munarriz et al., "Androgen replacement therapy with dehydroepiandrosterone for androgen insufficiency and female sexual dysfunction: androgen and questionnaire results," J Sex Marital Ther 2002 28 (Suppl 1) 165-173.

Nathorst-Boos et al., "Treatment with percutaneous testosterone gel in postmenopausal women with decreased libido—effects on sexuality and psychological general well-being," Maturitas 2006 53(1) 11-18.

Nieschlag et al., "Bioavailability and LH-suppressing effect of different testosterone preparations in normal and hypogonadal men," Horm Res 1976 7:138-145.

Nieschlag et al., "Transdermal Testosterone," The Lancet May 20, 1989; 1146-47.

Nieschlag et al., Testosterone: Action, Deficiency, Substiton 3rd Edition Cambridge University Press, Cambridge UK 2004.

(56) References Cited

OTHER PUBLICATIONS

Nieschlag, "Testosterone Treatment Comes of Age: New Options for Hypogonadal Men," Clin. ENdocrinol (Oxf) 2006; 65: 275-281.
Nijland et al., "Female sexual satisfaction and pharmaceutical intervention: a critical review of the drug intervention studies in female sexual dysfunction," J Sex Med 2006 3(5) 763-777.
Nobre et al., "Prevalence and comorbidity of sexual dysfunctions in Portuguese clinical sample," Journal of Sex and Marital Therapy 2006; 32:173-182.
Nogueira et al., "In-Vivo monitoring of neostriatal dopamine activity after nasal drug administration in the rat: relevance to Parkinson's Diseaseand addiction," Neuroscience Meeting, San Diego, CA 1995 Abstract.
Ohman et al., "17ß-Estradiol Levels in Blood and Cerebrospinal Fluid after Ocular and Nasal Administration inWomen and Female Rhesus Monkeys (*Macaca mulatta*)<" Contraception, vol. 22 No. 4, pp. 349-358, Oct. 1980.
Oldendorf et al., "Lipid solubility and drug penetration of the blood brain barrier," Proc. Soc. Exp. Biol. Med. 1974; 147:813-816.
Pabla et al., A comparative permeation/release study of different testosterone gel formulations, Drug Deliv. 2007; 14:389-96.
Padero et al., "Androgen supplementation in older women: too much hype, not enough data," J Am Geriatr Soc. 2002; 50:1131-40.
Panay et al., "Testosterone Treatment of HSDD in Naturally Menopausal Women: The ADORE Study," Climeteric 2010; 3(2): 21-131.
Pardridge, "Brain drug delivery and blood-brain barrier transport," Drug Deliv 1993; 1:83-101.
Parker et al., "Experience with transdermal testosterone replacement therapy for hepogonadal men," Clin Endocrinology 1999; 50(1) 57-62.
Pharmacopela (USP). Androgens (Systemic): In USP DI-Drug Information for the Health Care Professional (23rd Ed) (Micormedex—USP DI Editorial Group: ENglewood) 2003: 132-141.
Pharmacopeia (USP), "Guidance for Industry—Nasal Spray and Inhalation Solution, Suspension, and Spray Drug Products—Chemistry, Manufacturing, and Controls Documentation," 2002.
Place et al., "Transdermal delivery of testosterone with Testoderm to provide a normal circadian pattern of testosterona," Ann 1 V.Y. Acad Sci 1991; 618(1): 441-449.
Provasi et al., "Nasal delivery progesterone powder formulations comparison with oral administration," Biol Chim Farmaceutico, Anno 132 n. 10 poster, 1993; 402-404.
Pum et al., "Effects of intranasally applied dopamine on behavioral asymmetries in rats with unilateral 6-hydroxydopamine lesions of the nigro-striatal tract," Neuroscience Aug. 4, 2009; 162(1):174-83.
Redmond, "Hormones and sexual function," Int J Fertil Womens Med 1999; 44(4) 193-197.
Revay et al, "Dopamine transporter ummunohistochemistry in medial eminence, amygdala, and other areas of the rat brain," Synapse 1996; 22:93-99.
Reyes-Vallejo et al, "Subjective sexual response to testosterone replacement therapy based on initial serum levels on total testosterone," J Sex Med 2007; 4:1757-1762.
Rold et al., "Pharmacokinetics of a new transdermal testosterone gel in gonadotropin suppressed normal men," Eur J Endocrinol. 2002; 146(5) 673-679.
Rosen et al., "Minimal clinically important differences in the erectile function domain of the international index of erectile function scale," European Urology 2011; 60: 1010-1016.
Rosen et al., "Prevalence of Sexual Dysfunction in Women: Results of a Survey Study of 329 Women in an Outpatient Gynaecological Clinic," J Sex Martial Ther 1993 19(3) 171-188.
Rosen et al., "The Female Sexual Function Index (FSFI): A Multidimensional Self-Report Instrument for the Assessment of Female Sexual Function," J Sex and Marital Therapy 2000 26: 191-208.
Ruocco et al., "Intranasal application of dopamine reduces activity and improves attention in Naples High Excitability rats that feature the mesocortical variant of ADHD," Eur Neuropsychopharmacol Oct. 19, 2009(10) 693-701.

Saad et al., "A Dose-Response Study of Testosterone on Sexual Dysfunction and Features of the Metabolic Syndrome Using Testosterone Gel and Parenteral Testosterone Undercanoate," J Androl 2008 29:102-5.
Sakane et al., "Direct drug transport from the rat nasal cavity to the cerebrospinal fluid: the relation to the molecular weight of drugs," J Pharm Pharmacol 1995 47:379-381.
Sakane et al., "The transport of a drug to the cerebrospinal fluid directly from the nasal cavity: the relation to the lopophilicity of the drug," Chem Pharm Bull 1991; 39(9) 2456-2458.
Sakane et al., "Transport of cephalexin to the cerebrospinal fluid directly from the nasal cavity," J Pharm Pharmacol 1991: 43, 449-451.
Salehian et al., "Pharmacokinetics, bioefficacy, and safety of sublingual testosterone cyclodextrin in hypogonadal men: comparison to testosterone enanthate—a clinical research center study," J Clin Endocrinol Metab 1995; 80(12) 3567-3575.
Salmon et al., "Effect of Androgens upon Lipido in Women," J Clinical Endrocrinol 1943 3:235-238.
Salonia, "Minimal clinically important differences in the erectile function domain: Tough and challenging is beautiful," European Urology 2011 60:1017-1019.
Sarrel et al., "Estrogen andestrogen-androgen replacement in post-menopausal women dissatisfied with estrogen-only therapy, Sexual behavior and neuroendocrine responses,"J. Reprod Med 1998 43(10) 847-856.
Schultheiss et al., "Pilot study of the transdermal application of testosterone gel to the penile skin for the treatment of hypogonadotropic men with erectile dysfunction," World J Urol 2000; 18:431-435.
Seftel et al., "Restorative increases in serum testosterone levels are significantly correlated to improvements in sexual functioning," J Androl 2004 25(6) 963-72.
Segraves et al., "Hypoactive Sexual Desire Disorder: Prevalence and Comorbidity in 906 Subjects," J Sex and Marital Therapy 1991 17(1) 55-58.
Sharma et al., "Testosterone implants in Specific Neural Sites Activate Female Sexual Behaviour," J. Neuroendocrincl 1994 6:423-432.
Sherwin et al., "Androgen enhances sexual motivation in females: a prospective, crossover study of sex steroids administration in the surgical menopause," Physhosom Med 1985: 47(4) 339-351.
Sherwin et al., "The role of androgen in the maintenance of sexual functioning in oophorectomized women," Psychosomatic Med 1987 49; 397-409.
Sherwin, "Randomized clinical trials of combined estrogen-androgen preparations: effects on sexual functioning," Fertil Steril 2002 77(Suppl 4) S49-54.
Shifren et al., "Sexual Problems and Distress in United States Women: Prevalence and Correlates," Obstet Gynecol 2008 112(5) 970-978.
Shifren et al., "Testosterone patch for the treatment of hypoactive sexual desire disorder in naturally menopausal women: results from the Intimate NM1 study," Menopause 2006: 13(5) 770-779.
Shifren et al., "Transdermal testosterone treatment in women with impaired sexual function ater oophectomy," New Eng J Med 2000 343(10) 682-688.
Shifren et al., "Position Statement: The role of testosterone therapy in postmenopausal women: position statement of the North American Menopause Society," Menopause 2005 vol. 12 No. 5 pp. 497-511.
Shifren, "Androgen deficiency in the oophorectomized woman," Fertil Steril 2002 77(Suppl 4) S60-62.
Shifren, "The role of androgens in female sexual dysfunction," Mayo Clin Proc 2004 79(4 Suppl): S19-24.
Shipley, "Transport of molecules from nose to brain: transneuronal anterograde and retrograde labeling in the rat olfactory system by wheat germ agglutinin-horseradish peroxidase applied to the nasal epithelium," Brain Res Bull 1985 15, 129-142.
Sigurdsson et al., "Olfactory absorption of insulin in the brain," Drug Deliv 1997 4 195-200.
Simon et al., "Testosterone patch increases sexual activity and desire in surgically menopausal women with hypoactive sexual desire disorder," J Clin Endocrinol Metab 2005 90(9) 5226-5233.

(56) References Cited

OTHER PUBLICATIONS

Singh et al., "Pharmacokinetics of a transdermal testosterone system in men with end stage renal disease receiving maintenance hemodialysis and healthy hypogonadal men," J Clin Endocrinol Metab 2001 86(6) 243702445.
Sitruk-Ware, "Transdermal delivery of steroids," Contraception 1989; 39(1) 1-20.
Skipor et al., "Local transport of testosterone from the nasal mucosa to th carotid blood and the brain in the pig," Polish Veterinary Sciences vol. 3 No. 1 pp. 19-22, 2000.
Slater et al., "Pharmacokinetics of testosterone after percutaneous gel or buccal administration," Fertil Steril 2001 76(1) 32-37.
Slayden, "Risks of menopausal androgen supplementation," Semin Reprod Endocrinol 1998; 16(2) 145-52.
Somboonport, "Testosterone therapy for postmenupausal women: efficacy and safey," Semin Reprod Med 2006; 24(2) 115-23.
Spielberg, "Abnormal Testosterone Levels in Partners of Patients Using Testosterone Gels," J Sex Med 2005 2(2) 278.
Steege et al., "Bioavailability of nasally administered progesterone," Fertility and Sterility vol. 46 No. 4, 1986 pp. 727-729.
Steidle et al., "North american AA2500 T Gel Study Group. aa2500 Testosterone gel normalizes androgen levels in aging males with improvements in body composition and sexual function." J Clin Endocrinol Metab 2003 88(6) 2673-81.
Stein, "Brain damage, sex hormones and recovery: a new role for progesterone and estrogen?" Trends Neurosci 2001 24(7) 386-391.
Sturgeon et al., "Serum levels of sex hormones and breast cancer risk in premenopausal women: a case-control tudy (USA)" Cancer Causes Control 2004 15(1) 45-53.
Swerdloff et al., "Long Term Pharmacokinetics of Transdermal Testosterone Gel Versus Testosterone Patch in Hypogonadal Men," Jun. 22, 2000 2347 Male Reproductive Poster Session Board 578.
Swerdloff et al., "Long-term pharmacokinetics of transdermal testosterone gel in hypogonadal men," J Clin Endocrinot Metab 2000 85(12) 4500-4510.
Talengaonkar et al., "Intranasal Delivery: An Approach to Bypass the Blood Brain Barrier," Indian J. Pharmacol 2004 vl 36 issue 3 140-147.
Tavares et al., Effects of intra-nasally administered testosterone on sexual proceptive behavior in female capuchin monkeys (*Cebus apella*) Behav Brain Res Apr. 16, 2007; 179(1) 33-42.
Thorne et al., "Delivery of insulin-like growth factor-I to the rat brain and spinal cord along olfactory and trigeminal pathways following intranasal administration," Neuroscience 2004; 127; 481-496.
Thorne et al., "Delivery of neurotropic factors to the central nervous system: pharmacokinetic considerations," Clin Pharmacokinet 2001 40(12) 907-946.
Thorne et al., "Quantitative analysis of the olfactory pathway for drug delivery to the brain," Brain Res 1995; 692; 278-282.
Tjalve et al.,"Uptake of manganese and cadmium from the nasal mmucosa into the central nervious system via olfactory pathways in rats," Pharmacol Toxicol 1996; 79: 347-356.
Topic et al., "Evidence for antidepressant-like action of intranasal application of testosterone," CINP Biennial International Congress Munich, Germany Jul. 13-17 2008 Abstract.
Traish et al., "Testosterone therapy in women with gynecological and sexual disorders: a triumph of clinical endorinology from 1938 to 2008," J Sex Med 2009 6:334-351.
Tremblay et al., "Pharmacokinetic modeling of a novel testosterone formulation in hypogonadal subjects," Clinical Pharmacology & Therapeutics 2008; 83; S90.
Tuiten et al., "Can Sublingual Testosterone Increase Subjective and Physiological Measures of Laboratory-Induced Sexual Arousal," archives of General Psychiatry 2002; 59: 465-473.
Tuiten et al., "Discrepancies between genital responses and subjective sexual function during testosterone substitution in women with hypothalamic amenorrhea," Psychosomatic Medicine, 1996; 56, 234-241.
Tuiten et al., "Time Course of Effects of Testosterone Administration on Sexual Arousal in Women," Archives of General Psychiatry 2000 57: 149-153.
Turna et al., "Women with low libido: correlation of decreased androgen levels with female sexual function index," Int J Impot Res 2005; 17, 148-153.
Van Den Berg et al., "Uptake of estradiol or progesterone into the CSF following intranasal and intravenous in rats," Eur J Pharm Biopharm 2004 58:131-135.
Van Honk et al., "A single administration of testosterone induces cardiac accelerative responses to angry facts in healthy young women," Behav Neurosci 2001 115; 238-242.
Van Wingen et al., "Testosterone biases automatic memory processes in women towards potential mates," NeuroImage 2008 43 114-120.
Van Wingen et al., "Testosterone reduces amygdala-orbitofrontal complex coupling," Psychoneuroendocrinology 2010 vol. 35 issue 1, pp. 105-113.
Van Wingen et al., "Testosterone increases amygdala reactivity in middle-aged women to a young adulthood level," riNeuropsychopharmacology 2008 1-9.
Viggiano et al., Behavioural, pharmacological, morpho-functional molecular studies reveal a hyperfunctioning mesocortical dopamine system in an animal model of attention deficit and hyperactivity disorder Neurosci Biobehav Rev vol. 27, pp. 683-689, 2003.
Viggiano et al., "The Naples High- and -Low-Excitability rats: selective breeding, behavioral profile, morphometry, and molecular biology of the mesocortical dopamine system," Behav. Genet, 2002; 32(5): 315-333.
Wang et al., "Brain uptake of dihydroergotamine after intravenous and nasaladministration in the rat," Biopharmaceutics and Drug Disposition 1999, 19, 571-575.
Wang et al., "Effects of Transdermal Testosterone Gel on Bone Turnover Markers and Bone Mineral Density in Hypogandal Men," Clinical Science: Reproduction (Male) Prostate Jun. 22, 2000. Male Reproduction Poster Session No. 579.
Wang et al., "ISA, ISSAM, EAU, EAA and ASA recommendations: investigation, treatment and monitoring of late-onset hypogonadism in males," Int J of Impotence Research 20009 21(1) 1-9 Epub Sep. 3, 2008.
Wang et at., "Long-term testosterone gel (AndroGel), Treatment maintains Beneficial Effects on sexual Function and mood, Lean and Fat Mass, and Bone Mineral Density in Hypogonadal Men," J. Clin Endocrinol Metab. 2004 89(5) 2085-98.
Wang et al., "Pharmacokinetics of Transdermal Testosterone Gel in Hypogonadal Men," 80th Annual Meeting of the Enndocrine Society, Jun. 24-27, 1998 Poster Session No. P2-51.
Wang et al., "Pharmacokinetics of transdermal testosterone gel in hypogonadal men: application of gel at one site versus four sites: A General Clinical Research Center Study," J Clin Endocrinol Metab 2000 85(3) 964-969.
Wang et al., "Transdermal Testosterone Gel Improves Sexual Function, Mood, Muscle Strength, and Body Composition Parameters in Hypogonadal Men," Basic Science: Reproduction-Gonadal Control (Male) Jun. 24, 2000 Male Reproduction Oral Session, No. 1360.
Wang et al., "Transdermal testosterone gel improves sexual function, mood, muscle strength, and body composition parameters in hypogonadal men," J Clinical Endocrinology Metab. 2000 85(8) 2839-2853.
Warnock et al., "Combined esterified estrogens and methyltestosterone versus esterified estrogens alone in the treatment of loss of sexual interest in surgically menopausal women," Menopause 2005 12(4) 374-84.
Watson et al., "Development and validation of brief measures of positive and negative affect: the PANAS Scales," J of Personality and Social Psychology 1988 54(6) 1063-1070.
Wattanakumtornkul et al., "Intranasal hormone replacement therapy," Menopause: The Journal of the North American Menopause Society vol. 10 No. 1 pp. 88-98 2003.
Welling et al., "Raised salivary testosterone in women is associated with increased attraction to masculine faces," Hormones and Behavior 2007 52 156-161.

(56) References Cited

OTHER PUBLICATIONS

Wiegel et al., "The Female Sexual Function Index (FSFI): Cross-Validation and Development of Clinical Cutoff Scores," J Sex and Marital Therapy 2005 31: 1-20.

Wierman et al., "Androgen therapy in women: an Endocrine Society Clinical Practice Guideline," Journal of Clinical Endocrinology & Metabolism 2006 91(10 3697-3710.

Winters et al., "Serus LH Concentrations in Hypogonadal Men During Transdermal Testosterone Replacement Through Scrotal Skin: Further Evidence that Aging Enhances Testosterone Negative Feedback. The Testoderm Study Group," Clin Endocrinol 1997 47(3) 317-322.

Written Opinion of the International Search Authority of PCT Application No. PCT/IB2012/001113 dated Sep. 27, 2012.

Xing et al., "Transdermal testosterone delivery in castrated Yucatan minipigs: pharmacokinetics and metabolism," J Control Release 1998 52 (1-2) 89-98.

Yassin et al., "Improvement of sexual function in men with late-onset hypogonadism treated with testosterone only," J Sex Med 2007; 4:497-501.

Yialamas et al., "Androgens and the aging male and female," Best Pract Res Clin Endocrinol Metab 2003 17(2) 223-236.

Yoffey, "Passage of fluid and other substances through the nasal mucosa," J Laryngol Otol 1958 72, 377-383.

Yu et al., "Testosterone pharmacokinetics after application of an investigational transdermal system in hypogonadal men," J Clin Pharmacol 1997 37(12) 1139-1145.

Yu el al., "Transdermal testosterone administration in hypogonadal men: comparison of pharmacokinetics at different sites of application and at the first and fifth days of application," J Clin Pharmacol 1997 37(12) 1129-1138.

\* cited by examiner

VIAL CELL B#6 AT 2hr MISSING INJECTION, RELEASE RATE COMPARISON WILL BE CALCULATED BY 5 x6 =30 INDIVIDUAL T/R RATIOS.

METHODS OF TREATING HYPOGONADISM WITH TRANSNASAL TESTOSTERONE BIO-ADHESIVE GEL FORMULATIONS IN MALE WITH ALLERGIC RHINITIS, AND METHODS FOR PREVENTING AN ALLERGIC RHINITIS EVENT

RELATED APPLICATIONS

This application is a continuation of U.S. patent application Ser. No. 16/275,633, filed Feb. 14, 2019, which is a continuation of U.S. patent application Ser. No. 16/044,903, filed Jul. 25, 2018, which is a continuation of U.S. patent application Ser. No. 15/856,156 filed Dec. 28, 2017, which is a continuation of U.S. patent application Ser. No. 15/599,316, filed May 18, 2017, which is a continuation of U.S. patent application Ser. No. 15/284,479, filed Oct. 3, 2016, which is a continuation of U.S. patent application Ser. No. 15/045,208, filed Feb. 16, 2016, which is a continuation of U.S. patent application Ser. No. 14/753,552, filed Jun. 29, 2015, which is a continuation of U.S. patent application Ser. No. 14/536,130, filed Nov. 7, 2014, which is a continuation of U.S. patent application Ser. No. 14/215,882, filed Mar. 17, 2014, and claims the benefit of and priority to U.S. Provisional Patent Application No. 61/802,297, filed Mar. 15, 2013, the contents of which are incorporated herein by reference in their entirety.

FIELD OF THE INVENTION

The present invention relates to methods of treating hypogonadism in a male subject through administering intranasally to the male subject an intranasal testosterone bio-adhesive gel formulation to deliver a therapeutically effective amount of testosterone, thereby treating the hypogonadism. In particular, the present testosterone therapy remains effective for treating hypogonadism when an allergic rhinitis event occurs in the male or when the male subject uses a topical nasal vasoconstrictor or a topical intranasal decongestant during the hypogonadism treatment. Further, the present invention relates to a novel method of preventing the occurrence of an allergic rhinitis event in a male, who is undergoing a hypogonadism treatment with an intranasal testosterone bio-adhesive gel formulation of the present invention. In certain embodiments, the intranasal testosterone bio-adhesive gel formulation according to the present invention comprises 4.0% and 4.5% testosterone.

BACKGROUND

Androgens are a group of C19 steroids that cause masculinization of the genital tract and the development and maintenance of male secondary sex characteristics. They also contribute to muscle bulk, bone mass, libido, and sexual performance in men. Testosterone is the main androgen secreted by the Leydig cells of the testes, and its production increases during puberty. See. e.g., Tietz: Textbook of Clinical Chemistry and Molecular Diagnostics, 4th edition, Editors: Burtis C A, Ashwood E R, and Bruns D E (2006). Androgen deficiency is now recognized to be a relatively common condition in the aging male. See, e.g., 2. Wang C, Swerdloff R. S.: Androgen replacement therapy. Ann Med, 29: 365-370 (1997); Matsumoto A. M.: Andropause: clinical implications of the decline in serum Testosterone levels with aging in men. J Gerontol A Med Sci, 57: M76-M99 (2002); and Haren Mt et al.: Andropause: a quality-of-life issue in older males. Med Clin North Am, 90: 1005-1023 (2006).

Testosterone hormone therapy is indicated for replacement therapy and males having conditions associated with a deficiency or absence of endogenous testosterone, such as to treat male hypogonadism. This may cause sexual dysfunction, muscle loss, increase in fat, infertility, decreased beard and body hair and other conditions.

Hypogonadism is defined as testosterone deficiency. Male hypogonadism may be congenital or it may develop later in life due to, e.g., injury, trauma, surgery, infection, disease, drugs and/or aging. Generally, child-onset male hypogonadism has minimal consequences and generally remains undiagnosed until puberty is delayed. The symptoms or signs associated with child-onset male hypogonadism, if left untreated, include poor muscle and body hair development, including poor facial, pubic, chest and axillary hair growth, a high-pitched voice, excessive growth of arms and legs in relation to the trunk of the body, a small scrotum, abnormal phallic and testicular growth, and other growth problems, e.g., growth and maturation of the prostate and seminal vesicles. In adult-onset male hypogonadism, the symptoms may include a deficiency in spermatozoa production, osteoporosis, muscle loss or alterations in body musculature, fat distribution, fatigue and loss of energy, weakness, anemia, mood swings, e.g., depression and anger, a decline in cognitive skills, including memory loss and inability to concentrate, sleep disturbances, gynecomastia, a reduction in both beard and body hair, impotence, erectile dysfunction; a decrease in ejaculate volume, infertility, a decrease in sexual desire (loss of libido), and a regression of other secondary sexual characteristics.

Male hypogonadism is designated as either primary hypogonadism, which is due to a disorder of the testes, or central or secondary hypogonadism that results from a disorder in the hypothalamic-pituitary axis. In primary hypogonadism, there is a lack of testosterone production in the testes because the testes do not respond to FSH and LH. As a result, elevations in both hormones, FSH and LH, are observed in primary male hypogonadism. The most common cause of primary male hypogonadism is Klinefelter's syndrome. Other congenital causes of primary gonadism may include, e.g., Bilateral Congenital Anorchia, Leydig Cell Hypoplasia (Leydig Cell Aplasia), undescended testicles (Cryptorchidism), Noonan syndrome, Myotonic Dystrophy (MD) and defects in testosterone enzymatic synthesis. Causes of adult-onset primary hypogonadism may include aging, autoimmune disorders, surgery, chemotherapy, radiation, infection, disease, surgery, alcoholism, drug therapy and recreational drug use.

In secondary or central hypogonadism, insufficient amounts of FSH and LH are produced in the hypothalamus. Genital causes of secondary or central hypogonadism include, e.g., Kallmann syndrome, Prader-Willi syndrome (PWS), Dandy-Walker malformation, Isolated luteinizing hormone (LH) deficiency and Idiopathic hypogonadotropic hypogonadism (IHH). Causes of adult-onset secondary or central hypogonadism may include aging, disease, infections, tumors, bleeding, nutritional deficiencies, alcoholism, cirrhosis of the liver, obesity, weight loss, Cushing's syndrome, hypopituitarism, hyperprolactinemia, hemochromatosis, surgery, trauma, drug therapy, and recreational drug use.

In primary male hypogonadism, the levels observed for testosterone are below normal but are generally above normal for FSH and LH. In secondary or central male hypogonadism, the levels observed for testosterone, FSH and LH are below normal. Thus, diagnosis of primary or secondary male hypogonadism is typically confirmed by hormone levels and, on testing, blood levels of testosterone in both primary and secondary hypogonadism are characterized as low and should be replaced. Treatment generally varies with etiology, but typically includes testosterone replacement therapy. In the United States, testosterone may be administered as an intramuscular injection, a transdermal patch or a transdermal gel. In other countries, oral preparations of testosterone may be available.

In view of the fact that millions of men in the United States, as well as through out the world, suffer from hypogonadism, there is a real and immediate need for an effective and convenient medical therapy that can treat this disorder, so that the quality of life of these individuals can be improved. One therapeutic goal of one such therapy to solve this immediate need might be to restore testosterone levels in men to young adulthood levels in hopes to alleviate the symptoms generally associated with hypogonadism due possibly to testosterone deficiency.

SUMMARY OF THE INVENTION

The present invention offers effective methods for treating hypogonadism in a male with allergic rhinitis. In particular, the methods involve delivering a therapeutically effective amount of testosterone to the male through an intranasal administration of an intranasal testosterone bio-adhesive gel formulation. The current testosterone therapy remains effective if an allergic rhinitis event occurs in the male during the treatment. In addition, any topical nasal vasoconstrictor or topical intranasal decongestant used by the male during the hypogonadism treatment does not interfere with the efficacy of the testosterone therapy of the invention. Further, the present invention offers advantageous effects in a hypogonadism treatment, including, such as, preventing occurrence of an allergic rhinitis event in a male undergoing a hypogonadism treatment with an intranasal testosterone bioadhesive gel of the invention.

The term "a therapeutically effective amount" means an amount of testosterone sufficient to induce a therapeutic or prophylactic effect for use in testosterone replacement or supplemental therapy to treat male testosterone deficiency, namely, hypogonadism in males.

Thus, generally speaking, the present invention provides a novel method for treating hypogonadism in a male by administering intranasally to the male an intranasal testosterone bioadhesive gel formulation to deliver a therapeutically effective amount of testosterone. The hypogonadism treatment remains effective when an allergic rhinitis event occurs in the male during the treatment.

In another aspect, the invention provides a novel method of treating hypogonadism in a male, who is using a topical nasal vasoconstrictor or a topical intranasal decongestant during the treatment. In particular, the method comprises administering intranasally to the male an intranasal testosterone bio-adhesive gel formulation to deliver a therapeutically effective amount of testosterone.

The present invention also provides a novel method of preventing an allergic rhinitis event in a male, especially when the male is undergoing a hypogonadism treatment. The method of the invention comprises administering intranasally an intranasal testosterone bioadhesive gel formulation to the male to deliver a therapeutic effective amount of testosterone for treating hypogonadism.

The intranasal testosterone bioadhesive gel formulations used herein are formulated with testosterone in amounts of between about 4% and 8.0% by weight, and preferably between about 4.0% and about 4.5% by weight, and more preferably about 4.0%, about 4.5% and 8.0% by weight.

In accordance with the present invention, the rates of diffusion of the testosterone in the intranasal gel formulations of the present invention through a Franz cell membrane, as contemplated by the present invention, are between about 28 and 100 slope/mgT %, and preferably about 30 and 95 slope/mgT %. For those intranasal gels formulated with between about 4.0% and 4.5% testosterone, the preferred rates of diffusion of testosterone are between about 28 and 35 slope/mgT %.

The present invention is also directed to novel methods for pernasal administration of the nasal testosterone gels. Generally speaking, the novel methods involve depositing the intranasal testosterone gels topically into the nasal cavity of each nostril to deliver a therapeutically effective amount of testosterone in smaller volumes over dose life for providing constant effective testosterone brain and/or blood levels for use TRT, especially for effectively treating males in need of testosterone to treat hypogonadism.

More specifically, the present invention is directed to bioavailable intranasal testosterone gel formulations suitable for pernasal administration to for use in TRT and to treat hypogonadal subjects. In accordance with the present invention, and by way of example. The present invention contemplates:

Treatment with unit-dose devices pre-filled with 125 μL 4.0% testosterone gel to deliver about 5.0 mg of testosterone per nostril (intra-nasal) given, e.g., three times a day (total dose 30 mg/day);

Treatment with unit-dose devices pre-filled with about 150 μL 4.5% gel to deliver about 6.75 mg of Testosterone per nostril (intra-nasal) given, e.g., twice daily (total dose 27.0 mg/day); and/or Treatment with unit-dose devices pre-filled with about 125 μL 4.5% gel to deliver about 5.625 mg of Testosterone per nostril (intra-nasal) given, e.g., three times a day (total dose 33.75 mg/day).

Generally speaking, the intranasal testosterone gel formulations of the present invention are formulated with about 4% and 4.5% testosterone by weight, and the testosterone is well absorbed when such gel formulations are administered pernasally to hypogonadal subjects. More specifically, testosterone is rapidly absorbed following pernasal administration with a peak concentration reached within 36 minutes to 1 hour 6 minutes (mean Tmax) following intra-nasal administration and maximal serum concentration is reached after about 1-2 hours post nasal administration. The maximum Testosterone concentration over a 24-hour interval is observed during the first administration (0-10 hours) in approximately 57% to 71% of the hypogonadal men while approximately 29% to 43% of the subjects had their maximum 24-h Testosterone concentration during subsequent administrations.

The formulations containing 4% and 4.5% testosterone by weight provide surprising properties. Importantly, the solubility of testosterone in castor oil pure is 3.6% maximum, falling to 3.36% about with 4% Labrafil. Addition of fumed silica (Aerosil, CabOsil) can increase the solubility of testosterone in castor oil up to 4.5% even with 4.0% Labrafil. This is counter intuitive for a person skilled in the art. However, without wishing to be bound by any particular theory, it is believed that this increase in solubility in the presence of silica is due, at least in part, to the fact that $SiO_2$ adsorbs about 10% of the testosterone.

In accordance with the novel methods of the present invention, the intranasal testosterone gels are topically deposited on the outer external walls (opposite the nasal septum) inside the naval cavity of each nostril, preferably at about the middle to about the upper section of the outer external wall (opposite the nasal septum) just under the cartilage section of the outer external wall inside the naval cavity of each nostril. Once gel deposition is complete within each nostril of the nose, the outer nose is then gently and carefully squeezed and/or rubbed by the subject, so that the deposited gel remains in contact with the mucosal membranes within the nasal cavity for sustained release of the testosterone over dose life. Typical testosterone gel dosage amounts deposited pernasal application is between about 50 to about 150 microliters per nostril, and preferably about 125 to about 150 microliters per nostril.

In carrying out the methods of the present invention, approximately between about 50 microliters and about 150 microliters of an intranasal testosterone gel of the present invention is applied to each nostril of a subject once or twice daily or three times a day, e.g., for one, two, three, four or more consecutive weeks, or for two, three, four, five or six consecutive days or more, or intermittently such as every other day or once, twice or three times weekly, or on demand once or twice during the same day, as TRT or to treat male testosterone deficiency, including male hypogonadism.

In addition, the present invention contemplates testosterone gel formulations for nasal administration that are pharmaceutically equivalent, therapeutically equivalent, bioequivalent and/or interchangeable, regardless of the method selected to demonstrate equivalents or bioequivalence, such as pharmacokinetic methodologies, microdialysis, in vitro and in vivo methods and/or clinical endpoints described herein. Thus, the present invention contemplates testosterone gel formulations for nasal administration that are bioequivalent, pharmaceutically equivalent and/or therapeutically equivalent, especially testosterone gel formulations for nasal administration that are 0.15% testosterone by weight of the gel formulation, 0.45% testosterone by weight of the gel formulation and 0.6% testosterone by weight of the gel formulation, when used in accordance with the therapy of the present invention to treat anorgasmia and/or HSDD by intranasal administration. Thus, the present invention contemplates: (a) pharmaceutically equivalent testosterone gel formulations for nasal administration which contain the same amount of testosterone in the same dosage form; (b) bioequivalent testosterone gel formulations for nasal administration which are chemically equivalent and which, when administered to the same individuals in the same dosage regimens, result in comparable bioavailabilities; (c) therapeutic equivalent testosterone gel formulations for nasal administration which, when administered to the same individuals in the same dosage regimens, provide essentially the same efficacy and/or toxicity; and (d) interchangeable testosterone gel formulations for nasal administration of the present invention which are pharmaceutically equivalent, bioequivalent and therapeutically equivalent.

While the intranasal testosterone gels of the present invention are preferred pharmaceutical preparations when practicing the novel methods of the present invention, it should be understood that the novel topical intranasal gel formulations and methods of the present invention also contemplate the pernasal administration of any suitable active ingredient, either alone or in combination with testosterone or other active ingredients, such as neurosteroids or sexual hormones (e.g., androgens and progestins, like testosterone, estradiol, estrogen, oestrone, progesterone, etc.), neurotransmitters, (e.g., acetylcholine, epinephrine, norepinephrine, dopamine, serotonin, melatonin, histamine, glutamate, gamma aminobutyric acid, aspartate, glycine, adenosine, ATP, GTP, oxytocin, vasopressin, endorphin, nitric oxide, pregnenolone, etc.), prostaglandin, benzodiazepines like diazepam, midazolam, lorazepam, etc., and PDEF inhibitors like sildenafil, tadalafil, vardenafil, etc., in any suitable pharmaceutical preparation, such as a liquid, cream, ointment, salve or gel. Examples of additional topical formulations for practice in accordance with the novel methods of the present invention include the topical pernasal formulations disclosed in, for example, U.S. Pat. Nos. 5,578,588, 5,756,071 and 5,756,071 and U.S. Patent Publication Nos. 2005/0100564, 2007/0149454 and 2009/0227550, all of which are incorporated herein by reference in their entireties.

The present invention is also concerned with a novel titration method to determine the appropriate daily treatment regimen, i.e., a BID or TID treatment regimen, to administer the intranasal gels of the present invention to treat hypogonadism or TRT. While the preferred treatment regimen in accordance with the present invention for administering the intranasal testosterone gels, such as 4.0% or 4.5% TBS-1 as described in Examples 1, 2, 3, 5, 7, 8, 9 and 10 above, to treat hypogonadism or TRT is twice-daily (BID) treatment regimen, the present invention contemplates that certain subjects may be more effectively treated with a three-times-a-day (TID) treatment regimen. Thus, the novel titration method of the present invention has been developed to determine which subject will require a BID or TID treatment regimen to more effectively treat hypogonadism or TRT when treated with the intranasal testosterone gels of the present invention.

In carrying out the novel titration method in accordance with the present invention, subjects will have 2 blood draws, preferably at 7 am and at 8:20 am on the test day. The day before the first blood draw, the subject will take at 10 pm, his evening intranasal dose of TBS-1. On test day, the subject will take at about 8 am, his morning intranasal dose of TBS-1.

The 24-hour $C_{avg}$ of serum total testosterone will be estimated based on the sum of serum total testosterone levels collected at the 2 sampling points: the sample collected at about 9.0 hours (at 7 am, which is 1 hour before the morning 0800 h intranasal dose) and the sample collected at about 10.33 hours following the last evening's intranasal dose (20 minutes after the morning 0800 h dose+/−20 minutes). Note that, the blood draw times may be changed (+/−1 hour) but the delay between the last dose and the first blood draw is preferably 9 hours+/−20 minutes and the delay between the next dose administered at about 10 hours+/−20 minutes after the last dose and the second blood draw is preferably +/−20 minutes.

Testosterone serum concentrations are preferably measured by a validated method at a clinical laboratory and reported in ng/dL units.

The following titration criteria is preferably used:
If the sum of the serum total testosterone level values for PK samples collected at 9.0 hours and 10.33 hours is <755 ng/dL, then the estimated 24-hour $C_{avg}$ for the male patient is <300 ng/dL
If the sum of the serum total testosterone level values for PK samples collected at 9.0 hours and 10.33 hours is 755 ng/dL, then the estimated 24-hour $C_{avg}$ for the male patient is ≥300 ng/dL.

With respect to those subjects with an estimated serum total testosterone $C_{avg}$<300 ng/dL, i.e., those subjects who sum of the serum total testosterone level values for PK samples collected at 9.0 hours and 10.33 hours is <755 ng/dL, their BID treatment regimen should be titrated to a TID treatment regimen of TBS-1 to achieve a 24-hour $C_{avg}$ of ≥300 ng/dL. The decision to titrate the subject's daily dose to TID, however, will be made by the doctor based on the criteria specified above.

With respect to those subjects with an estimated serum total testosterone $C_{avg}$≥300 ng/dL, i.e., those subjects who sum of the serum total testosterone level values for pK samples collected at 9.0 hours and 10.33 hours is ≥755 ng/dL, their BID treatment regimen should remain unchanged at a BID treatment regimen of TBS-1 since their 24-hour $C_{avg}$ is ≥300 ng/dL. The decision to titrate the subject's daily dose to TID or remain at BID, however, will be made by the doctor based on the criteria specified above.

It should be understood that, while it is preferred to draw blood from a subject to test the subject's serum total testosterone level values for pK samples at 9 hours and at 10.33 hours after the last evening's BID dose, the difference in the total draw time, i.e., 10.33 hours, may vary by as much as about +/−60 minutes and preferably no more than about +/−20 minutes between one another. It should also be understood that while, serum total testosterone level values for PK samples is 755 ng/dL is the preferred level to use to determine if titration to TID is necessary, the serum total testosterone level values for PK samples may vary as much as +/−50 and preferably no more than +/−25.

As an alternative, it should be understood that, while the titration method is described above with starting the titration method based upon the last evening's BID dose, the titration method could also be used by starting the titration method based upon the first morning dose. For example, under this alternative embodiment, the first blood draw would be taken at about 9 hours and the second blood draw would be taken at about 10.33 hours after the morning dose, so long as the second blood draw is taken at about 20 minutes after the last BID dose of the day.

Thus, a titration method in accordance with the present invention for optimizing a treatment regimen for treating a male diagnosed with hypogonadism with an intranasal testosterone gel comprises:

(a) administering intranasally to the male the intranasal testosterone gel twice daily for a selected number of days;
(b) extracting a first blood sample from the male at a selected time before a selected dose (first or second dose) of the twice daily treatment regimen on the first day after the selected number of days;
(c) extracting a second blood sample from the male at a selected time after administration of the selected dose of the twice daily treatment regimen on the first day after the selected number of days;
(d) measuring the testosterone serum level in the first blood sample to generate a first testosterone ng/dl measurement;
(e) measuring the testosterone serum level in the second blood sample to generate a second testosterone ng/dl measurement;
(f) adding the first testosterone measurement and the second testosterone measurement together to generate a serum testosterone ng/dl concentration sum for predicting a testosterone $C_{avg}$ for the male; and
(g) comparing the serum testosterone concentration sum to a target serum testosterone level to determine an optimized intranasal treatment regimen for treating the male with the intranasal testosterone gel for maintaining in the male a testosterone 24 hour serum average at a level of at least about 300 ng/dl during the optimized treatment regimen; and wherein, if the serum testosterone concentration sum is (i) less than the target serum testosterone level, titrating the twice daily intranasal treatment regimen for the male to a treatment regimen that is three times a day (TID) to treat the male for hypogonadism, or (ii) is equal to or greater than the target serum testosterone level, continuing with the twice daily intranasal treatment regimen for the male to treat the male for hypogonadism.

The present invention is also directed to packaged pharmaceuticals comprising the novel and improved testosterone gel formulations for nasal administration of the invention. For example, the present invention contemplates pre-filled, single or multi-dose applicator systems for pernasal administration to strategically and uniquely deposit the nasal testosterone gels at the preferred locations within the nasal cavity for practicing the novel methods and teachings of the present invention. Generally, speaking the applicator systems of the present invention are, e.g., airless fluid, dip-tube fluid dispensing systems, pumps, pre-filled, unit-dose syringes or any other system suitable for practicing the methods of the present invention. The applicator systems or pumps include, for example, a chamber, pre-filled with a single dose or multiple doses of an intranasal testosterone gel of the present invention, that is closed by an actuator nozzle or cap. The actuator nozzle may comprise an outlet channel and tip, wherein the actuator nozzle is shaped to conform to the interior surface of a user's nostril for (a) consistent delivery of uniform dose amounts of an intranasal testosterone gel of the present invention during pernasal application within the nasal cavity, and (b) deposition at the instructed location within each nostril of a patient as contemplated by the novel methods and teachings of the present invention. Preferably, when inserted into a nasal cavity, the pump design is configured to help ensure that the nasal tip is properly positioned within the nasal cavity so that, when the gel is dispensed, the gel is dispensed within the appropriate location within the nasal cavity. See Steps 3 and 8 in FIG. 10A. Additionally, the nozzles of to pumps are preferably designed to dispense the gels from the side in a swirl direction, i.e., the tips of the nozzles are designed to dispense in a side distribution direction, as opposed to a direct distribution direction, onto the nasal mucosa, as shown in steps 4 and 9 of FIG. 10A. It is believed that the swirl action allows for better gel adhesion and side distribution from the nozzle tip avoids the dispensed gel from splashing back onto the tip. Finally, it is preferred to design the nozzle and tip to allow for any residual gel on the nozzle/tip to be wiped off as the tip is removed from the nasal cavity. See, e.g., FIGS. 10A and 10B. Examples of pre-filled, multi-dose applicator systems include, e.g., (a) the COMOD system available from Ursatec, Verpackung-GmbH, Schillerstr. 4, 66606 St. Wendel, Germany, (b) the Albion or Digital airless applicator systems available from Airlessystems, RD 149 27380 Charleval, France or 250 North Route 303 Congers, N.Y. 10950, (c) the nasal applicators from Neopac, The Tube, Hoffmann Neopac AG, Burgdorfstrasse 22, Postfach, 3672 Oberdiessbach, Switzerland, or (d) the syringes described in the Examples herein below.

A nasal multi-dose dispenser device according to embodiments of the present invention, such as the Albion or Digital airless applicator systems available from Airlessystems, is comprised of a fluid container and a distributor pump for delivery of multiple doses of a gel or other topical formulation. In one embodiment of the present invention, the nasal multi-dose dispenser device is adapted for an airless fluid dispensing system. In another embodiment of the present invention, the nasal multi-dose dispenser device is adapted for a dip tube fluid dispensing system.

An example of an airless system that is contemplated by the present invention is one that will deliver a liquid, including gel, without the need for a pressured gas or air pump to be in contact with the liquid (or gel). In general, an airless system of the present invention comprises a flexible pouch containing the liquid, a solid cylindrical container a moving piston, an aspirating pump, a dosing valve and a delivery nozzle, as depicted, for example, in FIGS. 1-4. See also FIGS. 7A, 7B, 8A, 8B, 9A, 9B, 10A, 10B and 11.

In accordance with the present invention, the multi-dose dispenser 100 of FIG. 1 is provided with a fluid container 120, a distributor pump 140 and a cap 102.

The fluid container 120 comprises a container body 122, a base 124 and a neck 126. The distributor pump 140 is fastened to the neck by a sleeve 128. The top end of the container body 122 is closed by the distributor pump 140. The sleeve 128 tightly pinches a neck gasket 150 against the top end of the container body 122. The container body 122 forms a vacuum and houses the fluid to be dispensed.

The distributor pump 140 is closed by its actuator nozzle 130, which retains the stem 144 at the stem head. The actuator nozzle 130 comprises an outlet channel 132 and tip 134.

The actuator nozzle 130 is shaped to conform with the interior surface of a user's nostril. The actuator nozzle 130 is moveable between a downward open position and upward closed position. The user removes the cap 102 and inserts the actuator nozzle 130 in the user's nostril. When the user pushes the actuator nozzle 130 downwards to the open position, fluid in the dosing chamber 180 is withdrawn by the distributor pump 140 and exits at the tip 134 via the outlet channel 132 of the actuator nozzle 130.

FIG. 2 shows a cross-sectional view of the distributor pump 140.

The distributor pump has a body 142 provided with a bottom intake having an inlet valve 160 with a ball 162 as its valve member. The ball 162 is held in place by a cage 164 and by a return spring 170.

At its bottom end, the stem 144 carries a spring cap 172. A piston 174 is located above the spring cap 172. The stem 144 passes through an axial orifice of the piston base 176.

The side walls of the piston 174 seals against the distributor pump body 142 via lips. The sleeve 128 tightly pinches a stem gasket 152 against the stem collar 146, distributor pump body 142 and top of the piston 174.

A precompression spring 178 placed between the piston base 176 and the stem collar 146. The precompression spring 178 biases the actuator nozzle 130 via the stem 144 to the closed position.

The return spring 170, which returns the piston 174 back upwards, is compressed between two opposed seats on the cage 164 and the spring cap 172.

The distributor pump 140 has a dosing chamber 180 formed between the cage 164 and piston 174. When the user pushes the actuator nozzle downwards to the open position, fluid in the dosing chamber is withdrawn by the distributor pump 140 and dispensed from the tip of the actuator nozzle 130.

When the user releases the actuator nozzle 130 upwards to the closed position, a fluid in the container body 122 is withdrawn into the dosing chamber 180 by the distributor pump 140. Thus, a dose of fluid is ready for the next actuation of the actuator nozzle by the user.

In another embodiment of the present invention, the dispenser 200 of FIG. 3 is provided with a fluid container 220, a distributor pump 240 and a cap 202.

The fluid container 220 comprises a container body 222, a base 224 and a neck 226. The distributor pump 240 is fastened to the neck by a sleeve 228. The top end of the container body 222 is closed by the distributor pump 240. The sleeve 228 tightly pinches a neck gasket 250 against the top end of the container body 222. The container body 222 houses the fluid to be dispensed.

The distributor pump 240 is closed by its actuator nozzle 230, which retains the stem 244 at the stem head. The actuator nozzle 230 comprises an outlet channel 232 and tip 234. The actuator nozzle 230 is shaped to conform with the interior surface of a user's nostril. The actuator nozzle 230 is moveable between a downward open position and upward closed position. The user removes the cap 202 and inserts the actuator nozzle 230 in the user's nostril. When the user pushes the actuator nozzle 230 downwards to the open position, fluid in the dosing chamber 280 is withdrawn by the distributor pump 240 and exits at the tip 234 via the outlet channel 232 of the actuator nozzle 230.

FIG. 4 shows a cross-sectional view of the distributor pump 240.

The distributor pump has a body 242 provided with a bottom intake having an inlet valve 260 with a ball 262 as its valve member. The ball 262 is held in place by a cage 264 and by a return spring 270. Optionally, a dip tube 290 can extend downward from the inlet valve 260 and is immersed in the liquid contained in the container body.

At its bottom end, the stem 244 carries a spring cap 272. A piston 274 is located above the spring cap 272. The stem 244 passes through an axial orifice of the piston base 276.

The side walls of the piston 274 seals against the distributor pump body 242 via lips. The sleeve 228 tightly pinches a stem gasket 252 against the stem collar 246, distributor pump body 242 and top of the piston 274.

A precompression spring 278 placed between the piston base 276 and the stem collar 246. The precompression spring 278 biases the actuator nozzle 230 via the stem 244 to the closed position.

The return spring 270, which returns the piston 274 back upwards, is compressed between two opposed seats on the cage 264 and the spring cap 272. The distributor pump 240 has a dosing chamber 280 formed between the cage 264 and piston 274. When the user pushes the actuator nozzle downwards to the open position, air enters the dosing chamber 280, which forces the fluid in the dosing chamber to be withdrawn by the distributor pump 240 and dispensed from the tip of the actuator nozzle 230.

When the user releases the actuator nozzle 230 upwards to the closed position, the air contained in the dosing chamber 280 forces the fluid in the container body 222 to be withdrawn into the dosing chamber 280. Thus, a dose of fluid is ready for the next actuation of the actuator nozzle by the user.

The amount of fluid withdrawn by the distributor pump into the dosing chamber may be a fixed volume. The distributor pumps may be of a variety of sizes to accommodate a range of delivery volumes. For example, a distributor pump may have a delivery volume of 140 μl.

The dispensers of the present invention may dispense topical intranasal gel or other topical intranasal formulations, preferably pernasally, which contain alternative or additional active ingredients, such as neurosteroids or sexual hormones (e.g., androgens and progestins, like testosterone, estradiol, estrogen, oestrone, progesterone, etc.), neurotransmitters, (e.g., acetylcholine, epinephrine, norepinephrine, dopamine, serotonin, melatonin, histamine, glutamate, gamma aminobutyric acid, aspartate, glycine, adenosine, ATP, GTP, oxytocin, vasopressin, endorphin, nitric oxide, pregnenolone, etc.), prostaglandin, benzodiazepines like diazepam, midazolam, lorazepam, etc., and PDEF inhibitors like sildenafil, tadalafil, vardenafil, etc., in the form of a liquid, cream, ointment, salve or gel. The dispensers may be suitable for cosmetic, dermatological or pharmaceutical applications. Examples of topical intranasal formulations for topical pernasal application, which can be dispensed in accordance with the present invention include the pernasal testosterone gels of the present invention or other intranasal topical gels wherein the testosterone is replaced or combined with a another active ingredient in effective amounts, such as those active ingredients discussed herein above. In addition, other testosterone formulations suitable and contemplated for dispensing from the dispensers and/or in accordance with the methods of the present invention include the formulations disclosed in, for example, U.S. Pat. Nos. 5,578,588, 5,756,071 and 5,756,071 and U.S. Patent Publication Nos. 2005/0100564, 2007/0149454 and 2009/0227550, all of which are incorporated herein by reference in their entireties.

It should be understood by those versed in this art that the amount of testosterone in a lower dosage strength intranasal testosterone gel of the present invention that will be therapeutically effective in a specific situation will depend upon such things as the dosing regimen, the application site, the particular gel formulation, dose longevity and the condition being treated. As such, it is generally not practical to identify specific administration amounts herein; however, it is believed that those skilled in the art will be able to determine appropriate therapeutically effective amounts based on the guidance provided herein, information available in the art pertaining to testosterone replacement therapy, and routine testing.

It should be further understood that the above summary of the present invention is not intended to describe each disclosed embodiment or every implementation of the present invention. The description further exemplifies illustrative embodiments. In several places throughout the specification, guidance is provided through examples, which examples can be used in various combinations. In each instance, the examples serve only as representative groups and should not be interpreted as exclusive examples.

BRIEF DESCRIPTION OF THE DRAWINGS

The foregoing and other objects, advantages and features of the present invention, and the manner in which the same are accomplished, will become more readily apparent upon consideration of the following detailed description of the invention taken in conjunction with the accompanying figures and examples, which illustrate embodiments, wherein.

DETAILED DESCRIPTION

Figure 1:
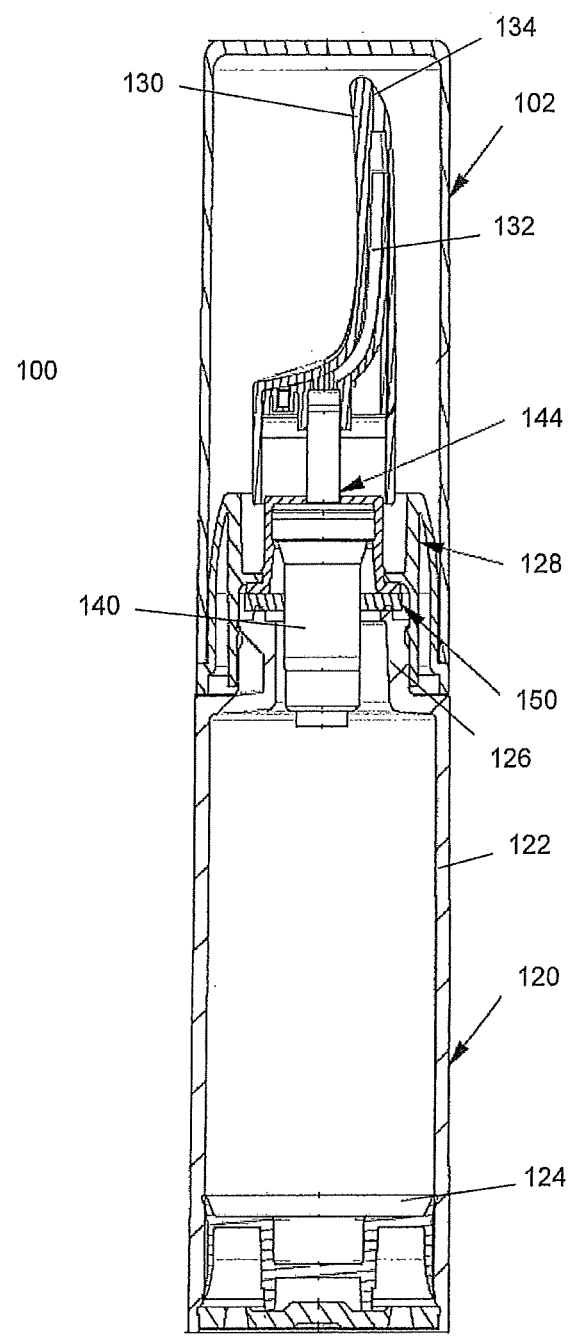
FIG. 1 is a side view of a first embodiment of the invention.
Figure 2:
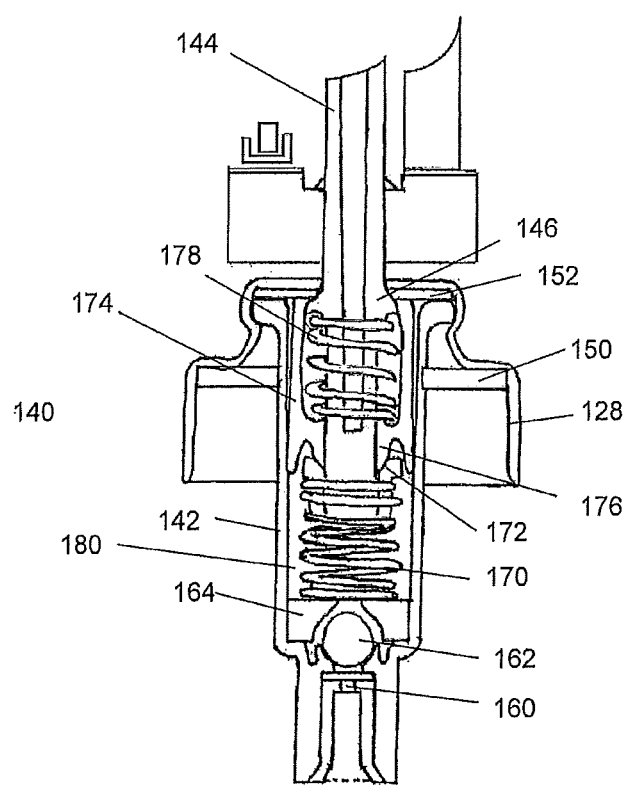
FIG. 2 is a cross-sectional side view of the distributor pump of the first embodiment of the invention.

By way of illustrating and providing a more complete appreciation of the present invention and many of the attendant advantages thereof, the following detailed description and examples are given concerning the novel lower dosage strength intranasal testosterone gels, application devices and methods of the present invention.

As used in the description of the invention and the appended claims, the singular forms "a", "an" and "the" are used interchangeably and intended to include the plural forms as well and fall within each meaning, unless the context clearly indicates otherwise. Also, as used herein, "and/or" refers to and encompasses any and all possible combinations of one or more of the listed items, as well as the lack of combinations when interpreted in the alternative ("or").

As used herein, "at least one" is intended to mean "one or more" of the listed elements.

Singular word forms are intended to include plural word forms and are likewise used herein interchangeably where appropriate and fall within each meaning, unless expressly stated otherwise.

Except where noted otherwise, capitalized and non-capitalized forms of all terms fall within each meaning.

Unless otherwise indicated, it is to be understood that all numbers expressing quantities, ratios, and numerical properties of ingredients, reaction conditions, and so forth used in the specification and claims are contemplated to be able to be modified in all instances by the term "about".

All parts, percentages, ratios, etc. herein are by weight unless indicated otherwise.

As used herein, "bioequivalence" or "bioequivalent", refers to nasally administered testosterone gel formulations or drug products which are pharmaceutically equivalent and their bioavailabilities (rate and extent of absorption) after administration in the same molar dosage or amount are similar to such a degree that their therapeutic effects, as to safety and efficacy, are essentially the same. In other words, bioequivalence or bioequivalent means the absence of a significant difference in the rate and extent to which testosterone becomes available from such formulations at the site of testosterone action when administered at the same molar dose under similar conditions, e.g., the rate at which testosterone can leave such a formulation and the rate at which testosterone can be absorbed and/or become available at the site of action to affect TRT, including hypogonadism. In other words, there is a high degree of similarity in the bioavailabilities of two testosterone gel formulation pharmaceutical products for nasal administration (of the same galenic form) from the same molar dose, that are unlikely to produce clinically relevant differences in therapeutic effects, or adverse reactions, or both. The terms "bioequivalence", as well as "pharmaceutical equivalence" and "therapeutic equivalence" are also used herein as defined and/or used by (a) the FDA, (b) the Code of Federal Regulations ("C.F.R."), Title 21, (c) Health Canada, (d) European Medicines Agency (EMEA), and/or (e) the Japanese Ministry of Health and Welfare. Thus, it should be understood that the present invention contemplates testosterone gel formulations for nasal administration or drug products that may be bioequivalent to other testosterone gel formulations for nasal administration or drug products of the present invention. By way of example, a first testosterone gel formulation for nasal administration or drug product is bioequivalent to a second testosterone gel formulation for nasal administration or drug product, in accordance with the present invention, when the measurement of at least one pharmacokinetic parameter(s), such as a Cmax, Tmax, AUC, etc., of the first testosterone gel formulation for nasal administration or drug product varies by no more than about ±25%, when compared to the measurement of the same pharmacokinetic parameter for the second testosterone gel formulation for nasal administration or drug product of the present invention.

As used herein, "bioavailability" or "bioavailable", means generally the rate and extent of absorption of testosterone into the systemic circulation and, more specifically, the rate or measurements intended to reflect the rate and extent to which testosterone becomes available at the site of action or is absorbed from a drug product and becomes available at the site of action. In other words, and by way of example, the extent and rate of testosterone absorption from a lower dosage strength gel formulation for nasal administration of the present invention as reflected by a time-concentration curve of testosterone in systemic circulation.

As used herein, the terms "pharmaceutical equivalence" or "pharmaceutically equivalent", refer to testosterone gel formulations for nasal administration or drug products of the present invention that contain the same amount of testosterone, in the same dosage forms, but not necessarily containing the same inactive ingredients, for the same route of administration and meeting the same or comparable compendial or other applicable standards of identity, strength, quality, and purity, including potency and, where applicable, content uniformity and/or stability. Thus, it should be understood that the present invention contemplates testosterone gel formulations for nasal administration or drug products that may be pharmaceutically equivalent to other testosterone gel formulations for nasal administration or drug products used in accordance with the present invention.

As used herein, "therapeutic equivalence" or "therapeutically equivalent", means those testosterone gel formulations for nasal administration or drug products which (a) will produce the same clinical effect and safety profile when utilizing testosterone drug product for TRT and to treat testosterone deficiency, including hypogonadism, in male subjects in accordance with the present invention and (b) are pharmaceutical equivalents, e.g., they contain testosterone in the same dosage form, they have the same route of administration; and they have the same testosterone strength. In other words, therapeutic equivalence means that a chemical equivalent of a lower dosage strength testosterone formulation of the present invention (i.e., containing the same amount of testosterone in the same dosage form when administered to the same individuals in the same dosage regimen) will provide essentially the same efficacy and toxicity.

As used herein a "testosterone gel formulation for nasal administration" means a formulation comprising testosterone in combination with a solvent, a wetting agent, and a viscosity increasing agent.

As used herein, "plasma testosterone level" means the level of testosterone in the plasma of a subject. The plasma testosterone level is determined by methods known in the art.

"Diagnosis" or "prognosis," as used herein, refers to the use of information (e.g., biological or chemical information from biological samples, signs and symptoms, physical exam findings, psychological exam findings, etc.) to anticipate the most likely outcomes, timeframes, and/or responses to a particular treatment for a given disease, disorder, or condition, based on comparisons with a plurality of individuals sharing symptoms, signs, family histories, or other data relevant to consideration of a patient's health status, or the confirmation of a subject's affliction, e.g., testosterone deficiency, including hypogonadism.

A "subject" according to some embodiments is an individual whose signs and symptoms, physical exams findings and/or psychological exam findings are to be determined and recorded in conjunction with the individual's condition (i.e., disease or disorder status) and/or response to a candidate drug or treatment.

"Subject," as used herein, is preferably, but not necessarily limited to, a human subject. The subject may be male or female, and is preferably female, and may be of any race or ethnicity, including, but not limited to, Caucasian, African-American, African, Asian, Hispanic, Indian, etc. Subject as used herein may also include an animal, particularly a mammal such as a canine, feline, bovine, caprine, equine, ovine, porcine, rodent (e.g., a rat and mouse), a lagomorph, a primate (including non-human primate), etc., that may be treated in accordance with the methods of the present invention or screened for veterinary medicine or pharmaceutical drug development purposes. A subject according to some embodiments of the present invention include a patient, human or otherwise, in need of therapeutic treatment of testosterone deficiency, including hypogonadism.

"Treatment," as used herein, includes any drug, drug product, method, procedure, lifestyle change, or other adjustment introduced in attempt to effect a change in a particular aspect of a subject's health (i.e., directed to a particular disease, disorder, or condition).

"Drug" or "drug substance," as used herein, refers to an active ingredient, such as a chemical entity or biological entity, or combinations of chemical entities and/or biological entities, suitable to be administered to a male subject to treat testosterone deficiency, including hypogonadism. In accordance with the present invention, the drug or drug substance is testosterone or a pharmaceutically acceptable salt or ester thereof.

The term "drug product," as used herein, is synonymous with the terms "medicine," "medicament," "therapeutic intervention," or "pharmaceutical product." Most preferably, a drug product is approved by a government agency for use in accordance with the methods of the present invention. A drug product, in accordance with the present invention, is an intranasal gel formulated with a drug substance, i.e., testosterone.

"Disease," "disorder," and "condition" are commonly recognized in the art and designate the presence of signs and/or symptoms in an individual or patient that are generally recognized as abnormal and/or undesirable. Diseases or conditions may be diagnosed and categorized based on pathological changes. The disease or condition may be selected from the types of diseases listed in standard texts, such as Harrison's Principles of Internal Medicine, 1997, or Robbins Pathologic Basis of Disease, 1998.

As used herein, "diagnosing" or "identifying a patient or subject having testosterone deficiency, such as hypogonadism, refers to a process of determining if an individual is afflicted with testosterone deficiency, such as hypogonadism.

As used herein, "control subject" means a subject that has not been diagnosed with testosterone deficiency or hypogonadism and/or does not exhibit any detectable symptoms associated with these diseases. A "control subject" also means a subject that is not at risk of developing testosterone deficiency or hypogonadism, as defined herein.

The testosterone gel formulations of the invention are viscous and thixotropic, oil-based formulations containing a solution of testosterone intended for intranasal application. The non-irritating formulation is designed to adhere to the inner nose. In addition, it acts as a controlling matrix, thus allowing sustained drug delivery through the nasal mucosa.

Other pharmacologically inactive ingredients in the testosterone intranasal gel are castor oil USP, oleoyl macrogolglycerides EP and colloidal silicon dioxide NF. None of these excipients are of human or animal origin. All excipients are well-known and listed in the "Inactive Ingredient" list for Approved Drug Products issued by the FDA.

The steroid hormone testosterone is the active ingredient in the testosterone gel formulations of the invention. The manufacture of the drug substance presents no potential risk for humans; the synthesis route is well-characterized,

TABLE 1

| Nomenclature Testosterone | |
|---|---|
| INN name | Testosterone |
| Compendial name | Testosterone |
| Chemical name | 17β-Hydroxyandrost-4-en-3-one |
| Other non-proprietary names | Androst-4-en-3-one, 17-hydroxy-, (17β)-Trans-testosterone Δ4-androsten-17β-ol-3-one |
| CAS registry number | 58-22-0 |
| Proquina code | 8139 |

Structural Formula

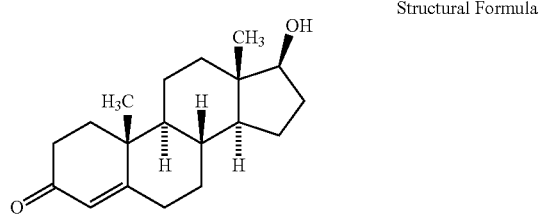

Molecular Formula $C_{19}H_{28}O_2$

Relative Molecular Mass
288.4

The physical chemical properties of testosterone are listed in Table 2.

TABLE 2

| General Properties of Testosterone | |
|---|---|
| Appearance | White or slightly creamy white crystals or crystalline powder. It is odourless, and stable in air. |
| Solubility | Practically insoluble in water (0.024 g/L), freely soluble in dehydrated alcohol, chloroform and in methylene chloride, soluble in dioxane and in vegetable oils; slightly soluble in ether. |
| Melting range | 153° C. to 157° C. |
| Specific rotation | +101° to +105° (dioxane) |
| Loss on drying | Not more than 1.0% |
| UV max | 238 nm |
| Storage | Protected from light |

Testosterone, for testosterone gel formulations of the invention, appears as white or slightly creamy white crystals or crystalline powder. It is freely soluble in methanol and ethanol, soluble in acetone and isopropanol and insoluble in n-heptane. It can also be considered as insoluble in water ($S_{20° C.}$=2.41×10$^{-2}$ g/L±0.04×10$^{-2}$ g/L); its n-Octanol/Water partition coefficient (log $P_{OW}$ determined by HPLC) is 2.84. The solubility of testosterone in oils was determined to be 0.8% in isopropylmyristate, 0.5% in peanut oil, 0.6% in soybean oil, 0.5% in corn oil, 0.7% in cottonseed oil and up to 4% in castor oil.

Because testosterone is fully dissolved within the formulations of the present invention, physical characteristics of the drug substance do not influence the performance of the drug product, testosterone gel formulations of the invention. The manufacturability of testosterone gel formulations of the invention, however is influenced by the particle size of testosterone. When using a particle size of 50%≤25 microns, 90%≤50 microns the solubility of the drug substance in the matrix is especially favorable.

In accordance with the present invention, the testosterone drug can be in, for instance, crystalline, amorphous, micronized, non-micronized, powder, small particle or large particle form when formulating to intranasal testosterone gels of the present invention. An Exemplary range of testosterone particle sizes include from about 0.5 microns to about 200 microns. Preferably, the testosterone particle size is in a range of from about 5 microns to about 100 microns, and the testosterone is in crystalline or amorphous and non-micronized or micronized form. Preferably, the testosterone is in crystalline or amorphous micronized form.

The molecular structure of testosterone contains no functional groups that can be protonated or deprotonated in the physiological pH-range. Therefore testosterone is to be considered as a neutral molecule with no pKa value in the range 1-14. Because it is neutral, testosterone is compatible with excipients.

The testosterone gel formulations of the invention are viscous and thixotropic, oil-based formulations containing a solution of testosterone intended for intranasal application. The non-irritating formulation is designed to adhere to the inner nose. In addition, it acts as a controlling matrix, thus allowing sustained drug delivery through the nasal mucosa.

Other pharmacologically inactive ingredients in the testosterone intranasal gel are castor oil USP, oleoyl macrogolglycerides EP and colloidal silicon dioxide NF. None of these excipients are of human or animal origin. All excipients are well-known and listed in the "Inactive Ingredient" list for Approved Drug Products issued by the FDA.

According to the "Handbook of Pharmaceutical Additives" oleoyl polyoxylglycerides are used as hydrophilic oil for topicals, injectables and nasals. In FDA-approved medicinal products it is used as co-emulsifier in topical emulsions/lotions/creams and in vaginal emulsions/creams. In France this excipient is approved for nasal preparations such as "Rhino-Sulforgan" (Laboratoire Jolly-Jatel, France; containing 10% oleoyl polyoxylglycerides) and "Huile Gomenolee 2% ("Laboratoire Goménol, France; containing 10% oleoyl polyoxylglycerides). Hence, like for castor oil it can be deduced that oleoyl polyoxylglycerides is suitable for an application route where safety and tolerability are of highest importance (e.g. injectables and nasal or vaginal preparations).

Oleoyl macrogolglycerides are also referred to as Labrafil M 1944 CS, apricot kernel oil PEG-6 esters, Peglicol-5-oleate, mixture of glycerides and polyethylene esters. The castor oil, which is used as a solvent for testosterone gel formulations of the invention, is a fixed oil. Such oils have the advantage of being non-volatile or spreading (in contrast to essential oils or liquid paraffin), but have the disadvantage of being hydrophobic. The nasal mucosa contains 95-97% water. Without the oleoyl macrogol-glycerides, the castor oil containing the active ingredient would form a non-interactive layer on the mucous membrane. In order to achieve adequate contact between the castor oil layer and the mucous membrane, the hydrophilic oleoyl macrogol-glycerides oil is added to the formulation to form an emulsion between the castor oil and the mucosa fluid.

Oleoyl macrogolglycerides are used in semi-solids at concentrations ranging from about 3 to 20%, depending on the application. The amount of oleoyl macrogol-glycerides in testosterone gel formulations of the invention is high enough to allow for a better contact of the carrier oil with the mucous membrane and low enough to have minimal impact on the amount of testosterone that can be incorporated into the carrier oil. A favourable concentration of oleoyl microgol-glycerides in testosterone gel formulations of the invention is found to be 4% of the formulation.

According to the "Handbook of Pharmaceutical Additives" colloidal silicon dioxide is used as an oil adsorbent, thermal stabiliser and gellant. In FDA-approved medicinal products it is used in dental gels, sublingual tablets, endocervical gel, suppositories, vaginal emulsions/creams/tablets/tampons and capsules for inhalation. Furthermore, it is used as an excipient in "Testoderm with adhesives" (Alza Corporation, approved in 1996) a testosterone transdermal patch. Hence, it can be deduced that colloidal silicon dioxide is suitable for an application route where safety and tolerability are of highest importance (e.g. inhalations, endocervical, vaginal or rectal preparations).

For clinical trial supplies, testosterone intranasal gel is supplied in unit-dose syringes consisting of a syringe body made from polypropylene, a plunger moulded from polyethylene and a syringe cap made from high density polyethylene. The syringes are wrapped in aluminum foil as secondary packaging. The pre-filled unit-dose syringes used in accordance with the study in the Examples are filled as follows: (a) 4% testosterone intranasal bio-adhesive gel—148 microliters and 5.92 mgs of testosterone; (b) 4.5% testosterone intranasal bio-adhesive gel—148 microliters and 6.66 mgs of testosterone; and (c) 4.5% testosterone intranasal bio-adhesive gel—148 microliters and 7.785 mgs of testosterone.

The oil in testosterone gel formulations of the invention is thickened with colloidal silicon dioxide, which acts as a gel-forming agent. This compound is used commonly for stiffening oleogels.

The intended dosage form for testosterone gel formulations of the invention is a semi-solid, not a liquid. The formulation is thickened with colloidal silicon dioxide. It is believed that colloidal silicon dioxide contributes to the thixotropic properties of the gel, simplifying drug delivery to the nostril.

Colloidal silicon dioxide is generally an inert material which is well tolerated as an excipient in mucosal applications such as suppositories. Colloidal silicon dioxide is typically used in these preparations at concentrations ranging from about 0.5 to 10%. The concentration of colloidal silicon dioxide in testosterone gel formulations of the invention is high enough to achieve gel formation but at a level that has minimal impact on testosterone incorporation into the carrier oil.

Preferably, the intranasal testosterone gels of the present invention have in general, a viscosity in the range of between about 3,000 cps and about 27,000 cps. It should nevertheless be understood by those versed in this art that, while the above-mentioned viscosity range is believed to be a preferred viscosity range, any suitable viscosities or viscosity ranges that do not defeat the objectives of the present invention are contemplated.

A detailed description of batches of a testosterone gel formulation of the invention is shown in Table 3.

TABLE 3

Composition of a testosterone gel formulation of the invention

| Component | Amount (% w/w) 4.0% | Amount (% w/w) 0.45% |
|---|---|---|
| Testosterone | 4.0% | 4.5% |
| Castor oil | 88% | 87.5% |

TABLE 3-continued

Composition of a testosterone gel formulation of the invention

| Component | Amount (% w/w) 4.0% | Amount (% w/w) 0.45% |
|---|---|---|
| Oledyl macrogol-glycerides | 4.0% | 4.0% |
| Colloidal silicon dioxide | 4.0% | 4.0% |

The testosterone gel formulations of the invention are stored at room temperature (20-25° C. or 68 to 77° F.). Temperature excursions from 15 to 30° C. or 59 to 86° F. are permissible for the testosterone gel formulations of the inventions. The stability data supports a 12-month shelf life. Unit dose syringes are chosen for the primary packaging of the clinical materials for the clinical trial described below to allow for ease of dosing, ability to generate multiple doses by varying the fill volume and consistency of dose delivered. The syringe consists of a syringe body, a plunger and a syringe cap. The syringes body is moulded from polypropylene, the plunger is moulded from polyethylene and the cap is HDPE. These syringes are designed and manufactured to deliver sterile and non-sterile solutions, liquids and gels at low volumes. For additional protection from the environment (i.e., exposure to dirt, light, humidity and oxygen), the syringes are packed in a foil-laminate overwrap pouch.

The syringes and caps are designed for use in a clinical setting and meet the requirements of the EU Medical Devices Directive 93/42/EEC of Jun. 14, 1993 and as amended. As this container closure is only intended for use in this portion of the clinical program, no additional studies will be performed on the syringe and syringe components.

For a further element of protection, two syringes are contained in secondary packaging consisting of an aluminium foil pouch. Two syringes are packaged in the aluminium foil pouch and each pouch is sealed.

The pouch consists of a flexible, 3-layered-foil-laminate of a) polyester 12 micron, b) aluminum 12 micron and c) a polyethylene 75 micron. It is manufactured by Floeter Flexibles GmbH, and supplied under the name "CLIMA-PAC II 12-12-75".

The invention provides for intranasal bio-adhesive gel formulations of testosterone to be administered intranasally, wherein the dosage of the formulation is from about 4.0% or 4.5% testosterone by weight of said gel.

The methods and treatments of the present invention are suitable for TRT in men and are especially suitable to treat testosterone deficient male subjects, such as those who are diagnosed with hypogonadism.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

EXAMPLES

Having now generally described the invention, the same will be more readily understood through reference to the following Examples which are provided by way of illustration, and are not intended to be limiting of the present invention, unless specified.

The following examples are put forth for illustrative purposes only and are not intended to limit the scope of what the inventors regard as their invention.

Example 1

Description and Composition of Testosterone

Gel Formulations of the Invention

The compositions of three different concentrations of the drug product to be administered in this clinical trial are provided in the tables below.
Description of Dosage Form The testosterone gel formulations of the invention are viscous and thixotropic, oil-based formulations containing solubilized testosterone intended for intranasal application. The drug product is formulated with the compendial inactive ingredients: castor oil, oleoyl polyoxylglycerides and colloidal silicon dioxide.

Two different doses of the testosterone gel formulations of the invention are intranasally administered: 0.4% w/w and 0.45% w/w. An overage is added to each syringe to account for the gel that is retained in the syringe after dosing. This overage remains consistent at 23 μl, regardless of volume of gel in the syringe.

4.0% and 4.5% Intranasal Testosterone Compositions

TABLE 1

Components, Quantity, Quality Standards and Function—4.0% testosterone gel formulation of the invention

| Component | Amount (% w/w) | Amount per Syringe (mg) | Amount Delivered per Dose (mg) | Function | Quality Standard |
|---|---|---|---|---|---|
| Testosterone | 4.0% | 5.92 | 5.0 | Active ingredient | USP |
| Castor oil | 88.0% | 130.24 | 110 | Solvent | USP |
| Oleoyl macrogol-glycerides | 4.0% | 5.92 | 5.0 | Wetting agent (hydrophilic oil) | Ph. Eur. |
| Colloidal silicon dioxide | 4.0% | 5.92 | 5.0 | Viscosity increasing agent | USP/NF |

TABLE 1A

Components, Quantity, Quality Standards and Function—0.6% testosterone gel formulation of the invention

| Component | Amount (% w/w) | Amount per Syringe (mg) | Amount Delivered per Dose (mg) | Function | Quality Standard |
|---|---|---|---|---|---|
| Testosterone | 0.6% | 0.74 | 0.6 | Active ingredient | USP |
| Castor oil | 91.4% | 112.42 | 91.4 | Solvent | USP |
| Oleoyl polyoxyl-glycerides | 4.0% | 4.92 | 4.0 | Wetting agent (hydrophilic oil) | Ph. Eur/NF. |

TABLE 1A-continued

Components, Quantity, Quality Standards and Function—0.6% testosterone gel formulation of the invention

| Component | Amount (% w/w) | Amount per Syringe (mg) | Amount Delivered per Dose (mg) | Function | Quality Standard |
|---|---|---|---|---|---|
| Colloidal silicon dioxide | 4.0% | 4.92 | 4.0 | Viscosity increasing agent | NF |
| Total | 100% | 123 mg | 100 mg | | |

TABLE 2

Components, Quantity, Quality Standards and Function, TBS-1: 5.6 mg/125 μl/syringe (4.5% gel)

| Component | Amount (% w/w) | Amount per Syringe (mg) | Amount Delivered per Dose (mg) | Function | Quality Standard |
|---|---|---|---|---|---|
| Testosterone | 4.5% | 6.66 | 5.63 | Active ingredient | USP |
| Castor oil | 87.5% | 129.5 | 109.37 | Solvent | USP |
| Oleoyl macrogol-glycerides | 4.0% | 5.92 | 5.0 | Wetting agent (hydrophilic oil) | Ph. Eur. |
| Colloidal silicon dioxide | 4.0% | 5.92 | 5.0 | Viscosity increasing agent | USP/NF |

TABLE 3

Components, Quantity, Quality Standards and Function, TBS-1: 6.75 mg/150 μl/syringe (4.5% gel)

| Component | Amount (% w/w) | Amount per Syringe (mg) | Amount Delivered per Dose (mg) | Function | Quality Standard |
|---|---|---|---|---|---|
| Testosterone | 4.5% | 7.79 | 6.75 | Active ingredient | USP |
| Castor oil | 87.5% | 151.37 | 131.25 | Solvent | USP |
| Oleoyl macrogol-glycerides | 4.0% | 6.92 | 6.0 | Wetting agent (hydrophilic oil) | Ph. Eur. |
| Colloidal silicon dioxide | 4.0% | 6.92 | 6.0 | Viscosity increasing agent | USP/NF |

Container

Testosterone gel formulations of the invention are supplied in unit-dose polypropylene syringes. Two syringes of each dosage are packaged in a protective aluminium foil pouch.

Example 2

Intranasal Testosterone Gel Formulations

The testosterone gel formulations of the invention are formulations of testosterone in an intranasal gel proposed for assessing the pharmacokinetic of two different doses of testosterone gel formulations of the invention for testosterone gel formulations of the invention in hypogonadal men.

The active ingredient, testosterone, is sourced from Bayer Schering. Challenges for nasal delivery include:

requirements for larger particles than pulmonary administration (i.e., only particles >10 μm are sufficiently heavy to avoid entering the respiratory tract);

concentrations must be higher due to the smaller volumes that can be administered;

rapid clearance of the therapeutic agent from the site of deposition results in a shorter time available for absorption;

potential for local tissue irritation; and limited formulation manipulation possibilities to alter drug delivery profiles.

Testosterone is indicated for TRT in males who are testosterone deficient for any number of reasons, including hypogonadism. The currently available options for administration of testosterone are oral, buccal, injectable, implantable and transdermal (patches and gels).

An intranasal testosterone (3.2%) gel is developed for the treatment of hypogonadism in men and has been administered to hypogonadal men in several clinical trials, see e.g., Mattern, C. et al., 2008 The Aging Male 11(4):171-178 (December 2008, which is incorporated herein by reference in its entirety. In a phase II study NCT00975650, which was performed in the U.S. in testosterone deficient men and which was supplemental to the Romanian study reported in Mattern et al., *Supra*, the 3.2% intranasal gel as reported in Mattern et al, *Supra*, failed to reach testosterone plasma levels required by the FDA to support TRT efficacy in testosterone deficient men. The intranasal testosterone gels formulations of the present invention are developed at concentrations of about 4.0% and 4.5% testosterone.

Example 3

Overages

Testosterone Gel Formulations of the Invention

No overage is added to the formulation. An overage is added to each syringe to account for the gel that is retained in the syringe after dosing. This overage remains consistent at 23 μl, regardless of volume of gel in the syringe. The theoretical fill and dispensed amounts for testosterone gel formulations of the invention are provided below.

| Syringe Dosage | Theoretical Fill Volume (μl) | Theoretical Dispensed Volume (μl) |
| --- | --- | --- |
| 4.0% Testosterone Gel formulation of the Invention | 148 | 125 |
| 4.5% Testosterone Gel formulation of the Invention | 148 | 125 |
| 4.5% Testosterone Gel formulation of the Invention | 173 | 150 |

Example 4

Physicochemical and Biological Properties

Testosterone Gel Formulations of the Invention

The testosterone bio-adhesive gel formulations of the invention has a viscosity in the range of 3,000 to 10,000 mPaxsec. The viscosity is important because it facilitates maintenance of the gel in the nasal cavity in contact with the nasal mucosa. When the viscosity is less than approximately 3,000 mPaxsec (i.e., 3,000 centipoise), the gel tends to be drawn by gravity out of the nasal cavity.

Example 5

Batch Formula

Testosterone Gel Formulations of the Invention

Three different concentrations of testosterone gel formulations of the invention, 0.15%, 0.45% and 0.6%, are manufactured for the proposed clinical trial. The batch formulae for these batches are presented in Table 5 below.

TABLE 5

200 KG Batch Formulae for 4.0% and 4.5% bio-adhesive testosterone gel formulations of the invention at the 8 kg Batch Size

| Components | 4.0% | 4.5% |
| --- | --- | --- |
| Testosterone, USP | 8 g | 9 g |
| Castor oil, USP | 176 g | 175 g |
| Oleoyl polyoxylglycerides, Ph. Eur./NF | 8 g | 8 g |
| Colloidal silicon dioxide, NF | 8 g | 8 g |

Example 6

Figure 34:
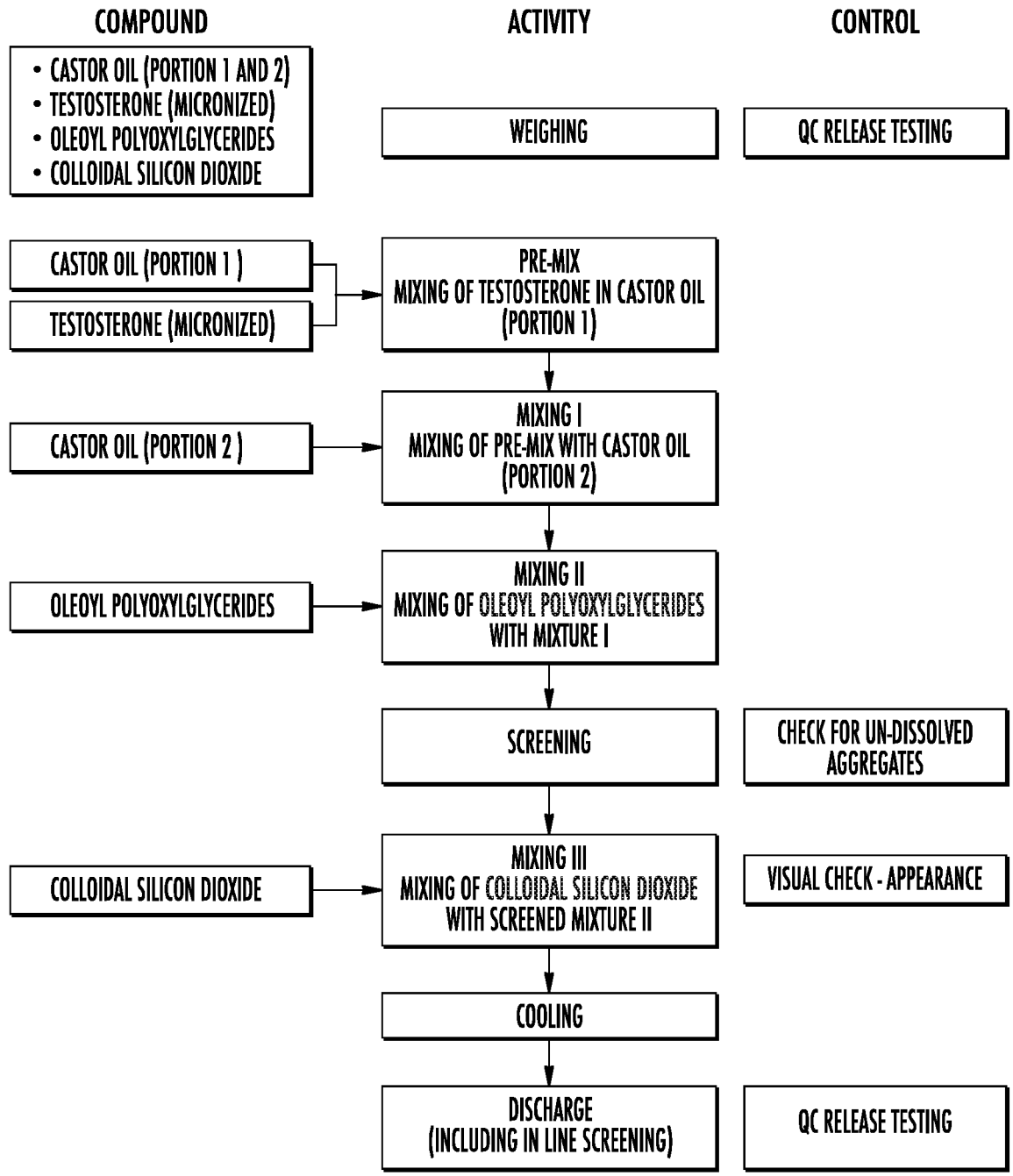
FIG. 34 is an operational diagram for manufacturing the testosterone gel formulations in accordance with the invention.

The Testosterone Gel Formulations of the Invention is manufactured according to the process shown in FIG. 34.

Mixing of the Ingredients—Bulk Gel

The Pre-Mix is prepared by mixing, with a propeller mixer, the full amount of Testosterone with portion 1 of the castor oil for 10 minutes.

Mixture I is prepared by adding the Pre-Mix to the remaining castor oil and mixing for 60 minutes. The product temperature is maintained below 50° C. for the entire mixing process.

The oleoyl polyoxoylglycerides are pre-heated to 40-50° C. and mixed for 10 minutes before being added to Mixture I. This is identified as Mixture II. It is mixed for 45 minutes while maintaining product temperature below 50° C. Mixture II is then screened through a sieve to remove any un-dissolved Testosterone aggregates.

Mixture III is prepared by adding the colloidal silicon dioxide to Mixture II and mixing for 15 minutes while maintaining product temperature below 50° C. A visual check is conducted after this step, to ensure that the gel is clear.

At the completion of mixing the gel is stirred and cooled to a product temperature below 30° C. The product is then discharged into stainless steel drums and the bulk gel sample is taken for analytical testing.

Filling and Packaging—Clinical Supplies

After release of the final gel mixture by the quality control laboratory, the filling and packaging process is carried out by filling a pre-determined volume into the syringe followed by the application of the syringe cap. Two syringes are packaged into a foil pouch.

The syringes are filled using a pipette with the gel taken from a holding tank. The tip of the pipette is discarded after the syringe is filled and the syringe cap is applied. Each syringe is individually labeled.

Following the application of the label, two syringes are packaged in a pre-formed foil pouch and the pouch is sealed. Each pouch is labelled.

Example 7

Drug Product TBS-1

The drug product, TBS-1, is a viscous and thixotropic, oil-based formulation containing solubilized testosterone intended for intranasal application for the treatment of hypogonadism in men.

The drug product is formulated with the following compendial inactive ingredients: castor oil, oleoyl macrogolglycerides, and colloidal silicon dioxide.

To allow for different doses to be administered in the Phase II program, a syringe is used as the unit dose container for the clinical supplies.

The syringes intended for use in the clinical program are needleless and a twist off cap is applied to the end of the syringe. The syringe consists of the syringe barrel and the plunger. The syringe barrel is formed from polypropylene. The plunger is formed from polyethylene. The syringe cap is formed from High Density Polyethylene (HDPE).

New dose formulation of TBS-1 is manufactured for clinical study TBS-1-2010-01 (submitted to the Agency on Jul. 28, 2010 Serial Number 0019). The quantity of testosterone in these formulations is 4.0% and 4.5% along with an adjustment of the amount of castor oil. The precise formulation is listed in Tables 1, 2 and 3. TBS-1 is concentrated so that the same dose is administered intranasally in a smaller volume.

Three different concentrations of TBS-1 gel will be administered in this clinical trial 5.0 mg/125 μl/syringe (4.0% gel), 5.6 mg/125 μl/syringe (4.5% gel) and 6.75 mg/150 μl/syringe (4.5% gel). An overage is added to each syringe to account for the gel that is retained in the syringe after dosing. This overage remains consistent regardless of volume of gel in the syringe.

Composition

The compositions of the three different concentrations of the drug product to be administered in this clinical trial are provided in Tables 1, 2 and 3.

TABLE 1

Components, Quantity, Quality Standards and Function, TBS-1: 5.0 mg/125 μl/syringe (4.0% gel)

| Component | Amount (% w/w) | Amount per Syringe (mg) | Amount Delivered per Dose (mg) | Function | Quality Standard |
|---|---|---|---|---|---|
| Testosterone | 4.0% | 2.92 | 5.0 | Active ingredient | USP |
| Castor oil | 88.0% | 130.24 | 110 | Solvent | USP |
| Oleoyl macrogolglycerides | 4.0% | 5.92 | 5.0 | Wetting agent (hydrophilic oil) | Ph. Eur. |
| Colloidal silicon dioxide | 4.0% | 5.92 | 5.0 | Viscosity increasing agent | USP/NF |

TABLE 2

Components, Quantity, Quality Standards and Function, TBS-1: 5.6 mg/125 μl/syringe (4.5% gel)

| Component | Amount (% w/w) | Amount per Syringe (mg) | Amount Delivered per Dose (mg) | Function | Quality Standard |
|---|---|---|---|---|---|
| Testosterone | 4.5% | 6.66 | 5.63 | Active ingredient | USP |
| Castor oil | 87.5% | 129.5 | 109.37 | Solvent | USP |
| Oleoyl macrogolglycerides | 4.0% | 5.92 | 5.0 | Wetting agent (hydrophilic oil) | Ph. Eur. |
| Colloidal silicon dioxide | 4.0% | 5.92 | 5.0 | Viscosity increasing agent | USP/NF |

TABLE 3

Components, Quantity, Quality Standards and Function, TBS-1: 6.75 mg/150 μl/syringe (4.5% gel)

| Component | Amount (% w/w) | Amount per Syringe (mg) | Amount Delivered per Dose (mg) | Function | Quality Standard |
|---|---|---|---|---|---|
| Testosterone | 4.5% | 7.79 | 6.75 | Active ingredient | USP |
| Castor oil | 87.5% | 151.37 | 131.25 | Solvent | USP |
| Oleoyl macrogolglycerides | 4.0% | 6.92 | 6.0 | Wetting agent (hydrophilic oil) | Ph. Eur. |
| Colloidal silicon dioxide | 4.0% | 6.92 | 6.0 | Viscosity increasing agent | USP/NF |

Container

TBS-1 gel is supplied in unit-dose polypropylene syringes. Two syringes of each dosage are packaged in a protective aluminium foil pouch.

Control of Drug Products [TBS-1, Gel]

Specification [TBS-1, Gel]

The TBS-1 bulk gel is tested to the following specifications for batch release.

TABLE 1

Specification for TBS-1 Bulk Gel

| Test Parameter | Method/Reference | Acceptance Criteria | |
|---|---|---|---|
| Appearance | Visually | Slightly yellowish gel | |
| Colour of formulation | APHA colour reference solution | Colour ≤ 250 | |
| Viscosity | Rotational viscosimeter USP <911> | 3,000-10,000 mPa × sec | |
| Density | Relative density USP <699> | 0.97-1.01 g/cm³ | |
| Identification | HPLC USP <621> UV USP <197U> | Retention time corresponds to reference sample UV spectrum corresponds to reference sample | |
| Impurities | HPLC USP <621> | Impurity C - Epitestosterone | ≤ 0.5% |
| | | Impurity I - Δ-6-testosterone | ≤ 0.2% |
| | | Each individual unknown impurity | ≤ 0.1% |
| | | Total impurities | ≤ 1.0% |
| Assay | HPLC USP <621> | 95-105% | |

Finished product TBS-1 gel packaged in unit dose syringes is tested to the following specifications for batch release.

TABLE 2

Specification for TBS-1 Gel Packaged in Unit Dose Syringes

| Test Parameter | Method/Reference | Acceptance Criteria | |
|---|---|---|---|
| Appearance | Visually | Slightly yellowish gel | |
| Identification | HPLC USP <621> UV USP <197U> | Retention time corresponds to reference sample UV spectrum corresponds to reference sample | |
| Impurities | HPLC USP <621> | Impurity C - Epitestosterone | ≤ 0.5% |
| | | Impurity I - Δ-6-testosterone | ≤ 0.2% |
| | | Each individual unknown impurity | ≤ 0.1% |
| | | Total impurities | ≤ 1.0% |
| Assay | HPLC USP <621> | 95-105% | |
| Microbial limits | USP <61> and <62> | TAMC | <10² cfu/g |
| | | TYMC | <10 cfu/g |
| | | P. aeruginosa | 0/g |
| | | S. aureus | 0/g |
| Mass variation | USP <905> | Complies with USP <905> | |

TAMC—total aerobic microbial count
TYMC—total combined yeast/mould count

Batch Analyses [TBS-1, Gel]

One preliminary batch (Batch No. 100304), four pilot scale batches (Batch No. ED 187, ED 188, ED 189 and ED 014), two pilot non-GMP batches (NA 090811-1 and NA090723-1) and three commercial scale (Batch 9256, 0823 and 0743) batches of TBS-1 have been produced. Data from the new batches, 0823 and 0743 are described in Tables 4 and 5.

TABLE 3

Description of TBS-1 Batches

| Formulation | 4.0% | 4.5% |
|---|---|---|
| Batch no. | 0823 | 0743 |
| Batch size | 200 kg | 200 kg |
| Date of manufacture | June 2010 | June 2010 |
| Manufacturing site | Haupt Pharma | Haupt Pharma |
| Batch no. testosterone | 89100760 (Bayer/Schering) | 89100760 (Bayer/Schering) |
| Equipment | Commercial Process | Commercial Process |
| Filling quantity per container | 148 □g | 173 □g |

Batch 0743, bulk 4.5% testosterone gel, is filled into two different dosage strengths, 5.6 mg (Batch 0943) and 6.75 mg (Batch 0744), by varying the weight of the gel in the finish syringe. Batch 0823, bulk 4.0% testosterone gel, is filled as one dose strength, 5.0 mg (Batch 0942).

TABLE 4

Batch Analysis - TBS-1 Batches 0743 and 0823

| Test Parameter | Acceptance Criteria | Batch No. 0743 | Batch No. 0823 |
|---|---|---|---|
| Appearance of formulation | Clear, slightly yellowish gel | Complies | Complies |
| Colour | ≤ APHA solution 250 | 150 | 150 |
| Viscosity | 3,000-10,000 mPas/30 s | 5,217 | 5,086 |
| Density | 0.97-1.01 g/cm³ | 0.99 | 0.99 |
| Identification | Retention time corresponds to reference sample | Complies 5.0 min | Complies 5.0 min |
| | UV spectrum corresponds to reference sample | Complies | Complies |
| Impurities | Impurity C-Epitestosterone ≤ 0.5% | 0.3 | 0.3 |
| | Impurity I Δ-6-testosterone ≤ 0.2% | <0.05 | <0.05 |
| | Single impurity ≤ 0.1 | <0.05 | <0.05 |
| | Total impurities ≤ 1.0 | 0.5 | 0.5 |

TABLE 4-continued

Batch Analysis - TBS-1 Batches 0743 and 0823

| Test Parameter | Acceptance Criteria | Batch No. 0743 | Batch No. 0823 |
|---|---|---|---|
| Assay | 95.0-105.0% | 100% | 100% |
| Microbial limits | TAMC < $10^2$ cfu/g | Complies | Complies |
| | TYMC < 10 cfu/g | Complies | Complies |
| | P. aeruginosa not detected/g | Complies | Complies |
| | S. aureus not detected/g | Complies | Complies |

TAMC—total aerobic microbial count
TYMC—total combined yeast/mould count

TABLE 5

Batch Analysis - TBS-1 Batches 00744, 0942 and 0943

| Test Parameter | Acceptance Criteria | 0744 | 0942 | 0943 |
|---|---|---|---|---|
| Batch No. Bulk | | 0743 | 0823 | 0743 |
| Appearance | Slightly yellowish gel | Complies | Complies | Complies |
| Identification | Retention time corresponds to reference sample | Complies 4.9 min | Complies 5.0 min | Complies 4.9 min |
| | UV spectrum corresponds to reference sample | Complies | Complies | Complies |
| Impurities | Impurity C ≤ 0.5% | 0.3% | 0.3% | 0.3% |
| | Impurity I ≤ 0.2% | <0.05% | <0.05% | <0.05% |
| | Each individual unknown impurity ≤ 0.1% | 0.05% | 0.05% | 0.05% |
| | Total impurities ≤ 1.0% | 0.3% | 0.3% | 0.3% |
| Assay | 95-105% | 99% | 100% | 100% |
| Microbial limits | TAMC < $10^2$ cfu/g | Complies | Complies | Complies |
| | TYMC < 10 cfu/g | Complies | Complies | Complies |
| | P. aeruginosa 0/g | Complies | Complies | Complies |
| | S. aureus 0/g | Complies | Complies | Complies |
| Mass variation | Complies with USP <905> | Complies | Complies | Complies |

Stability [TBS-1, Gel]
Stability Summary and Conclusions [TBS-1, Gel]

This section has been amended to include additional data on the on-going stability studies for the initial stability batches and to provide stability data on the drug product in the syringes utilized for the Phase II clinical study. Only the updated sections and new information have been included for review.

All stability studies of TBS-1 gel have been performed by ACC GmbH Analytical Clinical Concepts, Schöntalweg 9-11, 63849 Leidersbach/Aschaffenburg, Germany. Stability studies that meet ICH requirements are on-going.

TABLE 1

Stability Studies Conducted in Support of TBS-1

| Study Type | Container Closure System | Drug Product Batch No. | Storage Conditions | Stability Data available | Study End |
|---|---|---|---|---|---|
| ICH | White LDPE unit dose container; sterile air in pressure cushion; aluminum pouch secondary package (no nitrogen) | ED 187C ED 188 ED 189 | 25° C./60% RH 40° C./75% RH | 12 months 6 months | Study completed |
| ICH | | EI 014 | 25° C./60% RH | 36 months plus a 42 month analysis | Study completed |
| ICH Photostability | | ED 187B | 9 hours ≥ 200 Wh/m² (300-400 nm) 22 hours 1.2 Mill. Lxh. (400-800 nm) | Full exposure | Study completed |
| Thermal Cycling | | ED 188 | 12 hr −20° C. cycle to 12 hr + 40° C. | 4 weeks | Study completed |
| ICH | Syringe with Syringe Cap | Pilot Scale (non GMP) 4.0 mg 5.5 mg 7.0 mg | 25° C./60% RH 40° C./75% RH | 6 months | Study completed |
| ICH | Stainless Steel Drum under Nitrogen | 9256 | Ambient temperature | 6 months | On-going |
| ICH | Syringe with Syringe Cap | Bulk 9256 9445 - 4.0 mg 9246 - 5.5 mg 9247 - 7.0 mg | 25° C./60% RH 40° C./75% RH | 6 months | On-going |
| ICH | Stainless Steel Drum under Nitrogen | 0743 0823 | 25° C./60% RH 40° C./75% RH | Initial | Ongoing |

TABLE 1-continued

Stability Studies Conducted in Support of TBS-1

| Study Type | Container Closure System | Drug Product Batch No. | Storage Conditions | Stability Data available | Study End |
|---|---|---|---|---|---|
| ICH | Syringe with Syringe Cap | 0943 | 25° C./60% RH 40° C./75% RH | initial | Ongoing |

Overall, stability data provided in this section are concluded to support a 24 month "use by" period for TBS-1 stored at controlled room temperature conditions [i.e., 25° C. (77° F.); excursions 15-30° C. (59-86° F.)]. The data also show that special storage conditions for the drug product are not required. The packaging configuration is adequate to protect the drug product from light and the drug product does not degrade or change physically following exposure to temperature cycling stress.

The clinical supplies are applied a 1 year re-test period, when stored at controlled room temperature conditions [i.e., 25° C. (77° F.); excursions 15-30° C. (59-86° F.)], to reflect the duration of the trial and the data available. As additional data is available the re-test period will be extended as appropriate.

Stability Data [TBS-1, Gel]

In this section, the updated stability data tables for a commercial size bulk Batch 9256, 0743 and 0823 and finish product lots 9445, 9446, 9447, 0943 are provided.

A 6 month real time stability program is ongoing on the commercial scale bulk (Batch 9256). A 36 month real time and a 6 month accelerated stability program is ongoing on three different doses of Batch 9256 packaged in 1 ml syringes: Batch 9445 4.0 mg (3.2% gel), Batch 9446 5.5 mg (3.2% gel), Batch 9447 7.0 mg (3.2% gel).

A 6 month real time stability program is underway on the commercial scale bulk batch 0743 (4.5% gel) and 0823 (4.0% gel). A 36 month real time and a 6 month accelerated stability program is underway on Batch 0943 (bulk Batch 0743 filled in 1 ml syringes).

TABLE 2

Stability Schedule for Commerical Scale Bulk TBS-1 gel and Finished Product Filled in 1 mL Syringes

| Storage Conditions (° C., % RH) | Product | Completed Test Intervals (Outstanding Test Intervals) |
|---|---|---|
| Ambient temperature | 9256 | 0 m, 3 m, 6 m |
| 25 ± 2° C., 60 ± 5% | 9445 | 0 m, 6 m (12 m, 24 m, 36 m) |
| 40 ± 2° C., 75 ± 5% | 9445 | 0 m, 3 m, 6 m |
| 25 ± 2° C., 60 ± 5% | 9446 | 0 m, 6 m (9 m, 18 m, 30 m, 36 m) |
| 40 ± 2° C., 75 ± 5% | 9446 | 0 m, 3 m, 6 m |
| 25 ± 2° C., 60 ± 5% | 9447 | 0 m, 6 m (12 m, 24 m, 36 m) |
| 40 ± 2° C., 75 ± 5% | 9447 | 0 m, 3 m, 6 m |
| 25 ± 2° C., 60 ± 5% | 0943 | 0 m, (3 m, 9 m, 18 m, 30 m, 36 m) |
| 40 ± 2° C., 75 ± 5% | 0943 | 0 m, (3 m, 6 m) |
| Ambient temperature | 0743 | 0 m, (3 m, 6 m) |
| Ambient temperature | 0823 | 0 m, (3 m, 6 m) |

TABLE 3

Stability Data TBS-1 Batch 9256 (3.2% Bulk Gel) Manufactured July 2009 Stored at Ambient Temperature

| Test Parameter | Acceptance Criteria | 07/2009 Time 0 | 10/2009 3 months | 01/2010 6 months |
|---|---|---|---|---|
| Appearance | Slightly yellow gel | Complies | Complies | Complies |
| Colour of formulation | Colour ≤ 250 | 200 | 200 | 200 |
| Viscosity | 3,000-10,000 mPa × sec | 5504 | 5325 | 5198 |
| Density | 0.97-1.01 g/cm³ | 0.99 | 0.99 | 0.99 |
| Iodine value | FIPO | 78.62 | 77.39 | 76.40 |
| Acid value | FIPO ( mg KOH/g) | 1.98 | 2.00 | 2.16 |
| Peroxide value | FIPO (meq O₂/kg) | 3.56 | 3.16 | 2.63 |
| Identification | a. Retention time corresponds to RS | Complies | Complies | Complies |
| | b. UV spectrum corresponds to RS | Complies | Complies | Complies |
| Impurities | Imp C ≤ 0.5% | 0.166% | 0.148% | 0.189% |
| | Imp I ≤ 0.1% | <0.05% | 0.05% | <0.05% |
| | Each individual unknown imp. ≤ 0.1% | 0.064% | 0.05% | 0.075% |
| | Total imp. ≤ 1.0% | 0.230% | 0.198% | 0.264% |
| | Imp. D ≤ 0.2% | <0.2% | <0.2% | 0.2% |
| Assay | 95.0-105% | 99.4% | 98.3% | 100.4% |
| Microbial limits | TAMC <10² cfu/g | <10 cfu/g | <10 cfu/g | <10 cfu/g |
| | TYMC <10 cfu/g | <10 cfu/g | <10 cfu/g | <10 cfu/g |
| | S.aureus 0/g | Not detected/g | Not detected/g | Not detected/g |
| | P. aeruginosa 0/g | Not detected/g | Not detected/g | Not detected/g |

TABLE 4

Stability Data 4.0 mg TBS-1 Batch 9445 (3.2% gel) 1 ml Syringe ($25 \pm 2°$ C., $60 \pm 5\%$ RH, horizontal)

| Test Parameter | Acceptance Criteria | Time 0 | 6 months | 12 months |
|---|---|---|---|---|
| Appearance Colour of formulation | Slightly yellow gel Colour ≤ 250 | Complies 200 | | |
| Dissolution | ≥80% within 120 min | 87.8% within 120 minutes | | |
| Impurities | Imp C ≤ 0.5% | 0.127% | | |
| | Imp I ≤ 0.1% | <0.05% | | |
| | Each individual unknown imp. ≤ 0.1% | <0.05% | | |
| | Total imp. ≤ 1.0% | 0.127% | | |
| | Imp. D ≤ 0.2% | <0.2% | | |
| Assay | 95.0-105% | 99.3% | | |
| Microbial limits | TAMC < $10^2$ cfu/g | <10 cfu/g | | |
| | TYMC < 10 cfu/g | <10 cfu/g | | |
| | *S. aureus* 0/g | Not detected/g | | |
| | *P. aeruginosa* 0/g | Not detected/g | | |

TABLE 5

Stability Data 4.0 mg TBS-1 Batch 9445 (3.2% gel) 1 ml Syringe, ($40 \pm 2°$ C., $75 \pm 5\%$ RH, horizontal)

| Test Parameter | Acceptance Criteria | Time 0 | 3 months | 6 months |
|---|---|---|---|---|
| Appearance Colour of formulation | Slightly yellow gel Colour ≤ 250 | Complies 200 | Complies 200 | |
| Dissolution | ≥80% within 120 min | 87.8% within 120 minutes | 87.3% within 120 minutes | |
| Impurities | Imp C ≤ 0.5% | 0.127% | 0.128% | |
| | Imp I ≤ 0.1% | <0.05% | <0.05% | |
| | Each individual unknown imp. ≤ 0.1% | <0.05% | Rel RT 0.38: 0.177% Rel RT 2.93: 0.066% | |
| | Total imp. ≤ 1.0% | 0.127% | 0.371% | |
| | Imp. D ≤ 0.2% | <0.2% | <0.2% | |
| Assay | 95.0-105% | 99.3% | 99.3% | |
| Microbial limits | TAMC < $10^2$ cfu/g | <10 cfu/g | <10 cfu/g | |
| | TYMC < 10 cfu/g | <10 cfu/g | <10 cfu/g | |
| | *S. aureus* 0/g | Not detected/g | Not detected/g | |
| | *P. aeruginosa* 0/g | Not detected/g | Not detected/g | |

TABLE 6

Stability Data 5.5 mg TBS-1 Batch 9446 (3.2% gel) 1 ml Syringe, ($25 \pm 2°$ C., $60 \pm 5\%$ RH, horizontal)

| Test Parameter | Acceptance Criteria | Time 0 | 3 months | 6 mos |
|---|---|---|---|---|
| Appearance Colour of formulation | Slightly yellow gel Colour ≤ 250 | Complies 200 | Complies 200 | |
| Dissolution | ≥80% within 120 min | 86.8% within 120 minutes | 83.6% within 120 minutes | |
| Impurities | Imp C ≤ 0.5% | 0.125% | 0.126% | |
| | Imp I ≤ 0.1% | <0.05% | <0.05% | |
| | Each individual unknown imp. ≤ 0.1% | <0.05% | <0.05% | |
| | Total imp. ≤ 1.0% | 0.125% | 0.126% | |
| | Imp. D ≤ 0.2% | <0.2% | <0.2% | |
| Assay | 95.0-105% | 99.1% | 99.4% | |
| Microbial limits | TAMC < $10^2$ cfu/g | <10 cfu/g | <10 cfu/g | |
| | TYMC < 10 cfu/g | <10 cfu/g | <10 cfu/g | |
| | *S. aureus* 0/g | Not detected/g | Not detected/g | |
| | *P. aeruginosa* 0/g | Not detected/g | Not detected/g | |

TABLE 7

Stability Data 5.5 mg TBS-1 Batch 9446 (3.2% gel) 1 ml Syringe, ($40 \pm 2°$ C., $75 \pm 5\%$ RH, horizontal)

| Test Parameter | Acceptance Criteria | Time 0 | 3 months | 6 months |
|---|---|---|---|---|
| Appearance Colour of formulation | Slightly yellow gel Colour ≤ 250 | Complies 200 | Complies 200 | |
| Dissolution | ≥80% within 120 min | 86.8% within 120 minutes | 86.8% within 120 minutes | |
| Impurities | Imp C ≤ 0.5% | 0.125% | 0.127% | |
| | Imp I ≤ 0.1% | <0.05% | <0.05% | |
| | Each individual unknown imp. ≤ 0.1% | <0.05% | Rel RT 0.38: 0.102% Rel RT 3.01: 0.070 | |
| | Total imp. ≤ 1.0% | 0.125% | 0.299% | |
| | Imp. D ≤ 0.2% | <0.2% | <0.2% | |
| Assay | 95.0-105% | 99.1% | 97.9% | |
| Microbial limits | TAMC < $10^2$ cfu/g | <10 cfu/g | <10 cfu/g | |
| | TYMC < 10 cfu/g | <10 cfu/g | <10 cfu/g | |
| | *S. aureus* 0/g | Not detected/g | Not detected/g | |
| | *P. aeruginosa* 0/g | Not detected/g | Not detected/g | |

TABLE 8

Stability Data 7.0 mg TBS-1 Batch 9447 (3.2% gel) 1 ml Syringe, ($25 \pm 2°$ C., $60 \pm 5\%$ RH, horizontal)

| Test Parameter | Acceptance Criteria | Time 0 | 6 months | 12 months |
|---|---|---|---|---|
| Appearance Colour of formulation | Slightly yellow gel Colour ≤ 250 | Complies 200 | | |
| Dissolution | ≥80% within 120 min | 83.5% within 120 minutes | | |
| Impurities | Imp C ≤ 0.5% | 0.132% | | |
| | Imp I ≤ 0.1% | <0.05% | | |
| | Each individual unknown imp. ≤ 0.1% | <0.05% | | |
| | Total imp. ≤ 1.0% | 0.132% | | |
| | Imp. D ≤ 0.2% | <0.2% | | |
| Assay | 95.0-105% | 98.7% | | |
| Microbial limits | TAMC < $10^2$ cfu/g | <10 cfu/g | | |
| | TYMC < 10 cfu/g | <10 cfu/g | | |
| | *S. aureus* 0/g | Not detected/g | | |
| | *P. aeruginosa* 0/g | Not detected/g | | |

TABLE 9

Stability Data 7.0 mg TBS-1 Batch 9447 (3.2% gel) 1 ml Syringe, (40 ± 2° C., 75 ± 5% RH., horizontal)

| Test Parameter | Acceptance Criteria | Time 0 | 3 months | 6 months |
|---|---|---|---|---|
| Appearance Colour of formulation | Slightly yellow gel Colour ≤ 250 | Complies 200 | Complies 200 | |
| Dissolution | ≥80% within 120 min | | 83.5% within 120 minutes | 85.4% within 120 minutes |
| Impurities | Imp C ≤ 0.5% | | 0.132% | 0.132% |
| | Imp I ≤ 0.1% | | <0.05% | <0.05% |
| | Each individual unknown imp. ≤ 0.1% | | <0.05% | Rel RT 0.37: 0.074% Rel RT 3.13: 0.069 |
| | Total imp. ≤ 1.0% | | 0.132% | 0.275% |
| | Imp. D ≤ 0.2% | | <0.2% | <0.2% |
| Assay | 95.0-105% | | 98.7% | 99.1% |
| Microbial limits | TAMC < $10^2$ cfu/g | | <10 cfu/g | <10 cfu/g |
| | TYMC < 10 cfu/g | | <10 cfu/g | <10 cfu/g |
| | S. aureus 0/g | | Not detected/g | Not detected/g |
| | P. aeruginosa 0/g | | Not detected/g | Not detected/g |

TABLE 10

Stability Data 5.6 mg TBS-1 Batch 0943 (4.5% gel) 1 ml Syringe, (25 ± 2° C., 60 ± 5% RH, horizontal)

| Test Parameter | Acceptance Criteria | Time 0 | 3 months | 6 months |
|---|---|---|---|---|
| Appearance Colour of formulation | Slightly yellow gel Colour ≤ 250 | Complies Complies | | |
| Impurities | Imp C ≤ 0.5% | 0.3% | | |
| | Imp I ≤ 0.1% | <0.05% | | |
| | Each individual unknown imp. ≤ 0.1% | <0.05% | | |
| | Total imp. ≤ 1.0% | 0.3 | | |
| Assay | 95.0-105% | 100% | | |
| Microbial limits | TAMC < $10^2$ cfu/g | Complies | | |
| | TYMC < 10 cfu/g | Complies | | |
| | S. aureus 0/g | Complies | | |
| | P. aeruginosa 0/g | Complies | | |

TABLE 11

Stability Data 5.6 mg TBS-1 Batch 0943 (4.5% gel) 1 ml Syringe, (40 ± 2° C., 75 ± 5% RH, horizontal)

| Test Parameter | Acceptance Criteria | Time 0 | 3 months | 6 months |
|---|---|---|---|---|
| Appearance Colour of formulation | Slightly yellow gel Colour ≤ 250 | Complies Complies | | |
| Impurities | Imp C ≤ 0.5% | 0.3% | | |
| | Imp I ≤ 0.1% | <0.05% | | |
| | Each individual unknown imp. ≤ 0.1% | <0.05% | | |
| | Total imp. ≤ 1.0% | 0.3 | | |
| Assay | 95.0-105% | 100% | | |
| Microbial limits | TAMC < $10^2$ cfu/g | Complies | | |
| | TYMC < 10 cfu/g | Complies | | |
| | S. aureus 0/g | Complies | | |
| | P. aeruginosa 0/g | Complies | | |

TABLE 12

Stability Data TBS-1 Batch 0743 (4.5% gel) Bulk Stored at Ambient Temperature

| Test Parameter | Acceptance Criteria | Time 0 | 3 months | 6 months |
|---|---|---|---|---|
| Appearance Colour of formulation | Slightly yellow gel Colour ≤ 250 | Complies Complies | | |
| Impurities | Imp C ≤ 0.5% | 0.3% | | |
| | Imp I ≤ 0.1% | <0.05% | | |
| | Each individual unknown imp. ≤ 0.1% | <0.05% | | |
| | Total imp. ≤ 1.0% | 0.3 | | |
| Assay | 95.0-105% | 100% | | |
| Microbial limits | TAMC < $10^2$ cfu/g | Complies | | |
| | TYMC < 10 cfu/g | Complies | | |
| | S. aureus 0/g | Complies | | |
| | P. aeruginosa 0/g | Complies | | |

TABLE 14

Stability Data TBS-1 Batch 0823 (4.5% gel) Bulk Stored at Ambient Temperature

| Test Parameter | Acceptance Criteria | Time 0 | 3 months | 6 months |
|---|---|---|---|---|
| Appearance Colour of formulation | Slightly yellow gel Colour ≤ 250 | Complies Complies | | |
| Impurities | Imp C ≤ 0.5% | 0.3% | | |
| | Imp I ≤ 0.1% | <0.05% | | |
| | Each individual unknown imp. ≤ 0.1% | <0.05% | | |
| | Total imp. ≤ 1.0% | 0.3 | | |
| Assay | 95.0-105% | 100% | | |
| Microbial limits | TAMC < $10^2$ cfu/g | Complies | | |
| | TYMC < 10 cfu/g | Complies | | |
| | S. aureus 0/g | Complies | | |
| | P. aeruginosa 0/g | Complies | | |

Example 8

Phase 2 Study Designed to Investigate the Intranasal Absorption of 4% of the Drug Three Times a Day and 4.5% of the Drug Administered Twice a Day and Three Times a Day This is a Phase 2 study designed to investigate the intranasal absorption of 4% of the drug three times a day and 4.5% of the drug administered twice a day and three times a day, and to compare the absorption from the previous study in the same subjects that responded with a 3.2% testosterone gel. In the previous study, Nasobol-01-2009, a 3.2% Testosterone gel is used to deliver 4.0 mg, 5.5 mg and 7.0 mg of Testosterone intra-nasally using gel volumes of 125 μL, 172 μL and 219 μL, respectively. In this study, 5.0 mg, 5.65 mg and 6.75 mg of Testosterone is administered in gel volumes of 125 μL, 125 μL, and 150 μL, respectively. This study allowed investigating the delivery of similar Testosterone amounts in much smaller volumes.

In this open label study, subjects are equally randomized into three treatment arms. The treatments are administered for one week, in a parallel design. At the end of one week, the three treatments are compared by conducting a 24-hour pharmacokinetic investigation of the systemic absorption of the drug product testosterone and its two physiological metabolites dihydrotestosterone and estradiol.

8. Study Objectives 8.1 Primary Objective

The primary objective of this study is to determine the bioavailability through PK analysis of a 4% TBS-1 gel (applied three times a day) and 4.5% TBS-1 gel (applied twice a day and three times a day) in hypogonadal men.

8.2 Secondary Objective

The secondary objective of the study is to establish the safety profile for TBS-1.

9. Investigational Plan 9.1 Overall Study Design and Plan Description

This is an open label, randomized, balanced, three treatment (4.0% t.i.d. 4.5% b.i.d. and 4.5% t.i.d.), parallel design, pharmacokinetic study of TBS-1, administered intra-nasally. The serum concentrations of total Testosterone, Dihydrotestosterone and Estradiol are measured using validated LC/MS methods.

Hypogonadal subjects are required to visit the Clinic on three (3) occasions, of which one (1) visit (Visit 3) required an overnight stay for the previously described 24-hour pharmacokinetic profile.

The following pharmacokinetic parameters are determined for all subjects:

$AUC_{0-T}$, $C_{avg}$, $C_{min}$, $C_{max}$, $t_{max}$, PTF and PTS means and standard error of the means are calculated for the 24-hour interval.

The percentage of subjects with a $C_{avg}$ for Testosterone, Dihydrotestosterone and Estradiol, below, within and above the Reference Range for the respective analyte is calculated.

Erythrocytosis, anemia and infections are monitored by measuring complete blood counts at screening and the Close-Out visit.

It is planned to enroll approximately 30 subjects. Twenty-two (22) subjects completed the study. Study participation is 2 to 3 weeks.

9.2 Discussion of Study Design

Testosterone therapy for hypogonadal men should correct the clinical abnormalities of Testosterone deficiency, including disturbances of sexual function. Testosterone decreases body fat and increases lean muscle mass and bone density with minimal adverse effects.

There are several Testosterone replacement products available, which can be given intra-muscularly, orally, as a buccal tablet to the gums, or topically as a patch or gel. Current replacement therapies have certain drawbacks. Testosterone injections show wide fluctuations in serum Testosterone levels often at values above the reference range (5). Testosterone patches have a high rate of skin irritation (6,7). Testosterone gels although popular in North America are not always convenient and have a risk of skin-to-skin transfer to family members (8,9). Oral Testosterone undecanoate needs to be administered with a high fat meal and levels obtained are often low (10-12).

Intra-nasal administration of a new formulation of Testosterone (TBS-1) has been shown to be effectively absorbed and shows excellent potential as a therapeutic product in the treatment of male hypogonadism (13). The nasal mucosa offers an alternative route of administration that is not subject to the first pass effect, has high permeability and ease of administration with rapid absorption into the systemic circulation producing high plasma levels similar to those observed after intravenous administration.

The advantages of the Testosterone nasal gel, when compared to other formulations, are the following: Convenient application form permitting inconspicuous use, the much smaller amount of active ingredient needed for the subject, and knowing that this type of administration is less likely to contaminate other family members (wife and children).

Several studies have indicated the utility of testosterone administration using the nasal gel. The prior study conducted in 2009 is to demonstrate the efficacy of TBS-1 in the treatment of hypogonadal men requiring Testosterone replacement therapy. Efficacy is determined by establishing an optimal pharmacokinetic profile for serum Testosterone levels following a multiple-dose b.i.d. dosing profile for TBS-1, using three different strengths of Testosterone (8.0 mg, 11.0 mg and 14.0 mg) and comparing it to that of the active control, Androderm®. The secondary objective of this study is to establish a safety profile for TBS-1. This is to be achieved by monitoring adverse and serious adverse events during the course of the entire study, and comparing various safety parameters at follow-up to those obtained at baseline. These safety parameters consisted of vital signs, complete blood counts, a chemistry profile, an endocrine profile, and urinalysis. In addition, changes to the nasal mucosa and to the prostate at follow up are compared to baseline.

An important advantage of the power of the dose finding design of this study is that it minimizes the subject selection bias and the different host groups often observed in sequential study designs.

The three clinical sites are monitored by Schiff & Company to ensure the safety of the Subjects and performance of the clinical study according to ICH E6 and FDA guidelines.

A central laboratory is used for the analysis of hematology and biochemistry parameters in order to obtain consistent and unbiased laboratory results. A second central laboratory is used for the PK analysis.

The following are the specific activities in the study design during the subject visits:

| Visit Number: | In/Ex PERIOD 1 | Day 1 2 | Day 7 3 | Day 8 |
|---|---|---|---|---|
| PROCEDURE | | | | |
| Informed Consent[1] | x | | | |
| Medical History | x | | | |
| Physical Exam* & Vital Signs | x | x | x | x |
| Subject Demographic Data | x | | | x |
| PROCEDURE | | | | |
| Otorhinolaryngological Exam | x | | | x |
| Prostate Exam[2] | x | | | x |
| Chemistry Profile[3] | x | | | x |
| Hematology Profile[4] | x | | | x |
| Urinalysis[5] | x | | | x |
| Serum PSA | x | | | x |
| Hepatitis B, C, & HIV Testing | x | | | |
| Urine Drug Screen[6] | x | | | |
| Ethanol Test[7] | x | | | |
| Hemoglobin $A_1c$ | x | | | |
| Serum Testosterone[8] | x | | | |
| Serum T, DHT & Estradiol | | x | | |
| Serum T, DHT & Estradiol PK | | | x | |
| Concomitant Medications | x | x | x | x |
| Adverse Event Recording | x | x | x | x |

*Physical Exam on Screen and Day 8 only.

Informed consent will be signed prior to Screening Visit 1 In/Ex Period: Inclusion, and Exclusion Period
[2]If subject had a prior normal prostate exam in Nasobol-01-2009, it will not be required.
[3]Chemistry Profile: Na/K, Glucose, Urea, Creatinine, Total Bilirubin, Albumin, Calcium, Phosphate, Uric Acid, AST, ALT, ALP, GGT and CK.
[4]Complete Blood Count and Differential.
[5]Urine dipstick (no microscopic).
[6]Cocaine, Cannabinoids, Opiates, Benzodiazepines.
[7]Urine alcohol by dipstick.
[8]Serum Testosterone, Dihydrotestosterone & Estradiol will be measured by a reference lab using a validated LC-MS/MS method, for T and DHT and a validated LC-MS/MS or immunoassay method, for Estradiol.

Screening Visit 1

Subjects, after having voluntarily signed the Informed Consent Form, are interviewed by the Clinical Investigator or his/her designee Physician/Nurse Practitioner who took the medical and physical history, record demographic data, and performed a routine physical examination. Body weight and Height is measured and BMI calculated. Vital signs (seated 5 minutes) are measured (Blood Pressure, Heart Rate, Respiratory Rate, and Body Temperature).

If the subject had a normal digital rectal exam of the prostate in the recent Nasobol-01-2009 trial, it is not repeated.

The Clinical Investigator assessed the subject study eligibility based on the inclusion/exclusion criteria, and eligible subjects that are currently on Testosterone replacement therapy needed to undergo a wash-out period; four (4) weeks for depot products administered intra-muscularly (e.g., Testosterone enanthate 200 mg/mL), and two (2) weeks for products administered orally or topically (patch, gel, or buccal). At the end of the wash-out period, subjects are to return to have their serum Testosterone measured.

Treatment naïve subjects did not require a wash-out period.

Blood for serum Testosterone is drawn under fasting conditions, at 0900 h±30 minutes. The serum Testosterone level must be >150 ng/dL, and <300 ng/dL.

Blood is drawn for Clinical Laboratory investigations after an overnight fast (8-10 hour fast) and included the following:
  Complete Blood Count (Hemoglobin, Hematocrit, MCV, MCHC, RBC, WBC & Differential)
  Clinical Chemistry profile (Na/K, Glucose, Urea, Creatinine, Total Bilirubin, Albumin, Calcium, Phosphate, Uric Acid, AST, ALT, ALP, GGT and CK)
  Serum PSA
  Testing for HBV, HCV and HIV (Hepatitis B surface antigen, Hepatitis C antibody, HIV antibodies)
  Whole blood sample for Hemoglobin A1c
  Urine for dipstick urinalysis
  Urine for Drug screen (Cocaine, Cannabis, Opiates and Benzodiazepines). Subjects with positive test are not enrolled, unless the positive test is due to interference from a drug prescribed by a Physician
  Urine for alcohol testing The otorhinolaryngologic nasal endoscopy examination is done by an ENT specialist.

Subjects that met all of the inclusion and exclusion criteria are enrolled into the study and randomized into one of three treatment groups (A, B or C).

Visit 2 (Day 1)
  Subjects arrived at the Clinic under fasting conditions (6-8 hour fast) at 2000 hours or earlier.
  Instructions are given to subjects on the proper technique for intra-nasal dosing of TBS-1.
  Blood is drawn at 2045 hours for baseline serum Testosterone, Dihydrotestosterone, and Estradiol concentrations.
  Vital Signs (seated 5 minutes) are measured (Blood Pressure, Heart Rate, Respiratory Rate, and Body Temperature) to establish a baseline.
  Subjects are given a one week supply of pouches: 18 pouches for treatment A, 12 pouches for treatment B, and 18 pouches for treatment C. Pouches required for dosing during the pharmacokinetic profile remained with the Clinical Investigator. Each pouch contained two syringes pre-filled with TBS-1 gel for treatment A, B, or C.
  Subjects administered their first dose of TBS-1 at 2100 hours according to their treatment group.
  Vital Signs are measured at 2200 hours and subjects are sent home with their supply of pouches for their treatment group.

Telephone Check (Day 4)
  On Day 4, all subjects are called to check compliance of study drug administration, compliance to abstention from alcohol for 48 hours, and to document any adverse events that may have occurred. Subjects are reminded to bring in all syringes for counting at Visit 3.

Visit 3 (Day 7)
  Subjects arrived at the Clinic under fasting conditions (6-8 hour fast) at 2000 hours or earlier.
  Blood is drawn at 2045 hours for baseline serum Testosterone, Dihydrotestosterone, and Estradiol concentrations.
  Subject underwent a 24-hour pharmacokinetic profile immediately after the 2100 hour dosing. Vital signs are recorded hourly for two hours post dosing.
  Safety parameters are recorded.
  Subjects remained fasting for two hours post dose and then given supper. After supper, the subjects again fasted overnight and remained fasting until 0900 hours on Day 8. Lunch and supper on Day 8 occurred at the regular times and are not subject to fasting conditions.

Pharmacokinetic Blood Draws
  Administration of the drug should have occurred at ±5 minutes from the indicated time (2100 h and 0700 h for b.i.d. dosing and 2100 h, 0700 h and 1300 h for t.i.d. dosing).
  Blood draws should have been within ±5 minutes from the indicated times when blood draw intervals are 30 minutes and within ±15 minutes when blood draws are >30 minutes.
  Treatment A: Blood draws for serum Testosterone, Dihydrotestosterone, and Estradiol measurements: Blood draws for t.i.d. dosing are done at the following times after the 2100 hour drug administration; 0.33, 0.66, 1.0, 1.5, 2.0, 3.0, 6.0, 9.0, 9.75, 10.33, 10.66, 11.0, 11.5, 12.0, 13.0, 14.0, 15.75, 16.33, 16.66, 17.0, 17.5, 18.0, 20.0, 22.0 and 24.0 hours, (total blood draws; 25+baseline).
  Treatment B: Blood draws for serum Testosterone, Dihydrotestosterone, and Estradiol measurements: Blood draws for b.i.d. dosing are done at the following times after the 2100 hour drug administration; 0.33, 0.66, 1.0, 1.5, 2.0, 3.0, 6.0, 9.0, 9.75, 10.33, 10.66, 11.0, 11.5, 12.0, 13.0, 16.0, 19.0, 22.0, and 24.0 hours, (total blood draws; 19+baseline).
  Treatment C: Blood draws for serum Testosterone, Dihydrotestosterone, and Estradiol measurements: Blood draws for t.i.d. dosing are done at the following times after the 2100 hour drug administration; 0.33, 0.66, 1.0, 1.5, 2.0, 3.0, 6.0, 9.0, 9.75, 10.33, 10.66, 11.0, 11.5, 12.0, 13.0, 14.0, 15.75, 16.33, 16.66, 17.0, 17.5, 18.0, 20.0, 22.0 and 24.0 hours, (total blood draws; 25+baseline).
  The last blood draw in the pharmacokinetic profile included enough blood to measure the clinical laboratory safety parameters required at Close-out.

Visit 3 (Day 8), Close Out Visit
Subjects Underwent the Following Assessments:
  A routine physical examination including vital signs (Blood Pressure, Heart Rate, Respiratory Rate, and Body Temperature).
  Otorhinolaryngologic nasal examination.

Blood sample is taken for a Complete Blood Count (Hemoglobin, Hematocrit, RBC, WBC and differential, MCV, MCHC).

Blood sample for Chemistry Profile (Na/K, glucose, urea, creatinine, calcium, phosphate, uric acid, total bilirubin, albumin, AST, ALT, ALP, GGT, and CK).

Blood sample for PSA.

Urine sample for dipstick urinalysis.

9.3 Selection of Study Population

Subjects are included in the study according to the following inclusion/exclusion criteria:

9.3.1 Inclusion Criteria

1. Males who are responders to high-dose intra-nasal Testosterone in the Nasobol-01-2009 trial.
2. Written informed consent.
3. Males between 18 and 80 years of age.
4. Men with primary or secondary hypogonadism and a morning (0900 h±30 minutes) serum Testosterone levels >150 ng/dL and ≤300 ng/dL, on blood drawn under fasting conditions.
5. BMI between 18.5-35 kg/m$^2$.
6. All clinical laboratory assessments at the Screening Visit are from blood drawn or urine collected following an overnight fast (10 hours), and are within ±15% of the Clinical Laboratory's reference range, except for serum Testosterone.
7. Normal Otorhinolaryngological nasal endoscopy examination. See Appendix 16.1.1 for exclusion criteria pertaining to endoscopy examination.
8. Prior, normal prostate examination (no palpable prostatic mass) from the Nasobol-01-2009 trial.
9. A serum PSA≤4.0 ng/mL.

9.3.2 Exclusion Criteria

1. Significant inter-current disease of any type, in particular liver, kidney, or heart disease, any form of diabetes mellitus or psychiatric illness.
2. Limitations in mobility, defined as having difficulty walking two blocks on a level surface or climbing 10 steps
3. Hematocrit >54% at screening.
4. History of cancer, excluding skin cancer.
5. History of nasal surgery, specifically turbinoplasty, septoplasty, rhinoplasty, "nose job", or sinus surgery.
6. Subject with prior nasal fractures.
7. Subject with active allergies, such as rhinitis, rhinorrhea, and nasal congestion.
8. Subject with mucosal inflammatory disorders, specifically pemphigus, and Sjogren's syndrome.
9. Subject with sinus disease, specifically acute sinusitis, chronic sinusitis, or allergic fungal sinusitis.
10. History of nasal disorders (e.g., polyposis, recurrent epistaxis (>1 nose bleed per month), abuse of nasal decongestants) or sleep apnea.
11. Subject using any form of intra-nasal medication delivery, specifically nasal corticosteroids and oxymetazoline containing nasal sprays (e.g., Dristan 12-Hour Nasal Spray).
12. History of severe adverse drug reaction or leucopenia.
13. History of abnormal bleeding tendencies or thrombophlebitis unrelated to venipuncture or intravenous cannulation.
14. Positive test for Hepatitis B, Hepatitis C, or HIV.
15. History of asthma and on-going asthma treatment.
16. History of sleeping problems.
17. Smokers (>10 cigarettes per day).
18. Regular drinkers of more than four (4) units of alcohol daily (1 unit=300 mL beer, 1 glass wine, 1 measure spirit) or those that may have difficulty in abstaining from alcohol during the 48 hours prior to the 24-hour blood sampling visit.
19. History of, or current evidence of, abuse of alcohol or any drug substance, licit or illicit; or positive urine drug and alcohol screen for drugs of abuse and alcohol.
20. Current treatment with androgens (e.g., Dehydroepiandrostenedione, Androstenedione) or anabolic steroids (e.g., Testosterone, Dihydrotestosterone).
21. Treatment with Estrogens, GnRH antagonists, or Growth Hormone, within previous 12 months.
22. Treatment with drugs which interfere with the metabolism of Testosterone, such as Anastrozole, Clomiphene, Dutasteride, Finasteride, Flutamide, Ketoconazole, Spironolactone and Testolactone.
23. Androgen treatment within the past four weeks (intramuscular, topical, buccal, etc.).
24. Subject with poor compliance history or unlikely to maintain attendance.
25. Participation in any other research study during the conduct of this study or 30 days prior to the initiation of this study, with the exception of Nasobol-01-2009.
26. Blood donation (usually 550 mL) at any time during this study, and within the 12 week period before the start of this study.

9.3.3 Removal of Subjects from Therapy or Assessment

Subjects are informed that they are free to withdraw from the study at any time without having to give reasons for their withdrawal, and without consequences for their future medical care. They are asked to inform the investigator immediately of their decision. The subject's participation in the study may have been discontinued for any of the following reasons:

Subject's own wish.

Significant non compliance with the study protocol and procedures.

Inter-current illness which interferes with the progress of the study.

Intolerable adverse event, including clinically significant abnormal laboratory findings, where, in the opinion of the Clinical Investigator, these could interfere with the subject's safety.

Clinical Investigator's decision that the withdrawal from the study is in the best interest of the subject.

The Clinical Investigator had the right to terminate a study prematurely for safety reasons, after having informed and consulted with the Sponsor. The Sponsor had the right to terminate the study earlier if the clinical observations collected during the study suggested that it might not be justifiable to continue or for other reasons as described in the contract between Sponsor and the clinical sites (e.g., administrative, regulatory, etc.). However this is not necessary. There are no premature terminations or drops outs from the study.

9.4 Treatments 9.4.1 Treatments Administered

Subjects are centrally randomized to the following treatment groups in order to balance the numbers equally within the groups across the three centers:

Treatment A (n=10): TBS-1 syringes pre-filled with 125 μL 4.0% gel to deliver 5.0 mg of Testosterone per nostril (intra-nasal) given t.i.d. at 2100, 0700, and 1300 hours. (total dose 30 mg/day)

Treatment B (n=10): TBS-1 syringes pre-filled with 150 μL 4.5% gel to deliver 6.75 mg of Testosterone per nostril (intra-nasal) given b.i.d. at 2100 and 0700 hours. (total dose 27.0 mg/day)

Treatment C (n=10): TBS-1 syringes pre-filled with 125 μL 4.5% gel to deliver 5.625 mg of Testosterone per nostril (intra-nasal) given t.i.d. at 2100, 0700, and 1300 hours. (total dose 33.75 mg/day)

9.4.2 Identity of Investigational Products

Name of the drug: TBS-1 (Syringes are pre-filled to contain 5.0 mg, 5.625 mg, and 6.75 mg of Testosterone/syringe).

Pharmaceutical form: Gel for nasal administration.

Content: Active ingredient: Testosterone.

Excipients: Silicon dioxide, castor oil, Labrafil®.

Mode of administration: Nasally, as a single dose to each nostril.

Manufacturer: Haupt Pharma Amareg.

Batch numbers: 0744, 0942, and 0943

Storage conditions: Between 20-25° C.

Packaging

The TBS-1 study drug is delivered to the clinical trial site as a ready-for-use syringe in a foil pouch (two syringes per pouch). Examples of Syringe and Pouch Labels are described in Appendix 4 of the protocol.

9.4.3 Method of Assigning Subjects to Treatment

Subjects who met the entry criteria are assigned randomly on a 1:1:1 basis to one of the three treatment groups. At Screening, each subject is assigned a subject number by site in sequential order. Subject numbers consisted of 5 digits. The first 2 digits reflected the site number assigned to the investigator, followed by a 3-digit subject number. For example, 01-001 indicates site (01) and the first subject (001). The subject number was used to identify the subject throughout the study and was entered on all documents. The same subject number was not assigned to more than one subject.

9.4.4 Selection of Doses in the Study

In a previous study, Nasobol-01-2009, a 3.2% Testosterone gel is used to deliver 4.0 mg, 5.5 mg and 7.0 mg of Testosterone intra-nasally using gel volumes of 125 μL, 172 μL and 219 μL, respectively. In this study, 5.0 mg, 5.65 mg and 6.75 mg of Testosterone are administered in gel volumes of 125 μL, 125 μL, and 150 μL, respectively. This study permits the investigation of the delivery of similar Testosterone amounts in much smaller volumes.

9.4.5 Selection and Timing of Dose for Each Subject

This was based on the results of the prior study.

9.4.6 Blinding

There is no blinding, because this is an open label study. The rationale for not blinding is that analytical endpoints, which are quantitative rather than qualitative are measured, and are not subject to any bias being introduced by the subjects or the Investigators.

9.4.7 Prior and Concomitant Therapy

The following medications are prohibited during the course of the study:

Subject using any form of intra-nasal medication delivery, specifically nasal corticosteroids and oxymetazoline containing nasal sprays (e.g., Dristan 12-Hour Nasal Spray).

Current treatment with androgens (e.g., Dehydroepiandrostenedione, Androstenedione) or anabolic steroids (e.g., Testosterone, Dihydrotestosterone). Treatment with Estrogens, GnRH antagonists, or Growth Hormone, within previous 12 months.

Treatment with drugs which interfere with the metabolism of Testosterone, such as; Anastrozole, Clomiphene, Dutasteride, Finasteride, Flutamide, Ketoconazole, Spironolactone and Testolactone.

Androgen treatment within the past four weeks (intramuscular, topical, buccal, etc.).

9.4.8 Treatment Compliance

All drugs are dispensed in accordance with the protocol. It is the Principal Investigator's responsibility to ensure that an accurate record of drugs issues and return is maintained. At the end of the study, the used original packages are returned to the sponsor for destruction. Drug accountability is verified by the monitors during the course of the study and prior to destruction of remaining study drugs. During Visit 2, the subjects are given a one-week supply of pouches; 18 pouches for treatment A, 12 pouches for treatment B, and 18 pouches for treatment C. Each pouch contained two syringes prefilled with TBS-one gel for treatment A, B, or C. The subjects are instructed on how to administer the gel and are also given a diary to indicate the times of administration at their home.

9.5 Efficacy and Safety Variables 9.5.1 Efficacy and Safety Measurements Assessed The primary efficacy parameter is the AUC is obtained in the 24 hours post administration of TBS-1. From the AUC the 24 hour $C_{avg}$ is calculated.

Area under the concentration curve (AUC) for both b.i.d. and t.i.d. dosing is determined for the 0 to 24 hour time interval using the trapezoidal rule.

The average concentration in the dosing interval ($C_{avg}$) is calculated from the AUC using the following formula: $C_{avg}=AUC_{0-T}/T$, with T=dosing interval time.

Peak Trough Fluctuation (PTF) and Peak Trough Swing (PTS) is calculated as follows:

$$PTF=(C_{max}-C_{min})/C_{avg}$$

$$PTS=(C_{max}-C_{min})/C_{min}$$

$C_{min}$, $C_{max}$ and $t_{max}$ is taken from the actual measured values. Values are determined relative to the Testosterone administration time in treated subjects.

The percent of subjects with 24 hour $C_{avg}$ values for serum Testosterone, DHT and Estradiol concentration above, within, and below the respective reference range are calculated.

Additional exploratory analyses of PK parameters may have been performed as necessary.

Analysis of Safety Data

Erythrocytosis, anemia, and infections are monitored by measuring complete blood counts at screening, and the Close-Out visit. An Otorhinolaryngological physician examined subjects and identifies any clinically significant changes to the nasal mucosa at follow up compared to baseline.

Clinical chemistry and urinalysis testing at Screening Visit 1 and at Close Out are assessed, hypo or hyperglycemia, renal function, liver function (hepato-cellular or obstructive liver disease), skeletal/heart muscle damage, and changes in calcium homeostasis.

Serum PSA is measured as a cautionary measure to measure possible changes to the prostate, although changes to the prostate and to serum PSA is not expected in a short treatment time frame.

Measurement of serum Testosterone, Dihydrotestosterone and Estradiol, at Screening Visit 1 and Visit 3 permitted any excursions beyond the upper limit of the reference range for the two physiological products of Testosterone; DHT, and Estradiol to be observed.

The safety analysis is performed on all subjects who received TBS-1. Occurrence of adverse events are presented by treatment group, by severity, and by relationship to the study drugs. All adverse events are described and evaluated regarding causality and severity. Adverse events are classified using MedDRA. However they are very few and all but two are not related to the drug.

Subject Safety

Monitoring of subjects and emergency procedures: Emergency medication, equipment and Subject gurney are available at the Study Center. During the "at home" phase, the subjects have an emergency call number to be able to contact the Clinical Investigator.

Adverse events are defined as any untoward medical occurrence in a subject or clinical trial subject having administered a medicinal product and which may or may not have a causal relationship with this treatment. An adverse event can therefore be any unfavorable and unintended sign, laboratory finding, symptom or disease temporally associated with the use of an investigational medicinal product, whether considered related to it or not. Any pre-existing condition during the clinical trial which is worsened during the clinical study is to be considered an adverse event.

An adverse reaction is defined as any untoward and unintended response to an investigational product related to any dose administered. All adverse reactions judged by either the Clinical Investigator or the Sponsor to have reasonable causal relationship to a medicinal product qualified as adverse reactions. This is meant to convey in general that there is evidence or an argument to suggest a causal relationship.

An unexpected adverse reaction is defined as an adverse reaction, the nature, or severity of which is not consistent with the applicable product information.

A serious adverse event or serious adverse reaction is defined as any untoward medical occurrence or effect that, at any dose, results in death, is life threatening, requires hospitalization or prolongation of existing in-Subject hospitalization, results in persistent or significant disability or incapacity, or is a congenital anomaly or birth defect.

The observation period is extended from the time the subject began the study medication through the end of Visit 3 for hypogonadal subjects. AEs that are continuing at the end of the study period are followed until the Investigator believed that the AEs reached a stable clinical endpoint or are resolved.

The percent of subjects with a serum DHT and Estradiol greater than the upper limit of the reference range, for the respective analytes.

The Day 8 close-out findings are compared to the screening results, and clinically significant changes identified in the following:

Vital Signs and Adverse Events: Blood Pressure, Body Temperature, Respiratory Rate, Heart Rate.

Otorhinolaryngological examination.

Complete Blood Count to evaluate changes in white blood count, hemoglobin and hematocrit.

Clinical chemistry profile; Na/K, glucose, urea, creatinine, calcium, phosphate, uric acid, total bilirubin, albumin, AST, ALT, ALP, GGT, CK, and PSA.

Classifications:

A serious adverse event (SAE) or serious adverse reaction: Defined as any untoward medical occurrence or effect that at any dose; results in death, is life-threatening, requires in-Subject hospitalization or prolongation of existing in-Subject hospitalization, results in persistent or significant disability or incapacity, is a congenital anomaly or birth defect, a medically important condition, i.e., the AE jeopardized the subject, or requires intervention to prevent one of the outcomes listed above.

Non-serious AE: Any AE not meeting the SAE criteria.

Intensity: An adverse event/reaction is classified as Mild, Moderate, or Severe.

Causality: The adverse event may be considered an adverse reaction to an investigational medicinal product when a "reasonable causal relationship" exists between the event and the investigational product. The following degree of causal relationship might be considered:

Definite: plausible temporal relationship with drug administration and withdrawal, and re-appears after drug re-start.

Probable: plausible temporal relationship with drug administration.

Possible: plausible temporal relationship with drug administration but can reasonably be associated to other factors.

Unlikely: does not have plausible temporal relationship with drug administration.

Unknown: no sufficient elements to establish a correlation with drug intake.

Not Related: cannot be correlated to the drug administration.

Procedure to be followed in the case of adverse events: All adverse events detected by the Clinical Investigator are recorded in the special section of the Case Report Form. Any event that is classified as serious, regardless of causal relationship, is to have been reported to the CRO and Sponsor within 24 hours. There are no serious adverse events.

9.5.2 Appropriateness of Measurements

All measurements used in this study are standard indices of efficacy, PK and safety and are generally recognised as reliable, accurate and relevant.

9.5.3. Primary Efficacy Variable(s)

Pharmacokinetic profiles of serum Testosterone for subjects dosed in Treatments A, B, and C that have:

1. A 24 hour $C_{avg}$ value >300 ng/dL and <1050 ng/dL.
2. The percent of subjects in each treatment group with a 24 hour $C_{avg}$ less than, within and above the serum Testosterone reference range of 300 ng/dL-1050 ng/dL.

9.6 Data Quality Assurance

The CRF entries are verified by the monitors against source documents. All entries into the database included the CRF and Diary Card subject data, the PK results, and laboratory values. All data is 100% audited after being entered into the database for this report.

9.7 Statistical Methods Planned in the Protocol and Determination of Sample Size 9.7.1 Statistical and Analytical Plans The PK Analysis Plan is described above. The Analysis Plan for the Vital Signs and Laboratory Results are compared baseline results with final visit results after PK analysis. Other data including demographic data is descriptive. No statistical analysis is performed because group sizes are not selected on the basis of statistical significance.

9.7.2 Determination of Sample Size

Based on the results are obtained from conducting several pharmacokinetic studies in groups of 10 subjects per cohort, these are sufficient for an acceptable description of the pharmacokinetic parameters in this population. As this is a relatively modest Phase II PK study with the intent of investigating two higher concentrations of TBS-1 gel, a true sample size calculation is not performed.

9.8 Changes in the Conduct of the Study or Planned Analysis

The protocol is amended on Jul. 27, 2010. The change requested is in the timing of blood draws. The number of blood draws remained the same. This change is required to enable the full capture of the peak of testosterone absorption following the third TID dosing which occurred at 1300 hours on Day 8 or 1600 hours after the initial 2100 hour drug administration on the previous day (Day 7).

10. Study Subjects 10.1 Disposition of Subjects

The study is conducted at three centers located in Miami, Fla., Shreveport, L A and Tucson, Ariz.

The three treatment groups are equally divided amongst the three sites. Eight Subjects received Treatment A, seven Subjects received Treatments B and C, respectively. A total of 22 subjects are in the study. In addition, five subjects who participated in the previous clinical study failed screening and are therefore not randomized to the study.

TABLE 10.1

Disposition of Subjects by Site and Treatment

| SITE ID | Treatment A: TBS-1 syringe prefilled with 125 micro-liters of drug | Treatment B: TBS-1 syringe prefilled with 150 micro-liters of drug | Treatment C: TBS-1 syringe prefilled with 125 micro-liters of drug | Total |
|---|---|---|---|---|
| 01 | 3 | 3 | 3 | 9 |
| 02 | 3 | 2 | 2 | 7 |
| 03 | 2 | 2 | 2 | 6 |
| Total | 8 | 7 | 7 | 22 |

10.2 Protocol Deviations

There are no meaningful pharmacokinetic deviations.

11. Pharmacokinetics and Statistics 11.1 Datasets Analyzed

The PK population is defined as subjects who receive the Treatment A, B or C, and who complete the study without major protocol violation or for whom the PK profile can be adequately characterized. The PK population is used for the analysis of PK data.

Based on the above criteria, twenty-two (22) subjects are included in the PK population. The numbers of subjects by site and by treatment are displayed below.

TABLE 11.1.1

Disposition of Subjects in the PK population:

| Site | Number of Subjects |
|---|---|
| 1 | 9 |
| 2 | 7 |
| 3 | 6 |

| Treatment | Number of Subjects |
|---|---|
| A: TBS-1 125 µL of 4.0% Gel (t.i.d.) | 8 |
| B: TBS-1 150 µL of 4.5% Gel (b.i.d.) | 7 |
| C: TBS-1 125 µL of 4.5% Gel (t.i.d.) | 7 |

11.2 Demographic and Other Baseline Characteristics

The demographic data and characteristics are presented by dose group for all the treated subjects in Table 11.2. No meaningful differences are observed amongst the three groups for any of the characteristics.

TABLE 11.2

Summary of Demographic Characteristics-All Subjects

| Characteristic | Treatment A: TBS-1 syringe prefilled with 125 micro-liters of 4.0 percent gel | Treatment B: TBS-1 syringe prefilled with 150 micro-liters of 4.5 percent gel | Treatment C: TBS-1 syringe prefilled with 125 micro-liters of 4.5 percent gel | All Subjects |
|---|---|---|---|---|
| SEX | (N = 8) | (N = 7) | (N = 7) | (N = 22) |
| Male | 8 | 7 | 7 | 22 |
| RACE | | | | |
| Black or African American | | | 1 | 1 |
| White | 8 | 7 | 6 | 21 |
| ETHNIC | | | | |
| Hispanic or Latino | 4 | 3 | 3 | 10 |
| Non-Hispanic and Non-Latino | 4 | 4 | 4 | 12 |
| AGE | | | | |
| Mean | 52.38 | 53.86 | 51.57 | 52.59 |
| SD | 12.55 | 11.04 | 9.90 | 10.78 |
| Minimum | 37 | 36 | 35 | 35 |
| Maximum | 73 | 63 | 67 | 73 |
| Median | 51 | 59 | 52 | 54 |

The treated populations for Group A have a mean age of 52.38, for Group B 53.86, and for Group C 51.57. The standard deviations are 12.55, 11.04, and 9.90, respectively. The ethnic and racial distribution are essentially the same in each group.

11.3 Measurement of Treatments Compliance

Compliance of drug utilization during the home portion of the study is determined by a review of the diaries and used returned pouches and syringes. Although the method is not absolute, it is sufficient to establish reasonable compliance. One subject could not find his diary.

11.4 Pharmacokinetics and Statistical Results 11.4.1 Methods

The blood concentrations are received from ABL and transferred electronically from Trimel Biopharma SRL to the statistical unit of PharmaNet. Testosterone and Dihydrotestosterone serum concentrations are provided in ng/mL. However, the serum concentrations are converted to ng/dL for PK calculation to match the units of the literature's reference ranges.

During the trial, clinical site 1 performs PK sampling one day later than specified in the protocol that is it started on Day 8 rather than Day 7. This change is not planned. Consequently, the actual times are calculated relative to the 2100 drug administration on Day 8 for the subjects of clinical site 1 and the drug administration 21 h00 on Day 7 for the subjects of clinical sites 2 and 3.

For subject No. 02-003, the dosing time is not recorded on Day 7. Consequently, the schedule sampling times are used instead of the actual sampling times for PK calculations. The 16.33 h and 16.67 h samples for subject 01-001 are drawn at the same time due to technical reason. The schedule sampling time is used for sample 16.33 h while the actual sampling time is used for sample 16.67 h.

Excluding the above exceptions, time deviations during sampling are treated as follows: for all sampling times, the difference between the scheduled and the actual sampling time is considered acceptable if it is less than 1 minute. When the difference exceeded this time limit, the actual sampling times (rounded off to three decimal digits) are used to calculate pharmacokinetic parameters, except for pre-dose samples, which are always reported as zero (0.000), regardless of time deviations. Scheduled sampling times are presented in concentration tables and graphs in the statistical report.

PK calculations are performed using WinNonlin™ version 5.2 (or higher), validated according to industry's expectations and regulatory requirements. Descriptive statistical calculations are also performed using Microsoft® Office Excel 2003. Microsoft® Office Excel 2003 and Microsoft® Office Word 2003 are used for report data tabulation.

Descriptive statistics (N, mean, standard deviation (SD), coefficient of variation (CV), median, minimum value (Min.), and maximum value (Min.)) of the serum concentrations versus time as well as all pharmacokinetic parameters are provided for each treatment at each dose level using the evaluable population. All figures are presented using both linear (a) and semi-log (b) scales.

For the calculation of the PK parameters from the last three drug administrations (Treatments A and C: 0 hour to 10 hours, 10 hours and 16 hours and 16 hours and 24 hours; treatment B: 0 hour to 10 hours and 10 hours and 24 hours), the serum concentration values for Testosterone, Dihydrotestosterone, and Estradiol at time points 10 hours (pre-dose for the second drug administration) and 16 hours (pre-dose for the third drug administration under Treatments A and C) are obtained by imputing the serum concentration value observed at time points 9.75 hours and 15.75 hours, respectively.

The following pharmacokinetic parameters are determined for all subjects for Testosterone, Dihydrotestosterone and Estradiol:

For Treatments A and C (t.i.d.): $AUC_{0-T}$, $AUC_{0-10}$, $AUC_{10-16}$, $AUC_{16-24}$, $C_{max}$, $C_{max\ 0-10}$, $C_{max\ 10-16}$, $C_{max\ 16-24}$, $C_{min}$, $C_{min\ 0-10}$, $C_{min\ 10-16}$, $C_{min\ 16-24}$, $C_{avg}$, $C_{avg\ 0-10}$, $C_{avg\ 10-16}$, $C_{avg\ 16-24}$, $t_{max}$, $t_{max\ 0-10}$, $t_{max\ 10-16}$, $t_{max\ 16-24}$, $t_{max\ 10-24}$, PTF, PTS.

For Treatment B (b.i.d.): $AUC_{0-T}$, $AUC_{0-10}$, $AUC_{10-24}$, $C_{max}$, $C_{max\ 0-10}$, $C_{max\ 10-24}$, $C_{min}$, $C_{min\ 0-10}$, $C_{min\ 10-24}$, $C_{avg}$, $C_{avg\ 0-10}$, $C_{avg\ 10-24}$, $t_{max}$, $t_{max\ 0-10}$, $t_{max\ 10-24}$, PTF, PTS.

Additionally, the percent of subjects with $C_{avg}$ values for serum Testosterone, Dihydrotestosterone and Estradiol above, within, and below their respective reference range is calculated for each treatment. As well, the mean percent time of serum Testosterone, Dihydrotestosterone and Estradiol values above (% TimeAbove), within (% TimeWithin), and below (% TimeBelow) the corresponding reference range are provided for each treatment. The calculation of all these pharmacokinetic parameters is explained below.

11.4.1.1 Maximum and Minimum Observed Concentrations and Time of Observed Peak Concentrations $C_{max}$, the maximum is observed concentrations and $T_{max}$, the time to reach that peak concentrations, as well as $C_{min}$, the minimum observed concentrations are determined for each subject and for each treatment as follow:

$C_{max}$: Maximum observed concentration over the dosing interval. This parameter is calculated for Treatments A, B and C.

$C_{max\ 0-10}$: Maximum observed concentration from time zero to 10 hours. This parameter is calculated for Treatments A, B and C.

$C_{max\ 10-16}$: Maximum observed concentration from time 10 hours to 16 hours. This parameter is calculated for Treatments A and C.

$C_{max\ 16-24}$: Maximum observed concentration from time 16 hours to 24 hours. This parameter is calculated for Treatments A and C.

$C_{max\ 10-24}$: Maximum observed concentration from time 10 hours to 24 hours. This parameter is calculated for Treatment B only.

$C_{min}$: Minimum observed concentration over the dosing interval. This parameter is calculated for Treatments A, B and C.

$C_{min\ 0-10}$: Minimum observed concentration from time zero to 10 hours. This parameter is calculated for Treatments A, B and C.

$C_{min\ 10-16}$: Minimum observed concentration from time 10 hours to 16 hours. This parameter is calculated for Treatments A and C.

$C_{min\ 16-24}$: Minimum observed concentration from time 16 hours to 24 hours. This parameter is calculated for Treatments A and C.

$C_{min\ 10-24}$: Minimum observed concentration from time 10 hours to 24 hours. This parameter is calculated for Treatment B only.

$t_{max}$: Time of observed $C_{max}$ over the dosing interval. This parameter is calculated for Treatments A, B and C.

$t_{max\ 0-10}$: Time of observed $C_{max}$ from time zero to 10 hours. This parameter is calculated for Treatments A, B and C.

$t_{max\ 10-16}$: Time of observed $C_{max}$ from time 10 hours to 16 hours. This parameter is calculated for Treatments A and C.

$t_{max\ 16-24}$: Time of observed $C_{max}$ from time 16 hours to 24 hours. This parameter is calculated for Treatments A and C.

$t_{max\ 10-24}$: Time of observed $C_{max}$ from time 10 hours to 24 hours. This parameter is calculated for Treatment B only.

11.4.1.2 Areas Under the Concentration-Time Curves

The calculation of AUCs is performed using the linear trapezoidal method. $AUC_{0-T}$ is computed from dose time (0) to dose time □ (□=24 h). However, in case the 24-h sample is collected with a time deviation, the $AUC_0$_T is estimated based on the estimated concentration at 24 hours using the regression line calculated from the elimination phase, and not the concentration at the actual observation time.

In the case where the last concentration value (Y) is missing or does not correspond to a scheduled sampling time (i.e. 10 hours and 16 hours), $AUC_{X-Y}$ is extrapolated using the corresponding subject's elimination phase, if calculable.

The following AUCs are calculated:

$AUC_{0-T}$: Area under the concentration-time curve for one dosing interval. This parameter is calculated for Treatments A, B and C.

$AUC_{0-10}$: Area under the concentration-time curve from time zero to 10 hours. This parameter is calculated for Treatments A, B and C.

$AUC_{10-16}$: Area under the concentration-time curve from time 10 hours to 16 hours. This parameter is calculated for Treatments A and C.

$AUC_{16-24}$: Area under the concentration-time curve from time 16 hours to 24 hours. This parameter is calculated for Treatments A and C.

$AUC_{10-24}$: Area under the concentration-time curve from time 10 hours to 24 hours. This parameter is calculated for Treatment B only.

The $C_{avg}$ are calculated as follow:

$C_{avg}$: Average concentration during the dosing interval, calculated as $AUC_0$-T/T (T=24 hours). This parameter is calculated for Treatments A, B and C.

$C_{avg\ 0\text{-}10}$: Average concentration from time zero to 10 hours, calculated as AUC0-10/10. This parameter is calculated for Treatments A, B and C.

$C_{avg\ 10\text{-}16}$: Average concentration from time 10 hours to 16 hours, calculated as AUC10-16/6. This parameter is calculated for Treatments A and C.

$C_{avg\ 16\text{-}24}$: Average concentration from time 16 hours to 24 hours, calculated as AUC16-24/8. This parameter is calculated for Treatments A and C.

$C_{avg\ 10\text{-}24}$: Average concentration from time 10 hours to 24 hours, calculated as AUC10-24/14. This parameter is calculated for Treatment B only.

11.4.1.3 Average Drug Concentrations

The $C_{avg}$ are calculated as follow:

$C_{avg}$: Average concentration during the dosing interval, calculated as AUC0-T/T ($\tau$=24 hours). This parameter is calculated for Treatments A, B and C.

$C_{avg\ 0\text{-}10}$: Average concentration from time zero to 10 hours, calculated as AUC0-10/10. This parameter is calculated for Treatments A, B and C.

$C_{avg\ 10\text{-}16}$: Average concentration from time 10 hours to 16 hours, calculated as AUC10-16/6. This parameter is calculated for Treatments A and C.

$C_{avg\ 16\text{-}24}$: Average concentration from time 16 hours to 24 hours, calculated as AUC16-24/8. This parameter is calculated for Treatments A and C.

$C_{avg\ 10\text{-}24}$: Average concentration from time 10 hours to 24 hours, calculated as AUC10-24/14. This parameter is calculated for Treatment B only.

11.4.1.4 Peak Trough Fluctuation and Peak Trough Swing

The peak trough fluctuation (PTF) and the Peak trough swing are calculated as follow:

PTF: Peak trough fluctuation, calculated as $(C_{max}-C_{min})/C_{avg}$ This parameter is calculated for Treatments A, B and C.

PTS: Peak trough swing, calculated as $(C_{max}-C_{min})/C_{min}$.

This parameter is calculated for Treatments A, B and C.

11.4.1.5 Percent Time Above, within and Below the Reference Range and Percent of a Subjects with $C_{avg}$ Above, within and Below the Reference Range The percent times during which observations fall above (% TimeAbove), within (% TimeWithin), and below (% TimeBelow) the reference ranges are computed for each subject and treatment for the serum Testosterone, Dihydrotestosterone and Estradiol. The percent of subjects with $C_{avg}$ values for serum Testosterone, Dihydrotestosterone and Estradiol above, within, and below their respective reference range is calculated for each treatment. The reference ranges are 300 ng/dL to 1050 ng/dL for Testosterone, 25.5 ng/dL to 97.8 ng/dL for Dihydrotestosterone and 3 pg/mL to 81 pg/mL for Estradiol.

PTS: Peak trough swing, calculated as $(C_{max}-C_{min})/C_{min}$.

This parameter is calculated for Treatments A, B and C.

11.4.1.6 Statistical Analysis

Only descriptive statistics (N, mean, SD, CV, median, Min., and Max.) are calculated on the serum concentrations and the PK parameters for each treatment. No inferential statistical analysis is performed.

11.4.2 Analysis of Pharmacokinetics and Statistical Issues 11.4.2.2 Handling of Missing Data Samples that are not analyzed due to an insufficient volume (refer to the bioanalytical report) are recorded as INV (Insufficient volume for analysis) in the concentration tables.

These samples are set as missing for pharmacokinetic and statistical analyses. As the PK parameters could be estimated using the remaining data points, subjects with missing data are kept in the pharmacokinetic analysis.

11.4.2.3 Pharmacokinetic Analysis

The following pharmacokinetic parameters are determined for all subjects for Testosterone, Dihydrotestosterone and Estradiol:

For Treatments A and C $AUC_{0\text{-}T}$, $AUC_{0\text{-}10}$, $AUC_{10\text{-}16}$, $AUC_{16\text{-}24}$, $C_{max}$, $C_{max\ 0\text{-}10}$, $C_{max\ 10\text{-}16}$, $C_{max\ 16\text{-}24}$, $C_{min}$, $C_{min\ 0\text{-}10}$, $C_{min\ 10\text{-}16}$, $C_{min\ 16\text{-}24}$, $C_{avg}$, $C_{avg\ 0\text{-}10}$, $C_{avg\ 10\text{-}16}$, $C_{avg\ 16\text{-}24}$, $t_{max}$, $t_{max\ 0\text{-}10}$, $t_{max\ 10\text{-}16}$, $t_{max\ 16\text{-}24}$, $t_{max\ 10\text{-}24}$, PTF, PTS.

For Treatment B (b.i.d.): $AUC_{0\text{-}T}$, $AUC_{0\text{-}10}$, $AUC_{10\text{-}24}$, $C_{max}$, $C_{max\ 0\text{-}10}$, $C_{max\ 10\text{-}24}$, $C_{min}$, $C_{min\ 0\text{-}10}$, $C_{min\ 10\text{-}24}$, $C_{avg}$, $C_{avg\ 0\text{-}10}$, $C_{avg\ 10\text{-}24}$, $t_{max}$, $t_{max\ 0\text{-}10}$, $t_{max\ 10\text{-}24}$, PTF, PTS.

Additionally, the percent of subjects with $C_{avg}$ values for serum Testosterone, Dihydrotestosterone and Estradiol above, within, and below their respective reference range is calculated for each treatment. As well, the mean percent time of serum Testosterone, Dihydrotestosterone and Estradiol values above (% TimeAbove), within (% TimeWithin), and below (% TimeBelow) the corresponding reference range are provided for each treatment. The calculation of all these pharmacokinetic parameters is explained below.

With the exception of text Tables (numbered as 11.4.2.3-1 to 11.4.2.3-3) and text Figures (numbered as 11.4.2.3-1 to 11.4.2.3-3), all tables and figures referred to in this section are displayed in sections 14.2.1 and 14.2.2, respectively. For brevity, TBS-1 treatments are identified in the text of the statistical report by their treatment code: A (125 µL of 4% gel given t.i.d. for a total dose of 30 mg/day), B (150 µL of 4.5% gel is given b.i.d. for a total dose of 27.0 mg/day) and C (125 µL of 4.5% gel given t.i.d. for a total dose of 33.75 mg/day).

Blood samples for pharmacokinetic analysis are collected prior and post the 2100 hour drug administration on Day 7 at 0.333, 0.667, 1.00, 1.50, 2.00, 3.00, 6.00, 9.00, 9.75, 10.33, 10.66, 11.0, 11.5, 12.0, 13.0, 14.0, 15.75, 16.33, 16.66, 17.0, 17.5, 18.0, 20.0, 22.0, and 24.0 hours for Treatments A and C. Blood samples for pharmacokinetic analysis are collected prior and post the 2100 hour drug administration on Day 7 at 0.333, 0.667, 1.00, 1.50, 2.00, 3.00, 6.00, 9.00, 9.75, 10.33, 10.66, 11.0, 11.5, 12.0, 13.0, 16.0, 19.0, 22.0, and 24.0 hours for Treatment B. The actual sampling times is used for PK calculation are displayed in Tables 14.2.1.22, 14.2.1.23 and 14.2.1.24 for Treatments A, B and C, respectively.

Testosterone

The Testosterone serum concentrations measured for each subject at each sampling time appear in Tables 14.2.1.1, 14.2.1.2 and 14.2.1.3 according to treatment. The plots of the individual serum levels over the sampling period are presented using both linear (a) and semi-log (b) scales in FIGS. 14.2.2.1 through 14.2.2.22. Lines for the minimum (300 ng/dL) and maximum (1050 ng/dL) bound of the reference range for the testosterone serum concentrations are also presented for information purposes. As well, a line for the average drug concentration ($C_{avg}$) during the dosing interval ($\tau$=24 hours) is also presented on the individual profiles.

Figure 14:
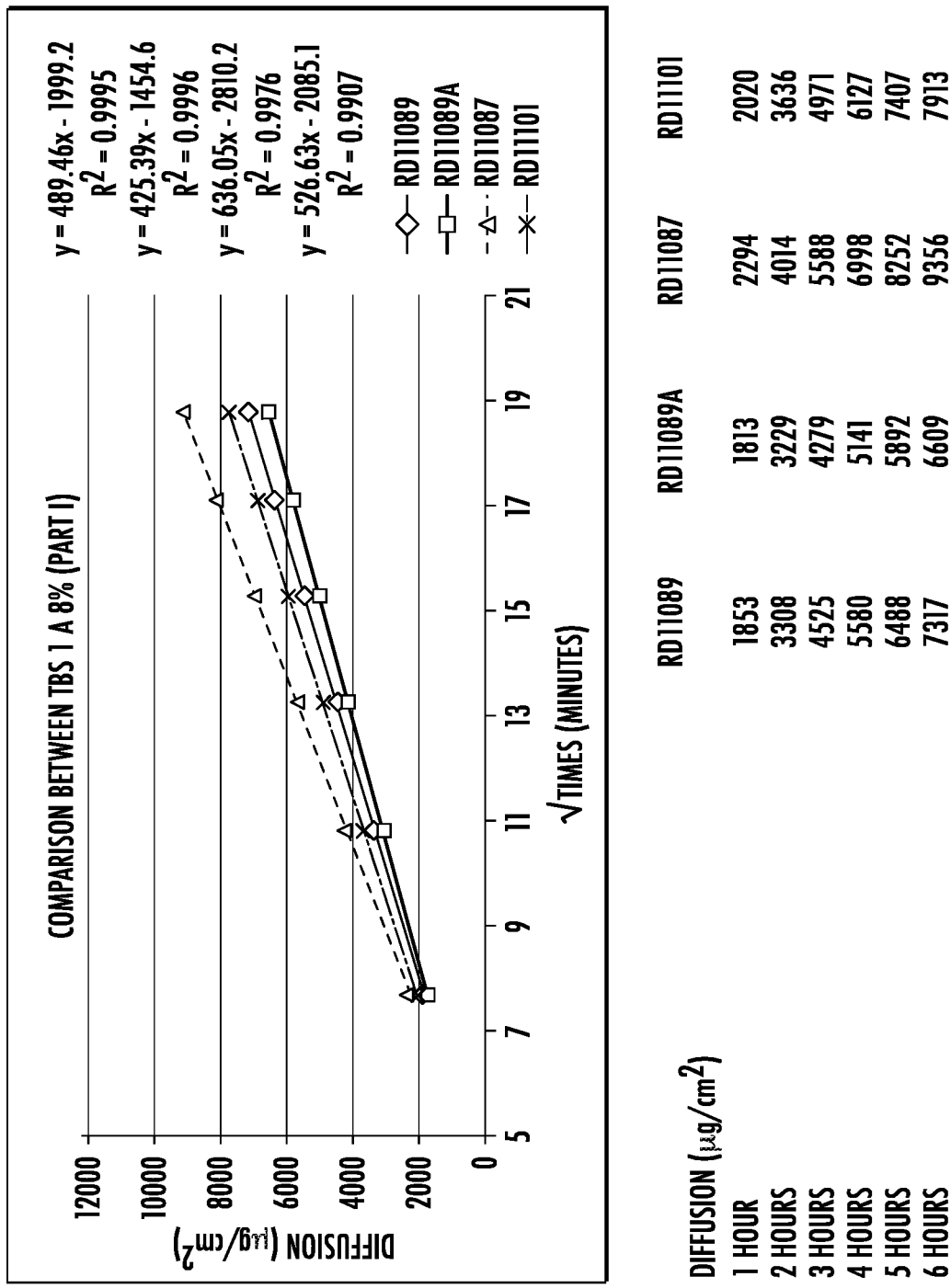
FIG. 14 depicts a comparison between TBS 1 A 8% (Part I)

The plots of the mean serum levels over the sampling period are also presented using both the linear (a) and semi-log (b) scales in FIGS. 14.2.2.23, 14.2.2.24 and 14.2.2.25 for Treatments A, B and C, respectively. The error bars on these mean profiles correspond to one standard deviation. The lines for the minimum and maximum bound of the reference ranges are also presented on the mean figures.

Figure 11:
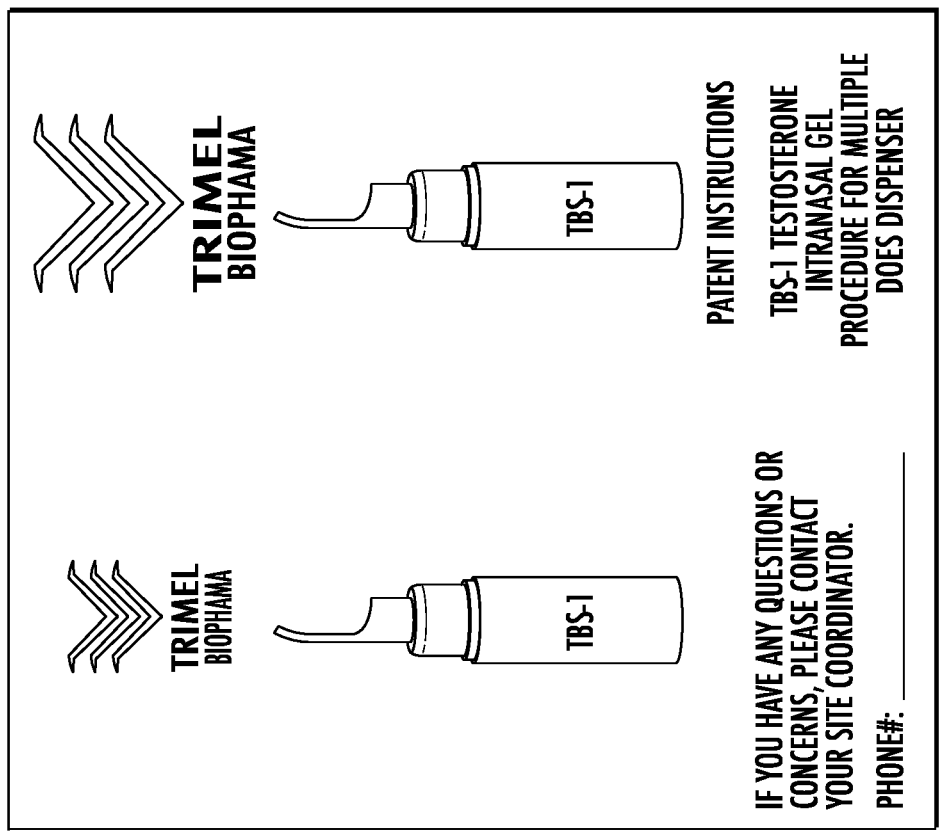
FIG. 11 illustrates a multiple dose dispenser in accordance with the present invention.
Figure 10B:
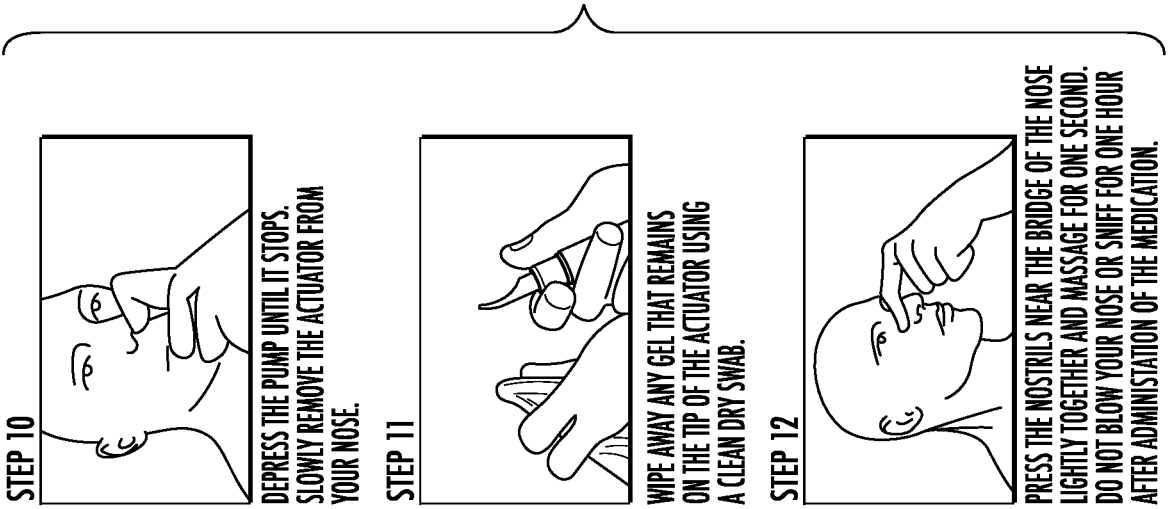

The mean plot on the linear scale for each treatment is also presented below in the text FIG. 11.4.2.3-1.

Figure 35:
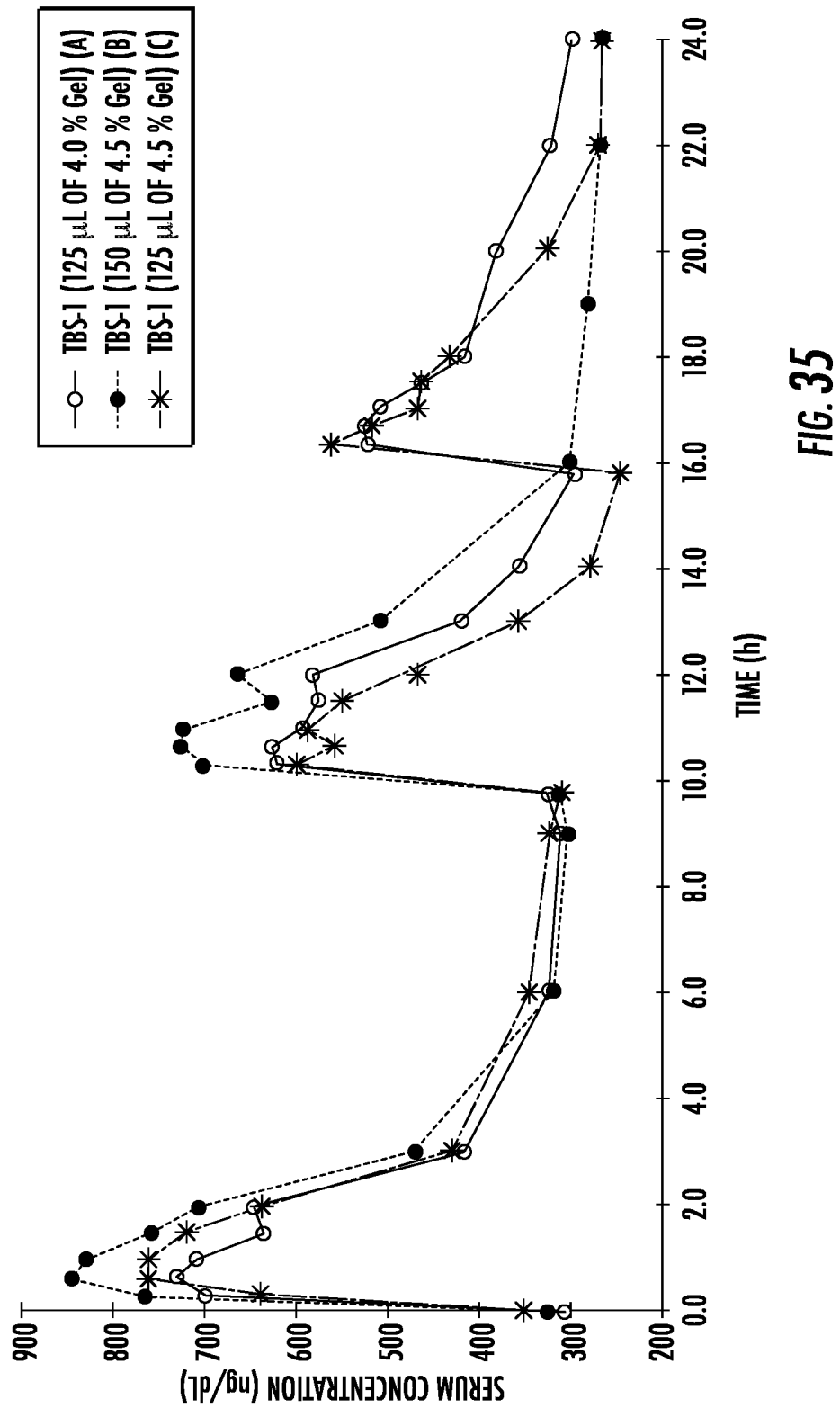
FIG. 35 depicts the mean testosterone serum concentration time profile.

As shown in FIG. 35 the mean testosterone serum concentration (ng/dL) Time Profile for Each Treatment.

Calculated pharmacokinetic parameters for each subject according to treatment are shown in Tables 14.2.1.4, 14.2.1.5 and 14.2.1.6 for Treatments A, B and C, respectively. They are summarized in the text Table 11.4.2.3-1.

calculated for each treatment and are presented in Table 14.2.1.7. These results are also summarized in text Table 11.4.2.3.1.

Dihydrotestosterone

The Dihydrotestosterone serum concentrations are measured for each subject at each sampling time appear in Tables 14.2.1.8, 14.2.1.9 and 14.2.1.10 according to treatment. The plots of the individual serum levels over the

TABLE 11.4.2.3-1

Summary of Testosterone Pharmacokinetic Parameters for Each Treatment

| | | Treatment A[1] (N = 8) | | | Treatment B[2] (N = 7) | | | Treatment C[3] (N = 7) | | |
|---|---|---|---|---|---|---|---|---|---|---|
| Parameter | Unit | Mean | SD | CV % | Mean | SD | CV % | Mean | SD | CV % |
| $AUC_{0-10}$ | h * ng/dL | 4178.68 | 1210.51 | 28.97 | 4451.64 | 1581.09 | 35.52 | 4355.19 | 1374.07 | 31.55 |
| $C_{max\ 0-10}$ | ng/dL | 786 | 209 | 26.53 | 894 | 500 | 55.90 | 857 | 323 | 37.72 |
| $C_{min\ 0-10}$ | ng/dL | 259 | 70.3 | 27.16 | 256 | 91.5 | 35.76 | 272 | 69.7 | 25.61 |
| $C_{avg\ 0-10}$ | ng/dL | 418 | 121 | 28.97 | 445 | 158 | 35.52 | 436 | 137 | 31.55 |
| $T_{max\ 0-10}$ | h | 1.01 | 0.678 | 67.21 | 0.695 | 0.279 | 40.18 | 0.905 | 0.422 | 46.62 |
| $AUC_{10-16}$ | h * ng/dL | 2635.05 | 1062.56 | 40.32 | — | — | — | 2301.51 | 658.44 | 28.61 |
| $C_{max\ 10-16}$ | ng/dL | 698 | 251 | 35.88 | — | — | — | 675 | 256 | 37.98 |
| $C_{min\ 10-16}$ | ng/dL | 270 | 90.7 | 33.63 | — | — | — | 230 | 53.9 | 23.48 |
| $C_{avg\ 10-16}$ | ng/dL | 439 | 177 | 40.32 | — | — | — | 384 | 110 | 28.61 |
| $T_{max\ 10-16}$ | h | 11.1 | 1.06 | 9.54 | — | — | — | 10.8 | 0.562 | 5.20 |
| $AUC_{10-24}$ | h * ng/dL | — | — | — | 5264.19 | 2176.63 | 41.35 | — | — | — |
| $C_{max\ 10-24}$ | ng/dL | — | — | — | 846 | 377 | 44.53 | — | — | — |
| $C_{min\ 10-24}$ | ng/dL | — | — | — | 228 | 100 | 43.88 | — | — | — |
| $C_{avg\ 10-24}$ | ng/dL | — | — | — | 376 | 155 | 41.35 | — | — | — |
| $T_{max\ 10-24}$ | h | — | — | — | 11.1 | 0.675 | 6.06 | — | — | — |
| $AUC_{16-24}$ | h * ng/dL | 3016.52 | 1083.58 | 35.92 | | | | 2766.97 | 838.13 | 30.29 |
| $C_{max\ 16-24}$ | ng/dL | 556 | 216 | 38.78 | — | — | — | 595 | 352 | 59.20 |
| $C_{min\ 16-24}$ | ng/dL | 271 | 86.9 | 32.08 | — | — | — | 225 | 59.1 | 26.26 |
| $C_{avg\ 16-24}$ | ng/dL | 377 | 135 | 35.92 | — | — | — | 346 | 105 | 30.29 |
| $T_{max\ 16-24}$ | h | 16.6 | 0.404 | 2.43 | — | — | — | 16.8 | 0.704 | 4.19 |
| $AUC_{0-\infty}$ | h * ng/dL | 9920.07 | 3300.65 | 33.27 | 9781.39 | 3532.43 | 36.11 | 9505.03 | 2650.59 | 27.89 |
| $C_{max}$ | ng/dL | 830 | 188 | 22.65 | 1050 | 463 | 44.19 | 883 | 346 | 39.23 |
| $C_{min}$ | ng/dL | 239 | 77.6 | 32.55 | 224 | 98.6 | 43.97 | 222 | 57.1 | 25.69 |
| $C_{avg}$ | ng/dL | 413 | 138 | 33.27 | 408 | 147 | 36.11 | 396 | 110 | 27.89 |
| $T_{max}$ | h | 4.61 | 5.27 | 114.31 | 4.99 | 5.43 | 108.81 | 4.50 | 6.44 | 143.18 |
| PTF | — | 1.51 | 0.39 | 26.03 | 2.04 | 1.07 | 52.23 | 1.61 | 0.47 | 28.92 |
| PTS | — | 2.63 | 0.73 | 27.70 | 4.49 | 3.92 | 87.27 | 3.04 | 1.65 | 54.27 |
| % TimeBelow * | % | 34.47 | 30.93 | 89.72 | 36.40 | 25.92 | 71.22 | 30.14 | 29.25 | 97.05 |
| % TimeWithin * | % | 65.16 | 30.46 | 46.75 | 59.47 | 23.10 | 38.84 | 68.21 | 28.77 | 42.17 |
| % TimeAbove * | % | 0.38 | 1.06 | 282.84 | 4.13 | 6.88 | 166.67 | 1.65 | 2.60 | 157.31 |
| $C_{avg}$ Below * [N (% of Subjects) | % | 1 (12.50%) | — | — | 1 (14.29%) | — | — | 1 (14.29%) | — | — |
| $C_{avg}$ Within * [N (% of Subjects) | % | 7 (87.50%) | — | — | 6 (85.71%) | — | — | 6 (85.71%) | — | — |
| $C_{avg}$ Above * [N (% of Subjects)] | % | 0 (0%) | — | — | 0 (0%) | — | — | 0 (0%) | — | — |

*Reference Range = 300-1050 ng/dL.
[1]TBS-1, 125 μL 4.0% gel given t.i.d. (total dose 30 mg/day)
[2]TBS-1, 150 μL of 4.5% gel given b.i.d. (total dose 27.0 mg/day)
[3]TBS-1, 125 μL of 4.5% gel given t.i.d. (total dose 33.75 mg/day)

The percent times during which observations fall above (% TimeAbove), within (% TimeWithin), and below (% TimeBelow) the reference range are computed for each subject and are presented in Tables 14.2.1.4, 14.2.1.5 and 14.2.1.6 for Treatments A, B and C, respectively. These results are also summarized in text Table 11.4.2.3.1.

The percent of subjects with $C_{avg}$ values for serum Testosterone above, within, and below the reference range is sampling period are presented using both linear (a) and semi-log (b) scales in FIGS. 14.2.2.26 through 14.2.2.47. Lines for the minimum (25.5 ng/dL) and maximum (97.8 ng/dL) bound of the reference range for the Dihydrotestosterone serum concentrations are also presented for information purposes. As well, a line for the average drug concentration ($C_{avg}$) during the dosing interval (τ=24 hours) is also presented on the individual profiles.

The plots of the mean serum levels over the sampling period are also presented using both the linear (a) and semi-log (b) scales in FIGS. 14.2.2.48, 14.2.2.49 and 14.2.2.50 for Treatments A, B and C, respectively. The error bars on these mean profiles correspond to one standard deviation. The lines for the minimum and maximum bound of the reference ranges are also presented on the mean figures.

The mean plot on the linear scale for each treatment is also presented below in the text FIG. 11.4.2.3-2.

Figure 36:
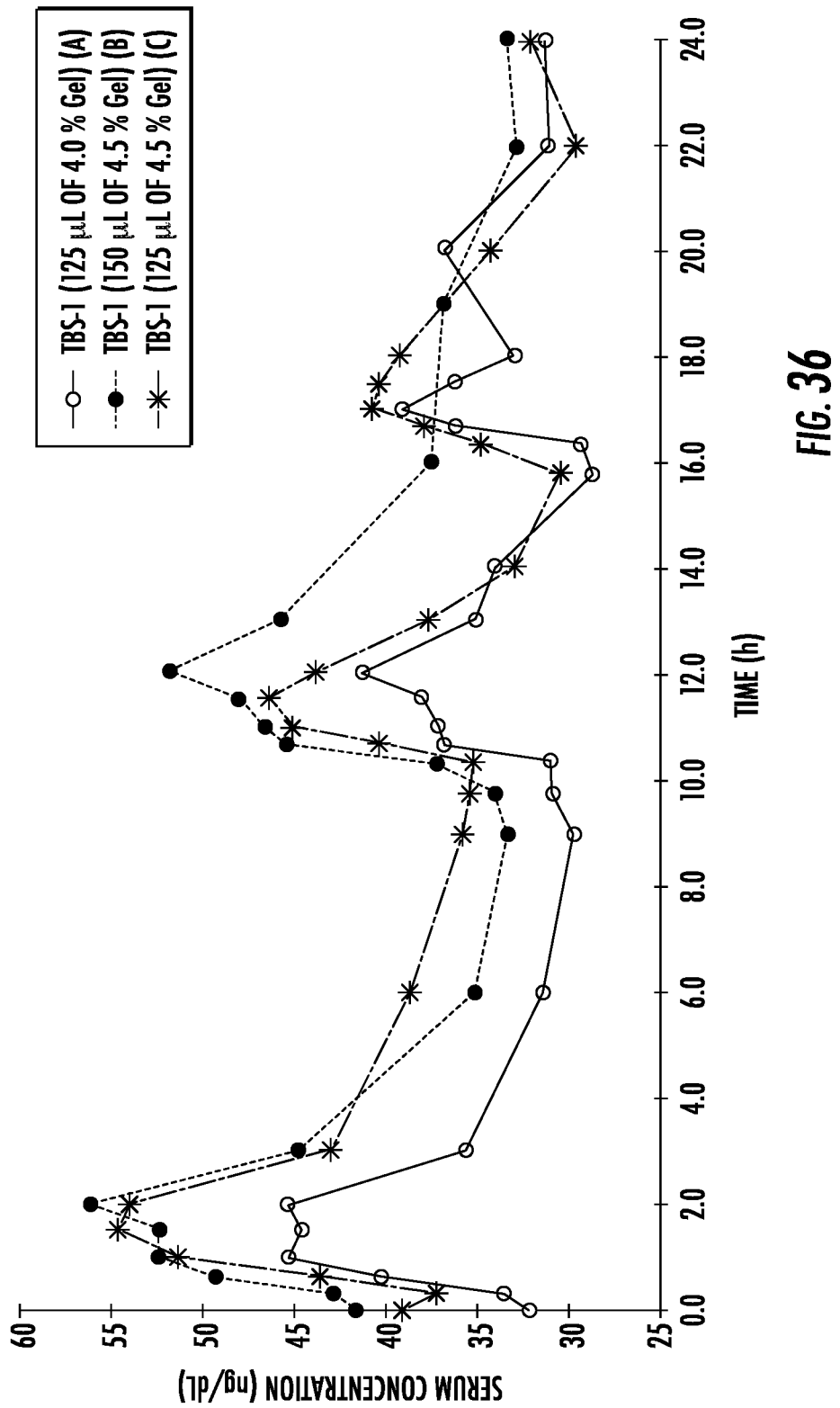
FIG. 36 depicts the mean dihydrotestosterone serum concentration time profile.

As shown in FIG. 36 depicts the Mean Dihydrotestosterone Serum Concentration (ng/dL) Time Profile for Each Treatment is depicted.

As per SAP, $AUC_{X-Y}$ is calculated based on the estimated concentration (Y) using the regression line calculated from the elimination phase data when the last concentration (Y) does not correspond to a schedule sampling time. For subject No. 01-002 and 02-007, the elimination phase is not well characterized due to fluctuation in the Dihydrotestosterone serum concentration for the 10 to 16 hours and 0 to 10 hours intervals, respectively. Therefore, $AUC_{10-16}$ and $C_{avg\ 10-16}$ (derived from $AUC_{10-16}$) could not be calculated for subject No. 01-002 for Treatment A (N=7 for these parameters). As well, $AUC_{0-10}$ and $C_{avg\ 0-10}$ (derived from $AUC_{0-10}$) could not be calculated for subject No. 02-007 for Treatment A (N=7 for these parameters).

Calculated pharmacokinetic parameters for each subject according to treatment are shown in Tables 14.2.1.11, 14.2.1.12 and 14.2.1.13 for Treatments A, B and C, respectively. They are summarized in the text Table 11.4.2.3-2.

TABLE 11.4.2.3-2

Summary of Dihydrotestosterone Pharmacokinetic Parameters for Each Treatment

| Parameter | Unit | Treatment A[1] (N = 8) | | | Treatment B[2] (N = 7) | | | Treatment C[3] (N = 7) | | |
|---|---|---|---|---|---|---|---|---|---|---|
| | | Mean | SD | CV % | Mean | SD | CV % | Mean | SD | CV % |
| $AUC_{0-10}{}^a$ | h * ng/dL | 345.77 | 133.49 | 38.61 | 402.77 | 133.11 | 33.05 | 411.10 | 131.22 | 31.92 |
| $C_{max\ 0-10}$ | ng/dL | 51.4 | 18.8 | 36.52 | 56.8 | 17.1 | 30.08 | 59.0 | 19.7 | 33.48 |
| $C_{min\ 0-10}$ | ng/dL | 26.6 | 10.1 | 38.15 | 30.1 | 13.4 | 44.57 | 31.7 | 9.33 | 29.41 |
| $C_{avg\ 0-10}{}^a$ | ng/dL | 34.6 | 13.3 | 38.61 | 40.3 | 13.3 | 33.05 | 41.1 | 13.1 | 31.92 |
| $T_{max\ 0-10}$ | h | 2.38 | 2.98 | 125.22 | 1.70 | 0.501 | 29.48 | 1.32 | 0.569 | 43.20 |
| $AUC_{10-16}{}^a$ | h * ng/dL | 186.33 | 65.10 | 34.94 | — | — | — | 222.62 | 53.52 | 24.04 |
| $C_{max\ 10-16}$ | ng/dL | 44.2 | 16.8 | 38.01 | — | — | — | 48.9 | 12.4 | 25.37 |
| $C_{min\ 10-16}$ | ng/dL | 26.6 | 10.4 | 38.95 | — | — | — | 30.1 | 8.41 | 27.94 |
| $C_{avg\ 10-16}$ | ng/dL | 31.1 | 10.8 | 34.94 | — | — | — | 37.1 | 8.92 | 24.04 |
| $T_{max\ 10-16}$ | h | 11.9 | 1.13 | 9.50 | — | — | — | 11.4 | 0.436 | 3.84 |
| $AUC_{10-24}$ | h * ng/dL | — | — | — | 543.29 | 235.71 | 43.39 | — | — | — |
| $C_{max\ 10-24}$ | ng/dL | — | — | — | 54.6 | 21.9 | 40.12 | — | — | — |
| $C_{min\ 10-24}$ | ng/dL | — | — | — | 28.3 | 12.7 | 45.02 | — | — | — |
| $C_{avg\ 10-24}$ | ng/dL | — | — | — | 38.8 | 16.8 | 43.39 | — | — | — |
| $T_{max\ 10-24}$ | h | — | — | — | 11.8 | 0.775 | 6.55 | — | — | — |
| $AUC_{16-24}$ | h * ng/dL | 269.16 | 114.13 | 42.40 | — | — | — | 275.21 | 74.02 | 26.89 |
| $C_{max\ 16-24}$ | ng/dL | 41.3 | 17.0 | 41.20 | — | — | — | 42.6 | 12.8 | 30.15 |
| $C_{min\ 16-24}$ | ng/dL | 26.5 | 11.3 | 42.63 | — | — | — | 26.6 | 6.41 | 24.11 |
| $C_{avg\ 16-24}$ | ng/dL | 33.6 | 14.3 | 42.40 | — | — | — | 34.4 | 9.25 | 26.89 |
| $T_{max\ 16-24}$ | h | 17.6 | 1.37 | 7.79 | — | — | — | 17.5 | 0.433 | 2.48 |
| $AUC_{0-\tau}$ | h * ng/dL | 818.95 | 315.07 | 38.47 | 946.89 | 361.03 | 38.13 | 909.68 | 249.37 | 27.41 |
| $C_{max}$ | ng/dL | 52.2 | 18.1 | 34.64 | 61.0 | 22.5 | 36.85 | 60.3 | 18.6 | 30.84 |
| $C_{min}$ | ng/dL | 25.3 | 10.1 | 40.14 | 27.8 | 13.0 | 46.69 | 26.6 | 6.41 | 24.11 |
| $C_{avg}$ | ng/dL | 34.1 | 13.1 | 38.47 | 39.5 | 15.0 | 38.13 | 37.9 | 10.4 | 27.41 |
| $T_{max}$ | h | 4.43 | 6.01 | 135.63 | 4.42 | 4.84 | 109.53 | 4.26 | 5.18 | 121.44 |
| PTF | — | 0.82 | 0.28 | 34.18 | 0.89 | 0.33 | 36.71 | 0.88 | 0.17 | 19.17 |
| PTS | — | 1.14 | 0.44 | 39.02 | 1.36 | 0.70 | 51.43 | 1.24 | 0.30 | 23.90 |
| % TimeBelow * | % | 32.64 | 35.13 | 107.62 | 26.22 | 30.06 | 114.63 | 13.87 | 36.41 | 262.41 |
| % TimeWithin * | % | 67.36 | 35.13 | 52.15 | 73.78 | 30.06 | 40.74 | 86.13 | 36.41 | 42.27 |
| % TimeAbove * | % | 0.0 | 0.00 | — | 0.0 | 0.000 | — | 0.0 | 0.000 | — |
| $C_{avg}$ Below * [N (% of Subjects)] | % | 3 (37.50%) | — | — | 1 (14.29%) | — | — | 1 (14.29%) | — | — |
| $C_{avg}$ Within * [N (% of Subjects)] | % | 5 (62.50%) | — | — | 6 (85.71%) | — | — | 6 (85.71%) | — | — |
| $C_{avg}$ Above * [N (% of Subjects)] | % | 0 (0%) | — | — | 0 (0%) | — | — | 0 (0%) | — | — |

*Reference Range = 25.5-97.8 ng/dL.

[1]TBS-1, 125 μL 4.0% gel given t.i.d. (total dose 30 mg/day)

[2]TBS-1, 150 μL of 4.5% gel given b.i.d. (total dose 27.0 mg/day)

[3]TBS-1, 125 μL of 4.5% gel given t.i.d. (total dose 33.75 mg/day)

[a]For these parameters, N = 7 for Treatment A.

The percent times during which observations fall above (% TimeAbove), within (% TimeWithin), and below (% TimeBelow) the reference range are computed for each subject and are presented in Tables 14.2.1.11, 14.2.1.12 and 14.2.1.13 for Treatments A, B and C, respectively. These results are also summarized in text Table 11.4.2.3.2. The percent of subjects with $C_{avg}$ values for serum Dihydrotestosterone above, within, and below the reference range is calculated for each treatment and are presented in Table 14.2.1.14. These results are also summarized in text Table 11.4.2.3.2.

Estradiol

The Estradiol serum concentrations are measured for each subject at each sampling time appear in Tables 14.2.1.15, 14.2.1.16 and 14.2.1.17 according to treatment. The plots of the individual serum levels over the sampling period are presented using both linear (a) and semi-log (b) scales in FIGS. 14.2.2.51 through 14.2.2.72. Lines for the minimum (3 pg/mL) and maximum (81 pg/mL) bound of the reference range for the Estradiol serum concentrations are also presented for information purposes. As well, a line for the average drug concentration ($C_{avg}$) during the dosing interval ($\tau$=24 hours) is also presented on the individual profiles.

The plots of the mean serum levels over the sampling period are also presented using both the linear (a) and semi-log (b) scales in FIGS. 14.2.2.73, 14.2.2.74 and 14.2.2.75 for Treatments A, B and C, respectively. The error bars on these mean profiles correspond to one standard deviation. The lines for the minimum and maximum bound of the reference ranges are also presented on the mean figures.

The mean plot on the linear scale for each treatment is also presented below in the text FIG. 11.4.2.3-3.

Figure 37:
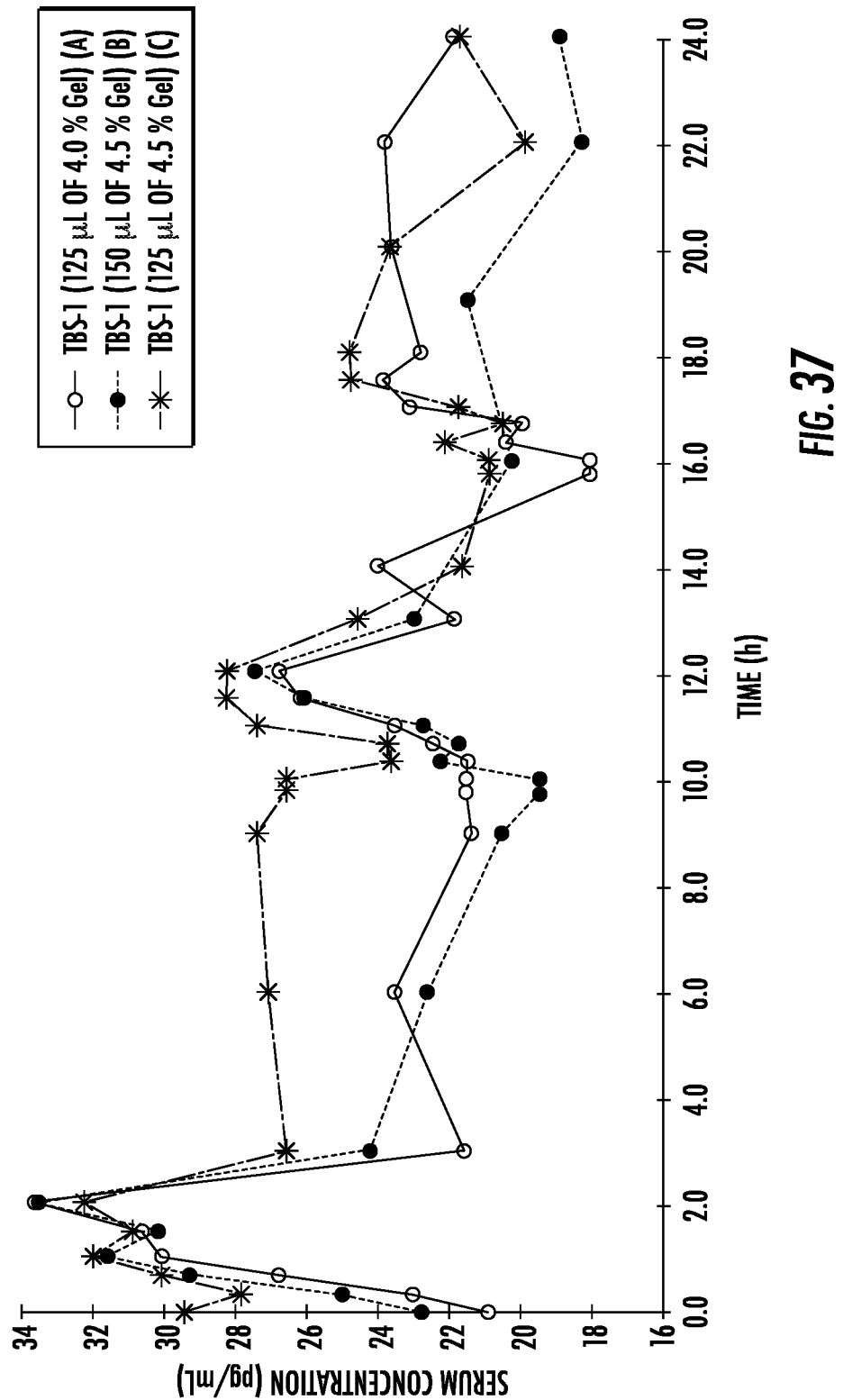
FIG. 37 depicts the mean estradiol serum concentration time profile.

As shown in FIG. 37 the mean estradiol serum concentration (pg/mL) Time Profile for Each Treatment is depicted.

As per SAP (section 8.3), $AUC_{X-Y}$ is calculated based on the estimated concentration (Y) using the regression line calculated from the elimination phase data when the last concentration (Y) does not correspond to a schedule sampling time. However, for some subjects the elimination phase is not well characterized due to fluctuation in the Estradiol serum concentration as follows:

Subject No.: 02-007 for the 0 to 10 hours and for the 0 to 24 hours time intervals for Treatment A. The following PK parameters could not be calculated for this subject: $AUC_{0-10}$, $C_{avg\ 0-10}$, $AUC_{0-T}$, $C_{avg}$ and PTF for Treatment A (N=7 for these parameters).

Subject Nos: 01-002 and 01-007 for the 10 to 16 hours time interval for Treatment A. The $AUC_{10-16}$ and $C_{avg\ 10-16}$ could not be calculated for these subjects for Treatment A (N=6 for these parameters).

Subject Nos. 02-004 and 02-007 for the 16 to 24 hours time interval for Treatment A. The $AUC_{16-24}$ and $C_{avg\ 16-24}$ could not be calculated for this subject for Treatment A (N=6 for these parameters).

Subject Nos. 02-003 and 02-005 for the 0 to 10 hours time interval for Treatment C. The $AUC_{0-10}$ and $C_{avg\ 0-10}$ could not be calculated for these subjects for Treatment C (N=5 for these parameters).

Calculated pharmacokinetic parameters for each subject according to treatment are shown in Tables 14.2.1.18, 14.2.1.19 and 14.2.1.20 for Treatments A, B and C, respectively. They are summarized in the text Table 11.4.2.3-3.

TABLE 11.4.2.3-3

Summary of Estradiol Pharmacokinetic Parameters for Each Treatment

| Parameter | Unit | Treatment A[1] (N = 8) | | | Treatment B[2] (N = 7) | | | Treatment C[3] (N = 7) | | |
|---|---|---|---|---|---|---|---|---|---|---|
| | | Mean | SD | CV % | Mean | SD | CV % | Mean | SD | CV % |
| $AUC_{0-10}$[b, c] | h * pg/mL | 234.96 | 95.96 | 40.84 | 242.02 | 64.26 | 26.55 | 267.78 | 75.37 | 28.15 |
| $C_{max\ 0-10}$ | pg/mL | 36.8 | 13.4 | 36.33 | 35.8 | 9.06 | 25.29 | 35.5 | 7.75 | 21.80 |
| $C_{min\ 0-10}$ | pg/mL | 17.7 | 6.43 | 36.35 | 17.4 | 5.67 | 32.63 | 22.1 | 8.07 | 36.43 |
| $C_{avg\ 0-10}$[b, c] | pg/mL | 23.5 | 9.60 | 40.84 | 24.2 | 6.43 | 26.55 | 26.8 | 7.54 | 28.15 |
| $T_{max\ 0-10}$ | h | 2.62 | 2.87 | 109.67 | 1.49 | 0.608 | 40.85 | 2.68 | 3.38 | 126.14 |
| $AUC_{10-16}$[d] | h * pg/mL | 144.76 | 51.60 | 35.65 | — | — | — | 144.30 | 53.70 | 37.21 |
| $C_{max\ 10-16}$ | pg/mL | 28.9 | 10.8 | 37.29 | — | — | — | 31.5 | 8.82 | 28.02 |
| $C_{min\ 10-16}$ | pg/mL | 16.3 | 5.42 | 33.32 | — | — | — | 19.2 | 8.62 | 45.02 |
| $C_{avg\ 10-16}$[d] | pg/mL | 24.1 | 8.60 | 35.65 | — | — | — | 24.0 | 8.95 | 37.21 |
| $T_{max\ 10-16}$ | h | 12.1 | 1.15 | 9.49 | — | — | — | 11.2 | 0.693 | 6.19 |
| $AUC_{10-24}$ | h * pg/mL | — | — | — | 295.12 | 81.19 | 27.51 | — | — | — |
| $C_{max\ 10-24}$ | pg/mL | — | — | — | 30.6 | 8.16 | 26.70 | — | — | — |
| $C_{min\ 10-24}$ | pg/mL | — | — | — | 15.9 | 4.46 | 27.95 | — | — | — |
| $C_{avg\ 10-24}$ | pg/mL | — | — | — | 21.1 | 5.80 | 27.51 | — | — | — |
| $T_{max\ 10-24}$ | h | — | — | — | 12.4 | 1.74 | 14.00 | — | — | — |
| $AUC_{16-24}$[d] | h * pg/mL | 153.02 | 42.87 | 28.02 | — | — | — | 177.97 | 48.79 | 27.41 |
| $C_{max\ 16-24}$ | pg/mL | 27.2 | 10.4 | 38.23 | — | — | — | 26.9 | 7.99 | 29.74 |
| $C_{min\ 16-24}$ | pg/mL | 17.4 | 5.75 | 33.11 | — | — | — | 17.0 | 5.65 | 33.28 |
| $C_{avg\ 16-24}$[d] | pg/mL | 19.1 | 5.36 | 28.02 | — | — | — | 22.2 | 6.10 | 27.41 |
| $T_{max\ 16-24}$ | h | 18.81 | 1.88 | 10.01 | — | — | — | 18.5 | 1.92 | 10.36 |
| $AUC_{0-T}$[b] | h * pg/mL | 530.27 | 196.8 | 37.12 | 537.16 | 137.99 | 25.69 | 601.91 | 188.18 | 1.26 |
| $C_{max}$ | pg/mL | 37.9 | 13.6 | 35.97 | 36.2 | 8.69 | 24.04 | 36.4 | 8.44 | 23.18 |
| $C_{min}$ | pg/mL | 16.1 | 5.36 | 33.31 | 15.7 | 4.40 | 28.03 | 17.0 | 5.65 | 33.28 |
| $C_{avg}$[b] | pg/mL | 22.1 | 8.20 | 37.12 | 22.4 | 5.75 | 25.69 | 25.1 | 7.84 | 31.26 |
| $T_{max}$ | h | 4.13 | 7.13 | 172.74 | 4.51 | 5.25 | 116.25 | 4.88 | 5.27 | 107.94 |

TABLE 11.4.2.3-3-continued

Summary of Estradiol Pharmacokinetic Parameters for Each Treatment

| | | Treatment A[1] (N = 8) | | | Treatment B[2] (N = 7) | | | Treatment C[3] (N = 7) | | |
|---|---|---|---|---|---|---|---|---|---|---|
| Parameter | Unit | Mean | SD | CV % | Mean | SD | CV % | Mean | SD | CV % |
| PTF[b] | — | 0.97 | 0.35 | 36.08 | 0.93 | 0.28 | 30.25 | 0.81 | 0.21 | 25.16 |
| PTS | — | 1.36 | 0.48 | 35.44 | 1.35 | 0.49 | 35.88 | 1.21 | 0.31 | 25.44 |
| % TimeBelow * | % | 0.00 | 0.00 | — | 0.00 | 0.00 | — | 0.00 | 0.00 | — |
| % TimeWithin * | % | 100.00 | 0.00 | 0.00 | 100.00 | 0.00 | 0.00 | 100.00 | 0.00 | 0.00 |
| % TimeAbove * | % | 0.00 | 0.00 | — | 0.00 | 0.00 | — | 0.00 | 0.00 | — |
| $C_{avg}$ Below [b, *] [N (% of Subjects)] | % | 0 (0%) | — | — | 0 (0%) | — | — | 0 (0%) | — | — |
| $C_{avg}$ Within [b, *] [N (% of Subjects)] | % | 7 (100.00%) | — | — | 7 (100.00%) | — | — | 7 (100.00%) | — | — |
| $C_{avg}$ Above [b, *] [N (% of Subjects)] | % | 0 (0%) | — | — | 0 (0%) | — | — | 0 (0%) | — | — |

* Reference Range = 3-81 μg/mL.
[1] TBS-1, 125 μL 4.0% gel given t.i.d. (total dose 30 mg/day)
[2] TBS-1, 150 μL of 4.5% gel given b.i.d. (total dose 27.0 mg/day)
[3] TBS-1, 125 μL of 4.5% gel given t.i.d. (total dose 33.75 mg/day)
[b] or these parameters, N = 7 for Treatment A.
[c] For these parameters, N = 6 for Treatment A.
[d] For these parameters, N = 5 for Treatment C.

The percent times during which observations fall above (% TimeAbove), within (% TimeWithin), and below (% TimeBelow) the reference range are computed for each subject and are presented in Tables 14.2.1.18, 14.2.1.19 and 14.2.1.20 for Treatments A, B and C, respectively. These results are also summarized in text Table 11.4.2.3.3.

The percent of subjects with $C_{avg}$ values for serum Estradiol above, within, and below the reference range is calculated for each treatment and are presented in Table 14.2.1.21. These results are also summarized in text Table 11.4.2.3.3.

11.4.2.4 Pharmacodynamic Analysis

No pharmacodynamic analysis is planned or performed during this study.

11.4.7 Pharmacokinetic and Statistical Conclusions

In this Phase II study, subjects are randomized into three treatment arms (4.0% TBS-1 administered t.i.d. and 4.5% TBS-1 administered bid. and t.i.d.). The treatments are administered for one week by intra-nasal route, in a parallel design. At the end of one week, the three treatments are compared by conducting a 24 hour pharmacokinetic investigation of the systemic absorption of the drug product Testosterone, and its two physiological metabolites Dihydrotestosterone and Estradiol.

Testosterone

The pharmacokinetic profile of TBS-1 following single and repeat dosing is examined in 2 previous studies (TST-PKP-01-MAT/04 and TST-DF-02-MAT/05). It is demonstrated in these studies that Testosterone is well absorbed following intra-nasal administration. The maximal serum concentration is reached after 1-2 hours post administration. In the current study, the Testosterone formulations (4.0% TBS-1 is administered t.i.d. and 4.5% TBS-1 is administered bid. and t.i.d.) are rapidly absorbed with a peak concentration reached within 36 minutes to 1 hour 6 minutes (mean $T_{max}$) following intra-nasal administration. The maximum Testosterone concentration over the 24-hour interval is observed during the first administration (0-10 hours) in approximately 57% to 71% of the hypogonadal men while approximately 29% to 43% of the subjects had their maximum 24-h Testosterone concentration during the subsequent administrations.

When TBS-1 administrations are compared separately for the t.i.d. treatments, although the mean AUC is similar between formulations, a greater AUC is observed following the first administration compared to the two subsequent administrations ($AUC_{0-10}$: 4178.68 and 4355.19 h*ng/dL>$AUC_{10-16}$: 2635.05 and 2301.51 h*ng/dL<$AUC_{16-24}$: 3016.52 and 2766.97 h*ng/dL for Treatments A and C, respectively). A greater AUC is observed for the second administration when compared to the first administration for Treatment B ($AUC_{0-10}$: 4451.64 h*ng/dL~$AUC_{10-24}$: 5264.19 h*ng/dL). The difference in AUC between administrations for both the t.i.d. and b.i.d. formulations could be due to the different time periods elapsed between each administration. The mean $AUC_{0-T}$ calculated over the 24-hour dosing interval, is comparable between all treatments ($AUC_{0-T}$: 9920.07, 9781.39 and 9505.03 h*ng/dL for Treatments A, B and C, respectively).

Although the mean $C_{max}$ is similar between Treatments A and C, a trend toward a decrease in $C_{max}$ with subsequent administrations is observed ($C_{max\ 0-10}$: 786 and 857 ng/dL>$C_{max\ 10-16}$: 698 and 675 ng/dL>$C_{max\ 16-24}$: 556 and 595 ng/dL for Treatments A and C, respectively). Comparable mean Testosterone $C_{max}$ is observed for both administrations of Treatment B ($C_{max\ 0-10}$: 894 ng/dL~$C_{max\ 10-24}$: 846 ng/dL). The difference in $C_{max}$ between administrations for the t.i.d. formulations could be due to the different time periods that are elapsed between each administration. The mean $C_{max}$ calculated over the 24-hour dosing interval, is slightly greater for Treatment B (150 μL of 4.5% gel (b.i.d.)) ($C_{max}$: 1050 ng/dL) comparatively to Treatments A and C ($C_{max}$: 830 and 883 ng/dL, respectively). The upper limit of the physiological reference range (1050 ng/dL) is exceeded by 1 of 8 subjects for Treatment A and 3 of 7 subjects for Treatments B and C.

A trend toward a slight decrease in $C_{avg}$ is observed when administrations are compared separately for t.i.d. and b.i.d. treatments ($C_{avg\ 0-10}$: 418 and 436 ng/dL>$C_{avg\ 10-16}$: 439 and 384 ng/dL>$C_{avg\ 16-24}$: 377 and 346 ng/dL for Treatments A and C, respectively and $C_{avg\ 0-10}$: 445 ng/dL>$C_{avg\ 10-24}$: 376 ng/dL for Treatment B). The difference in $C_{avg}$ between administrations could be due to the different time periods that are elapsed between each administration. The mean $C_{avg}$ calculated over the 24-hour dosing interval, is comparable for all treatments ($C_{avg}$: 413, 408, 396 ng/dL for Treatments A, B and C, respectively).

These results suggest a decrease in exposure (AUC, $C_{avg}$ and $C_{max}$) between each dose for the t.i.d. administrations (Treatments A and C), but not for the b.i.d. administration (Treatment B). This decrease in exposure for the t.i.d. administrations could be partly explained by the negative feedback on endogenous Testosterone production from the HPG axis. In other words, due to the smaller time intervals between each administration for the t.i.d. groups, the recovery of the HPG system from negative feedback would be less that for the b.i.d. group.

Independently of the formulation, approximately 86%-88% of the subjects had an average drug concentration ($C_{avg}$) within the physiological reference range (300 to 1050 ng/dL), 13%-14% of the subjects had a $C_{avg}$ below the reference range and no subjects had a $C_{avg}$ above the reference range.

The period of time during a day (24 hours) for which serum Testosterone concentrations are below, within and above the physiological reference range is covered respectively 30 to 35%, 59% to 68% and 0% of the 24-hour period for all formulations. That is to say that the testosterone levels are within normal range for about 14 to 16 hours a day.

Dihydrotestosterone

The Dihydrotestosterone peak concentration is reached within 1 hour 24 minutes and 2 hours 23 minutes (mean $T_{max}$) following the TBS-1 administrations. When TBS-1 administrations are compared separately for the t.i.d. treatments, although the mean AUC is similar between formulations, a trend toward a decrease in AUC with subsequent administrations is observed ($AUC_{0-10}$: 345.77 and 411.10 h*ng/dL>$AUC_{10-16}$: 186.33 and 222.62 h*ng/dL> $AUC_{16-24}$: 269.16 and 275.21 h*ng/dL for Treatments A and C, respectively). Comparable AUC is observed for both administrations of Treatment B ($AUC_{0-10}$: 402.77 h*ng/dL~$AUC_{10-24}$: 543.29 h*ng/dL). The difference in AUC between administrations for the t.i.d. formulations could be due to the different time periods elapsed between each administration. The mean $AUC_{0-T}$ calculated over the 24-hour dosing interval, is comparable between all treatments ($AUC_{0-T}$: 818.95, 946.89 and 909.68 h*ng/dL for Treatments A, B and C, respectively).

Although the mean $C_{max}$ is similar between the t.i.d. formulations, a trend toward a decrease in $C_{max}$ with subsequent administrations is observed ($C_{max\ 0-10}$: 51.4 and 59.0 ng/dL>$C_{max\ 10-16}$: 44.2 and 48.9 ng/dL>$C_{max\ 16-24}$: 41.3 and 42.6 ng/dL for Treatments A and C, respectively). Comparable mean Testosterone $C_{max}$ is observed for both administrations of Treatment B ($C_{max\ 0-10}$: 56.8 ng/dL~$C_{max\ 10-24}$: 54.6 ng/dL). The difference in $C_{max}$ between administrations for the t.i.d. formulations could be due to the different time periods elapsed between each administration. The mean $C_{max}$ is calculated over the 24-hour dosing interval, is comparable for all treatments ($C_{max}$: 52.2, 61.0 and 60.3 ng/dL for Treatments A, B and C, respectively). The upper limit of the physiological reference range (97.8 ng/dL) is not exceeded by any subjects for any treatment.

The $C_{avg}$ calculated by administration are comparable between treatments and administrations ($C_{avg\ 0-10}$: 34.6 and 41.1 ng/dL>$C_{avg\ 10-16}$: 31.1 and 37.1 ng/dL>$C_{avg\ 16-24}$: 33.6 and 34.4 ng/dL for Treatments A and C, respectively and $C_{avg\ 0-10}$: 40.3 ng/dL>$C_{avg\ 10-24}$: 38.8 ng/dL for Treatment B). The mean $C_{avg}$ calculated over the 24-hour dosing interval, is comparable for all treatments ($C_{avg}$: 34.1, 39.5, 37.9 ng/dL for Treatments A, B and C, respectively).

Approximately 63% of subjects had their $C_{avg}$ included in the physiological reference range for DHT (25.5 to 97.8 ng/dL) following administration of Treatment A, whereas this number rises to about 86% when Treatments B and C are administered. No subject had their $C_{avg}$ above the normal range while 38% and 14% of the subjects have their $C_{avg}$ below the normal range for Treatment A and both Treatments B and C, respectively.

The period of time during a day (24 hours) for which serum DHT concentrations are below, within and above the physiological reference range is covered respectively 32.64%, 67.36% and 0% for Treatment A, 26.22%, 73.78% and 0% for Treatment B and 13.87%, 86.13% and 0% for Treatment C. That is to say that the DHT levels are within normal range for about 16, 18 and 21 hours a day for Treatments A, B and C, respectively.

Estradiol

The Estradiol peak concentration is reached within 1 hour 12 minutes and 2 hours 41 minutes (mean $T_{max}$) following the TBS-1 administrations.

When TBS-1 administrations are compared separately for the t.i.d. treatments, although the mean AUC is similar between formulations, a trend toward a decrease in AUC with subsequent administrations is observed ($AUC_{0-10}$: 234.96 and 267.78 h*pg/mL>$AUC_{10-16}$: 144.76 and 144.30 h*pg/mL<$AUC_{16-24}$: 153.02 and 177.97 h*pg/mL for Treatments A and C, respectively). Comparable AUC is observed for both administrations of Treatment B ($AUC_{0-10}$: 242.02 h*pg/mL~$AUC_{10-24}$: 295.12 h*pg/mL). The difference in AUC between administrations for the t.i.d. formulations could be due to the different time periods elapsed between each administration. The mean $AUC_{0-T}$ calculated over the 24-hour dosing interval, is comparable between all treatments ($AUC_{0-T}$: 530.27, 537.16 and 601.91 h*pg/mL for Treatments A, B and C, respectively).

Although the mean $C_{max}$ is similar between the t.i.d. formulations, a trend toward a decrease in $C_{max}$ with subsequent administrations is observed ($C_{max\ 0-10}$: 36.8 and 35.5 pg/mL>$C_{max\ 10-16}$: 28.9 and 31.5 pg/mL>$C_{max\ 16-24}$: 27.2 and 26.9 pg/mL for Treatments A and C, respectively). Comparable mean Testosterone $C_{max}$ is observed for both administrations of Treatment B ($C_{max\ 0-10}$: 35.8 pg/mL~ $C_{max\ 10-24}$: 30.6 pg/mL). The difference in $C_{max}$ between administrations for the t.i.d. formulations could be due to the different time periods elapsed between each administration. The mean $C_{max}$ calculated over the 24-hour dosing interval, is comparable for all treatments ($C_{max}$: 37.9, 36.2 and 36.4 pg/mL for Treatments A, B and C, respectively). The upper limit of the physiological reference range (81 pg/mL) is not exceeded by any subjects for any treatment.

e $C_{avg}$ calculated by administration are comparable between treatments and administrations ($C_{avg\ 0-10}$: 23.5 and 26.8 pg/mL>$C_{avg\ 10-16}$: 24.1 and 24.0 pg/mL>$C_{avg\ 16-24}$: 19.1 and 22.2 pg/mL for Treatments A and C, respectively and $C_{avg\ 0-10}$: 24.2 pg/mL>$C_{avg\ 10-24}$: 21.1 pg/mL for Treatment B). The mean $C_{avg}$ is calculated over the 24-hour dosing interval, is comparable for all treatments ($C_{avg}$: 22.1, 22.4, 25.1 pg/mL for Treatments A, B and C, respectively).

All subjects have their $C_{avg}$ included in the physiological reference range for $E_2$ (3 to 81 pg/mL) following administration of all treatments. All subjects have $E_2$ concentrations within the normal range over the 24 hours period. No subjects have $E_2$ levels below or above the normal range at any time of the day.

12. Safety Evaluation 12.1 Extent of Exposure

Subjects use the drug for 7 days at two sites and 8 days in another.

12.2 Adverse Events 12.2.1 Brief Summary of Adverse Events

There are eight adverse events that occurred in six subjects. Six of the events occur during treatment A and two occur during treatment B. Subjects 01-002 and 01-007 both experience dizziness and both are indicated as possibly related to the study drug. Subject 01-002 has moderate severity which resolved after 5 days. Seven of the 8 adverse events are mild. Six of the 8 events are not related to study drug. Individual 02-004 is classified as having anemia by the investigator. The hemoglobin is at the minimal normal level and is deemed unrelated to the drug. Table 12.2.2 summarizes the events.

12.2.2 Display of Adverse Events

TABLE 12.2.2

Adverse Events

| Treatment | Subject | Age | Preferred Term | Severity | Relation to Drug | Start Date | End Date | Duration (days) |
|---|---|---|---|---|---|---|---|---|
| A | 01-002 | 40 | Dizziness | MODERATE | POSSIBLY RELATED | 2010 Oct. 25 | 2010 Oct. 30 | 5 |
| A | 01-007 | 49 | Dizziness | MILD | POSSIBLY RELATED | 2010 Oct. 23 | 2010 Oct. 28 | 5 |
| A | 02-004 | 53 | Anemia | MILD | NOT RELATED | 2010 Oct. 4 | | |
| A | 03-006 | 73 | Pain of skin | MILD | NOT RELATED | 2010 Sep. 27 | 2010 Nov. 4 | 37 |
| A | 03-006 | 73 | Excoriation | MILD | NOT RELATED | 2010 Sep. 2 | 2010 Nov. 4 | 62 |
| A | 03-006 | 73 | Excoriation | MILD | NOT RELATED | 2010 Sep. 27 | 2010 Nov. 4 | 37 |
| B | 03-001 | 59 | Respiratory tract congestion | MILD | NOT RELATED | 2010 Sep. 5 | 2010 Sep. 13 | 8 |
| B | 03-005 | 62 | Gastrooesophageal reflux disease | MILD | NOT RELATED | 2010 Sep. 14 | 2010 Sep. 27 | 13 |

2.2.4 Listing of Adverse Events by Subjects

Table 12.2.2 list of adverse events by subject.

12.3 Deaths, Other Serious Adverse Events, and Other Significant Adverse Events

There are no deaths, other serious adverse events or other significant adverse events during the course of this study.

12.4.2 Evaluation of Each Laboratory Parameter

There are no clinically significant changes in laboratory values from the beginning to the end of the study as determined by the principle investigators. All subjects did have some abnormal values at the initial visit and/or at the third visit. There are no consistent changes throughout the visits.

Subject 01-007 had a uric acid level of 539 U/L with 289 as the upper end of normal at the third visit. There are elevated glucose values in about half the subjects compared to a normal first visit value. This is spread across all three dosages and are only slightly elevated. There is no clinical significance.

12.5 Vital Signs, Physical Findings, and Other Observations Related to Safety

There are no meaningful or significant changes in vital signs after test drug administration.

12.6 Safety Conclusions

The TBS-1 gel demonstrates in this and other studies that it is safe for use. There are no serious adverse events or any events of consequence during this PK study or during the seven days of self administration. Tables 14.3.2.1 through 14.3.2.8 show all the laboratory values for visit 1 and visit 3.

13. Discussion and Overall Conclusions

The primary objective of this study is to determine the bioavailability of a 4.0% TBS-1 gel (applied t.i.d.) and 4.5% TBS-1 gel (applied b.i.d. and t.i.d.) in hypogonadal men.

In a previous study, Nasobol-01-2009, a 3.2% Testosterone gel is used to deliver 4.0 mg, 5.5 mg and 7.0 mg of Testosterone intra-nasally using gel volumes of 125 µL, 172 µL and 219 µL, respectively. In this study, 5.0 mg, 5.65 mg and 6.75 mg of Testosterone are administered in gel volumes of 125 µL, 125 µL, and 150 µL, respectively. This study allowed investigating the delivery of similar Testosterone amounts in much smaller volumes.

The secondary objective of this study is to establish a safety profile for TBS-1. In this Phase II study, subjects are randomized into three treatment arms (4.0% TBS-1 administered t.i.d. and 4.5% TBS-1 administered bid. and t.i.d.). The treatments are administered for one week by intra-nasal route, in a parallel design. At the end of one week, the three treatments are compared by conducting a 24 hour pharmacokinetic investigation of the systemic absorption of the drug product Testosterone, and its two physiological metabolites Dihydrotestosterone and Estradiol.

There are eight adverse events described by six subjects. Six of the events occurred during treatment A and two occurred during treatment B. Subjects 01-002 and 01-007 both experienced dizziness and both are indicated as possibly related to the study drug. The remainder are unrelated to study drug.

There are no vital signs or laboratory changes that are significant or meaningful. No erythrocytosis, anemia or infections are observed after measurement of complete blood counts at screening and close-out. Clinical chemistry and urinalysis showed no changes at close-out in hypo or hyperglycemia, renal function, liver function, skeletal/heart muscle damage or changes in calcium homeostasis. There are no clinically significant changes to the nasal mucosa.

The PK population is defined as subjects who received the Treatment A, B or C, and who completed the study without major protocol violation or for whom the PK profile can be adequately characterized. The PK population is used for the analysis of PK data. Based on these criteria, twenty-two (22) subjects are included in the PK population.

Testosterone

The pharmacokinetic profile of TBS-1 following single and repeat dosing is examined in 2 previous studies (TST-PKP-01-MAT/04 and TST-DF-02-MAT/05). It is demonstrated in these studies that Testosterone is well absorbed following intra-nasal administration. The maximal serum concentration is reached after 1-2 hours post administration. In the current study, the Testosterone formulations (4.0% TBS-1 administered t.i.d. and 4.5% TBS-1 administered bid. and t.i.d.) are rapidly absorbed with a peak concentration reached within 36 minutes to 1 hour 6 minutes (mean $T_{max}$) following intra-nasal administration. The maximum Testosterone concentration over the 24-hour interval is observed during the first administration (0-10 hours) in approximately 57% to 71% of the hypogonadal men while approximately 29% to 43% of the subjects had their maximum 24-h Testosterone concentration during the subsequent administrations.

When TBS-1 administrations are compared separately for the t.i.d. treatments, although the mean AUC is similar between formulations, a greater AUC is observed following the first administration compared to the two subsequent administrations ($AUC_{0-10}$: 4178.68 and 4355.19 h*ng/dL>$AUC_{10-16}$: 2635.05 and 2301.51 h*ng/dL<$AUC_{16-24}$: 3016.52 and 2766.97 h*ng/dL for Treatments A and C, respectively). A greater AUC is observed for the second administration when compared to the first administration for Treatment B ($AUC_{0-10}$: 4451.64 h*ng/dL~$AUC_{10-24}$: 5264.19 h*ng/dL). The difference in AUC between administrations for both the t.i.d. and b.i.d. formulations could be due to the different time periods elapsed between each administration. The mean $AUC_{0-t}$ calculated over the 24-hour dosing interval, is comparable between all treatments ($AUC_{0-t}$: 9920.07, 9781.39 and 9505.03 h*ng/dL for Treatments A, B and C, respectively).

When TBS-1 administrations are compared separately for the t.i.d. treatments, although the mean $C_{max}$ is similar between formulations, a trend toward a decrease in $C_{max}$ with subsequent administrations is observed ($C_{max\ 0-10}$: 786 and 857 ng/dL>$C_{max\ 10-16}$: 698 and 675 ng/dL>$C_{max\ 16-24}$: 556 and 595 ng/dL for Treatments A and C, respectively). Comparable mean Testosterone $C_{max}$ is observed for both administrations of Treatment B ($C_{max\ 0-10}$: 894 ng/dL~$C_{max\ 10-24}$: 846 ng/dL). The difference in $C_{max}$ between administrations for the t.i.d. formulations could be due to the different time periods elapsed between each administration. The mean $C_{max}$ calculated over the 24-hour dosing interval, is slightly greater for Treatment B (150 µL of 4.5% gel (b.i.d.)) ($C_{max}$: 1050 ng/dL) comparatively to Treatments A and C ($C_{max}$: 830 and 883 ng/dL, respectively). The upper limit of the physiological reference range (1050 ng/dL) is exceeded by 1 of 8 subjects for Treatment A and 3 of 7 subjects for Treatments B and C.

A trend toward a slight decrease in $C_{avg}$ is observed when administrations are compared separately for t.i.d. and b.i.d. treatments ($C_{avg\ 0-10}$: 418 and 436 ng/dL>$C_{avg\ 10-16}$: 439 and 384 ng/dL>$C_{avg\ 16-24}$: 377 and 346 ng/dL for Treatments A and C, respectively and $C_{avg\ 0-10}$: 445 ng/dL>$C_{avg\ 10-24}$: 376 ng/dL for Treatment B). The difference in $C_{avg}$ between administrations could be due to the different time periods elapsed between each administration. The mean $C_{avg}$ calculated over the 24-hour dosing interval, is comparable for all treatments ($C_{avg}$: 413, 408, 396 ng/dL for Treatments A, B and C, respectively).

These results suggest a decrease in exposure (AUC, $C_{avg}$ and $C_{max}$) between each dose for the t.i.d. administrations (Treatments A and C), but not for the b.i.d. administration (Treatment B). This decrease in exposure for the t.i.d. administrations could be partly explained by the negative feedback on endogenous Testosterone production from the HPG axis. In other words, due to the smaller time intervals between each administration for the t.i.d. groups, the recovery of the HPG system from negative feedback would be less that for the b.i.d. group.

Independently of the formulation, approximately 86%-88% of the subjects had an average drug concentration ($C_{avg}$) within the physiological reference range (300 to 1050 ng/dL), 13%-14% of the subjects had a $C_{avg}$ below the reference range and no subjects had a $C_{avg}$ above the reference range.

The period of time during a day (24 hours) for which serum Testosterone concentrations are below, within and above the physiological reference range covered respectively 30 to 35%, 59% to 68% and 0% of the 24-hour period for all formulations. That is to say that the Testosterone levels are within normal range for about 14 to 16 hours a day.

Dihydrotestosterone

The Dihydrotestosterone peak concentration is reached within 1 hour 24 minutes and 2 hours 23 minutes (mean $T_{max}$) following the TBS-1 administrations. When TBS-1 administrations are compared separately for the t.i.d. treatments, although the mean AUC is similar between formulations, a trend toward a decrease in AUC with subsequent administrations is observed ($AUC_{0-10}$: 345.77 and 411.10 h*ng/dL>$AUC_{10-16}$: 186.33 and 222.62 h*ng/dL>$AUC_{16-24}$: 269.16 and 275.21 h*ng/dL for Treatments A and C, respectively). Comparable AUC is observed for both administrations of Treatment B ($AUC_{0-10}$: 402.77 h*ng/dL~$AUC_{10-24}$: 543.29 h*ng/dL). The difference in AUC between administrations for the t.i.d. formulations could be due to the different time periods elapsed between each administration. The mean $AUC_{0-t}$ calculated over the 24-hour dosing interval, is comparable between all treatments ($AUC_{0-t}$: 818.95, 946.89 and 909.68 h*ng/dL for Treatments A, B and C, respectively).

Although the mean $C_{max}$ is similar between the t.i.d. formulations, a trend toward a decrease in $C_{max}$ with subsequent administrations is observed ($C_{max\ 0-10}$: 51.4 and 59.0 ng/dL>$C_{max\ 10-16}$: 44.2 and 48.9 ng/dL>$C_{max\ 16-24}$: 41.3 and 42.6 ng/dL for Treatments A and C, respectively). Comparable mean Testosterone $C_{max}$ is observed for both administrations of Treatment B ($C_{max\ 0-10}$: 56.8 ng/dL~$C_{max\ 10-24}$: 54.6 ng/dL). The difference in $C_{max}$ between administrations for the t.i.d. formulations could be due to the different time periods elapsed between each administration. The mean $C_{max}$ calculated over the 24-hour dosing interval, is comparable for all treatments ($C_{max}$: 52.2, 61.0 and 60.3 ng/dL for Treatments A, B and C, respectively). The upper limit of the physiological reference range (97.8 ng/dL) is not exceeded by any subjects for any treatment.

The $C_{avg}$ calculated by administration are comparable between treatments and administrations ($C_{avg\ 0-10}$: 34.6 and 41.1 ng/dL>$C_{avg\ 10\text{-}16}$: 31.1 and 37.1 ng/dL>$C_{avg\ 16\text{-}24}$: 33.6 and 34.4 ng/dL for Treatments A and C, respectively and $C_{avg\ 0\text{-}10}$: 40.3 ng/dL>$C_{avg\ 10\text{-}24}$: 38.8 ng/dL for Treatment B). The mean $C_{avg}$ calculated over the 24-hour dosing interval, is comparable for all treatments ($C_{avg}$: 34.1, 39.5, 37.9 ng/dL for Treatments A, B and C, respectively).

Approximately 63% of subjects had their $C_{avg}$ included in the physiological reference range for DHT (25.5 to 97.8 ng/dL) following administration of Treatment A, whereas this number rises to about 86% when Treatments B and C are administered. No subject had their $C_{avg}$ above the normal range while 38% and 14% of the subjects had their $C_{avg}$ below the normal range for Treatment A and both Treatments B and C, respectively.

The period of time during a day (24 hours) for which serum DHT concentrations are below, within and above the physiological reference range covered respectively 32.64%, 67.36% and 0% for Treatment A, 26.22%, 73.78% and 0% for Treatment B and 13.87%, 86.13% and 0% for Treatment C. That is to say that the DHT levels are within normal range for about 16, 18 and 21 hours a day for Treatments A, B and C, respectively.

Estradiol

The Estradiol peak concentration is reached within 1 hour 12 minutes and 2 hours 41 minutes (mean $T_{max}$) following the TBS-1 administrations.

When TBS-1 administrations are compared separately for the t.i.d. treatments, although the mean AUC is similar between formulations, a trend toward a decrease in AUC with subsequent administrations is observed ($AUC_{0\text{-}10}$: 234.96 and 267.78 h*pg/mL>$AUC_{10\text{-}16}$: 144.76 and 144.30 h*pg/mL<$AUC_{16\text{-}24}$: 153.02 and 177.97 h*pg/mL for Treatments A and C, respectively). Comparable AUC is observed for both administrations of Treatment B ($AUC_{0\text{-}10}$: 242.02 h*pg/mL~$AUC_{10\text{-}24}$: 295.12 h*pg/mL). The difference in AUC between administrations for the t.i.d. formulations could be due to the different time periods elapsed between each administration. The mean $AUC_{0\text{-}t}$ calculated over the 24-hour dosing interval, is comparable between all treatments ($AUC_{0\text{-}t}$: 530.27, 537.16 and 601.91 h*pg/mL for Treatments A, B and C, respectively).

Although the mean $C_{max}$ is similar between the t.i.d. formulations, a trend toward a decrease in $C_{max}$ with subsequent administrations is observed ($C_{max\ 0\text{-}10}$: 36.8 and 35.5 pg/mL>$C_{max\ 10\text{-}16}$: 28.9 and 31.5 pg/mL>$C_{max\ 16\text{-}24}$: 27.2 and 26.9 pg/mL for Treatments A and C, respectively). Comparable mean Testosterone $C_{max}$ is observed for both administrations of Treatment B ($C_{max\ 0\text{-}10}$: 35.8 pg/mL~$C_{max\ 10\text{-}24}$: 30.6 pg/mL). The difference in $C_{max}$ between administrations for the t.i.d. formulations could be due to the different time periods elapsed between each administration. The mean $C_{max}$ calculated over the 24-hour dosing interval, is comparable for all treatments ($C_{max}$: 37.9, 36.2 and 36.4 pg/mL for Treatments A, B and C, respectively). The upper limit of the physiological reference range (81 pg/mL) is not exceeded by any subjects for any treatment.

The $C_{avg}$ calculated by administration are comparable between treatments and administrations ($C_{avg\ 0\text{-}10}$: 23.5 and 26.8 pg/mL>$C_{avg\ 10\text{-}16}$: 24.1 and 24.0 pg/mL>$C_{avg\ 16\text{-}24}$: 19.1 and 22.2 pg/mL for Treatments A and C, respectively and $C_{avg\ 0\text{-}10}$: 24.2 pg/mL>$C_{avg\ 10\text{-}24}$: 21.1 pg/mL for Treatment B). The mean $C_{avg}$ calculated over the 24-hour dosing interval, is comparable for all treatments ($C_{avg}$: 22.1, 22.4, 25.1 pg/mL for Treatments A, B and C, respectively).

All subjects had their $C_{avg}$ included in the physiological reference range for $E_2$ (3 to 81 pg/mL) following administration of all treatments. All subjects had $E_2$ concentrations within the normal range over the 24 hours period. No subjects had $E_2$ levels below or above the normal range at any time of the day.

Conclusions

The TBS-1 formulations (4.0% TBS-1 gel (applied t.i.d.) and 4.5% TBS-1 gel (applied b.i.d. and t.i.d.)) are rapidly absorbed with mean Testosterone peak observed within 1 hour.

Overall, the Testosterone exposure ($AUC_{0\text{-}t}$ and $C_{max}$) at steady-state is comparable between all treatments. Independently of the formulation, approximately 86%-88% of the subjects had an average Testosterone drug concentration ($C_{avg}$) within the physiological reference range (300 to 1050 ng/dL).

The Testosterone levels are within normal range for about 14 to 16 hours a day.

TBS-1 is safe for intranasal administration at the dosages and frequency indicated. There are no meaningful adverse events, changes in vital signs or changes in laboratory results when compared to baseline.

Based on these results, no clear evidence is found to indicate a better performance from one of the formulations.

Example 9

TBS1A Report for 4% and 8% Bulk Gel

Objective:
To follow up on IMP-Clinical batch manufacture. Main points concern process flow and bulk appearance on stability.
  Process flow improvement
  Viscosity of bulk Gel
  Stability (re-crystallization)
  Evaluation of alternate materials sources and grades
  In Vivo results, formulation changes to impact onset of release
  Testing of trials using Franz Cell, trial selection
  List of Raw-materials identified for use in trials:

| Material name | Grade | Spec # | Source | Comments |
|---|---|---|---|---|
| Castor Oil | (Crystal O) | RM004A | Cas-Chem | |
| Castor Oil | (Virgin) | RM004B | — | |
| Labrafil | M1944CS | RM002A | Gattfosse | |
| DMI | — | RM009A | Croda | |
| Transcutol P | — | RM008A | Gattfosse | |
| Plasdone | K17 | RM011A | ISP | |
| Plasdone | S630 | RM013A | ISP | |
| Plasdone | K29-32 | Sample | ISP | |
| Plasdone | K90 | Sample | ISP | |
| HPC | Klucel HF | RM014A | Hercules | |
| HPC | Nisso H | Sample | Nisso | |
| HPC | Nisso M | Sample | Nisso | |
| HPC | Nisso L | Sample | Nisso | |
| Cab-O-Sil | M-5P | RM003A | Cabot | |
| Aerosil | 200 | RM003B | Evonik | |
| Purified water | — | — | Trimel | |
| Testosterone | micronized | RM001A | Proquina | |
| Oleic Acid | Super-refined | sample | Croda | |
| Testosterone | Not micronized | RM | Proquina | |

Equipment Used:
In addition to the Silverson High Shear mixer, used only during the manufacture of the TBS1A IMP Clinical batches, included also a propeller type mixing unit for the trials on several pre-mix operations. The only application for the High shear action is for dispersion of the active in the Co-Solvents.

For more uniform mixing and control of temperature, recommend a jacketed container with wiping blades to remove material from inner bowl wall (especially critical for uniform bulk temperature during heating as well as cooling cycles.

Background Info on IMP Bath Manufacture

Observation during the IMP Clinical batch manufacture included high viscosity during preparing the pre-mixture of the DMI/Transcutol co-solvent mix consisting of PVP K17/5640, Klucel HF and Testosterone micronized. Mixture resulting in a sticky mass when added to the Castor oil using the high shear mixer set up. With the same high shear mixer set up for the addition of the Cab-O-Sil (referenced in future to SiO2) could not obtain a vortex to incorporate the material and required additional manual mixing during addition stage, hence the recommendation for propeller type mixing unit). Even though the material was viscous during that addition stage, on further mixing the viscosity of the final Bulk Gel dropped to approximately 1,500-2,000 cps. Mixing time and speed had to be controlled not to overshoot targeted gel temperature (no cooling system).

Outline of Trials:

The initial trials (Placebo) concentrated on changing the order of addition to identify impact on viscosity. Previous process included the addition of the SiO2 at the final stage (see comments above), changed to dispersion of the SiO2 into the Castor oil prior to addition of the alternate active mixture. The resulting viscosity of the Castor Oil/SiO2 mixture, used various percentages, increased with the addition of a small percentage of Arlasolve (DMI).

Next step was to duplicate these results using the active mixture (Co-solvents/PVP/HPC/active) and added that mixture to the premix of Castor oil and SiO2. This however resulted in a low viscosity solution, indicating an impact of the active mixture on formation of a viscous gel.

Since the co-solvent mix without additional materials resulted in an increase of viscosity, the quantities of solvent were split into 2 parts, adding part of the solvent mix only to the Oil mixture and remaining solvent mix used to disperse the PVP, HPC and active. The active mixture with the reduced co-solvent ended up more viscose, plus similar low viscosity when added to the castor Oil premix. Additional trials included the prep of active in only DMI (no PVP) and obtained good viscosity. HPC was prepared separately in the Transcutol P, creating problems of stringing when added to the mixture (similar to IMP observations). Addition of SiO2 at a level of 0.1-0.3% resolved the problem.

The above process to dissolve active in the Co-solvents is sufficient and doesn't require PVP to increase solubility for the 4% formulation, however not sufficient co-solvents in the formulation to achieve solubility for the 8% strength. Trials on the 8% included an alternate successful approach for preparing the active dispersion containing PVP by including SiO2 into that mixture. As demonstrated on evaluation trials evaluating impact of SiO2 added to the DMI as well as Transcutol P, resulted in good viscosity forming with DMI, however not with Transcutol. Active dispersion therefore id prepared by dissolving the PVP in DMI only, followed by addition of the active at 55 C (50-60 C) and portion of available SiO2.

Please note that this process was only developed during the trial work on the 8%, hence it can be scaled down to the 4% strength if PVP indicate additional functionality (Franz Cell test).

Comments related to addition of purified water (noted in Table xxx) indicate increase in viscosity with trials containing HPC, no viscosity increase in trials using only PVP. These trials were only included for information to study water uptake and impact on viscosity after application into the nasal cavity.

Critical step during HPC set up is to provide at least 24 hours of solvating to obtain a clear solution.

As outlined in the trial objectives, formulation ratios were implemented using also alternate grades and sources of materials and are identified in the formulation table. To identify the impact of the process change (such as reaction of viscosity increase adding the co-solvents), performed trials to study impact if related to DMI or Transcutol P. Trials were initiated to disperse SiO2 (at the same ratio as used for Castor Oil mixture) in DMI only as well as in Transcutol P only. The Mixture with the DMI resulted in a viscous mixture while Transcutol P mixture was very fluid.

Similar trials were initiated to use the co-solvents individually to study solubility of the Polymers as well as active for potential reduction in Transcutol P. No noticeable difference in solubility using the mixture or individual solvents at the 4% strength. However, if PVP and HPC are prepared only in DMI, observed separation of the two materials when stored overnight (not apparent when mixed in the co-solvent mixture). To eliminate the stickiness of the dispersion when adding the active/polymer mixture, removed the HPC from the formulation and using PVP only (individual grades K17-K29/32-K90, no mixtures). This resulted in various degrees of viscosity related to the grade used.

Material also included the use of Labrafil M 1944 CS and are outlined in batch description and selected for testing in Franz Cell.

Comments:

The various trials are outlined below for 4% strength as well as 8%.

Trial lots of both strength have been selected for testing on the Franz Cell. Selected lots are identified.

All trials will be monitored for physical evidence of re-crystallization and change in appearance (separation), tested for change in viscosity. Viscosity values of the trials will be documented and updated Pending Franz Cell result evaluation, optimization of formulation and process can be implemented. This is critical to identify since the trial outline did not include impact on viscosity related to all process parameters (need to include analytical testing and stability data).

Observations during viscosity test using the Brookfield Viscometer Model DV-II+, with Spindle #6, at 50 rpm for 30 seconds, did actually show an increase in viscosity values over the test time in samples prepared with higher viscosity grade HPC. This can be attributed to the stickiness of the Gel causing agglomeration to the spindle shaft and disk creating a drag (not a true viscosity value of the results reported). The bulk Gel of several trials is not thixotropic. Also tested on some trials viscosity at 37 C.

Tested several trials using the new Haupt method with spindle 4 at 6 rpm.

The various attached tables show the trial numbers for active Gels, pre-mixes and Placebos Discussion and Considerations for Follow Up Trials with Both Strength Even though 'viscosity improvement' was not the primary target to initiate trials, it was certainly a designed effort to study the cause for low viscosity considering the high percentage of SiO2 present in the formulation. A cross check against SiO2 alternate source comparison did not indicate major differences, nor did various ratios of Co-Solvents, limited adjustment since a certain percentage required to dissolve the Testosterone. Changes in grades of PVP indicated impact on viscosity when used in the active dispersion, however not when added to the rest of the mixture. Changes in grades of HPC (used alternate source of fine material) showed impact on the final Gel, however the higher the Molecular weight of the HPC, impact of stickiness and stringing in the final Gel. Testing viscosity after several weeks did show a separation in the Gel of viscose settlement on the bottom of the container.

With indication of SiO2 retaining Testosterone, adding more to increase viscosity was not an option, aim was to reduce the % used. especially for the TBS1A 4% strength which indicated a much higher percentage of T retained compared to the 8% TBS1A. Target was to at least obtain the same ratio of SiO2 to T of the 8% strength for the 4% strength (hence aimed for scale down to 3%). With the trials completed and showing impact on viscosity related to process and formulation changes, a reduction in SiO2 for the definitely possible for the 4% strength that would also include the use of PVP in the formulation by taking advantage of the process change on the 8% strength. The above is only based on viscosity; however impact on the changes in formulation to slow down initial absorption rate in vivo can only be evaluated from the data obtained on the trials used for the analytical test using the Franz Cell. These results will be reviewed and evaluated with potential recommendations for further trials to either duplicate earlier trials or based on DOE.

The attached Tables for viscosity show the date of manufacture and latest test results (to help with trial selection on Franz Cell). In the Comment column original data will be reference or referenced in the Trial process description. Further alternate material source evaluation is recommended once a primary formulation and process for each strength has been established for direct comparison.

Formulation/Composition of TBS1A—4%

TABLE 1A (See the formulations in the Examples above and including Example 10)

| Trial number | Active % | Castor oil % | Labrafil % | PVP grade % | DMI % | TranscutolP % | HPC Nisso % | SiO2 % C = Cabosil A = Aerosil200 |
|---|---|---|---|---|---|---|---|---|
| RD11037 | 4 | 52 | 000000 | K17 = 3<br>S630 = 2 | 25 | 10 | 0000000 | C = 4 |
| RD11038 | 4 | 57 | 000000 | K17 = 3<br>S630 = 2 | 20 | 10 | 0000000 | C = 4 |
| RD11039 | 4 | 29 | 29 | K17 = 3<br>S630 = 2 | 20 | 10 | 0000000 | C = 3 |
| RD11040 | 4 | 57 | 0000000 | 0000000 | 25 | 10<br>6 + 4 | 00000000 | C = 4 |
| RD11041 | 4 | 53 | 0000000 | K17 = 3<br>S630 = 2 | 25 | 10<br>6 + 4 | 0000000 | C = 3 |
| RD11042 | 4 | 29 | 29 | 00000000 | 25 | 10<br>6 + 4 (split) | 000000 | C = 3 |
| RD11050 | 4 | 66.7 | 000000 | K17 = 3 | 24<br>20 + 4 | 0000000 | N − H = 0.3 | A = 2 |
| RD11050A | 4 | 66.7 | 000000 | K17 = 3 | 24<br>20 + 4 | 0000000 | N − H = 0.3 | 1% additional to final 11050 |
| RD11051 | 4 | 66.7 | 000000 | K30 = 3 | 24<br>20 + 4 | 0000000 | N − M = 0.3 | A = 2 |
| RD11051A | 4 | 66.7 | 000000 | K30 = 3 | 24<br>20 + 4 | 0000000 | N − M = 0.3 | 1% additional to final 11051 |
| RD11053 | 4 | 61.7 | 000000 | K17 = 3 | 22<br>16 + 6 | 6<br>4 + 2 | N − H = 0.3 | A = 3 |
| RD11054 | 4 | 61.4 | 000000 | K30 = 3 | 23<br>16 + 7 | 5<br>4 + 1 | N − M = 0.6 | A = 3 |
| RD11055 | 4 | 62.0 | 000000 | K90 = 3 | 23<br>16 + 7 | 5<br>4 + 1 | 0000000 | C = 3 |
| RD11056 | 4 | 62.0 | 000000 | K90 = 3 | 28<br>20 + 8 | 00000 | 0000000 | C = 3 |
| RD11059 | 4 | 75.0 | 000000 | K30 = 2.5 | 14<br>10 + 4 | 2 | 0000000 | C = 2.5 |
| RD11060 | 4 | 71.5 | 000000 | K30 = 2.0 | 18<br>9 + 9 | 1 | 00000000 | C = 3.5 |
| RD11061 | 4 | 71.0 | 2 | K17 = 2 | 16 | 2 | 0000000 | C = 3 |
| RD11062 | 4 | 62.35 | 0000000 | K17 = 1.5<br>K30 = 1.0 | 22<br>6 + 16 | 6<br>2 + 4 | N − H = 0.15 | A = 3 |
| RD11063 | 4 | 70.5 | 000000oo | K17 = 1.5<br>K30 = 1.5 | 18<br>6 + 12 | 00000000 | N − H = 0.2 | A = 4 |
| RD11064 | Transfer from RD11062 | Add 0.3% H2O | Increase in viscosity | | | | | Formula includes HPC |
| RD11065 | Transfer from RD11063 | Add 0.3% H2O | Increase in viscosity | | | | | Formula includes HPC |

TABLE 1A-continued (See the formulations in the Examples above and including Example 10)

| Trial number | Active % | Castor oil % | Labrafil % | PVP grade % | DMI % | TranscutolP % | HPC Nisso % | SiO2 % C = Cabosil A = Aerosil200 |
|---|---|---|---|---|---|---|---|---|
| RD11066 | Transfer from RD11041 | Add 0.3% H2O | No increase in viscosity | | | | N0 HPC | |
| RD11070 | Transfer from RD11037 | Add 0.3% H2O | No increase in viscosity | | | | N0 HPC | |
| RD11071 | Transfer from RD11042 | Add 0.3% H2O | No increase in viscosity | | | | N0 HPC | |
| RD11072 | Transfer from RD11040 | Add 0.3% H2O | No increase in viscosity | | | | N0 HPC | |
| RD11073 | 4 | 70.5 | 000000 | 0000000 | 16 10 + 6 (3) | 6 (3) | N − M = 0.5 (0.25) | A = 3 |
| RD11074 | Transfer from RD11073 | Add 0.3% H2O | | | | | Transfer from RD11040 | Add 0.3% H2O |
| RD11075 (base) | 4 | 68.0 | 000000 | K30 = 1.0 | 16 6 + 10 | 0000000 | See HPC pre-mixes | A = 3 |
| RD11076 | Base of RD11075 | — | — | — | — | — | Addition RD11067 | — |
| RD11077 | Base of RD11075 | — | — | — | — | — | Addition RD11068 | — |
| RD11078 | Base of RD11075 | — | — | — | — | — | Addition RD11069 | — |
| RD11079 | Transfer from RD11076 | Add 0.3% H2O | — | — | — | — | Formula includes HPC | — |
| RD11080 | Transfer from RD11077 | Add 0.3% H2O | — | — | — | — | Formula includes HPC | — |
| RD11081 | Transfer from RD11078 | Add 0.3% H2O | — | — | — | — | Formula includes HPC | — |
| RD11082 | 4 | 81.0 | 000000 | 0000000 | 10 See RD11073 (3 | See RD11073 (3 | See RD11073 (0.25) | 00000000 |
| RD11085 | 4 | 70.7 | 000000 | 0000000 | 16 10 + 6 | 6 | N − L = 0.2 N − M = 0.3 | A = 2.8 |
| RD11086 | 4 | 70.7 Add 0.3% H2O | 000000 | 0000000 | 16 10 + 6 | 6 | N − L = 0.2 N − M = 0.3 | A = 2.8 |

Lot #RD11037

Process duplication of IMP batch (4%) without HPC. K17 and S630 dissolved in DMI/Transcutol mixture followed by addition of the active. Clear solution. Castor oil preheated and added the above active mixture. Clear solution observed. Followed with the addition of the Cabosil with low shear. Viscosity at time of manufacture 500 cps, followed with test after 48 hours resulted in 620 cps.

Lower viscosity primarily due to missing HPC (note that IMP 4% had approx 1,500 cps)

Lot #RD11038

Change in order of addition using the same formulation with a reduction of DMI/Transcutol and adjusted with castor oil. Cabosil was mixed into the Castor oil obtaining a clear viscous solution. The active mixture was prepared as per RD11037. Viscosity of the Castor oil/Cabosil mixture changed to 1180 cps (expected higher viscosity based on addition of Co Solvents during the Placebo trials). Potential impact of PVP and active to solvent mixture.

Lot #RD11039

Duplicated performance based on Placebo mixture also containing Labrafil in castor oil plus Cabosil (for IP). Same reaction of reduced viscosity when adding the active mixture.

Lot #RD11040

Duplicated Placebo process adding to the Castor oil/Cabosil mixture a portion of the DMI/Transcutol P co-solvent mixture. Viscosity of the oil mixture increased. Prepared the active mixture with the remaining co-solvents without the PVP and added to the oil mixture. Final viscosity of the bulk Gel was 10,400 cps. Potential for F/C.

Lot #RD11041

Process was repeated as per RD11040 including the PVP K17 and S630 with the active mixture and viscosity was reduced to 500 cps (increased to 1,500 cps after 3 weeks). Clear indication of PVP impact on lowering viscosity using K17 and S630.

Lot #RD11042

Repeat of trial with Castor oil/Labrafil addition as per RD11037, and reduced Cabosil, with active co solvent mixture but no PVP. Viscosity of 1,750 cps The following trials were designed to identify impact of changing to higher PVP grades as well as alternate source of HPC (2 grades). Pre mixture were made as outlined in table 3 concentrating on mixtures without Labrafil, using Castor oil native and Aerosil 200.

Lot #RD11050

Dispersion (pre-mix I) of Castor Oil and Aerosil 200 was prepared and viscosity increased by adding part of the DMI (4%). The preparation of the active mixture use the pre-mix of RD11047A (PVP K17-3%) in DMI only, added 0.3% of HPC Nisso H followed by addition of active. Active mixture was added to the Pre-mix I Lot #RD11050A Same basic formulation as RD11050 with change of adding to a portion additional 1% of Aerosil 200

Lot #RD11051

Dispersion (pre-mix I) of Castor Oil and Aerosil 200 was prepared and viscosity increased by adding part of the DMI (4%). The preparation of the active mixture use the pre-mix of RD11047B (PVP K30-3%) in DMI only, added 0.3% of HPC Nisso M followed by addition of active. Active mixture was added to the Pre-mix I Lot #RD11051A Same basic formulation as RD11051 with change of adding to a portion additional 1% of Aerosil 200

Lot #RD11053

Dispersion (pre-mix I) of Castor Oil and Aerosil 200 was prepared and viscosity increased by adding part of the DMI and Transcutol P. The preparation of the active mixture use the pre-mix of RD11048A (PVP K17-3%), added 0.3% of HPC Nisso H followed by addition of active. Active mixture was added to the Pre-mix I Lot #RD11054

Dispersion (pre-mix I) of Castor Oil and Aerosil 200 was prepared and viscosity increased by adding part of the DMI and Transcutol P. The preparation of the active mixture use the pre-mix of RD11048B (PVP K30-3%), added 0.3% of HPC Nisso H followed by addition of active. Active mixture was added to the Pre-mix I Lot #RD11055

Dispersion (pre-mix I) of Castor Oil and Aerosil 200 was prepared and viscosity increased by adding part of the DMI and Transcutol P. The preparation of the active mixture use the pre-mix of RD11048C (PVP K90-3%). No HPC added. Active mixture was added to the Pre-mix I Lot #RD11056

Dispersion (pre-mix I) of Castor Oil and Aerosil 200 was prepared and viscosity increased by adding part of the DMI. The preparation of the active mixture use the pre-mix of RD11047C (PVP K90-3%). No HPC added Active mixture was added to the Pre-mix I Lot #RD11059

Prepared mixture of Castor Oil and Cabosil (2.5%). Active was dissolved in DMI and Transcutol P. Resulted in milky appearance. Adding that mix to the Castor Oil premix, mixture did not clear up. Prepared the PVP (K30) solution with DMI, added to the mix, no change in appearance however reduced viscosity.

Note, no change in evaluation adding a mixture of 0.1% HPC to appearance, slight increase in viscosity. Trial not reported under trial a lot number.

Lot #RD11060

Prepared the Castor Oil adding 3.5% Cabosil, followed by addition of a mixture of DMI/Transcutol P for thickening. The active dispersion was prepared in a PVP (K30) with DMI as co-solvent. (no HPC)

Lot #RD11061

Prepared the Castor Oil adding 3% Cabosil, followed by addition of Labrafil (2%) for thickening. The active dispersion was prepared in a DMI mixture containing PVP K17 (2%). Mix resulted in low viscosity, however could be considered for F/C test.

Lot #RD11062

Castor Oil native mixed with Aerosil 200 (3%) and added a mixture of DMI/Transcutol P (6+2) for thickening. A PVP mixture of K17 and K30 was dissolved in DMI/Transcutol P and followed with HPC H and solvate for 4 days. Mixture was reheated prior to addition of active. Castor Oil premix was heated prior to adding the active dispersion. Recommended for F/C Lot #RD11063

Castor Oil native mixed with Aerosil 200 (4%) and added the DMI (6%) resulting in a high viscose mix. A mixture of PVP K17 and L29/32 was dissolved in DMI, plus HPC Nisso H (0.2). On overnight setup, noticed a separation, required re-mixing. Active was added to the high viscosity Castor Oil premix. To be followed up with modification to composition Potential for F/C or to use RD11065

Lot #RD11064

Addition of 0.3% to portion of lot RD11062

Lot #RD11065

Addition of 0.3% to portion of lot RD11063

Lot #RD11066

Addition of 0.3% to portion of lot RD11041

Lot #RD11070

Addition of 0.3% to portion of lot RD11037

Lot #RD11071

Addition of 0.3% to portion of lot RD11042

Lot #RD11072

Addition of 0.3% to portion of lot RD11040

Lot #RD11073

Prepared Castor Oil/Aerosil 200 pre-mixture. Dissolve in DMI (6%) without PVP, the Testosterone and add to the Castor oil pre-mix. Obtained a viscosity of 6,300 cps. In a mixture of Transcutol P and DMI disperse the HPC M (only used 0.25% of prep) and add to main mix. Proposed for F/C Lot #RD11074

Addition of 0.3% to portion of lot RD11072

Lot #RD11075

Prepared a stock mixture to complete 3×500 g trials consisting of Castor-Oil (68%) Aerosil 200 (3%) DMI (6%). To this mix was added PVP K29-32 (1%) in DMI (10) and active. Bulk split into 3 parts to be completed for 3 trials containing different mixtures and grades of HPC Nisso in Transcutol (ref lots RD11067/68/69)

Lot #RD11076

Used bulk from RD11075 and added HPC mix RD11067 (Transcutol P with Nisso H (0.15%)

Lot #RD11077

Used bulk from RD11075 and added HPC mix RD11068 (Transcutol P with Nisso H (0.2%)

Lot #RD11078

Used bulk from RD11075 and added HPC mix RD11069 (Transcutol P with Nisso H (0.1) and M (0.1)

Lot #RD11079

Addition of 0.3% to portion of lot RD11076

Lot #RD11080

Addition of 0.3% to portion of lot RD11077

Lot #RD11081

Addition of 0.3% to portion of lot RD11078

Lot #RD11082

Trial attempt to prepare a batch without the use of SiO2 failed

Lot #RD11085

Prepared Castor-Oil pre-mix adding 2.5% Aerosil 200 followed with a mix of DMI (10) and Testosterone. Obtained viscosity of 3,100 cps. Followed with the addition of HPC Nisso L (0.2%) and Nisso M (0.3%) mixed in DMI and Transcutol plus 0.3% Aerosil 200 to reduce stickiness. Material was added without any stringing to the main mixture and obtained a viscosity of 4,800 cps at day of manufacture and 4,900 cps 3 weeks later. Proposed for F/C Lot #RD11086

Addition of 0.3% to portion of lot RD11085

TABLE 2

TBS1A 4% strength
Viscosity values using spindle 6, 20 rpm, Repeat test ref to Franz Cell: F/C

| Lot number | Trial Manuf date | Test date and values | Comments |
| --- | --- | --- | --- |
| RD11037 | Jul. 15, 2011 | Oct. 4, 2011 940 cps | Clear solution, previous results in July 620 cps and follow up test Sep. 15, 2011 was 900 cps |
| RD11038 | Jul. 15, 2011 | Oct. 4, 2011 1,800 cps | Clear solution, original test 1,180 cps, follow up Sep. 15, 2011 1,660 cps |
| RD11039 | Jul. 20, 2011 | Oct. 4, 2011 1,380 cps | Clear solution, previous results in July 980 cps and follow up test Sep. 15, 2011 was 1,300 cps |
| RD11040 | Jul. 20, 2011 | Oct. 4, 2011 11,040 cps | Clear Gel, previous results in July 10,400 cps and follow up test Sep. 15, 2011 was 10,140 cps |
| RD11041 | Jul. 21, 2011 | Oct. 4, 2011 1,420 cps | Clear solution, previous results in July 500 cps and follow up test Sep. 15, 2011 was 1,500 cps |
| RD11042 | Jul. 21, 2011 | Oct. 4, 2011 1,430 cps | Clear solution, test Sep. 15, 2011 was 1,720 cps |
| RD11050 | Aug. 9, 2011 | Oct. 4, 2011 Test not valid | Original comment sticky mixture, Sep. 15, 2011 results 2,460 Do not use trial lot for F/C Poor mixture, HPC settled to bottom as a slug |
| RD11050A | Aug. 9, 2011 | Oct. 4, 2011 Test not valid | Original comment sticky mixture, results Sep. 15, 2011 3,000 cps (increased during test from 2,400) Do not use trial lot for F/C Poor mixture, HPC settled to bottom as a slug |
| RD11051 | Aug. 9, 2011 | Oct. 4, 2011 2,100 cps▲ | Clear, results Sep. 15, 2011 1,940 cps Note: viscosity values increase during 30 sec test |
| RD11051A | Aug. 9, 2011 | Oct. 4, 2011 2,540 cps▲ | Clear, results Sep. 15, 2011 2,560 cps Note: viscosity values increase during 30 sec test |
| RD11053 | Aug. 10, 2011 | Oct. 4, 2011 4,500 cps▲ | Clear but sticky with air bubbles, results Sep. 15, 2011 4,060 cps Note: viscosity values increase during 30 sec test |
| RD11054 | Aug. 10, 2011 | Oct. 4, 2011 14,000 cps▲ | Sep. 15, 2011 test HPC globules, 15,000 cps Do not use trial lot for F/C, Note: viscosity values increase during 30 sec test Build up of HPC on spindle |
| RD11055 | Aug. 10, 2011 | Oct. 4, 2011 EEEEEE | Sep. 15, 2011, EEEEEE Do not use trial lot for F/C Note, error message indicates above 20,000 tester limit at that setting |
| RD11056 | Aug. 10, 2011 | Oct. 4, 2011 EEEEEE | Sep. 15, 2011, EEEEEE Do not use trial lot for F/C Note, error message indicates above 20,000 tester limit at that setting |
| RD11059 | Aug. 22, 2011 | Oct. 4, 2011 Test not valid | Do not use trial lot for F/C Separation of HPC (?)Build up of HPC on spindle |
| RD11060 | Aug. 23, 2011 | Oct. 5, 2011 3,540 cps | Uniform texture |
| RD11061 | Aug. 23, 2011 | Oct. 5, 2011 960 cps | Uniform texture |
| RD11062 | Aug. 24, 2011 | Oct. 5, 2011 3,200 cps | Original viscosity 2,400 cps |
| RD11063 | Aug. 24, 2011 | Oct. 5, 2011 3,460 cps | Original viscosity 1,600 cps |
| RD11064 | Aug. 31, 2011 | Oct. 5, 2011 6,440 cps | Original viscosity 5,800 cps Clear, thick, |
| RD11065 | Aug. 31, 2011 | Oct. 5, 2011 12,500 cps | Added .3% H2O to RD11063 Sep. 31, 2011 resulted in 9,100 cps Air bubbles |
| RD11066 | Aug. 31, 2011 | Oct. 5, 2011 2,600 cps | Added .3% H2O to RD11041 Sep. 31, 2011 resulted in 1,500 cps Clear, thick |
| RD11070 | Aug. 31, 2011 | Oct. 5, 2011 1,540 cps | Added .3% H2O to RD110370 Sep. 31, 2011 resulted in 720 cps Liquid and clear |

TABLE 2-continued

TBS1A 4% strength
Viscosity values using spindle 6, 20 rpm, Repeat test ref to Franz Cell:
F/C

| Lot number | Trial Manuf date | Test date and values | Comments |
|---|---|---|---|
| RD11071 | Aug. 31, 2011 | Oct. 5, 2011 1,820 cps | Added .3% H2O to RD11042 Sep. 31, 2011 resulted in 1,760 cps Liquid and clear |
| RD11072 | Aug. 31, 2011 | Oct. 5, 2011 7,920 cps | Added .3% H2O to RD11040 resulted in 7,920 cps Clear and thick, no change in viscosity |
| RD11073 | Sep. 7, 2011 | Oct. 5, 2011 9,980 cps | Started off in Sept with viscosity of 5,500 cps |
| RD11074 | Sep. 7, 2011 | Oct. 5, 2011 10,100 cps | Added .3% H2O to RD11073 increases viscosity to 7,200 cps. |
| RD11076 | Sep. 6, 2011 | Oct. 5, 2011 1,700 cps | Clear, however noticed separation in bulk |
| RD11077 | Sep. 6, 2011 | Oct. 5, 2011 1,600 cps | Clear |
| RD11078 | Sep. 6, 2011 | Oct. 5, 2011 2,700 cps | Clear and fluid |
| RD11079 | Sep. 6, 2011 | Oct. 5, 2011 3,500 cps | Added 0.3% H2O to RD11076 Clear, fluid |
| RD11080 | Sep. 6, 2011 | Oct. 5, 2011 3,900 cps | Added 0.3% H2O to RD11077 Clear, fluid |
| RD11081 | Sep. 6, 2011 | Oct. 5, 2011 2,600 cps | Added 0.3% H2O to RD11078 Clear, fluid |
| RD11085 | Sep. 14, 2011 | Oct. 5, 2011 4,900 cps | Original test 4,800 cps Thick and clear |
| RD11086 | Sep. 20, 2011 | Oct. 5, 2011 5,180 cps | Addition of 0.3% H2O to RD11085 = 5,200 cps original Thick gel and clear |

TBS1A 8% Formulation/Composition

TABLE 3

| Trial number | Active micronized % | Castor oil % | Labrafil % | PVP grade % | DMI % | TransbutolP % | HPC Nisso % | SiO2 % C = Cabosil A = Aerosil200 |
|---|---|---|---|---|---|---|---|---|
| RD11087 | 8 | 55.9 | 0000000 | 0000000 | 27 20 + 7 | 6 | N − L = 0.2 N − M = 0.3 | A = 2.6 |
| RD11088 | 8 | same | 0000000 | 0000000 | same | same | same | Same plus (0.3% H2O) |
| RD11089 | 8 | 46.5 | 0000000 | K17 = 3 S630 = 2 | 25 | 10 | N − M = 0.5 | C = 5 |
| RD11089A | 8 | same | 0000000 | same | same | same | same | Same plus (0.3% H2O) |
| RD11090 | 8 | 39.0 | 0000000 | K17 = 5.0 | 32 | 12 | N − H = 0.3 N − M = 0.2 | C = 3.5 |
| RD11100 | 8 | same | 0000000 | same | same | same | same | Added C = 2% for total of 5.5 |
| RD11101 | 8 | 46.1 | 0000000 | K17 =5.0 | 25 | 10 | N − L = 0.4 N − M = 0.4 | C = 5.1 |
| RD11102 | 8 | 46.1 | 0000000 | K17 = 5.0 | 25 | 10 | N − L = 0.4 N − M = 0.4 | C = 5.1 plus Addition of 1% for total of 6.1 |
| RD11103 | 8 | 46.1 | 0000000 | K17 =5.0 | 25 | 10 | N − L = 0.4 N − M = 0.4 | C = 5.1 plus addition of 0.3% water |
| RD11104 | 8 | 42.2 | 4.0 | K17 = 5.0 | 25 | 10 | N − L = 0.4 N − M = 0.4 | A = 5.0 |
| RD11105 | 8 | same | same | same | same | same | same | A = 5.0 addition of 0.5% total 5.5% |

Process Outline for Active Trials:

Lot #RD11087

Trial was initiated without PVP to identify impact on T solubility. The active dispersion in % DMI used did not provide a clear solution and did not clear up when adding to the Castor Oil/SiO2 mix. Even the co-solvents present in the HPC mixture did not provide a clear bulk Gel. To the HPV mixture 0.1% SiO2 was added to reduce stringing and stickiness.

Viscosity at 4,400

This trial however will be selected for the Franz Cell test to identify diffusion rate eliminating PVP.

Lot #RD11088

0.3% water was added to a portion of Lot RD11087 to identify impact on viscosity. As observed on 4% trials, increase in viscosity is not evident on the bulk mixed with SiO2 in the HPC. This trial not considered for F/C.

Lot #RD11089

This trial used the same quantitative formulation as the IMP Clinical 8%, however using an alternate source of HPC (original HPC source Klucel HF). Also made minor process changes, dissolved PVP in DMI only and added active. HPC was prepared in Transcutol and added to main bulk separately.

Obtained a clear solution when adding the active co-solvent mixture into the Castor-oil and no significant stringing with the addition of the HPC after addition of SiO2.

Viscosity of Gel on day of manufacture was 1,800 cps, when retested after 24 hours, 3,700 and after 48 hours up to 4,300. The re-test on October 3 (see table) recorded 4,500 cps.

This trial was selected for F/C test

Lot #RD11089A 0.3% water was added to a portion of Lot RD11089 to identify impact on viscosity.

Viscosity change over time similar to above trial, day of manufacture 2,700 cps, when retested after 24 hours, 3,920 and after 48 hours up to 4,600. The re-test on October 3 (see table) recorded 5,040 cps.

Selected for study on impact of water

Lot #RD11090

Used higher percentage of DMI and Transcutol to be split for various pre-mixes, similar with SiO2 to be added HPC. Made a pre-mix of Castor oil and SiO2, however due to the lower ratio between the 2 excipients, the mixture became quite thick and further thickened up when adding part of the DMI.

Did finish off the trial, ended up at low viscosity, day of manufacture 900 cps, test October 03-1,260 cps. Lower level of SiO2 was considered for study impact, however considering the processing issue (see RD11100) not suitable for F/C test Lot #RD11100

Using a portion of above trial RD11090, added an additional 2% SiO2 (for total of 5.5%) to study impact on Viscosity. Increased to 1,900 cps on day of manufacture and retest October 03 (see table) resulted in a value of 3.060

Lot #RD11101

To potentially reduce the impact of PVP, required to dissolve the active, during the addition to the Castor oil/SiO2 mixture, added 2% of SiO2 to the DMI-PVP-Testosterone mix, obtaining a viscous mix. After addition of that mixture to a dispersion of Castor oil containing 1% SiO2, maintained a viscous mixture at the temperature of 50% (would thicken up further on cooling). Further increase in viscosity with the addition of the HPC mix and final amount of SiO2.

Viscosity after cooling Gel to 21 C was 3,800 cps. (note that re-testing over time will be required, batch manufactured October 03)

This trial selected for F/C

Lot #RD11102

With the target for a 5,000 cps viscosity for the TBS1A project, the above RD11101 was so far the best candidate to evaluate impact of further addition of SiO2, hence to a portion of that lot additional 1% SiO2 was added. The rational for 6% was to obtain the same ratio of active to SiO2 as the targeted level of 3% SiO2 for the 4% strength.

Viscosity increase to 8,000 cps, this lot was selected for F/C study to identify impact of viscosity on rate of diffusion compared to RD11101 of same composition with exception of 1% addition in SiO2, may need to consider on assay obtained.

Lot #RD11103

Addition of water for impact on viscosity, not considered for follow up testing (see viscosity table for results, increase to RD11101 from 3,800 to 4,500 cps)

Lot #RD11104

Included this trial to evaluate addition of Labrafil. Labrafil was added to the Castor Oil mixed with SiO2 at 1%. As observed previously, addition of Labrafil to the Castor oil containing SiO2 increases viscosity. All other mixture prepared and added as per trial RD11101, with addition of 2% SiO2 to complete mixture. This mixture contains a larger percentage of air bubbles, common on formulations containing Labrafil. Viscosity obtained of 3,300 cps, will be followed up and tested at various time points.

Selected for F/C testing.

Lot #RD11105

Added to RD11104 an additional 0.5% SiO2 (% adjusted to avoid high increase observed on RD11102)

Increase from 3,300 to 4,100 cps

Not selected for F/C test

Note: Placebo trials are drawn up to identify impact on viscosity using the 2 different sources for Castor Oil and SiO2. These trials will also answer potential questions related to TBS1 and TBS2.

TABLE 4

TBS1A 8% strength
Viscosity values using spindle #6, 20 rpm, Franz Cell = F/C

| Lot number | Trial Manuf date | Test date and values | Comments |
| --- | --- | --- | --- |
| RD11087 | Sep. 20, 2011 | Oct. 3, 2011 4,400 cps | No PVP, solution not clear, 2.6% SiO2 Selected for Franz Cell |
| RD11088 | Sep. 20, 2011 | Oct. 3, 2011 4,040 cps | Added 0.3% H2O to RD11087 |

TABLE 4-continued

TBS1A 8% strength
Viscosity values using spindle #6, 20 rpm, Franz Cell = F/C

| Lot number | Trial Manuf date | Test date and values | Comments |
|---|---|---|---|
| RD11089 | Sep. 25, 2011 | Oct. 3, 2011 4,500 cps | Based on original IMP, change in HPC source and minor process step changes Selected for Franz Cell |
| RD11089A | Sep. 25, 2011 | Oct. 3, 2011 5,040 cps | As RD11089 plus 0.3% H2O Selected for Franz Cell |
| RD11090 | Sep. 26, 2011 | Oct. 3, 2011 1,260 cps | 3.5% SiO2 Potential for F/C |
| RD11091 | Sep. 26, 2011 | Oct. 3, 2011 | Added 0.3% H2O to RD11090 |
| RD11100 | Sep. 26, 2011 | Oct. 3, 2011 3,060 cps | Added to RD11090 to reach 5% SiO2 content |
| RD11101 | Oct. 3, 2011 | Oct. 4, 2011 3,800 cps | 5% SiO2 Selected for Franz Cell |
| RD11102 | Oct. 4, 2011 | Oct. 4, 2011 8,000 cps | 6% SiO2 Selected for Franz Cell |
| RD11103 | Oct. 4, 2011 | Oct. 4, 2011 4,500 cps | 0.3% with 5% SiO2 |
| RD11104 | Oct. 4, 2011 | Oct. 5, 2011 3,300 cps | Includes 4% Labrafil, same comp for polymers as RD11101 (air-bubbles) Selected or Franz Cell |
| RD11105 | Oct. 5, 2011 | Oct. 5, 2011 4,100 cps | Added additional 0.5% of SiO2 to RD11104 |

Pre-Mix RD Trials (Used for Addition in Active Trials)

TABLE 5

| Trial #/ observation test | Evaluation | Composition | Results/comments | Used in RD trial # |
|---|---|---|---|---|
| EV001A (pg 41) | Dissolving HPC Nisso grade M | DMI-100 g Transcutol P 50 g Nisso HPC M-2.5 g | Low viscosity grade Stored for hydration 72 hrs Suitable viscosity for further additions | Not transferred for use to RD trials |
| EV001B (pg 41) | Dissolving HPC Nisso grade H | DMI-100 g Transcutol P 50 g Nisso HPC H-2.5 g | high viscosity grade Stored for hydration 72 hrs Viscosity too high | Not transferred for use to RD trials |
| EV002A (pg 41) | Dispersing Cabosil in DMI (purpose to study impact on viscosity in final Gel) | DMI-125 g Cabosil 10 g Ratio related to Castor oil/Cabosil | Obtained clear and viscous dispersion | Not transferred for use to RD trials |
| EV002B (pg 41) | Dispersing Cabosil in Transcutol P (purpose to study impact on viscosity in final Gel) | Transcutol P 250 g Cabosil 20 g Ratio related to Castor oil/Cabosil | Obtained no increase viscosity, Solution milky in appearance | Not transferred for use to RD trials |
| RD11047 A | Addition of PVP K17 in DMI only. | DMI-100 g PVP K17 15 g Ratio represents 3% of PVP based on final Bulk Gel formula | Suitable for additional mixing with HPC H and active. Note: used higher viscosity HPC grade with lower viscosity PVP grade | Used in RD trial for addition of HPC-H and active (see RD1150 and RD1150A) |
| RD11047B | Addition of PVP K29/32 in DMI only. | DMI-100 g PVP K29/32 15 g Ratio represents 3% of PVP based on final Bulk Gel formula | Suitable for additional mixing with HPC M and active. Note: used lower viscosity HPC grade with higher viscosity PVP grade | Used in RD trial for addition of HPC-M and active (see RD1151 and RD1151A) |
| RD11047C | Addition of PVP K90 in DMI only. | DMI-100 g PVP K90 15 g Ratio represents 3% of PVP based on final Bulk Gel formula | Not suitable to add any grade HPC, however suitable to add the active portion. | Used in RD trial without HPC addition RD11056 |

TABLE 5-continued

| Trial #/observation test | Evaluation | Composition | Results/comments | Used in RD trial # |
|---|---|---|---|---|
| RD11048 A | Addition of PVP K17 in DMI and Transcutol P | DMI-80 g Transcutol P 20 g PVP K17 15 g Ratio represents 3% of PVP based on final Bulk Gel formula | Suitable for additional mixing with HPC H and active. Note: used higher viscosity HPC grade with lower viscosity PVP grade | Used in RD trial for addition of HPC-H and active (see RD11053 |
| RD11048B | Addition of PVP K29/32 in DMI and Transcutol P. | DMI-80 g Transcutol P 20 g PVP K29/32 15 g Ratio represents 3% of PVP based on final Bulk Gel formula | Suitable for additional mixing with HPC M and active. Note: used lower viscosity HPC grade with higher viscosity PVP grade | Used in RD trial for addition of HPC-M and active (see RD11054 |
| RD11048C | Addition of PVP K90 in DMI and Transcutol P | DMI-100 g PVP K90 15 g Ratio represents 3% of PVP based on final Bulk Gel formula | Not suitable to add any grade HPC, however suitable to add the active portion. | Used in RD trial without HPC addition RD11055 |
| RD11067 | Prep of HPC in Transcutol P only | TP = 40 g N—H = 0.75 g | | Used in RD11076 |
| RD11068 | Prep of HPC in Transcutol P only | TP = 40 g N—H = 1.0 g | | Used in RD11077 |
| RD11069 | Prep of HPC in Transcutol P only | TP = 40 g N—H = 0.5 g N—M = 0.5 g | | Used in RD11078 |
| RD11075 | Prep of base solution used RD11076/RD11077/RD11078 Details in Table 2 | Castor oil/ Aerosil200/ DMI/ PVP K30 Testosterone | | |

Placebo TBS1A Trials

TABLE 6

| Trial lot # | Evaluation | Composition | Results/comments |
|---|---|---|---|
| RD11032 | Evaluate change in viscosity using Labrafil versus Castor Oil Cr 0 | Labrafil M 1944 CS-500 g Cab-O-Sil - - - 40 g | Viscosity 10,460 cps |
| RD11033 | Evaluate change viscosity adding Cabosil first in Castor Oil Cr 0 | Castor Oil - - - 500 g Cab-O-Sil - - - 40 g Note: ratio used in IMP | Viscosity 14 460 cps |
| RD11034 | Impact on adding DMI and Transcutol to mixture RD11032 | RD11032-270 g DMI-125 g Transcutol P 50 g | Viscosity reduced to 8,740 |
| RD11035 | Impact on adding DMI and Transcutol to mixture RD11033 | Impact on adding DMI and Transcutol to mixture RD11032 | Viscosity reduced to 3,600 |
| RD11036A | Mixture of Castor Oil and Labrafil, adding Cabosil followed by DMI/Transcutol P | Castor oil . . . 125 g Labrafil . . . 125 g Cabosil . . . 20 g DMI . . . 125 g Transcutol P 50 g | High viscosity out of range |
| RD11036B | Mixture of Castor Oil and Labrafil followed by DMI/Transcutol P, add Cabosil last | Castor oil 0 . . . 125 g Labrafil . . . 125 g Cabosil . . . 20 g DMI . . . 125 g Transcutol P 50 g | Viscosity 7,680 cps |
| RD11043 | Castor oil and Cab0sil, followed by mixture of DMI/Transcutol P and HPC H | Castor oil 0 . . . 285 g Cabosil . . . 20 g DMI . . . 100 g Transcutol P 50 g HPC H . . . 2.5 g | |
| RD11043 | Castor oil and Cab0sil, followed by mixture of DMI/Transcutol P and HPC M and PVP K17 | Castor oil 0 . . . 285 g Cabosil . . . 20 g DMI . . . 100 g Transcutol P 50 g HPC M . . . 2.5 g PVP K15 . . . 15 g | |

TABLE 6-continued

| Trial lot # | Evaluation | Composition | Results/comments |
|---|---|---|---|
| RD11057P | TBS-2 Placebo for Analytical Lab Method | — | — |
| RD11058P A-B-C-D-E-F | Castor oil an Cabosil Mix followed by addition of Labrafil | A to D represents % Labrafil of 2-4% with change in viscosity E impact of adding Oleic acid F impact of adding DMI to RD11058-A | RD11058P = 2740 cps Part A 2% = 11,400 Part B 3% = 14,000 Part C 3.5% = 14,440 Part D 4% = 14,900 Part E with Oleic = 1,520 Part F-10% DMI to part A = 13,500 cps (incr. from 11,400) |
| RD11083P | Purpose of trial to decrease stringing and stickiness of HPC mixture when adding to base mix of castor oil/Aerosil and DMI | HPC mix prep of DMI/TranscutolP solvents plus Nisso HPC L and M Solvated for 48 hours followed by addition of SiO2 | Viscosity of base prior to addition of HPC mixture was 5,300 cps, after addition of HPC mixture (no stringing |
| RD11084P | Used part of RD1108P to add 0.3% H2O to evaluate impact on viscosity | | |

Example 10

Franz Cell Studies—Testosterone Rates of Diffusion

Generally speaking, soak the membrane for 30 minutes in the diffusion solution. After put the membrane on the Franz Cell. Put the ring and the donor chamber on the membrane and clamp it. Add approx. one gram of gel (TBS 1 A 4% or 8%). Check the level of diffusion solution in Franz Cells. It's supposed to be on the mark. Put "parafilm" on the sampling port to avoid evaporation. Withdraw 0.3 mL of sample at 60, 120, 180, 240, 300 and 360 minutes using syringe. Add diffusion solution to make up to the mark of Franz Cells. Each sample should be collected in insert.

Figure 12:
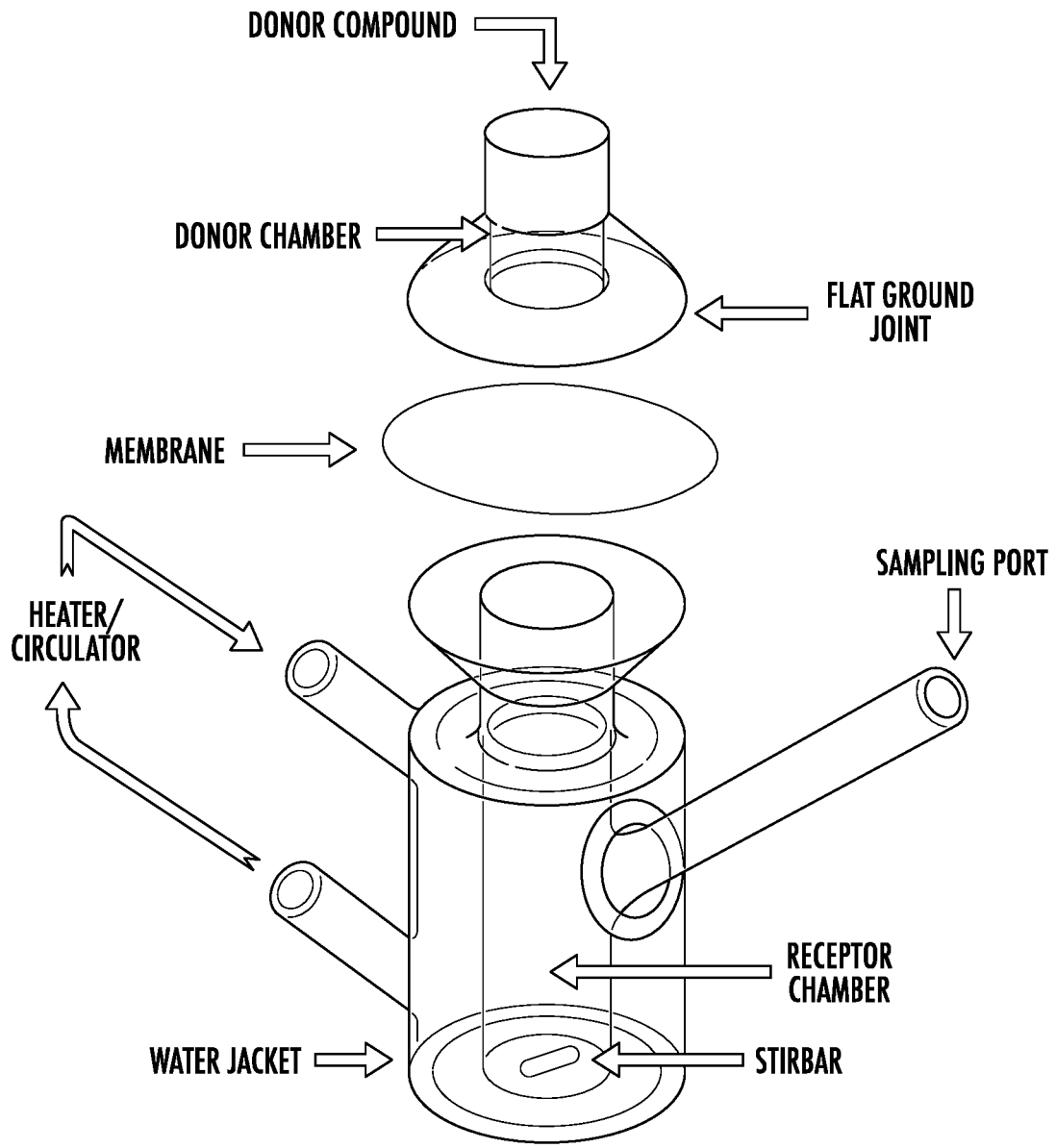
FIG. 12 depicts a Franz Cell apparatus position layouts for comparing testing in accordance with Example 5.

A typical Fanz cell used in accordance with this Example 9 and the invention is depicted in FIG. 12. The materials include:

Diffusion solution: Ethanol/Water 50:50

Membrane: Millipore 0.45 μm.

Temperature: 37°±0.5° C.

Stirring speed: 600 rpm.

Medium volume: 20 mL.

Surface area: 1.7671 cm$^2$

Number of Franz Cells: 6.

Sampling time (minutes): 60, 120, 180, 240, 300 and 360.

Aliquot volume: 0.3 mL.

Insert: 0.4 mL.

The TBS1A formulations are as follows and as reported in the Examples above and herein. The rate of diffusion results of testosterone through the Franz cell membrane, normalized for each gel concentrations being tested, measured as slope/mgT %, are reported below in the Franz Cell Table.

| 4% TBS1A Trial formulations used in Franz Cell ||||
|---|---|---|---|
| Raw Materials/grade | % | Process | comments |
| Trial Lot # RD11063 Batch size 500 g ||||
| Testosterone micronized | 4.0 | 12% DMI to disperse PVP and active | 24 hr Franz Cell |
| Castor Oil (V-O) | 70.8 | 4% SiO2 in Castor oil plus 6% of DMI | Steps: |
| PVP K17 | 1.5 | | A: add all SiO2 to Castor Oil |
| PVP K30 | 1.5 | | Followed by DMI portion |
| PVP K90 | 0.0 | | B: to the DMI add PVP, follow |
| Co PVP S630 | 0.0 | | With HPC and hold 24 hrs |
| DMI | 18.0 | | C: add active |
| Transcutol P | 0.0 | | D: add to mix A) |
| HPC Nisso L | 0.0 | | |
| HPC Nisso M | 0.0 | | Temp range NMT 60 C. |
| HPC Nisso H | 0.2 | | Homogenize active mixture |
| SiO2 (Cabosil-Aerosil 200) | 4.0 | | Viscosity 3,650 cps Oct. 5, 2011) |
| Trial Lot # RD11085 Batch size 500 g ||||
| Testosterone micronized | 4.0 | 10% DMI used to dissolve active | 24 hrs Franz Cell |
| Castor Oil (V-O) | 70.7 | 2.5% of SiO2 mixed into Castor Oil | Steps: |
| PVP K17 | 0.0 | — | A: Active /DMI mixture added |
| PVP K30 | 0.0 | — | to Castor Oil/SiO2 mix |
| PVP K90 | 0.0 | — | B: add SiO2 to HPC after 24 h |
| Co PVP S630 | 0.0 | — | |
| DMI | 16.0 | 6% DMI used for HPC dispersion | C: add HPC mixture to main |
| Transcutol P | 6.0 | Used to disperse HPC and solvate for 24 hrs | bulk |
| HPC Nisso L | 0.2 | 0.3% of SiO2 mixed into HPC mixture | |

-continued

| 4% TBS1A Trial formulations used in Franz Cell | | | |
|---|---|---|---|
| Raw Materials/grade | % | Process | comments |
| HPC Nisso M | 0.3 | | Temp range NMT 60 C. |
| HPC Nisso H | 0.0 | | Homogenize active mixture |
| SiO2 (Cabosil-Aerosil 200) | 2.8 | | Viscosity 4,900 cps (Oct. 5, 2011) |
| | | Trial Lot # RD11038 Batch size 500 g | |
| | | | 6 hr Franz Cell |
| Testosterone micronized | 4.0 | Add to PVP mixture | |
| Castor Oil (V-O) | 57.0 | All Cabosil into Castor Oil | A: add to the Castor Oil/SiO2 |
| PVP K17 | 3.0 | | Mix the PVP active mixture |
| PVP K30 | 0.0 | | |
| PVP K90 | 0.0 | | |
| Co PVP S630 | 2.0 | | |
| DMI | 20.0 | All DMI and Transcutol P to disperse PVP | |
| Transcutol P | 10.0 | | |
| HPC Nisso L | 0.0 | | |
| HPC Nisso M | 0.0 | | Homogenize active mixture |
| HPC Nisso H | 0.0 | | |
| SiO2 (Cabosil-Aerosil 200) | 4.0 | | Viscosity 1,800 cps |
| | | Trial Lot # RD11039 Batch size 500 g | |
| | | | 6 hr Franz Cell |
| Testosterone micronized | 4.0 | | |
| Castor Oil (V-O) | 29.0 | Mix Castor oil + Labrafil + Cabosil | |
| PVP K17 | 3.0 | | |
| PVP K30 | 0.0 | | |
| PVP K90 | 0.0 | | |
| Co PVP S630 | 2.0 | PVP into DMI + Tr-P followed by active | |
| DMI | 20.0 | | |
| Transcutol P | 10.0 | | |
| Labrafil | 29.0 | | |
| HPC Nisso M | 0.0 | | |
| HPC Nisso H | 0.0 | | |
| SiO2 (Cabosil-Aerosil 200) | 3.0 | | Viscosity 1,380 |
| | | Trial Lot # RD11040 Batch size 500 g | |
| | | | 6 hr Franz Cell |
| Testosterone micronized | 4.0 | Mix in 12% DMI and 6% Tr-P | |
| Castor Oil (V-O) | 57.0 | Combine Castor oil + SiO2 + 13% DMI + 4% TrP | |
| PVP K17 | 0.0 | | |
| PVP K30 | 0.0 | | |
| PVP K90 | 0.0 | | |
| Co PVP S630 | 0.0 | | |
| DMI | 25.0 | | |
| Transcutol P | 10.0 | | |
| HPC Nisso L | 0.0 | | |
| HPC Nisso M | 0.0 | | |
| HPC Nisso H | 0.0 | | |
| SiO2 (Cabosil-Aerosil 200) | 4.0 | | Viscosity 11,040 |
| | | Trial Lot # RD11042 Batch size 500 g | |
| | | | 6 hr Franz Cell |
| Testosterone micronized | 4.0 | Active dissolve in 13% DMI + 4% Tr-P | |
| Castor Oil (V-O) | 29.0 | Castor oil + Labrafil + SiO2 + 12% DMI + 6% Tr-P | |
| PVP K17 | 0.0 | | |
| PVP K30 | 0.0 | | |
| PVP K90 | 0.0 | | |
| Co PVP S630 | 0.0 | | |
| DMI | 25.0 | | |
| Transcutol P | 10.0 | | |
| Labrafil | 29.0 | | |
| HPC Nisso M | 0.0 | | |
| HPC Nisso H | 0.0 | | |
| SiO2 (Cabosil-Aerosil 200) | 3.0 | | Viscosity 1,430 cps |
| | | Trial Lot #RD11051 Batch size 500 g | |
| | | | 6 hr Franz Cell |
| Testosterone micronized | 4.0 | 20% DMI + PVP + N − M + 0.2% iO2 | |
| Castor Oil (V-O) | 66.7 | Castor Oil + SiO2 1.8% + 4% DMI | |
| PVP K17 | 0.0 | | Easier addition of HPC adding |
| PVP K30 | 3.0 | | Small % of SiO2 |
| PVP K90 | 0.0 | | |
| Co PVP S630 | 0.0 | | |
| DMI | 24.0 | | |
| Transcutol P | 0.0 | | |

4% TBS1A Trial formulations used in Franz Cell

| Raw Materials/grade | % | Process | comments |
|---|---|---|---|
| HPC Nisso L | 0.0 | | |
| HPC Nisso M | 0.3 | | |
| HPC Nisso H | 0.0 | | |
| SiO2 (Cabosil-Aerosil 200) | 2.0 | | Viscosity 2,100 cps |
| | | Trial Lot # RD11055 Batch size 500 g | |
| | | | 6 hr Franz Cell |
| Testosterone micronized | 4.0 | DMI 16% + Transc 4% + pvp + active | |
| Castor Oil (V-O) | 62.0 | Castor Oil + SiO2 3% + 7% DMI + Trans 1% | |
| PVP K17 | 0.0 | | |
| PVP K30 | 0.0 | | |
| PVP K90 | 3.0 | | |
| Co PVP S630 | 0.0 | | |
| DMI | 23.0 | | |
| Transcutol P | 5.0 | | |
| HPC Nisso L | 0.0 | | |
| HPC Nisso M | 0.0 | | |
| HPC Nisso H | 0.0 | | |
| SiO2 (Cabosil-Aerosil 200) | 3.0 | | Exceeded test range |
| | | Trial Lot # RD11078 Batch size 500 g | |
| | | | 6 hr Franz Cell |
| Testosterone micronized | 4.0 | | |
| Castor Oil (V-O) | 68.0 | Castor oil + SiO2-3% + 6% DMI | To be corrected to 67.8% |
| PVP K17 | 0.0 | | for repeat (base) |
| PVP K30 | 1.0 | DMI 10% + pvp + active | Base prep RD11075 |
| PVP K90 | 0.0 | | |
| Co PVP S630 | 0.0 | | |
| DMI | 16.0 | | |
| Transcutol P | 8.0 | Transc P + both HPC | Prep on RD11069 |
| HPC Nisso L | 0.0 | | |
| HPC Nisso M | 0.1 | | Requires adjustment of |
| HPC Nisso H | 0.1 | | Castor oil by 0.2% |
| SiO2 (Cabosil-Aerosil 200) | 3.0 | | Viscosity 2,700 cps |
| | | Trial Lot #RD11054 Batch size 500 g | |
| | | | 6 hr Franz Cell |
| Testosterone micronized | 4.0 | | |
| Castor Oil (V-O) | 61.4 | Castor Oil + SiO2 3% + DMI 7% + Transc 1% | |
| PVP K17 | 0.0 | | |
| PVP K30 | 3.0 | DMI 16% + Trans 4% + pvp + HPC + active | |
| PVP K90 | 0.0 | | |
| Co PVP S630 | 0.0 | | |
| DMI | 23.0 | | |
| Transcutol P | 5.0 | | |
| HPC Nisso L | 0.0 | | |
| HPC Nisso M | 0.6 | | |
| HPC Nisso H | 0.0 | | |
| SiO2 (Cabosil-Aerosil 200) | 3.0 | | Viscosity 14,000 cps |
| | | Trial Lot #RD11061 Batch size 500 g | |
| | | | 6 hr Franz Cell |
| Testosterone micronized | 4.0 | | |
| Castor Oil (V-O) | 71.0 | Castor oil + SiO2 + Labrafil | |
| PVP K17 | 2.0 | DMI 16% + Transc 2% + PVP + active | |
| PVP K30 | 0.0 | | |
| PVP K90 | 0.0 | | |
| Co PVP S630 | 0.0 | | |
| DMI | 16.0 | | |
| Transcutol P | 2.0 | | |
| Labrafil | 2.0 | | |
| HPC Nisso M | 0.0 | | |
| HPC Nisso H | 0.0 | | |
| SiO2 (Cabosil-Aerosil 200) | 3.0 | | Viscosity 960 cps |

TABLE 2

TBS1A 4% strength
Viscosity values using spindle 6, 20 rpm, Repeat test ref to Franz Cell: F/C

| Lot number | Trial Manuf date | Test date and values | Comments |
|---|---|---|---|
| RD11037 | Jul. 15, 2011 | Oct. 4, 2011 940 cps | Clear solution, previous results in July 620 cps and follow up test Sep. 15, 2011 was 900 cps |
| RD11038 | Jul. 15, 2011 | Oct. 4, 2011 1,800 cps | Clear solution, original test 1,180 cps, follow up Sep. 15, 2011 1,660 cps |
| RD11039 | Jul. 20, 2011 | Oct. 4, 2011 1,380 cps | Clear solution, previous results in July 980 cps and follow up test Sep. 15, 2011 was 1,300 cps |
| RD11040 | Jul. 20, 2011 | Oct. 4, 2011 11,040 cps | Clear Gel, previous results in July 10,400 cps and follow up test Sep. 15, 2011 was 10,140 cps |
| RD11041 | Jul. 21, 2011 | Oct. 4, 2011 1,420 cps | Clear solution, previous results in July 500 cps and follow up test Sep. 15, 2011 was 1,500 cps |
| RD11042 | Jul. 21, 2011 | Oct. 4, 2011 1,430 cps | Clear solution, test Sep. 15, 2011 was 1,720 cps |
| RD11050 | Aug. 9, 2011 | Oct. 4, 2011 Test not valid | Original comment sticky mixture, Sep. 15, 2011 results 2,460 Do not use trial lot for F/C Poor mixture, HPC settled to bottom as a slug |
| RD11050A | Aug. 9, 2011 | Oct. 4, 2011 Test not valid | Original comment sticky mixture, results Sep. 15, 2011 3,000 cps (increased during test from 2,400) Do not use trial lot for F/C Poor mixture, HPC settled to bottom as a slug |
| RD11051 | Aug. 9, 2011 | Oct. 4, 2011 2,100 cps▲ | clear, results Sep. 15, 2011 1,940 cps Note: viscosity values increase during 30 sec test |
| RD11051A | Aug. 9, 2011 | Oct. 4, 2011 2,540 cps▲ | clear, results Sep. 15, 2011 2,560 cps Note: viscosity values increase during 30 sec test |
| RD11053 | Aug. 10, 2011 | Oct. 4, 2011 4,500 cps▲ | Clear but sticky with air bubbles, results Sep. 15, 2011 4,060 cps Note: viscosity values increase during 30 sec test |
| RD11054 | Aug. 10, 2011 | Oct. 4, 2011 14,000 cps▲ | Sep. 15, 2011 test HPC globules, 15,000 cps Do not use trial lot for F/C, Note: viscosity values increase during 30 sec test Build up of HPC on spindle |
| RD11055 | Aug. 10, 2011 | | Sep. 15, 2011, EEEEEE |

The TBS-1A Gel In Vitro Release Rate Validation concerning Release Rate Study Summary for TBS-1A Gel 4.0% and TBS-1A Gel 4.5% are presented in Exhibits A and B submitted herewith.

These summaries summarize the release rate experiment data for exemplary TBS-1A Gels. There are four Nasobol Gels (0.15%, 0.6%, 4.0% and 4.5%) for the method validation. The purpose of the Day1 and Day2 test are to determine the specificity and intraday/interday precision of the slope (release rate), Day3 and Day4 are to evaluate the slope sensitivity to the sample strength variation.

See Exhibit A (4.0%) and Exhibit B (4.5%) submitted herewith, both of which are incorporated herein by reference in their entireties.

Example 11

In Vitro Release Rate (Ivrt) Comparison Testing

IVRT experimental approach is used for comparison of products in semi-solid dosage form through evaluation of the drug release. In order to have fair comparison, products to be compared should be of comparable age and their release rates should be determined on the same day, under the same conditions. To ensure an unbiased comparison, sample position within the bank of Franz cells are randomized. The test (T) product and reference (R) product in each run is randomized or pre-assigned in a mixed arrangement.

| Method Parameter Main | Alternate parameters |
|---|---|
| Franz Cells | Franz Cells |
| membrane: durapore 0.45 μm, HVLP02500 | membrane: durapore 0.45 μm, HVLP02500 |
| ring diameter 15 mm | diameter 15 mm |
| surface: 1.767 mm" | surface: 1.767 mm" |
| thickness: 3.2 mm | thickness: 1.63 mm |
| Gel Volume: 565.44 mm" | gel Volume: 288.02 mm" |
| receiving media volume: 12 ml | Volume media recptor: 7.5 ml |
| Ethanol Water 50/50 | ETOH/water 50/50 |
| 600 rpm | 600 rpm |
| Assay | Assay |
| UPLC | HPLC |
| Concentrations from 3 μg/ml to 200 μg/ml | Concentrations 5 μg/ml to 100 μg/ml |

The slope comparison test recommended by the FDA is performed and provides the evidence of the reproducibility of the IVRT method.

Figure 13:
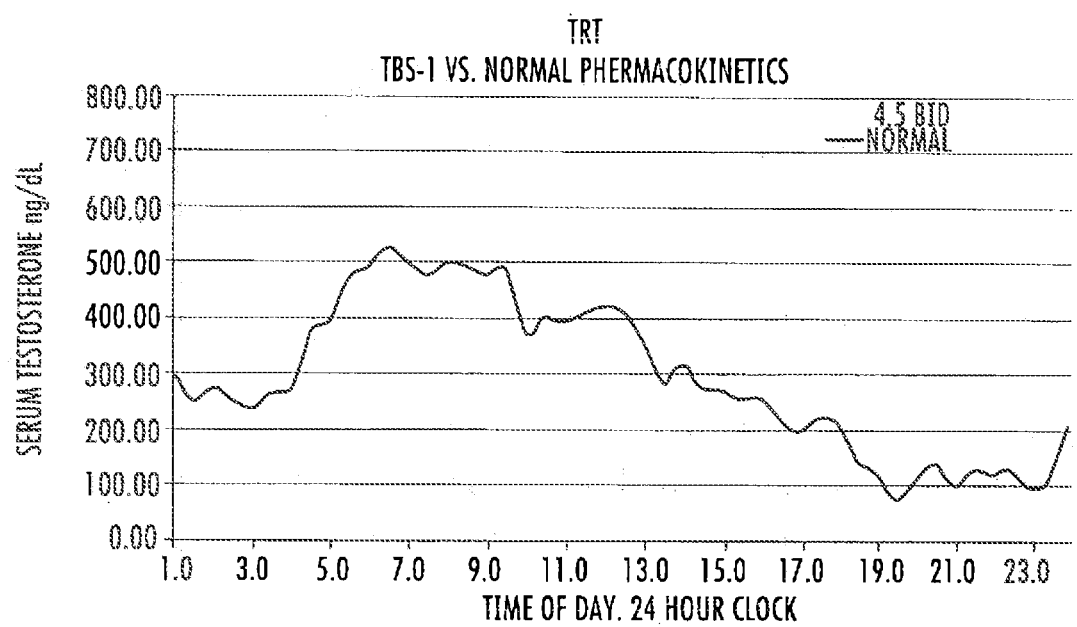
FIG. 13 is a graph showing the change in testosterone levels in serum over time for a 4.5% testosterone bioadhesive gel administered in each nostril of a hypogonadal male twice daily in accordance with the present invention as compared to normal testosterone pharmacokinetics in young healthy adult males, as reported in Diver M J. et al: Diurnal rhythms of total, free and bioavailable testosterone and of SHBG in middle-aged men compared with those in young men. Clinical Endocrinology, 58: 710-717 (2003)

The two different formulations of the testosterone gel products, Table 1, are applied on 12 cells of the modified Franz-Cell apparatus system: 6 cells for reference product (R) and 6 cells for test product (T), as depicted in FIG. 13. The two gel products, Testosterone Nasabol Gel 4%, lot #E10-007, and TBS1A Testosterone Nasal Gel 4%, lot #IMP 11002, are described in Example 6 and designated as 4% TSA-1A and TBS1.

TABLE 1

| Material | TBS1 | TBS-1A 4% (A) |
|---|---|---|
| Dimethyl isosorbide | 0 | 25.0 |
| Diethyleneglycol ethyl ether | 0 | 10.0 |
| Povidone | 0 | 3.0 |
| Copovidone | 0 | 2.0 |
| Hydroxypropyl cellulose | 0 | 0.5 |
| Testosterone micronized | 4.0 | 4.0 |
| Castor oil | 88.0 | 50.5 |
| Labrafil M1944CS | 4.0 | 0 |
| Colloidal silicon dioxide | 4.0 | 5.0 |
| Water | 0 | 0 |
| Total | 100.0 | 100.0 |

Samples are collected at 1, 2, 3, 4, 5 and 6 hours and are tested.

Franz Cell Apparatus Position Layouts for Comparison Testing

The Release Rates (slope) from the six cells of T-product and from the other six cells of the R-product are obtained. A 90% Confidence Interval (CI) for the ratio (T/R) of median release rates is computed.

A table with six rows and seven columns is generated and reference slopes (RS) are listed across the first row and test slopes (TS) are listed down the first column of Table 2. Individual T/R ratios (30) between each test slope and each reference slope are computed and the corresponding values are entered in the table.

TABLE 2

Calculation of T/R Ratios

| Slope | RS1 | RS2 | RS3 | RS4 | RS5 | RS6 |
|---|---|---|---|---|---|---|
| TS1 | TS 1/RS 1 | TS 1/RS2 | TS 1/RS3 | TS 1/RS4 | TS 1/RS5 | TS 1/RS6 |
| TS2 | TS2/RS 1 | TS2/RS2 | TS2/RS3 | TS2/RS4 | TS2/RS5 | TS2/RS6 |
| TS3 | TS3/RS 1 | TS3/RS2 | TS3/RS3 | TS3/RS4 | TS3/RS5 | TS3/RS6 |
| TS4 | TS4/RS I | TS4/RS2 | TS4/RS3 | TS4/RS4 | TS4/RS5 | TS4/RS6 |
| TS5 | TS5/RS 1 | TS5/RS2 | TS5/RS3 | TS5/RS4 | TS5/RS5 | TS5/RS6 |
| TS6 | TS6/RS 1 | TS6/RS2 | TS6/RS3 | TS6/RS4 | TS6/RS5 | TS6/RS6 |

These 30 T/R ratios are ranked from lowest to highest. The sixth and twenty-fifth ordered ratios represent low and upper limits of the 90% CI for the ratios of median release rates.

Standard Criteria:

Test and reference product are considered to be the same if the 90% CI falls within the limits of 75%-133.3%.

Two batches of Testosterone Nasabol Gel 4%, lot #E10-007, and TBS1A Testosterone Nasal Gel 4%, lot #IMP 11002, are tested and evaluated for sameness.

A statistical comparison is carried out by taking the ratio of release rates from 6 cells of the reference lot #E10-007 (R) against 5 cells of the test batch lot #IMP 11002 (T).

During the in vitro drug releases test, the reference batch and the test batch are applied in a randomized manner on the cells on Apparatus A and B of the modified Franz Cell System.

Release Rate (slope) from five cells of the test product (T) and six cells of the reference product (R) are compared. A 90% Confidence Interval (CI) for the ratio (T/R) of median release rates is computed.

The 90% Confidence Interval is represented by the sixth and twenty-fifth Release Rate ratios when ranked from lowest to highest. These ratios correspond to 160.77% and 202.90% respectively and do not meet the limits for sameness (CI 75%-133.33%). Therefore, the two batches of Testosterone Nasabol Gel 4%, lot #E10-007 and TBS1A Testosterone Nasal Gel 4%, lot #IMP 11002 are not considered the same.

Two gel products, Testosterone Nasabol Gel 4%, lot #E10-007, and TBS1A Testosterone Nasal Gel 4%, lot #IMP 11002, are tested and evaluated for sameness. The Mean Release Rate (slope) for the Test lot #IMP 11002 is about 1.8 times higher than for the Reference lot #E10-007. The two tested products are found to be not the same.

Figure 47:
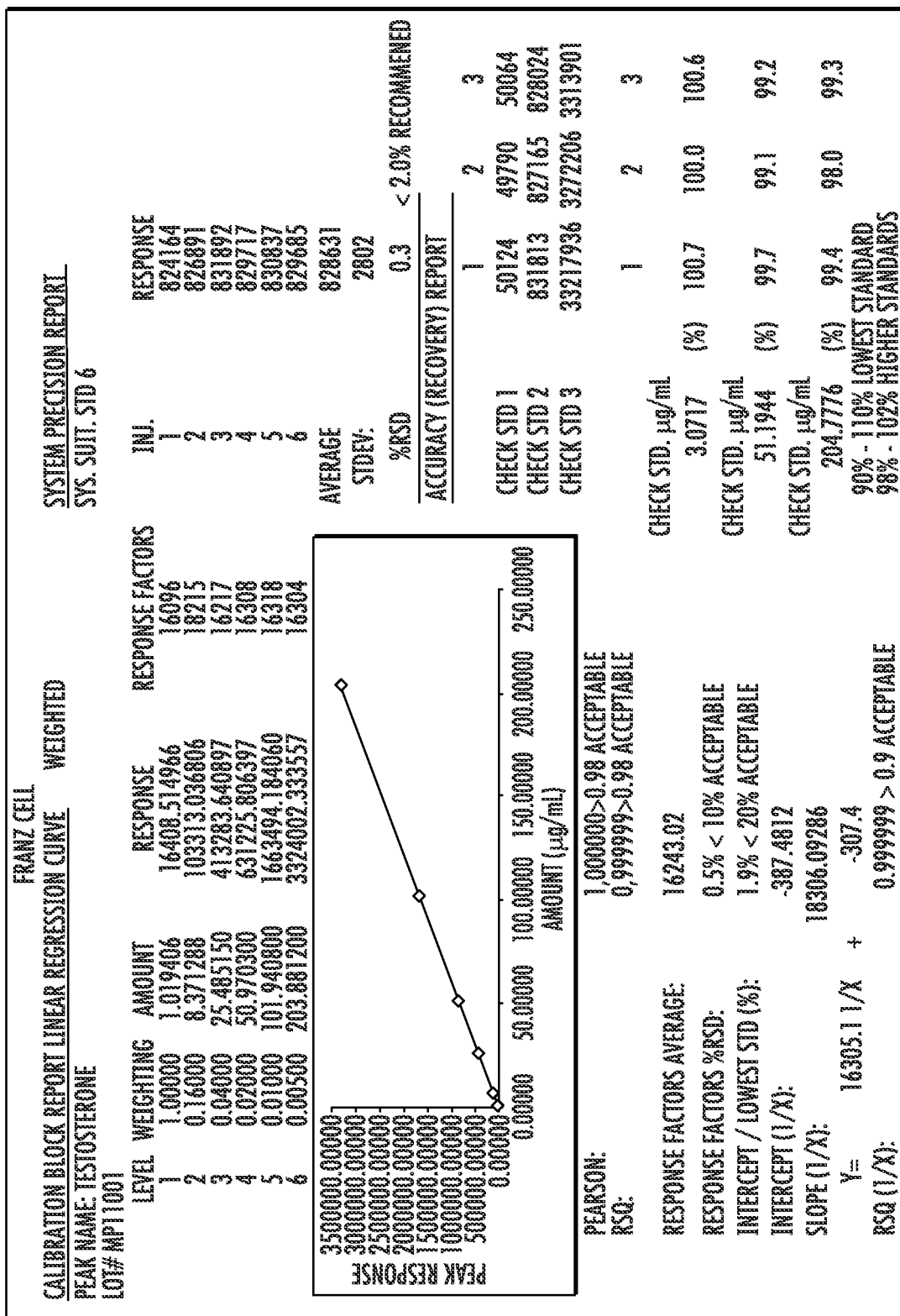
FIG. 47 depicts the In Vitro Release Rate (IVRT) testing results and new data.

The In Vitro Release Rate (IVRT) testing results and raw data are in Tables 3-8 below FIGS. 23 and 47.

Figure 38:
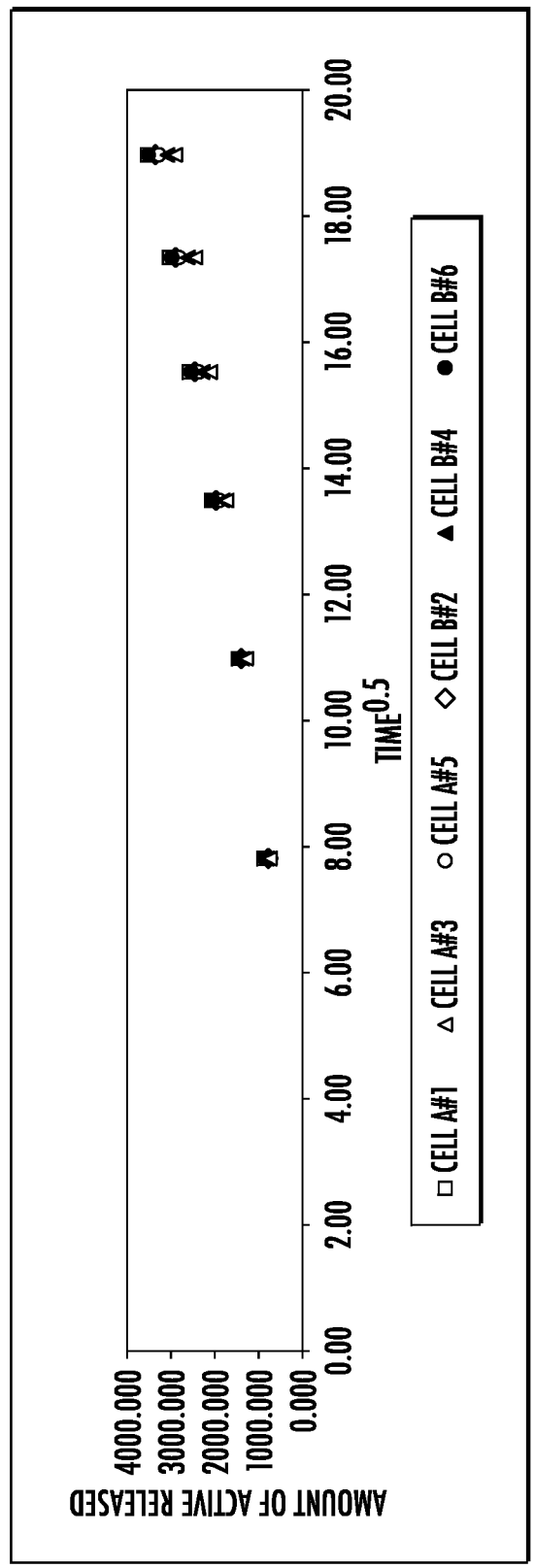
FIG. 38 depicts the peak response as a function of dosage.
Figure 39:
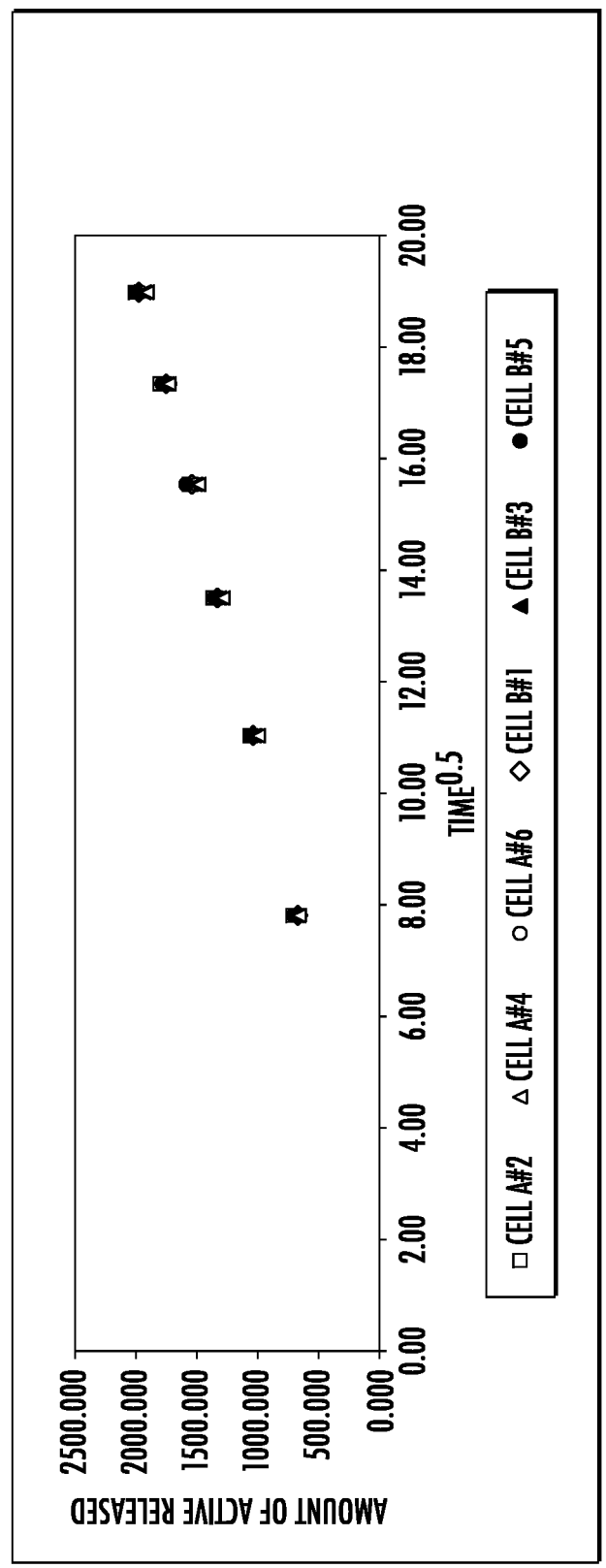
FIG. 39 depicts the active release amount over time.

Tables 4 and 5 are graphically represented in FIGS. 38 and 39 respectively.

TABLE 5

4% Gel Release Rate Comparison
Testosterone Nasobol Gel 4% Gel
Reference Lot# E10-007

Concentration of Active (µg/mL) versus Time
Amount Released (µg/mL) Calculation by Linear Regression Curve

| Time | Cell A #2 | Cell A#4 | Cell A#5 | Cell B#1 | Cell B#3 | Cell B#5 | Mean 1-6 | % RSD 1-6 |
|---|---|---|---|---|---|---|---|---|
| 60.00 | 96.792 | 104.726 | 101.499 | 98.956 | 96.994 | 101.074 | 100.341 | 2.7 |
| 120.00 | 143.746 | 153.402 | 151.866 | 148.611 | 146.111 | 152.389 | 149.356 | 2.6 |
| 180.00 | 181.187 | 191.204 | 190.149 | 185.651 | 182.536 | 188.818 | 186.591 | 2.2 |
| 240.00 | 206.803 | 219.307 | 216.557 | 214.046 | 212.670 | 218.650 | 214.672 | 2.2 |
| 300.00 | 234.373 | 243.717 | 243.534 | 239.656 | 238.437 | 241.174 | 240.165 | 1.5 |
| 360.00 | 253.244 | 262.615 | 261.716 | 259.500 | 255.210 | 263.639 | 259.321 | 1.6 |

TABLE 5-continued

4% Gel Release Rate Comparison
Testosterone Nasobol Gel 4% Gel
Reference Lot# E10-007

Actual Amont of Active Released (µg/cm$^2$) versus Time$^{0.5}$
Amount Released (µg/cm$^2$)

| | Cell A#2 | Cell A#4 | Cell A#6 | Cell B#1 | Cell B#3 | Cell B#5 | Mean 1-6 | % RSD 1-6 |
|---|---|---|---|---|---|---|---|---|
| Time$^{0.5}$ | | | | | | | | |
| 7.71 | 657.294 | 711.172 | 689.258 | 672.003 | 672.247 | 686.372 | 681.391 | 2.7 |
| 10.95 | 1003.536 | 1071.352 | 1060.212 | 1037.186 | 1020.219 | 1063.304 | 1042.635 | 2.6 |
| 13.42 | 1298.462 | 1371.463 | 1382.858 | 1330.766 | 1308.915 | 1353.934 | 1337.750 | 2.2 |
| 15.49 | 1523.682 | 1616.405 | 1596.093 | 1576.120 | 1565.197 | 1609.943 | 1581.240 | 2.2 |
| 17.32 | 1769.419 | 1844.221 | 1841.242 | 1810.596 | 1800.351 | 1824.766 | 1815.099 | 1.5 |
| 18.97 | 1963.883 | 2041.513 | 2032.959 | 2013.163 | 1981.718 | 2045.561 | 2013.135 | 1.7 |
| Slope | 116.80 | 119.04 | 120.10 | 119.69 | 118.02 | 129.59 | 119.04 | 1.2 |
| R$^2$ | 0.9998 | 0.9997 | 0.9996 | 0.9996 | 0.9992 | 0.9997 | 0.9995 | 0.0 |

TABLE 6

Comparison Study Franz Cell
Release Rate Comparison

R - Reference Lot# E10-007    Testosterone Nasobol Gel 4% Gel
T - Test Lot# IMP 11002    TBS1A Testosterone Nasal Gel 4%

| | R | | | | | |
|---|---|---|---|---|---|---|
| T | 116.80 | 119.04 | 120.10 | 119.69 | 118.02 | 120.59 |
| 242.85 | 2.0792 | 2.0401 | 2.0221 | 2.0290 | 2.0577 | 2.0138 |
| 187.78 | 1.6077 | 1.5775 | 1.5635 | 1.5689 | 1.5911 | 1.5572 |
| 217.83 | 1.8650 | 1.8299 | 1.8137 | 1.8200 | 1.8457 | 1.8064 |
| 239.55 | 2.0509 | 2.0123 | 1.9946 | 2.0014 | 2.0297 | 1.9865 |
| 213.29 | 1.8261 | 1.7918 | 1.7759 | 1.7820 | 1.8072 | 1.7687 |

Note:
Test Lot Vial# B#6 at 2 hour was missing injection. Comparison calculated by 5 × 6 = 30 individual T/R ratios, and the limits of 90% would be sixth and twenty-fifth order individual T/R ratios.

TABLE 7

| Sixth Ordered Ratio: | 160.77% |
|---|---|
| Twenty-fifth Ordered Ratio: | 202.90% |

Test and reference products are considered to be the "same" if the 90% CI falls within the limits of 75%-133.33%.

TABLE 8

Amount of Active Released (µg/cm$^2$)

| Time$^{0.5}$ | Lot# IMP11002 | Lot# E10-007 |
|---|---|---|
| 7.75 | 807.400 | 681.391 |
| 10.95 | 1360.268 | 1042.635 |
| 13.42 | 1922.042 | 1337.75 |
| 15.49 | 2378.231 | 1581.24 |
| 17.32 | 2816.161 | 1815.099 |
| 18.97 | 3285.301 | 2013.135 |

TABLE 9

In Vitro release Rate Testing
Products: TBS1A Testosterone Nasal Gel 4% and Testosterone Nasobol Gel 4%
Objective: Release rate comparison between the two testosterone gel products.

| Side | Sample Information | Release Rate Results |
|---|---|---|
| Reference Batch | Testosterone Nasobol Gel 4% The reference Lot #E10-007 Expiry date: N/A Diteba Sample ID: CSB-SPL-00200 Number of Cells: 6 Position of Cells: System (1) A#2, #4, #6; System (2) B#1, #3, #5 | Average slope: 119.87 µg/cm$^2$ · min$^{-0.5}$ RSD of Slopes: 1.8% R$^2$ of Lowest Linearity: 0.9995 |
| Test Batch | TBS1A Testosterone Nasal Gel 4% The test batch (Lot #IMP 11001) Expiry date: N/A Diteba Sample ID: CSB-SPL-00209 Number of Cells: 6 Position of Cells System (1) A#1, #3, #5; System (2) B#2, #4, #6 | Average slope: 300.02 µg/cm$^2$ · min$^{-0.5}$ RSD of Slopes: 9.3% R$^2$ of Lowest Linearity: 0.9995 |

TABLE 9-continued

In Vitro release Rate Testing
Products: TBS1A Testosterone Nasal Gel 4% and Testosterone Nasobol Gel 4%
Objective: Release rate comparison between the two testosterone gel products.

| Side | Sample Information | Release Rate Results |
|---|---|---|
| Release Rate Comparison | | Comparison Results<br>Comparison Limits: 75.00% to 1.33.33% |
| | Stage One | $8^{th}$ ordered ratio: 228.50%<br>$29^{th}$ ordered ratio: 264.03% |
| | Stage Two | $110^{th}$ ordered ratio: N/A<br>$215^{th}$ ordered ratio: N.A |

Example 12

A Phase-1 Open Label, Balanced, Randomized, Crossover, Two Groups, Two-Treatments, Two-Period, Pilot Study in Healthy Male Subjects A phase-1 open label, balanced, randomized, crossover, two groups, two-treatments, two-period, pilot study in healthy male subjects to determine the feasibility of a multiple dose dispenser for testosterone intranasal gel as measured by pharmacokinetics Testosterone replacement therapy aims to correct testosterone deficiency in hypogonadal men. Trimel BioPharma has developed an intranasal testosterone gel (TBS-1) as alternative to the currently available testosterone administration forms. To date, a syringe was used to deliver TBS-1 in clinical studies. Trimel identified a multiple dose dispenser intended for commercial use. The purpose of this study was to demonstrate the relative performance of the multiple dose dispenser in comparison to the syringe used previously in clinical trials.

This was an open label, balanced, randomized, crossover, two-group, two-treatment, two-period, pharmacokinetic study of TBS-1 testosterone nasal gel in healthy, male subjects aged 18 to 28. Treatment consisted of 4.5% TBS-1 testosterone gel as a single dose of 5.5 mg of testosterone per nostril, delivered using either a syringe or the multiple dose dispenser, for a total dose of 11.0 mg given at 21:00 hours. Prior to first administration, subjects were admitted to the unit for blood sampling in order to determine a baseline testosterone profile. Wash-out between drug administrations was at least 48 hours.

All subjects completed the study successfully and treatment was well tolerated.

The total exposure to testosterone as estimated by the mean area under the serum concentration-time curve ($AUC_{0-12}$ in ng·hr/dL), is higher after TBS-1 administration using the dispenser or syringe than endogenous levels alone (7484 and 7266, respectively, versus 4911 ng*h/dL. Mean $C_{max}$ is higher after administration with the dispenser than after administration using a syringe (1028 versus 778.8 ng/dL, respectively). $T_{max}$ occurs earlier following administration using the dispenser compared to the syringe (2.75 versus 5.6 hours, respectively. Thus, testosterone absorption seems to be faster with the multiple dose dispenser than with a syringe, but the total absorbed amount is similar. Also, in previous studies the syringe Tmax obtained in patient was closer to 1.0 or 2.0 hours.

Figure 3:
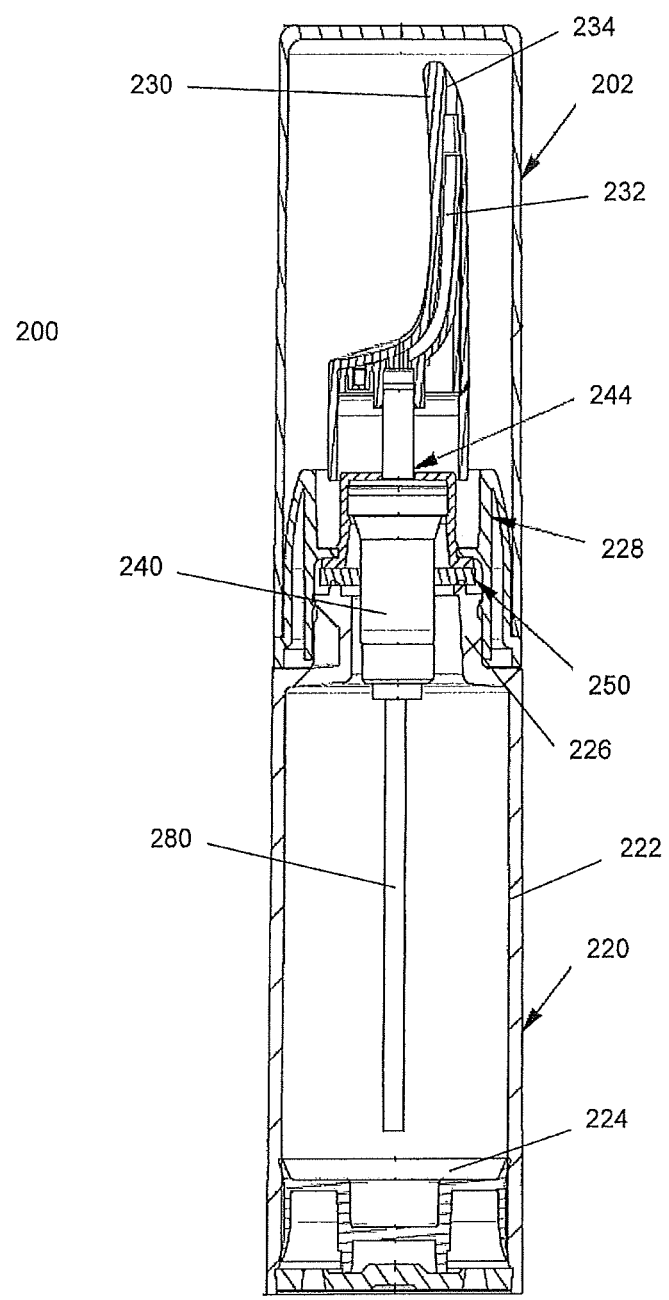
FIG. 3 is a side view of a second embodiment of the invention.
Figure 4:
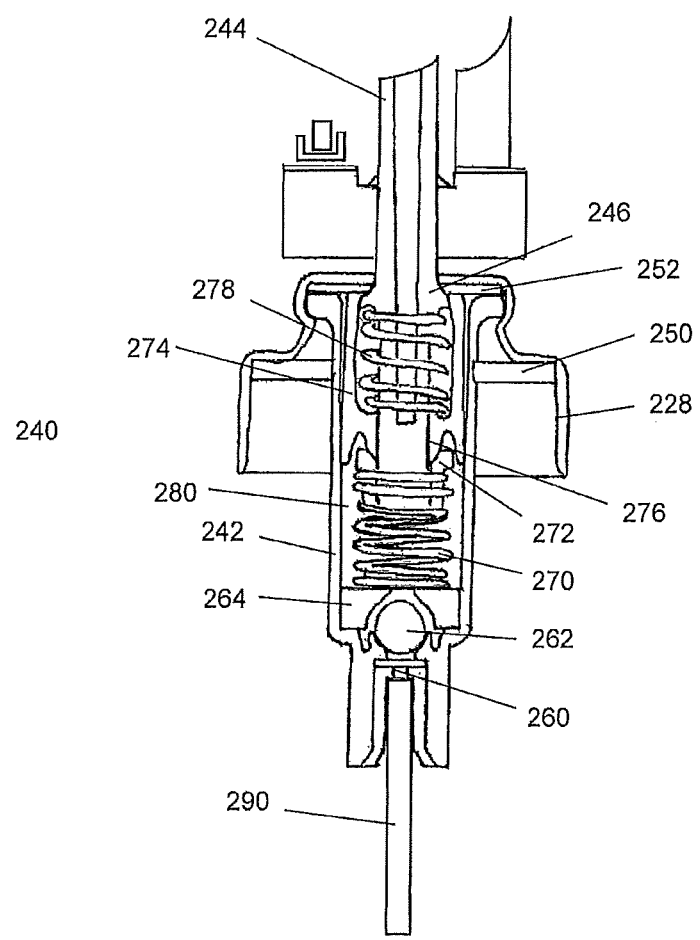
FIG. 4 is a cross-sectional side view of the distributor pump of the second embodiment of the invention.
Figure 5:
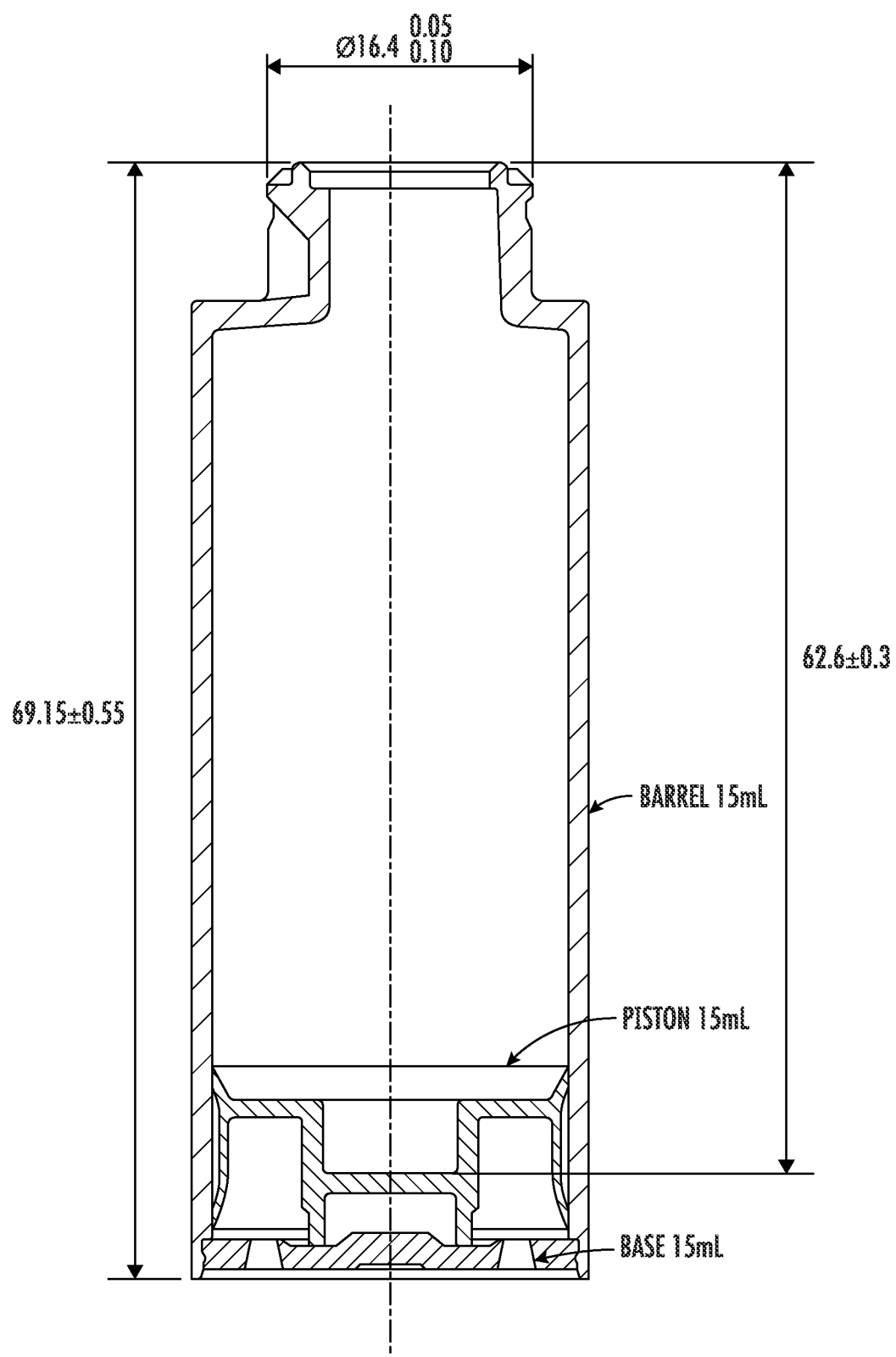
FIG. 5 is a side view of a second embodiment of the invention concerning an airless bottle assembly of the invention.
Figure 6:
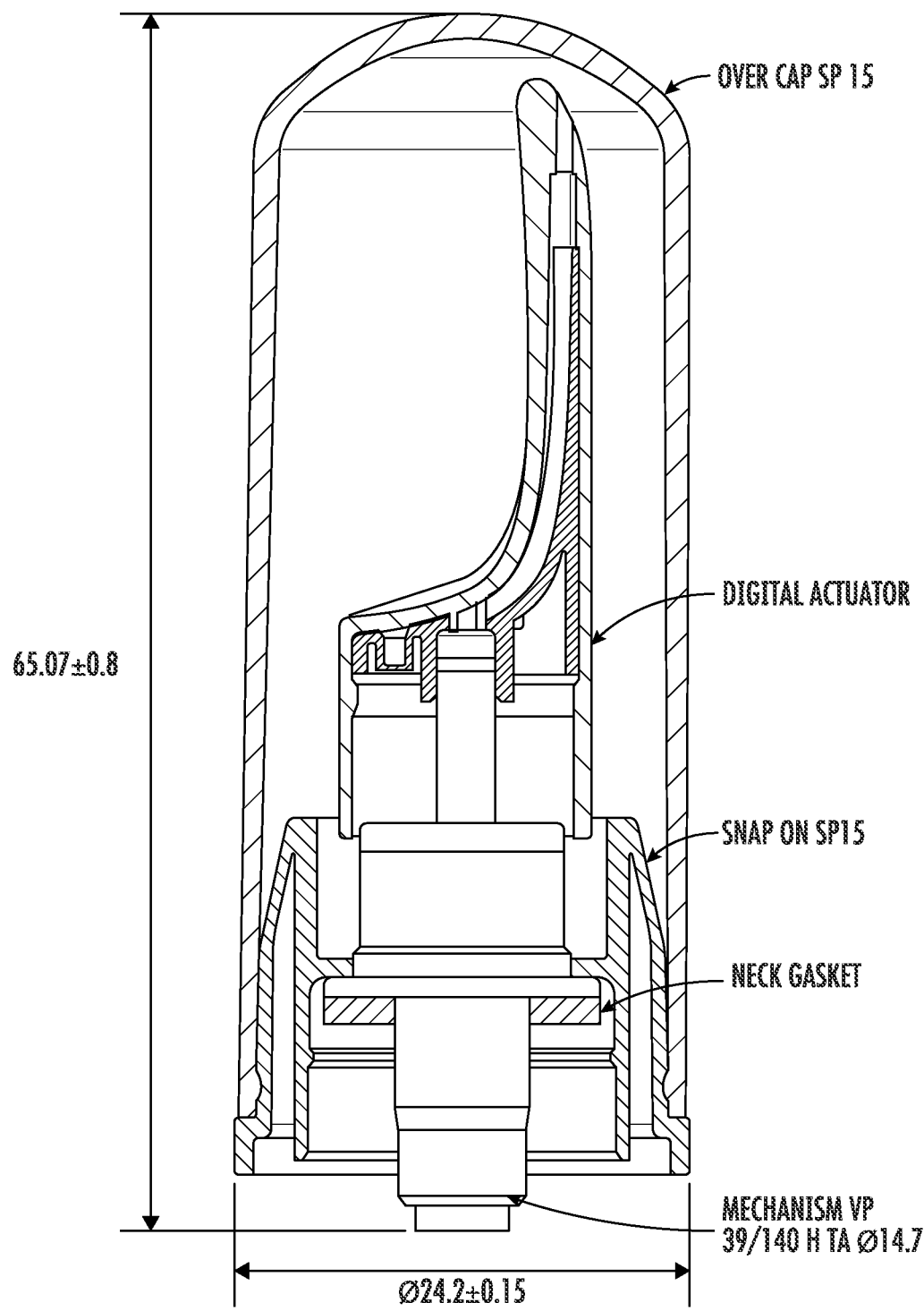
FIG. 6 is a side view of a second embodiment of the invention concerning digital actuator and rounded cap.
Figure 7A:
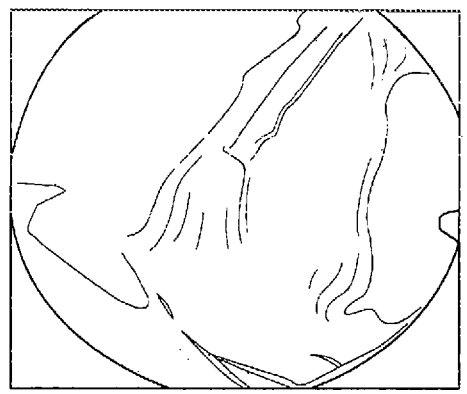
FIG. 7A depicts the right nostril of subject #1 after a single dose syringe administration.
Figure 7B:
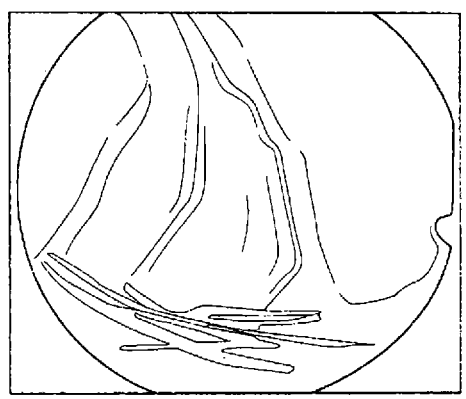
FIG. 7B depicts the left nostril of subject #1 after a multiple dose dispenser administration.
Figure 8A:
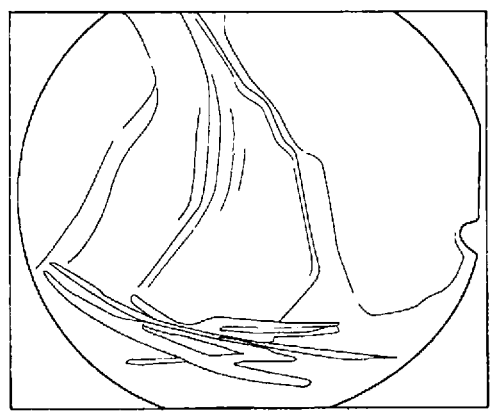
FIG. 8A depicts the right nostril of subject #2 after a single dose syringe administration.
Figure 8B:
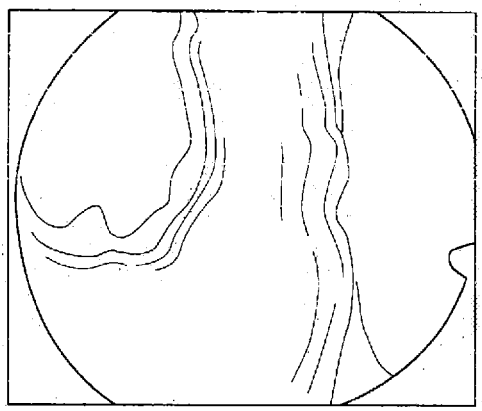
FIG. 8B depicts the left nostril of subject #2 after a multiple dose dispenser administration.
Figure 9A:
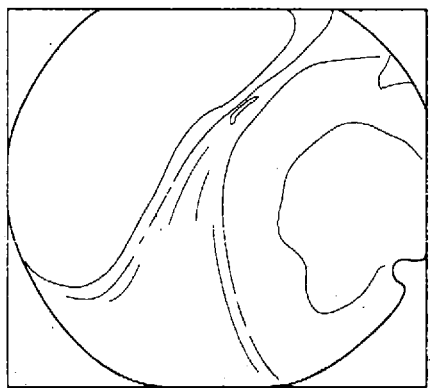
FIG. 9A depicts the right nostril of subject #3 after a single dose syringe administration.
Figure 9B:
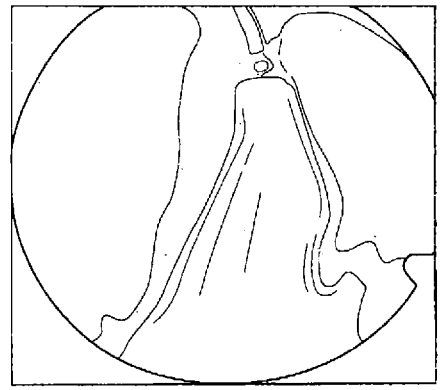
FIG. 9B depicts the left nostril of subject #3 after a multiple dose dispenser administration.
Figure 10A:
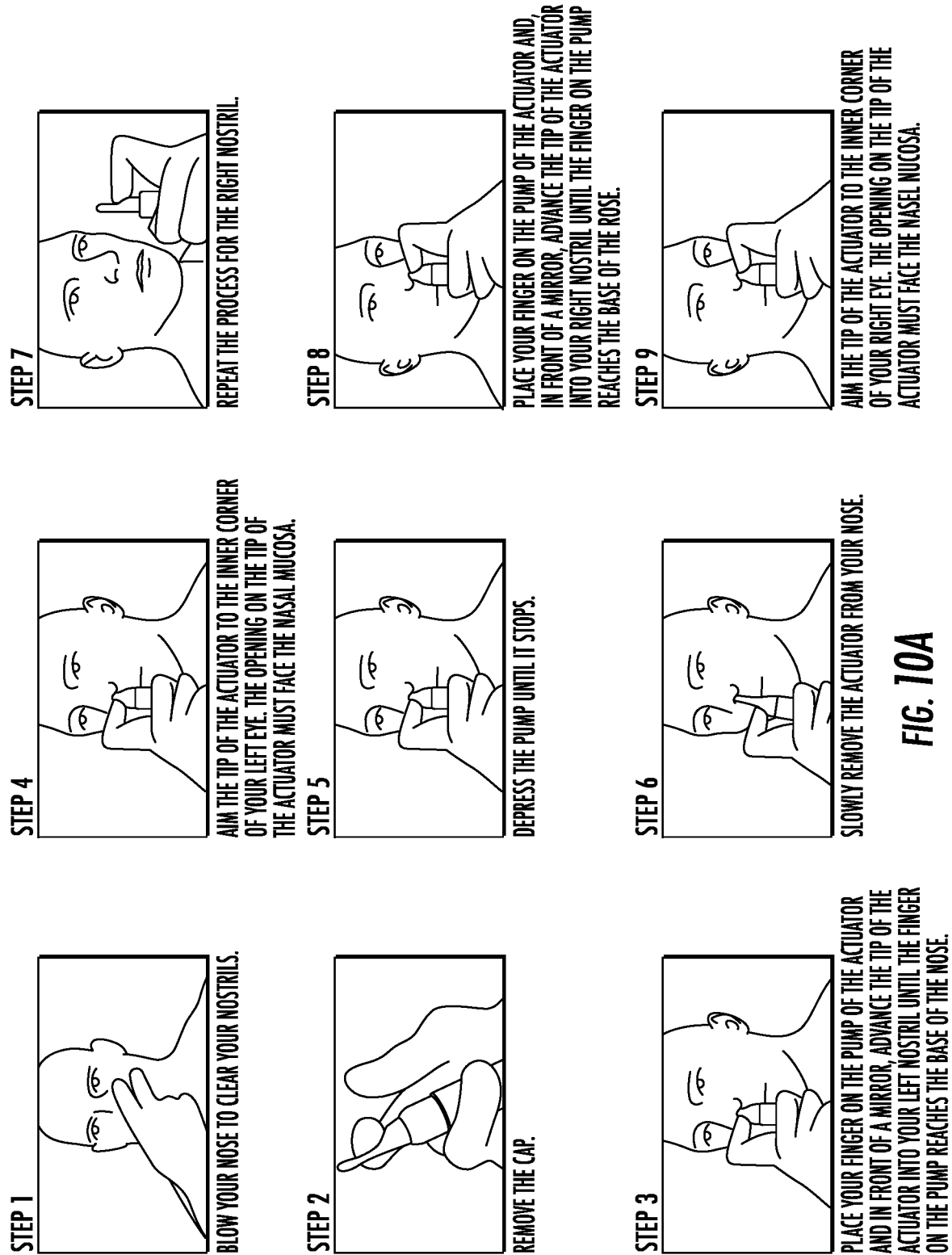
FIGS. 10A and 10B illustrate use of a multiple dose dispenser in accordance with the present invention.

When plotting probability density of the log ratio of testosterone levels reached with the multiple dose dispenser over levels reached with the syringe as shown in FIG. 3, no significant difference was demonstrated for either $AUC_{0-12}$ or $C_{max}$ within the lower and upper limit of the 95% confidence intervals. There is a trend toward a difference for $C_{max}$. However, this data does not confirm bioequivalence at a confidence interval level of 90% for either $AUC_{0-12}$ or $C_{max}$. If the trends found here are confirmed in a larger data set, the routes of administration would be almost equivalent for $AUC_{0-12}$, but t for $C_{max}$ further investigation may be required as the Cmax/tmax profile obtained in volunteers does not seem to match the one obtained in patients.

Testosterone as a Treatment for Hypogonadism

Endogenous androgens are responsible for the normal growth and development of the male sex organs as well as promoting secondary sex characteristics including the growth and maturation of the prostate, seminal vesicles, penis, and scrotum; the development of male hair distribution, such as beard, pubic, chest, and axillary hair, laryngeal enlargements, vocal cord thickening, alterations in body musculature, and fat distribution.

Hypogonadism in men is characterized by a reduced concentration of serum testosterone resulting in signs and symptoms that may include decreased libido, erectile dysfunction, decreased volume of ejaculate, loss of body and facial hair, decreased bone density, decreased lean body mass, increased body fat, fatigue, weakness and anaemia.

The causes of hypogonadism can be primary or secondary in nature. In primary hypogonadism (congenital or acquired) testicular failure can be caused by cryptorchidism, bilateral torsion, orchitis, vanishing testis syndrome, orchidectomy, Klinefelter's syndrome, chemotherapy, or toxic damage from alcohol or heavy metals. These men usually have low serum testosterone levels and serum gonadotropin levels (FSH, LH) above the normal range.

In secondary hypogonadism (Hypogonadotropic Hypogonadism (congenital or acquired)) the defects reside outside the testes, and are usually at the level of the hypothalamus or the pituitary gland. Secondary hypogonadism can be caused by Idiopathic Gonadotropin or LHRH deficiency, or pituitary hypothalamic injury from tumors, trauma, or radiation. These men have low serum testosterone levels but have serum gonadotropin levels in the normal or low ranges.

Testosterone hormone therapy is indicated as a hormone replacement therapy in males for conditions associated with a deficiency or absence of endogenous testosterone. The currently available options for administration of testosterone are oral, buccal, injectable, and transdermal.

Trimel BioPharma has developed an intranasal testosterone gel (TBS-1) as a hormone replacement therapy for the treatment of male hypogonadism. The nasal mucosa offers an alternative route of administration that is not subjected to first pass metabolism, has high permeability, with rapid absorption into the systemic circulation. The advantages of the testosterone intranasal gel when compared to other formulations include ease of administration and no transference of testosterone to other family members.

Investigational Medicinal Product

The investigational medicinal product in this trial was TBS-1, an intranasal testosterone dosage form. A description of its physical, chemical and pharmaceutical properties can be found in the Investigator's Brochure.

Summary of Non-Clinical and Clinical Studies

Summary of Non-Clinical Studies

An overview of the pharmacology, toxicology and pre-clinical pharmacokinetics of different testosterone preparations and administration routes is provided in the Investigator's Brochure Product-specific repeat dose toxicity and tolerance studies have been performed in ex vivo models and in different animal species.

Summary of Previous TBS-1 Clinical Studies

To date, Trimel has completed four Phase II clinical trials in hypogonadal men. The most recently conducted study, TBS-1-2010-01, is described below and the other studies are summarized in the Investigator's Brochure.

The objective of study TBS-1-2010-01 is to examine the efficacy and tolerability of 4.0% and 4.5% TBS-1 testosterone gel in hypogonadal men. In this study, TBS-1 is administered using a syringe, not the commercial multiple dose dispenser. The doses and dosing regimens that were used in study TBS-1-2010-01 are described in Table 1 below.

The results from all treatment groups met the FDA criteria for efficacy; defined as that at least 75% of subjects should achieve an average total T concentration ($C_{avg}$) in the normal range, a 24 hour $C_{avg}$ value ≥300 ng/dL and ≤1050 ng/dL.

TABLE 1

Summary of previous TBS-1 studies

| Dosing regimen | Total daily dose | $C_{avg}$ (% of subjects with $C_{avg}$ within the reference range) |
|---|---|---|
| 13.5 mg of TBS-1 (4.5%) BID | 27 mg/day | 419 ng/dL (100%) |
| 10.0 mg of TBS-1 (4.0%) TID | 30 mg/day | 413 ng/dL (87%) |
| 11.25 mg of TBS-1 (4.5%) TID | 33.75 mg/day | 396 ng/dL (85%) |

Summary of Benefits and Risks to Subjects

Benefits

Testosterone replacement therapy for hypogonadal men should correct the clinical abnormalities of testosterone deficiency. Since this was a Phase I study enrolling normal healthy men between the ages of 18-45, for a short period of time, it was not anticipated that these volunteers would directly benefit by taking part in this study. Volunteers were financially compensated for their participation.

Risks

The risk to the subject by participating in this study was considered to be minimal. Testosterone replacement therapy is indicated for the treatment of hypogonadism and TBS-1 has been administered to over 100 men with minimal side effects.

As TBS-1 is an investigational drug that is in clinical development, the complete side effect profile was not fully known. Epistaxis, nasal congestion, nasal discomfort, nasal dryness and nasal inflammation have been reported following use of TBS-1. Side effects from approved (prolonged) testosterone replacement therapy include elevated liver enzymes (alanine aminotransferase, aspartate aminotransferase), increased blood creatine phosphokinase, increase in prostatic specific antigen, decreased diastolic blood pressure, increased blood pressure, gynecomastia, headache, increased hematocrit/hemoglobin levels, hot flushes, insomnia, increased lacrimation, mood swings, smell disorder, spontaneous penile erection, and taste disorder.

The main benefit of the intranasal drug delivery route is that with this method many of the different disadvantages observed with other products would not be expected. This would include skin-to-skin transfer, stickiness, unpleasant smell (gels), skin irritation (patches), elevated DHT (patches and oral), injection pain and high T and DHT peaks (intramuscular injection), food interaction (oral).

Trial Rationale

Trimel identified a multiple dose dispenser that was intended as the commercial dispenser to be used in this clinical trial program. To date, a syringe has been used to deliver TBS-1 in the previous clinical trials. The purpose of this study was to demonstrate the comparability of the pharmacokinetic results obtained with a multiple dose dispenser or a syringe.

REFERENCES

1. Nasobol® Investigator Brochure Release Date 19 Aug. 2010, Edition No: 5.
2. http://www.androgel.com/pdf/500122-00127_Rev_1E_Sep_2009_FPI_with_MedGuide.pdf (Last accessed on 6 Sep. 2010).
3. http://www.mattern-pharmaceuticals.com/downloads/Nasobol.pdf (Last accessed on 6 Sep. 2010).
4. http://www.medicines.org.uk/EMC/medicine/22159/SPC/Testim+Gel/(Last accessed on 6 Sep. 2010).

Study Objectives

The primary study objective is to compare a pharmacokinetic profile of testosterone after administration of TBS-1 using two different dispensers in healthy male subjects.

The secondary objective is to assess the safety of TBS-1.

Investigational Plan

Overall Study Design and Plan

This is an open label, balanced, randomized, crossover, two-group, two-treatment, two-period, pharmacokinetic study of testosterone nasal gel formulation in healthy, adult, male human subjects. The study event schedule is summarized in Section?????in Table 2.

Healthy male volunteers, aged 18 to 45 years (inclusive) were screened for this study. The goal was to randomize 12 male subjects for the study.

There was a washout period of 6 days between each drug administration.

Discussion of Study Design

As this is a relatively small Phase I PK study with the intent to compare a pharmacokinetic profile of testosterone after administration of TBS-1 from two different dispensers in healthy male subjects, a true sample size calculation is not performed. Based on typical early-stage, pharmacokinetic studies, groups of 6 subjects per cohort are sufficient for an acceptable description of the pharmacokinetic parameters after single dose administration.

Selection of Study Population

Inclusion Criteria

The following eligibility assessments have to be met for subjects to be enrolled into the study:
1. Healthy male human subjects within the age range of 18 to 45 years inclusive
2. Willingness to provide written informed consent to participate in the study
3. Body-mass index of ≤35 kg/m²

4. Absence of significant disease or clinically significant abnormal laboratory values on laboratory evaluations, medical history or physical examination during screening
 5. Normal otorhinolaryngological examination
 6. Non-smokers for at least six months
 7. Comprehension of the nature and purpose of the study and compliance with the requirement of the protocol Exclusion Criteria A subject is not eligible for inclusion in this study if any of the following criteria applied:
 1. Personal/family history of allergy or hypersensitivity to testosterone or related drugs
 2. Past history of anaphylaxis or angioedema
 3. Any major illness in the past three months or any clinically significant ongoing chronic medical illness e.g. congestive heart failure, hepatitis, pancreatitis etc.
 4. Presence of any clinically significant abnormal values during screening e.g. significant abnormality of Liver Function Test (LFT), Renal (kidney) Function Test (RFT), etc.
 5. Hemoglobin <13 g/dl and Hematocrit >52% during screening
 6. Any cardiac, renal or liver impairment, any other organ or system impairment
 7. History of seizure or clinically significant psychiatric disorders
 8. Presence of disease markers for HIV 1 and/or 2, Hepatitis B and/or C virus
 9. History of nasal surgery, specifically turbinoplasty, septoplasty, rhinoplasty, ("nose job"), or sinus surgery
 10. Subject with prior nasal fractures
 11. Subject with active allergies, such as rhinitis, rhinorrhea, or nasal congestion
 12. Subject with mucosal inflammatory disorders, specifically pemphigus, or Sjogren's syndrome
 13. Subject with sinus disease, specifically acute sinusitis, chronic sinusitis, or allergic fungal sinusitis
 14. History of nasal disorders (e.g. polyposis, recurrent epistaxis (>1 nose bleed per month), abuse of nasal decongestants) or sleep apnea
 15. Subject using any form of intranasal medication delivery, specifically nasal corticosteroids and oxymetazoline containing nasal sprays (e.g. Dristan 12-Hour Nasal Spray)
 16. History of asthma and/or on-going asthma treatment
 17. Regular drinkers of more than three (3) units of alcohol daily (1 unit=300 ml beer, 1 glass wine, 1 measure spirit), or consumption of alcohol within 48 hours prior to dosing and during the study.
 18. Volunteer demonstrating a positive test for alcohol consumption (using breath alcohol analyzer) at the time of check-in during the admission periods.
 19. History of, or current evidence of, abuse of alcohol or any drug substance, licit or illicit
 20. Volunteers demonstrating a positive test for drugs of abuse in urine (Opiates, Benzodiazepines, Amphetamines, THC and cocaine) at the time of check-in during admission periods
 21. Inaccessibility of veins in left and right arm
 22. Receipt of any prescription drug therapy within four weeks of the first admission period.
 23. Difficulty in abstaining from OTC medication (except occasional paracetamol/aspirin) for the duration of the study
 24. Volunteers demonstrating serum PSA 4 ng/ml
 25. Participation in any other research study during the conduct of this study or 30 days prior to the initiation of this study.
 26. Blood donation (usually 550 ml) at any time during this study, or within the 12 week period before the start of this study.

Removal of Patients from Therapy or Assessment

All 12 subjects who enroll, complete the study successfully, and no subjects are replaced.

Treatments

Treatments Administered

For the drug administration, subjects are instructed on how TBS-1 is applied intranasally with the pre-filled syringes or the multiple dose dispensers. Self-administration of TBS-1 is monitored by the study personnel. Each subject is instructed not to sniff or blow his nose for the first hour after administration.

TABLE 2

| | | Treatment schedule | | |
|---|---|---|---|---|
| GROUP | Subject number | BASELINE Day 1/2 Time 21:00-09:00 | PERIOD I Day 2/3 Time 21:00-09:00 | PERIOD II Day 4/5 Time 21:00-09:00 |
| A | 1-6 | 12 hour baseline T profile | TREATMENT 1 | TREATMENT 2 |
| B | 7-12 | 12 hour baseline T profile | TREATMENT 2 | TREATMENT 1 |

Treatment 1 consists of TBS-1 syringes that are pre-filled with 4.5% testosterone gel to deliver a single dose of 5.5 mg of testosterone per nostril, for a total dose of 11.0 mg that is administered at 21:00 hours (±30 minutes) on Day 2 of Period I for Group A and Day 4 of Period II for Group B.

Treatment 2 consists of a TBS-1 multiple dose dispensers that are pre-filled with 4.5% testosterone gel to deliver a single dose of 5.5 mg of testosterone per nostril, for a total dose of 11.0 mg that is administered at 21:00 hours (±30 minutes) on Day 2 of Period I for Group B and Day 4 of Period II for Group A.

Identity of Investigational Product(s)

The investigational product in this trial is TBS-1, an intranasal testosterone dosage form.

Study medication consists of TBS-1 gel and is packed either in a single use syringe that is designed to expel 125 μl of gel, with two syringes packaged per foil pouch, or in a multiple dose dispenser that is designed to expel 125 μl of gel/actuation.

Study medication is dispensed by the study pharmacist who prepares the individual study kits which contained two syringes in a pouch or the multiple dose dispenser.

Method of Assigning Patients to Treatment Groups

Treatment assignment is determined according to the randomization schedule at the end of Visit 1. Subjects who met the entry criteria are assigned randomly on a 1:1 basis to one of the two treatment groups (Group A or Group B). The randomization is balanced and the code is kept under controlled access. The personnel that are involved in dispensing of study drug is accountable for ensuring compliance to the randomization schedule.

Selection and Timing of Dose

As healthy males have endogenous testosterone levels that fluctuate with a circadian rhythm which peaks in the early morning, it is decided to dose the study medication at night.

Blinding

This is an open-label study for both the subjects and the investigator, as the physical differences in the intranasal dosing dispensers prevent blinding.

Prior and Concomitant Therapy

None of the subjects use prescription medication immediately prior to, during or the 2 weeks after the study. One subject receives a single dose of paracetamol (2 tablets of 500 mg) just before discharge on the morning after the baseline visit (before administration of any study medication). There are no other reports of medication use.

Treatment Compliance

All subjects receive both doses of study medication according to the instructions and are monitored by study personnel for one-hour post-dosing to assure conformity to the TBS-1 instructions. All subjects remain in the clinic during the 12-hour PK sampling time period; during which they are monitored closely.

Screening

The screening visit (visit 1) takes place at a maximum of 21 days before the first study day. After giving informed consent, the suitability of the subject for study participation is assessed at screening which consists of the following items:

Medical history

Physical examination and Vital Signs.

A fasting blood sample is taken to determine the following: Complete Blood Count, Chemistry profile; testing for HBV, HCV, HIV and PSA.

Urinalysis, urine drug screen, and Breath Alcohol Testing.

An otorhinolaryngological nasal endoscopic examination is performed by an ENT specialist.

Subjects meeting all of the inclusion and no exclusion criteria are enrolled into the study and are randomized into one of two treatment groups (1 or 2).

Study Days

Subjects are admitted to the clinical research centre at 19:30 hours on Day 1 (Visit 2, baseline), 2 (Visit 3, Period 1) and 4 (Visit 4, Period 2). After check-in tests for drug-abuse and alcohol consumption are performed. Vital signs are recorded and subjects are questioned about changes in their health.

During Visit 2, a 12 hour baseline testosterone profile is measured. Blood for the 12 hour baseline testosterone profile is drawn according to the following schedule: first sample at 20:45 hours and then at 0.33, 0.66, 1.00, 1.50, 2.00, 3.00, 4.00, 5.00, 6.00, 8.00, 10.00, and 12.00 hours relative to 21:00 time point (a total of 13 samples). On Day 2 vital signs are measured and safety parameters (symptoms, AEs) recorded before check-out.

Dosing is performed on the evenings of Day 2 and 4, at 21:00 hr. Before dosing an ENT examination is performed and a pre-dose, baseline serum testosterone blood sample is drawn. After dosing, a 12 hour testosterone PK profile is measured. The blood samples are drawn according to the following schedule after the 21:00 hour dosing: 0.33, 0.66, 1.00, 1.50, 2.00, 3.00, 4.00, 5.00, 6.00, 8.00, 10.00, and 12.00 hr time points (a total of 13 samples per period).

On Day 3 and 5 vital signs are measured, ENT examination are performed and safety parameters are recorded (symptoms, AEs) after the last PK sampling and before check-out. On Day 5 a final examination is performed, consisting of a general physical examination and clinical laboratory investigation (Complete Blood Count, Chemistry profile and Urinalysis).

Pharmacokinetic Sampling

Blood samples for analysis of testosterone levels are collected in 4 ml standard clotting tubes using an intravenous cannula. Tubes are left to clot for 30-45 minutes. Samples are centrifuged within one hour at 2000 g for 10 minutes at 4° C. The serum is then transferred directly to two aliquots of 1 ml each and frozen at −40° C.

Safety

Blood samples for hematology are collected in 4 ml EDTA tubes and sent to the hematology laboratory of the Leiden University Medical Center (LUMC) for routine analysis. Blood samples for blood chemistry are collected in 4 ml Heparin tubes and sent to the clinical chemistry laboratory for routine analysis.

Drug Concentration Measurements

Frozen serum samples for PK analysis are stored in the freezer at −40° C. and are shipped on dry ice to the laboratory, at the end of the study. Samples are analyzed using a validated LC-MS method for the determination of testosterone levels. It is not possible to discriminate endogenous and exogenous testosterone from each other using this method.

Quality Assurance

The study is conducted in compliance with the pertaining CHDR Standard Operating Procedures and CHDR's QA procedures.

Calculation of Pharmacokinetic Parameters

A validated LC-MS/MS method is employed to determine serum testosterone. All samples from study participant completing both the periods are analyzed.

Incurred sample reanalysis is performed:

$C_{min}$, $C_{max}$, and $t_{max}$ actual measured values. Values are determined relative to the testosterone administration time in treated subjects.

Area under the concentration curve (AUC) is estimated for the 0 to 12 hour time interval using the trapezoidal rule.

Significance is evaluated using the t-test. Additional exploratory analyses of PK parameters could be performed as necessary.

The relative pharmacokinetic profile of the pre-filled syringe and the multiple dose dispenser is determined using the $AUC_{0-12h}$ and $Cmax_{0-12h}$ corrected for the endogenous serum testosterone concentration. For bioequivalence, the relative mean of the dispenser to the pre-filled syringe using log transformed data for $AUC_{0-12h}$ and $Cmax_{0-12h}$ is corrected for the endogenous serum testosterone concentration, is determined to be between 80% to 125%.

Analysis of Safety Parameters

The Day 5 close-out findings is compared to the screening results and clinically significant changes were to be identified in the following:

1. Vital Signs and Adverse Events: Blood Pressure, Body Temperature, Respiratory Rate, Heart Rate.
2. Otorhinolaryngological examination with the nasal tolerance data presented in summary tables.
3. Complete Blood Count: white blood count, hemoglobin and hematocrit.
4. Clinical chemistry profile: sodium, potassium, chloride, glucose, urea, creatinine, calcium, phosphate, uric acid, total bilirubin, albumin, AST, ALT, ALP, GGT, CK and cholesterol.
5. Urinalysis.

Determination of Sample Size

As this is a relatively small Phase I PK study with the intent to compare a pharmacokinetic profile of testosterone after administration of TBS-1 from two different dispensers in healthy male subjects, a true sample size calculation is not performed.

Subjects

26 Subjects are enlisted
2 subjects are not screened due to planning problems
1 subject is not screened because he does not have a general practitioner
23 Subjects are screened
3 screening failures due to ENT abnormalities
1 screening failure due to positive hepatitis B test
1 screening failure due to positive hepatitis C test
18 Subjects passed screening
12 subjects are randomized and completed the study
1 subject is cancelled before the baseline visit due to concurrent illness
5 subjects are reserves, but not needed
No subjects discontinue after randomization.

Efficacy Evaluation

Data collected is used in the analysis. This yields three PK curves of 12 hours each, one without treatment (baseline), and one each after administration of TBS-1 using the multiple dose dispenser or syringe.

Demographic Characteristics

Subject demographics are summarized in Table 4 below.

TABLE 4

Subject demographics

| Variable | N | MEAN | STD | MIN | MAX |
|---|---|---|---|---|---|
| Age (yrs) | 12 | 23.4 | 3.0 | 18 | 28 |
| BMI (kg/m$^2$) | 12 | 23.55 | 2.45 | 20.9 | 28.4 |
| Height (cm) | 12 | 184.43 | 8.46 | 173.5 | 197.0 |
| Weight (kg) | 12 | 80.08 | 9.76 | 63.2 | 98.2 |

Measurements of Treatment Compliance

The nasal gel is self-administered by subjects. All administrations are successful.

Efficacy Results and Tabulations of Individual Patient Data

Figure 24:
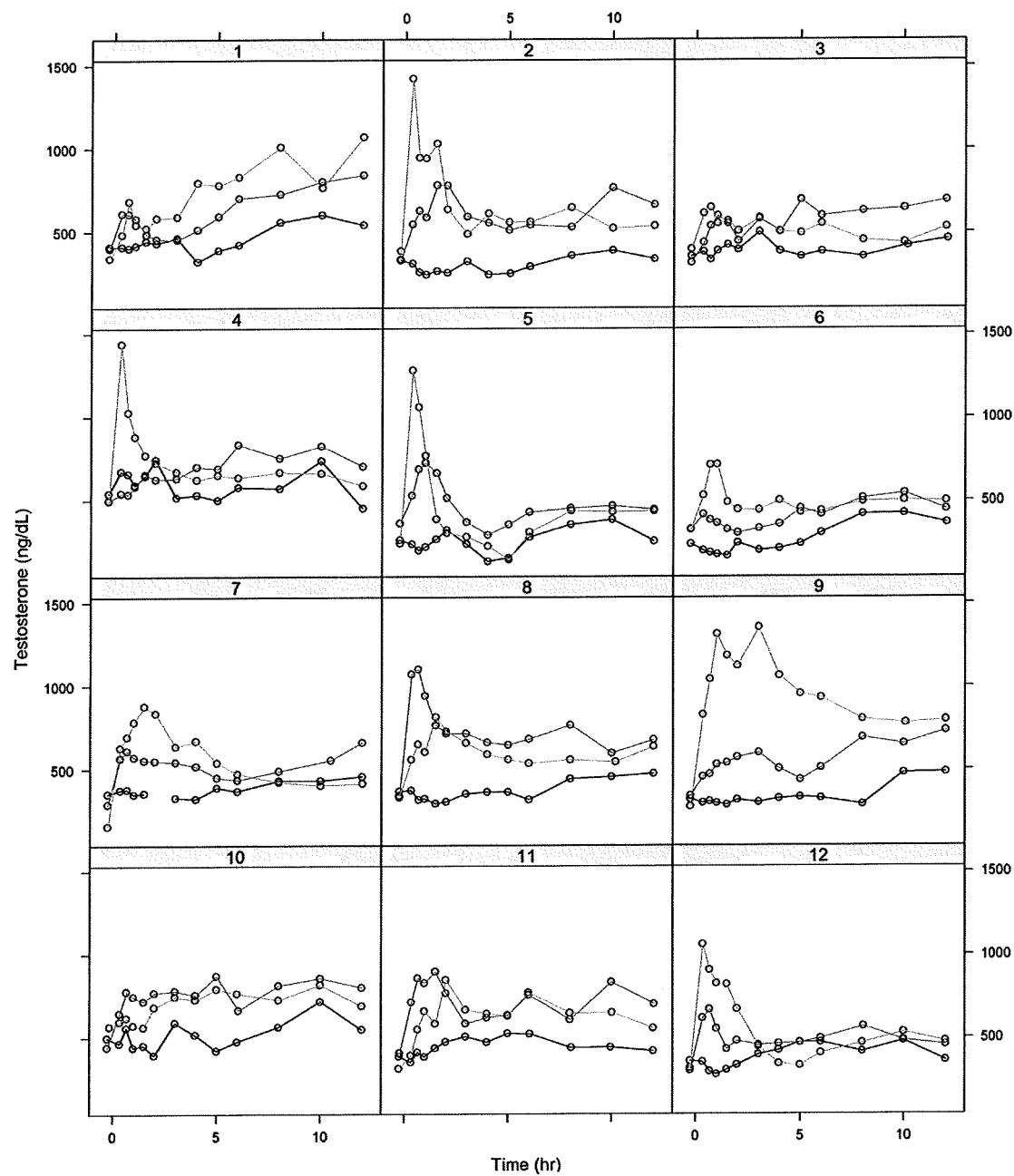
FIG. 24 depicts individual testosterone concentration versus time (linear y-axis), that are grouped by subject in accordance with Example 13. Number. Black: baseline; blue: syringe; salmon: multiple dose dispenser. T=0 is at 21:00 clock-time (±30 minutes), t=12 is at 9:00 (±30 minutes) clock-time.
Figure 25:
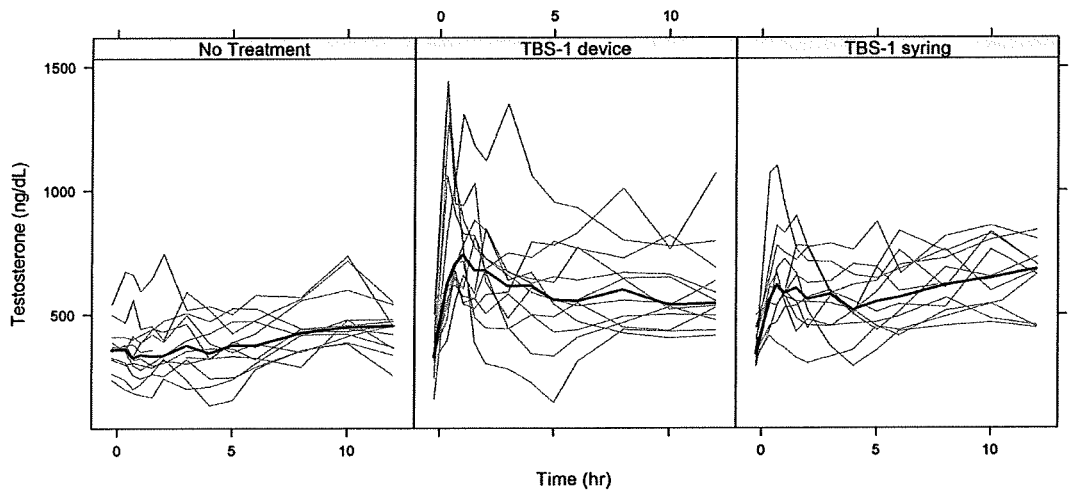
FIG. 25 depicts individual (blue) and median (black) testosterone concentration versus time (linear y-axis), that are grouped by treatment.
Figure 26:
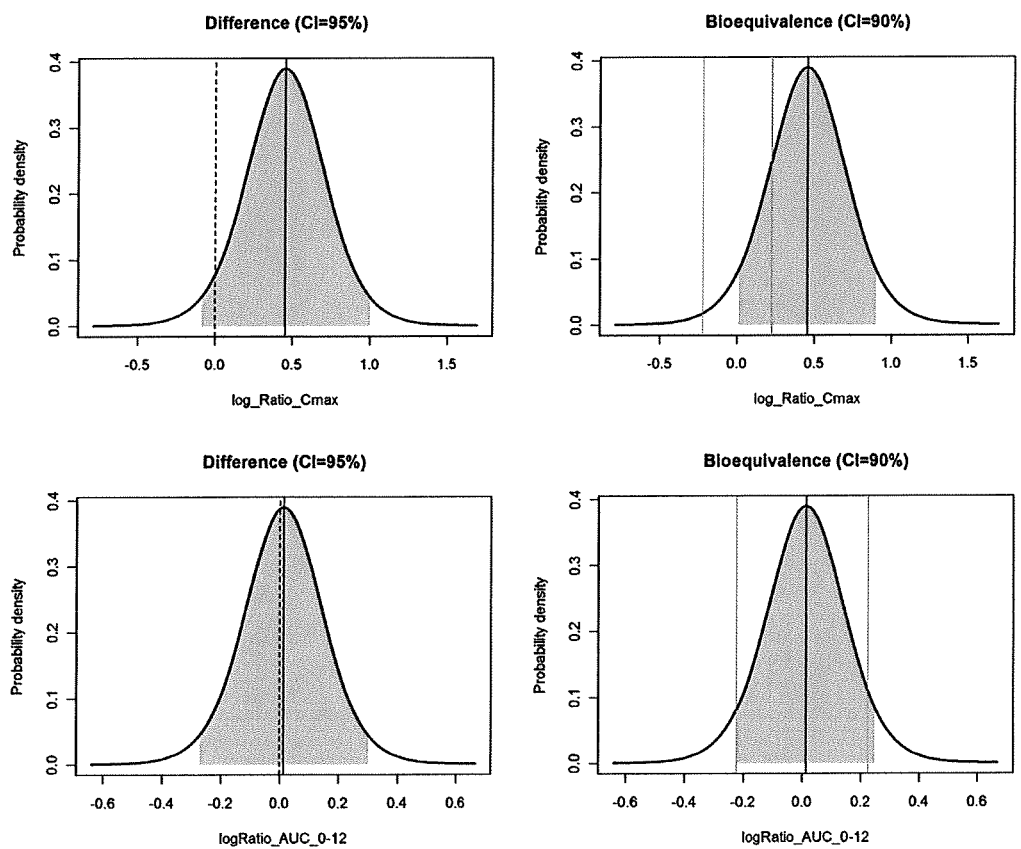
FIG. 26 depicts the probability density of the log ratio of testosterone levels that are reached with the multiple dose dispenser over levels that are reached with the syringe.
Figure 27:
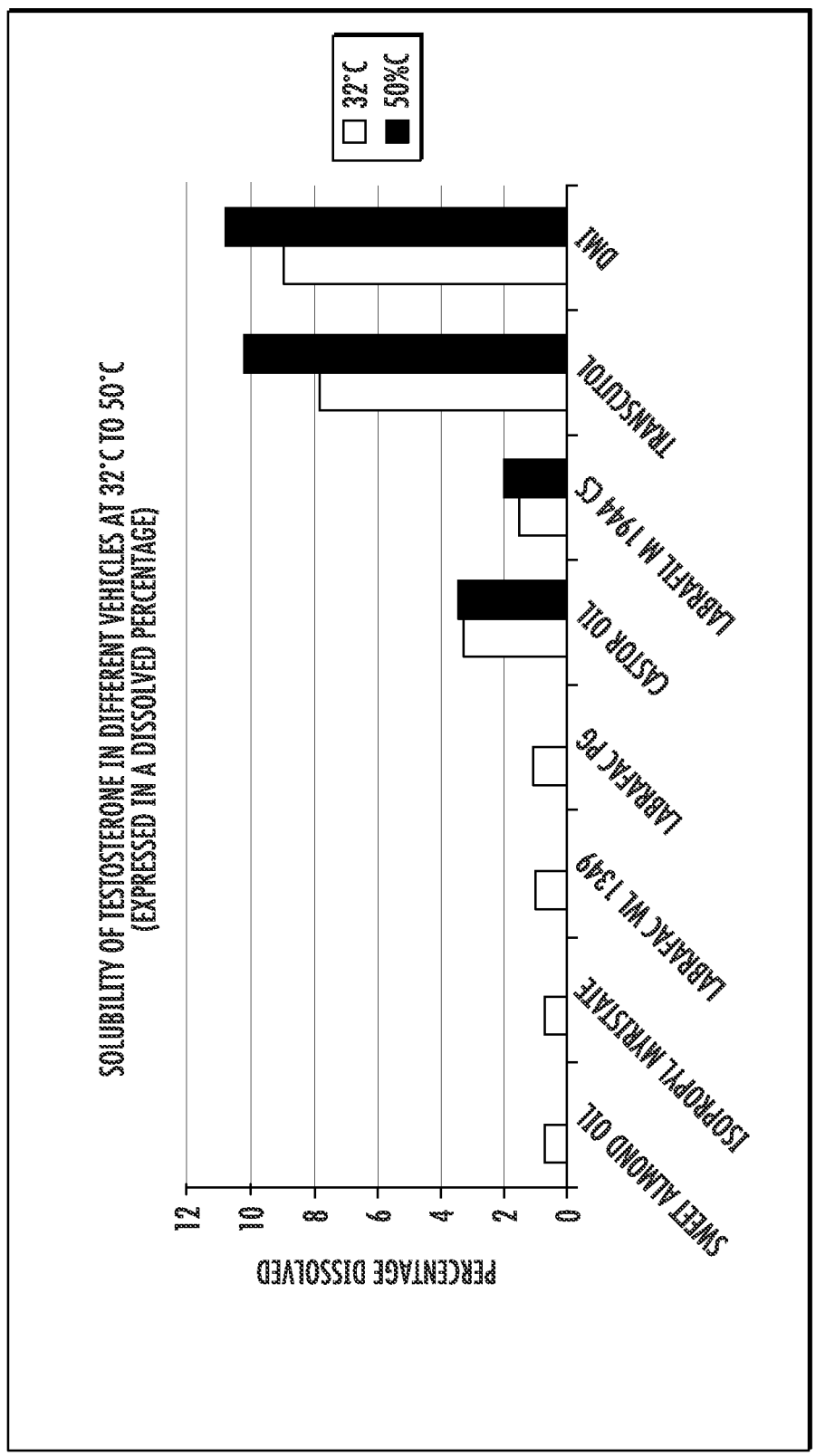
FIG. 27 depicts solubility of testosterone in different vehicles at 32° C. and at 50° C.
Figure 28:
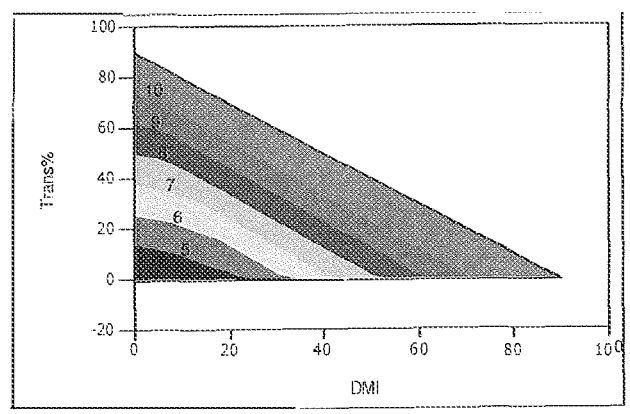
FIG. 28 depicts Ternary solvent mixture optimization: Contour plot shows that, in order to achieve more than 6% testosterone solubility, higher levels of DMI and Transcutol are required.
Figure 29:
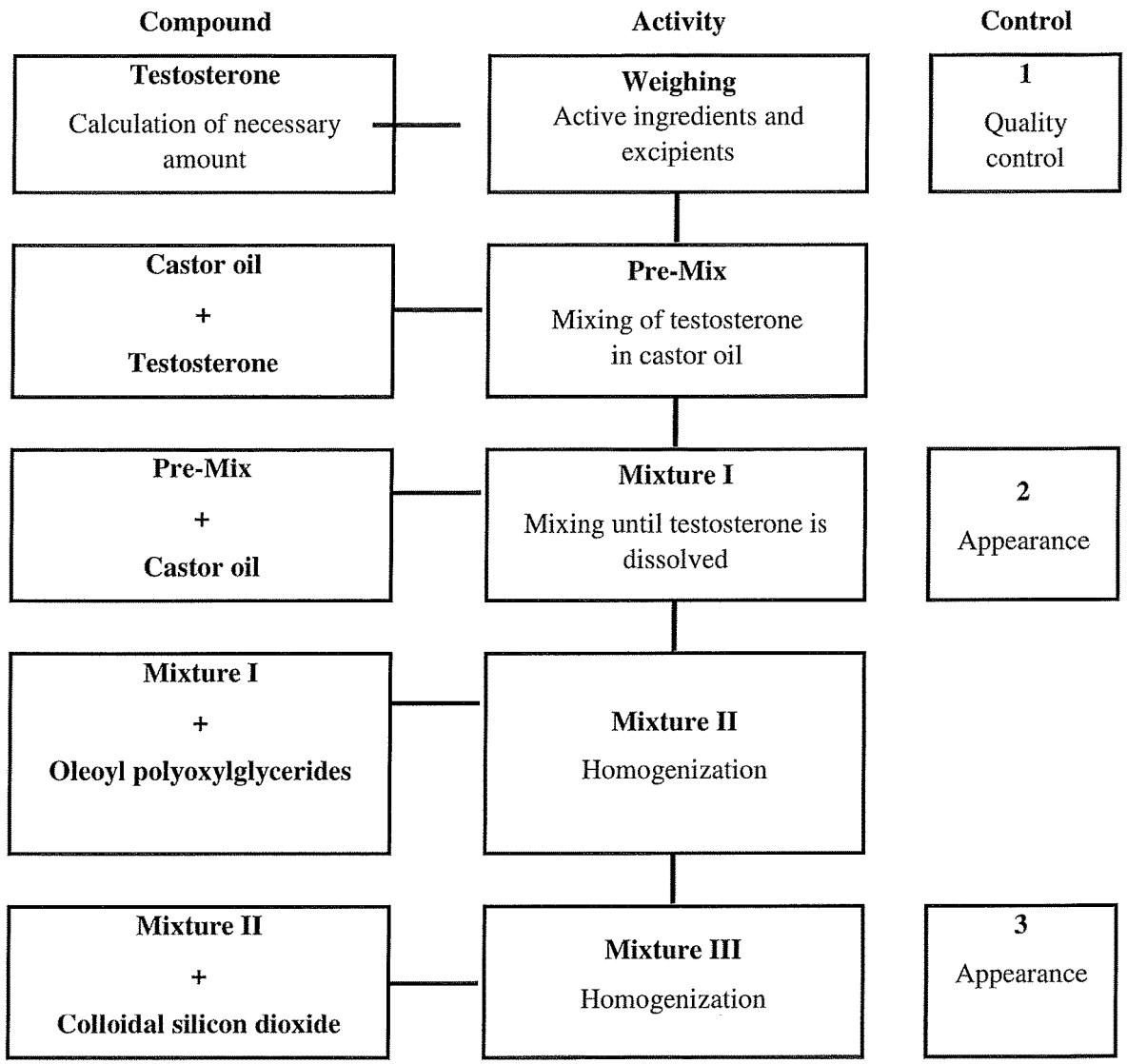
FIG. 29 depicts a flow diagram for manufacturing TBS-1.
Figure 30A:
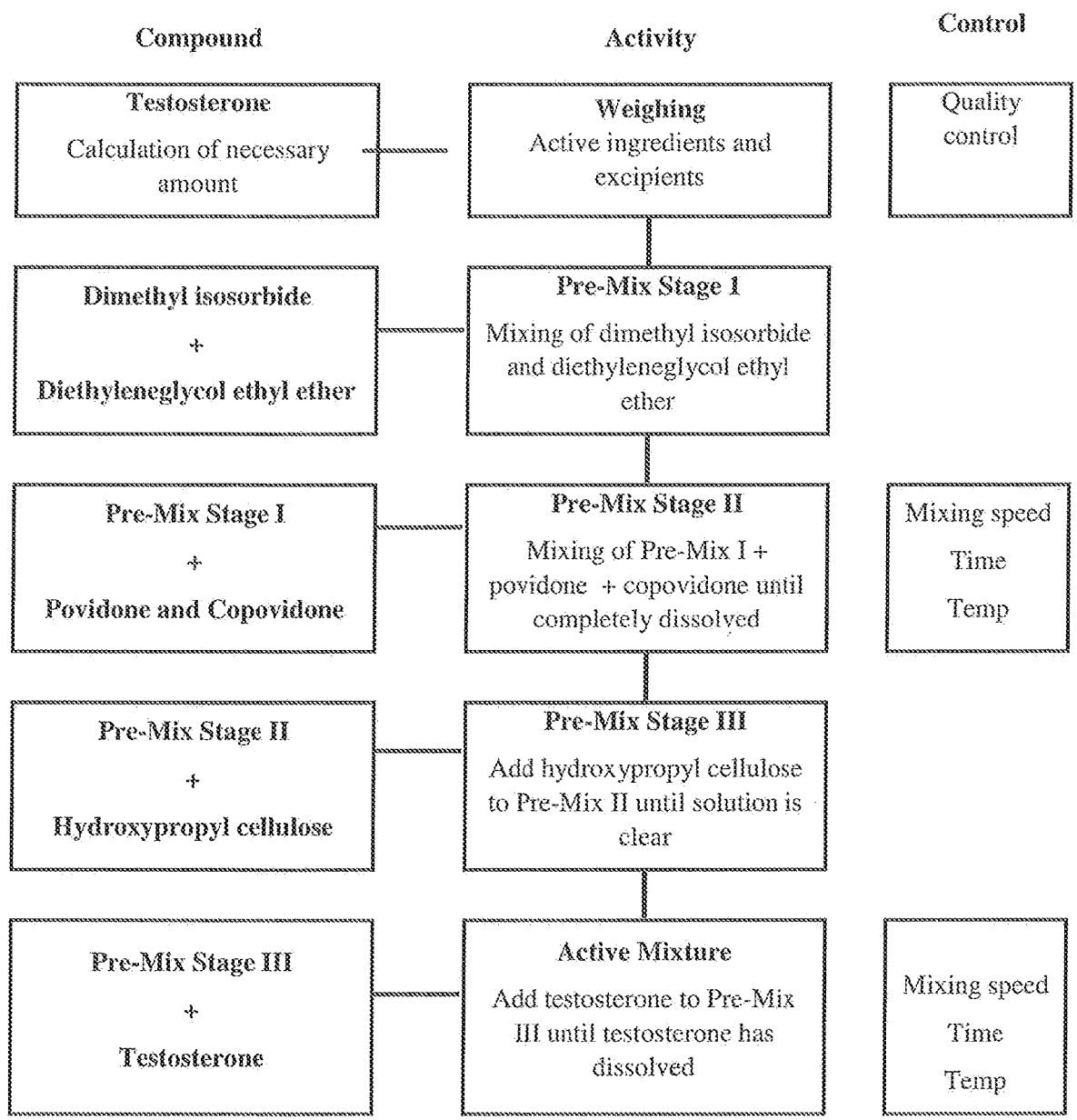
FIG. 30A and FIG. 30B depict a flow diagram of a manufacturing process of an intranasal testosterone gel of the present invention.
Figure 30B:
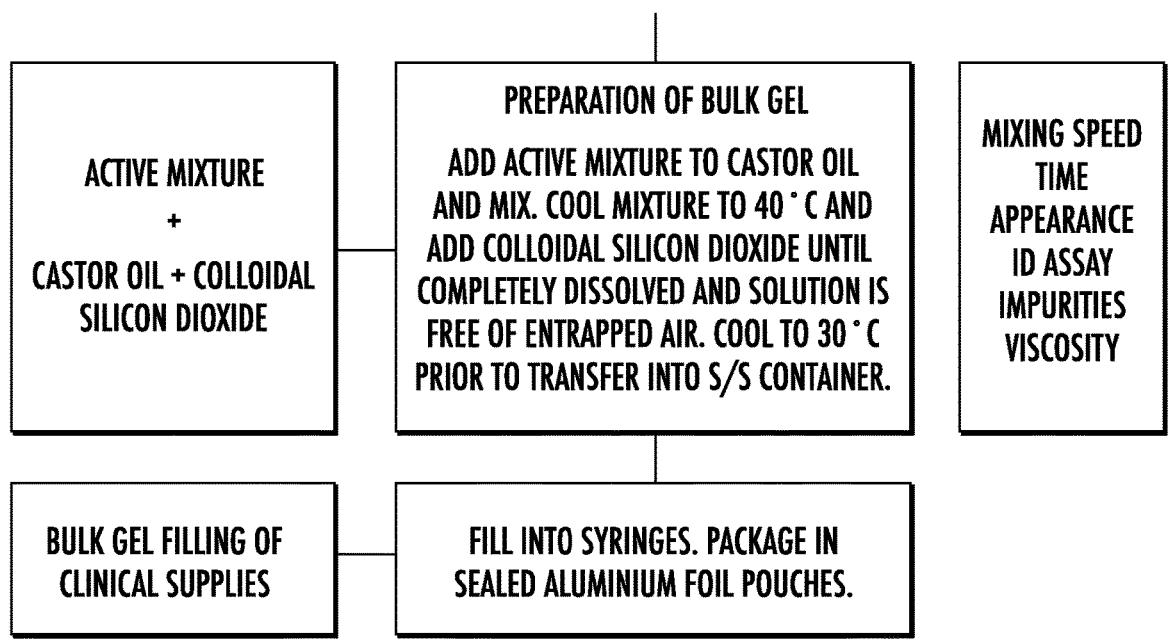
Figure 31:
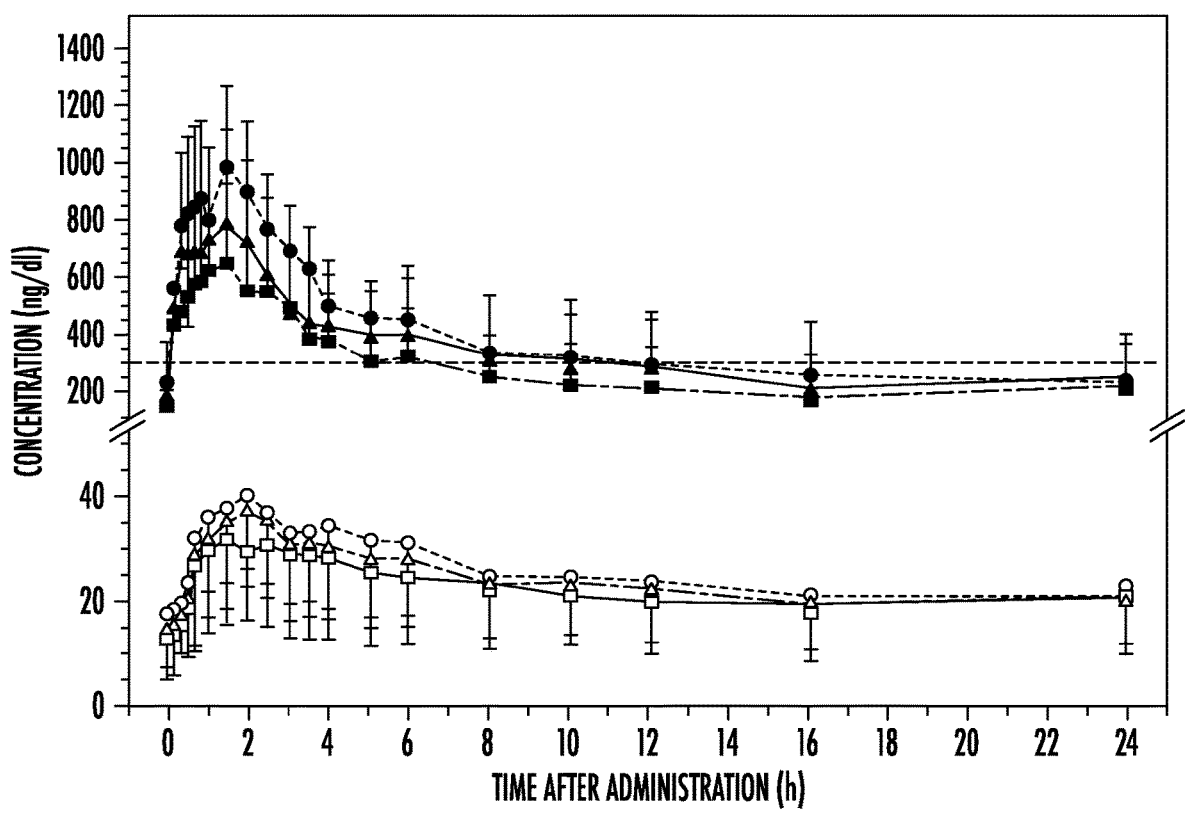
FIG. 31 depicts a mean concentration-time curves of testosterone (solid squares) and DHT (open squares) after single-dose administration of 3 different TBS-1 strengths (7.6 mg=squares; 15.2 mg=circles; 22.8 mg triangles). The lower limit of normal range for testosterone is indicated with the dashed line (based on morning serum samples)
Figure 32:
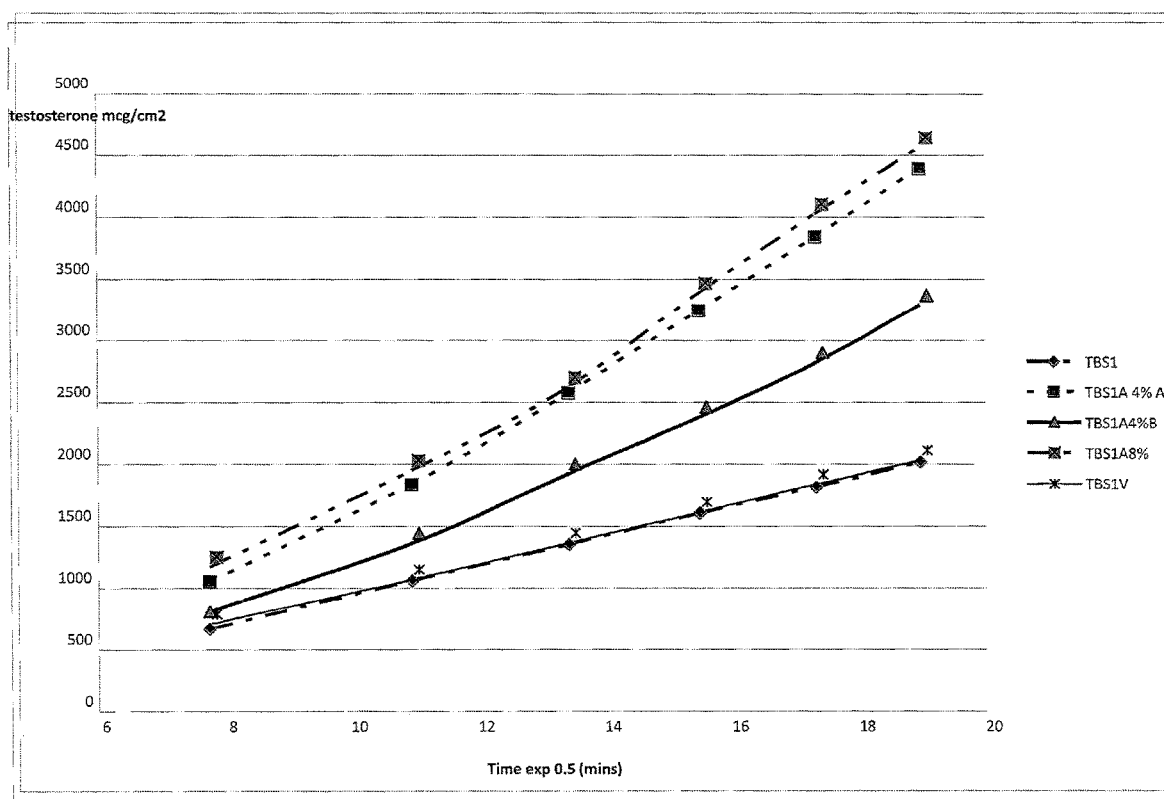
FIG. 32 depicts testosterone diffusion rate of intranasal testosterone gel formulations of Example 13 using Franz cells method.
Figure 33:
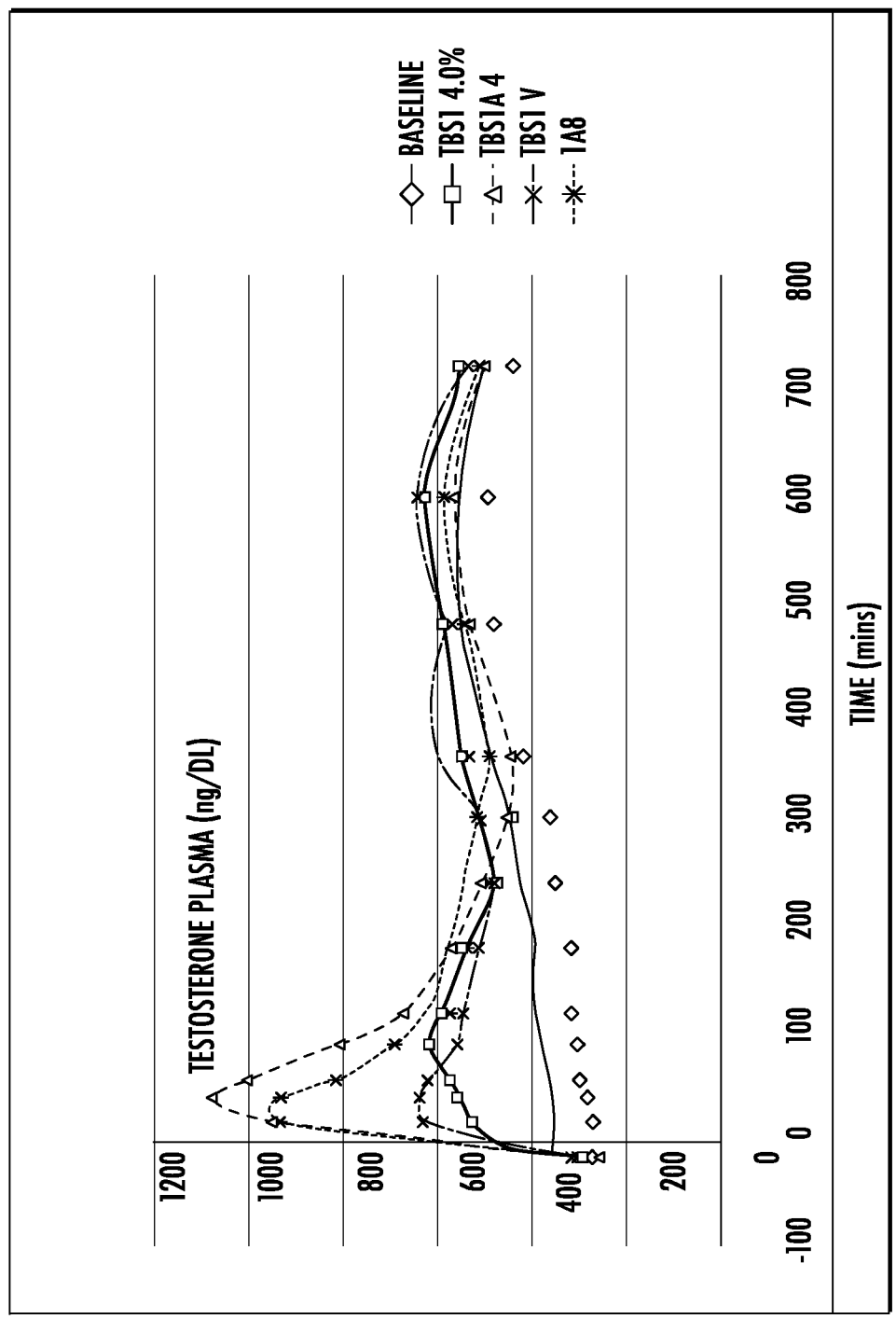
FIG. 33 depicts the pharmacokinetic profiles of 15 male subjects using the formulas of Example 13.

FIG. 24 shows the individual serum testosterone levels per occasion (baseline without medication, TBS-1 using the multiple dose dispenser and TBS-1 using syringes), where T=0 occurred at 21:00 hours clock time. FIG. 24 shows the individual and median testosterone concentration versus time grouped by treatment.

All subjects have testosterone levels within the normal range (24 hour $C_{mean} \geq 300$ ng/dL and $\leq 1050$ ng/dL). The baseline curves clearly show the slow circadian fluctuations in testosterone levels that are expected in a young, healthy population with the highest levels in the early morning.

Figure 15:
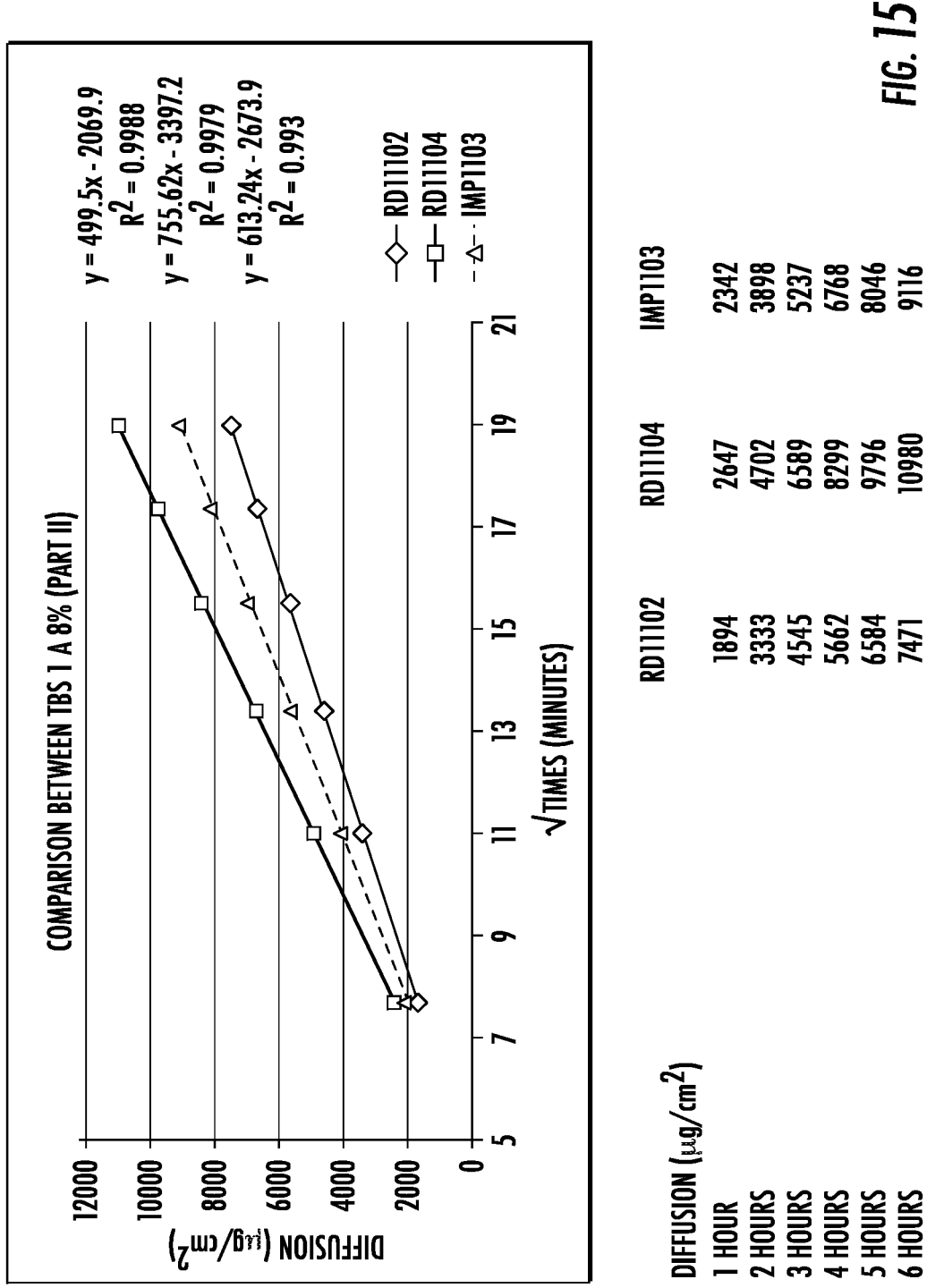
FIG. 15 depicts a comparison between TBS 1 A 8% (Part I)
Figure 16:
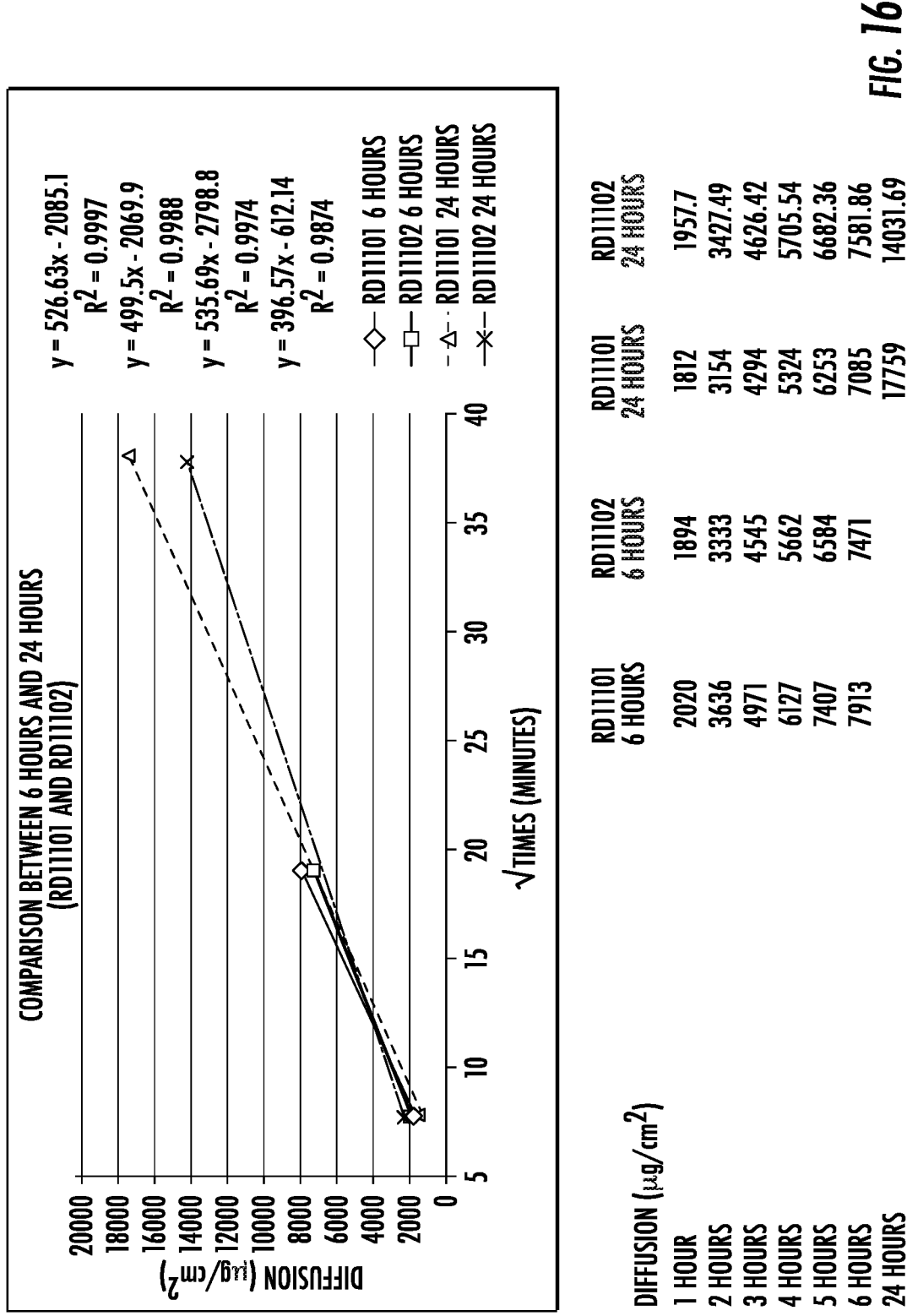
FIG. 16 depicts a comparison between 6 hours and 24 hours run (RD11101 and RD11102)

Although dose and volume of TBS-1 that is administered is exactly the same for both forms of administration, the graphs in FIGS. 15 and 16 suggest that there are differences in pharmacokinetic profile.

Pharmacokinetic Parameters

The following primary pharmacokinetic parameters, per occasion, are calculated:

$AUC_{0-12}$: Area under the serum concentration-time curve (ng·hr/dL) for each occasion from 21:00 to 9:00 hrs, is calculated using the linear trapezoidal method.

$C_{mean}$: Mean concentration (ng/dL) during each occasion from 21:00 to 9:00 hrs, is calculated as AUC_0-12/12.

$C_{max}$: Maximum is observed concentration (ng/dL) during each occasion.

$C_{min}$: Minimum is observed concentration (ng/dL) during each occasion.

$t_{max}$: Time (hr) at which $C_{max}$ is observed.

Tables 5 to 7 below summarize the primary pharmacokinetic parameters for endogenous testosterone during the baseline visit when no treatment is administered, for TBS-1 when administered using the multiple dose dispenser, and for TBS-1 when administered using a syringe.

Testosterone, Baseline, No Treatment

TABLE 5

Testosterone, no treatment

| Parameter | Mean | SD | Median | Min | Max | N |
|---|---|---|---|---|---|---|
| $AUC_{0-12}$ | 4911 | 1156 | 4726 | 3337 | 7164 | 12 |
| $t_{max}$ | 8.833 | 3.486 | 10.0 | 2.0 | 12 | 12 |
| $C_{max}$ | 514.2 | 117.5 | 480.0 | 384.0 | 746 | 12 |
| $C_{min}$ | 298.6 | 89.01 | 308.0 | 134.0 | 453 | 12 |
| $C_{mean}$ | 409.0 | 96.4 | 392.8 | 278.1 | 597 | 12 |

$AUC_{0-12}$ in ng*hr/dL; $t_{max}$ in hours; $C_{max}$, $C_{min}$ and $C_{mean}$ in ng/dL Testosterone, TBS-1 Multiple Dose Dispenser

TABLE 6

Testosterone, TBS-1 multiple dose dispenser

| Parameter | Mean | SD | Median | Min | Max | N |
|---|---|---|---|---|---|---|
| $AUC_{0-12}$ | 7484 | 1798 | 7347 | 4847 | 11350 | 12 |
| $t_{max}$ | 2.751 | 3.961 | 1.25 | 0.3333 | 12 | 12 |
| $C_{max}$ | 1028 | 283.1 | 970.5 | 645 | 1440 | 12 |
| $C_{min}$ | 337.9 | 119.7 | 328.5 | 145 | 565 | 12 |
| $C_{mean}$ | 623.6 | 149.9 | 612.3 | 403.9 | 945.7 | 12 |

$AUC_{0-12}$ in ng*hr/dL; $t_{max}$ in hours; $C_{max}$, $C_{min}$ and $C_{mean}$ in ng/dL Testosterone, TBS-1 Syringe

TABLE 7

Testosterone, TBS-1 syringe

| Parameter | Mean | SD | Median | Min | Max | N |
|---|---|---|---|---|---|---|
| $AUC_{0-12}$ | 7266 | 1360 | 7237 | 5186 | 9371 | 12 |
| $t_{max}$ | 5.612 | 4.736 | 5.0 | 0.667 | 12 | 12 |
| $C_{max}$ | 778.8 | 144.1 | 754.5 | 543 | 1100 | 12 |
| $C_{min}$ | 355.9 | 66.96 | 337.0 | 291 | 498 | 12 |
| $C_{mean}$ | 605.4 | 113.2 | 603.1 | 432.2 | 780.9 | 12 |

$AUC_{0-12}$ in ng*hr/dL; $t_{max}$ in hours; $C_{max}$, $C_{min}$ and $C_{mean}$ in ng/dL The listing of individual primary pharmacokinetic parameters is included in Table 7A.

TABLE 7A

Efficacy Data
Individual PK Parameters
Individual PK parameters 0-12 hrs for each occasion

| Subject | Occasion | Treatment | AUC_0-12 | t_max | C_max | C_mean | C_min |
|---|---|---|---|---|---|---|---|
| 1 | 1 | No Treatment | 5722 | 10.0000 | 600 | 476.9 | 321 |
| 1 | 2 | TBS-1 mdd | 9394 | 12.0000 | 1070 | 782.9 | 340 |
| 1 | 3 | TBS-1 syringe | 7802 | 12.0000 | 840 | 650.1 | 400 |
| 2 | 1 | No Treatment | 3731 | 10.0000 | 388 | 310.9 | 242 |

TABLE 7A-continued

Efficacy Data
Individual PK Parameters
Individual PK parameters 0-12 hrs for each occasion

| Subject | Occasion | Treatment | AUC_0-12t_max | C_max | C_mean | C_min |
|---|---|---|---|---|---|---|
| 2 | 2 | TBS-1 syringe | 7367 | 1.5000 | 779 | 613.9 | 333 |
| 2 | 3 | TBS-1 mdd | 7592 | 0.3333 | 1420 | 632.7 | 386 |
| 3 | 1 | No Treatment | 4771 | 3.0000 | 498 | 395.4 | 332 |
| 3 | 2 | TBS-1 mdd | 6056 | 0.6667 | 645 | 504.7 | 395 |
| 3 | 3 | TBS-1 syringe | 7107 | 5.0000 | 691 | 592.3 | 312 |
| 4 | 1 | No Treatment | 7164 | 2.0000 | 746 | 597.0 | 453 |
| 4 | 2 | TBS-1 syringe | 8639 | 6.0000 | 837 | 720.0 | 498 |
| 4 | 3 | TBS-1 mdd | 8370 | 0.3333 | 1440 | 697.5 | 500 |
| 5 | 1 | No Treatment | 3337 | 10.0000 | 384 | 278.1 | 134 |
| 5 | 2 | TBS-1 mdd | 4847 | 0.3500 | 1280 | 403.9 | 145 |
| 5 | 3 | TBS-1 syringe | 5439 | 1.0000 | 725 | 453.3 | 292 |
| 6 | 1 | No Treatment | 3673 | 10.0000 | 422 | 305.2 | 166 |
| 6 | 2 | TBS-1 syringe | 5186 | 10.0200 | 543 | 432.2 | 304 |
| 6 | 3 | TBS-1 mdd | 5851 | 1.0000 | 715 | 487.6 | 325 |
| 7 | 1 | No Treatment | 4681 | 12.0000 | 456 | 390.1 | 324 |
| 7 | 2 | TBS-1 syringe | 6250 | 12.0000 | 661 | 520.8 | 291 |
| 7 | 3 | TBS-1 mdd | 6503 | 1.5000 | 881 | 541.2 | 159 |
| 8 | 1 | No Treatment | 4632 | 12.0000 | 473 | 386.0 | 295 |
| 8 | 2 | TBS-1 mdd | 7102 | 1.5000 | 813 | 591.9 | 332 |
| 8 | 3 | TBS-1 syringe | 8529 | 0.6667 | 1100 | 710.7 | 343 |
| 9 | 1 | No Treatment | 4222 | 12.0000 | 481 | 351.8 | 287 |
| 9 | 2 | TBS-1 mdd | 11350 | 3.0000 | 1350 | 945.7 | 276 |
| 9 | 3 | TBS-1 syringe | 6992 | 12.0000 | 730 | 582.7 | 341 |
| 10 | 1 | No Treatment | 6503 | 10.0000 | 718 | 541.9 | 397 |
| 10 | 2 | TBS-1 syringe | 9371 | 5.0000 | 874 | 780.9 | 445 |
| 10 | 3 | TBS-1 mdd | 8747 | 10.0000 | 820 | 728.9 | 565 |
| 11 | 1 | No Treatment | 5541 | 5.0000 | 525 | 461.7 | 353 |
| 11 | 2 | TBS-1 mdd | 7823 | 2.0000 | 848 | 651.9 | 315 |
| 11 | 3 | TBS-1 syringe | 8550 | 1.5000 | 898 | 710.6 | 408 |
| 12 | 1 | No Treatment | 4950 | 10.0000 | 479 | 412.5 | 279 |
| 12 | 2 | TBS-1 syringe | 5962 | 0.6667 | 668 | 496.8 | 304 |
| 12 | 3 | TBS-1 mdd | 6171 | 0.3333 | 1060 | 514.2 | 317 | mdd - multiple dose dispenser

Total testosterone exposure is estimated by the mean area under the serum concentration-time curve ($AUC_{0-12}$ in ng·hr/dL) is higher after TBS-1 administration using the dispenser or syringe than endogenous levels alone (7484 and 7266, respectively, versus 4911 ng*h/dL). Between the methods of administration, the difference in mean $AUC_{0-12}$ is small. The significance of this difference is explored below.

Unexpectedly, mean $C_{max}$ is higher after administration with the dispenser than when with a syringe (1028 versus 778.8 ng/dL, respectively). $T_{max}$ occurs sooner after administration using the dispenser than after the syringe (2.75 versus 5.6 hours, respectively). Thus, after administration using the multiple dose dispenser serum testosterone seems to be absorbed faster than with a syringe. The significance of these differences is explored below.

Two subjects reach $t_{max}$ of testosterone only 10 and 12 hours after administration with the dispenser. In three subjects, $t_{max}$ is 10 and 12 hours after administration with the syringe, and $t_{max}$ is 5 and 6 hours in two others. Most likely, the endogenous testosterone peak fluctuation exceeded levels that is caused by exogenous testosterone administration. Thus, the calculated mean $t_{max}$ may be faster when testosterone is dosed high enough that the peak caused by exogenous administration exceeds the endogenous peak.

Derived Pharmacokinetic Parameters

The following derived pharmacokinetic parameters, combining results from occasions, are calculated:

$AUC_{0-12\_drug}$: difference between $AUC_{0-12}$ after treatment (syringe or dispenser) and no treatment (baseline occasion)

$C_{max\_drug}$: difference between $C_{max}$ after treatment (syringe or dispenser) and the observed concentration at $t_{max}$ in absence of treatment (baseline occasion)

Ratio $AUC_{0-12\_drug}$: % ratio between $AUC_{0-12\_drug}$ using dispenser and syringe Ratio $C_{max\_drug}$: % ratio between $C_{max\_drug}$ using dispenser and syringe Mean and uncertainty (95%, 90% and 80% confidence interval) of the log of Ratio $AUC_{0-12\_drug}$ Mean and uncertainty (95%, 90% and 80% confidence interval) of the log of Ratio $C_{max\_drug}$ Testosterone Level Using TBS-1, Baseline Subtracted Tables 8 and 9 below show the AUC and $C_{max}$ for the different TBS-1 delivery methods after subtracting baseline levels of testosterone.

TABLE 8

Testosterone level using TBS-1 multiple dose dispenser, baseline subtracted

| Parameter | Mean | SD | Median | Min | Max | N |
|---|---|---|---|---|---|---|
| $AUC_{0-12\_drug}$ | 2573.0 | 1679.0 | 2211 | 1207 | 7126 | 12 |
| $C_{max\_drug}$ | 630.8 | 314.7 | 534 | 102 | 1111 | 12 |

TABLE 9

Testosterone level TBS-1 syringe, baseline subtracted

| Parameter | Mean | SD | Median | Min | Max | N |
|---|---|---|---|---|---|---|
| $AUC_{0-12\_drug}$ | 2356.0 | 900.9 | 2219 | 1012 | 3897 | 12 |
| $C_{max\_drug}$ | 379.9 | 177.1 | 357 | 121 | 782 | 12 |

Testosterone Level TBS-1 Dispenser Over Syringe Ratio

Table 10 below shows the ratio of serum testosterone levels that are reached with the dispenser or syringe, after subtracting baseline testosterone levels. There is clearly a difference in $C_{max}$ between the administration forms (mean ratio dispenser over syringe $C_{max}$ 2.057), but the AUCs are comparable (mean ratio dispenser over syringe AUC 1.12).

TABLE 10

Testosterone, ratio of TBS-1 multiple dose dispenser over syringe

| Parameter | Mean | SD | Median | Min | Max | N |
|---|---|---|---|---|---|---|
| Ratio $AUC_{0-12\_drug}$ | 1.122 | 0.580 | 0.940 | 0.550 | 2.572 | 12 |
| Ratio $C_{max\_drug}$ | 2.057 | 1.339 | 1.983 | 0.227 | 4.455 | 12 |
| logRatio $AUC_{0-12\_drug}$ | 0.014 | 0.453 | −0.071 | −0.598 | 0.945 | 12 |
| logRatio $C_{max\_drug}$ | 0.455 | 0.860 | 0.684 | −1.484 | 1.494 | 12 |

Table 11 below shows the log of the ratio of serum testosterone levels that are reached when administering using the multiple dose dispenser over syringe, after subtracting baseline testosterone levels, with 95%, 90% and 80% confidence intervals.

Figure 17:
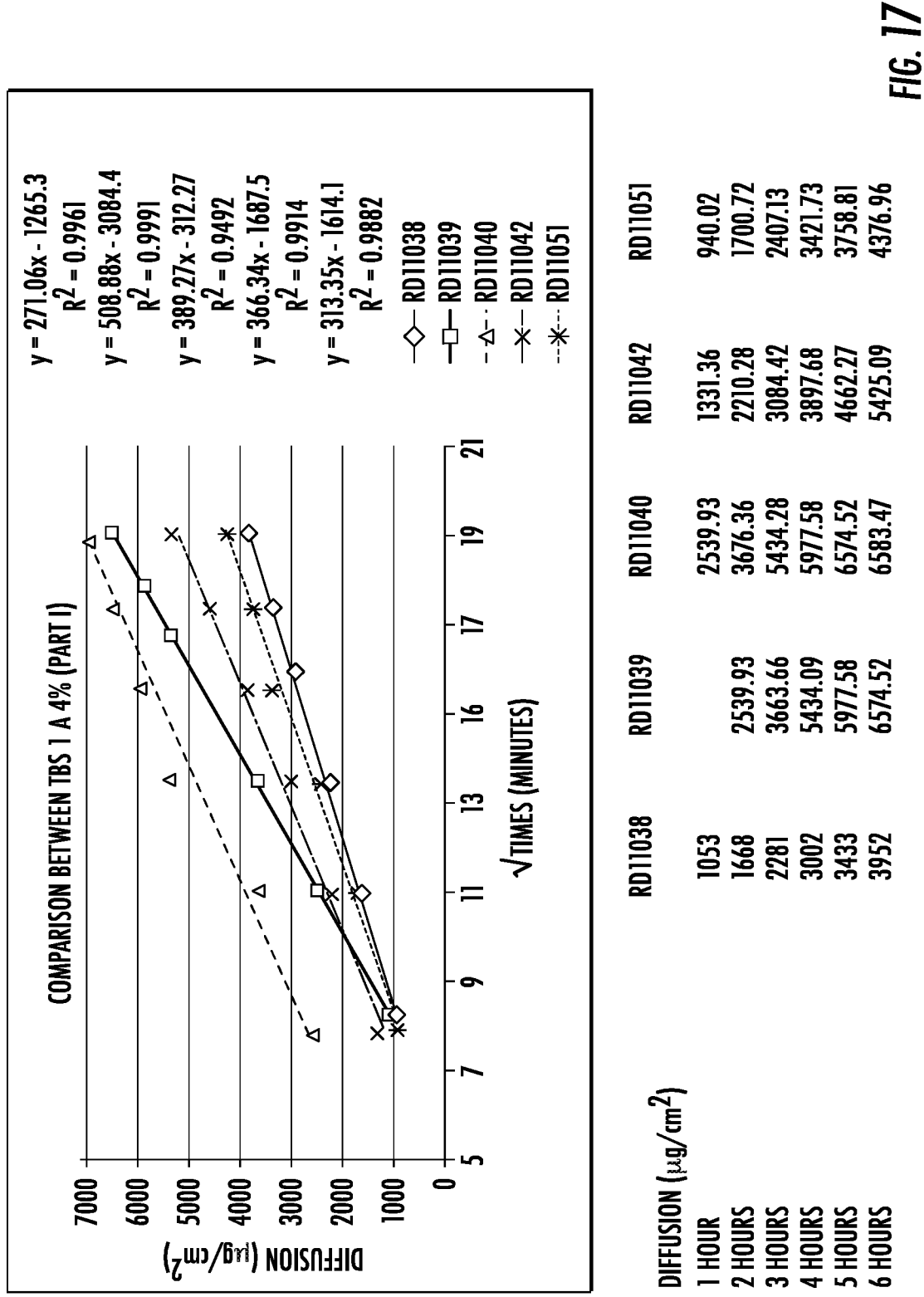
FIG. 17 depicts a comparison between TBS 1 A 4% (Part I)
Figure 18:
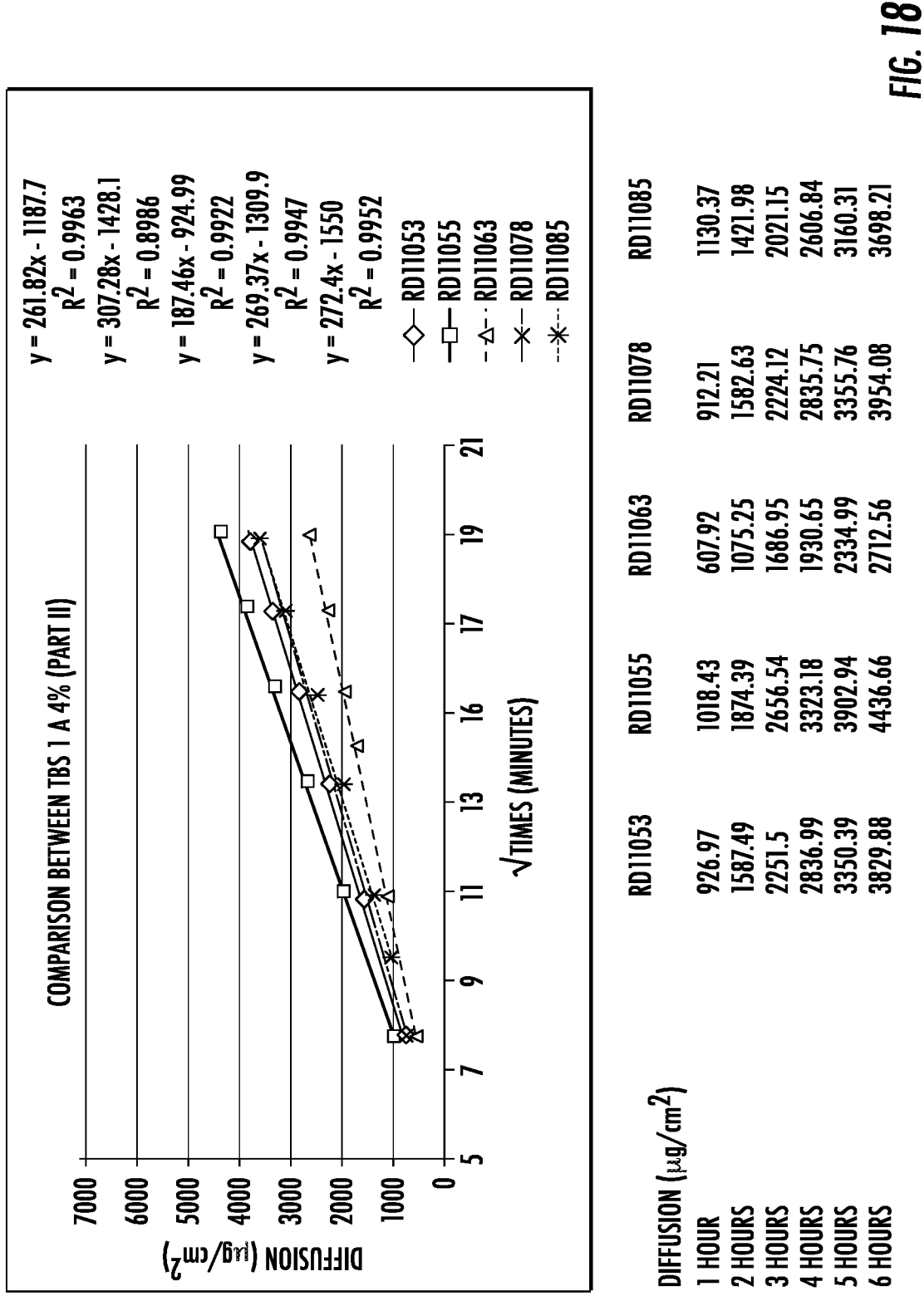
FIG. 18 depicts a comparison between TBS 1 A 4% (Part II)
Figure 19:
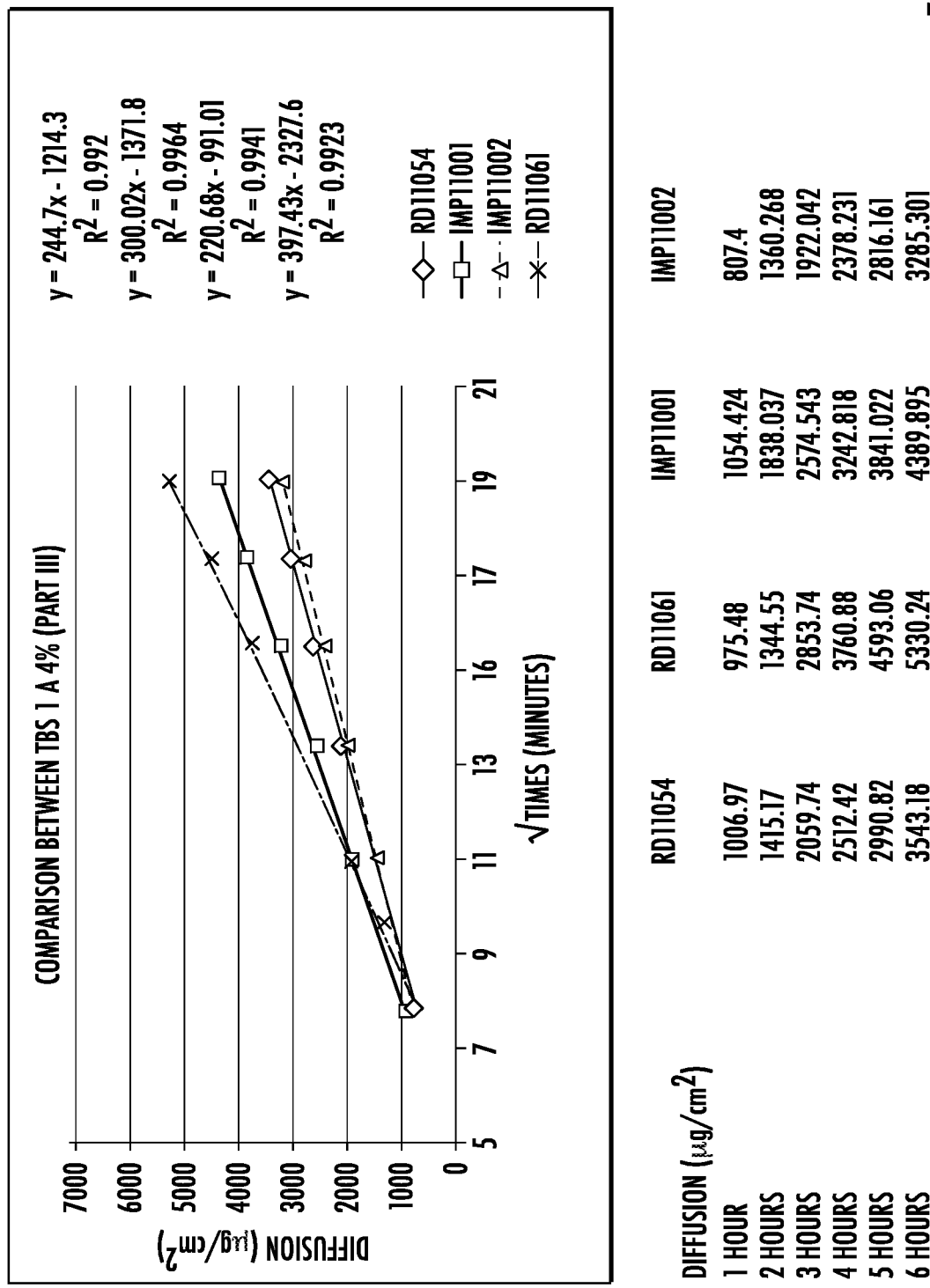
FIG. 19 depicts a comparison between TBS 1 A 4% (Part III)
Figure 20:
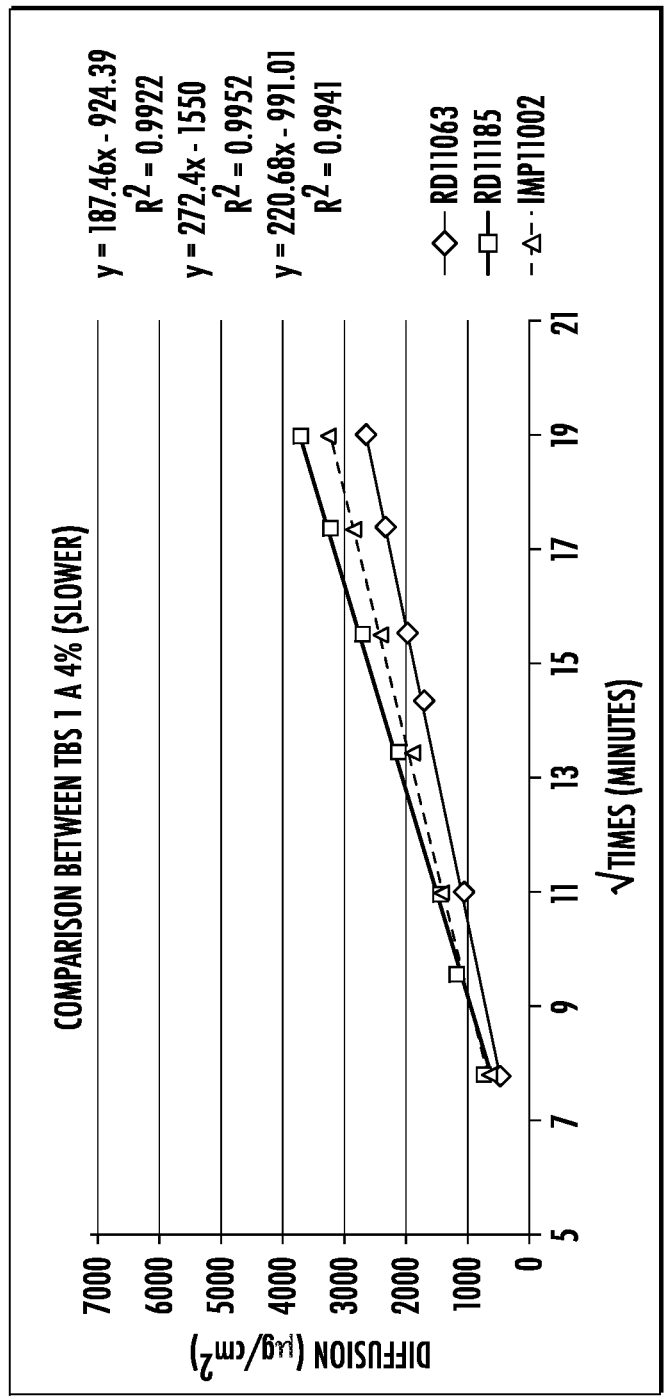
FIG. 20 depicts a comparison slower diffusion.
Figure 21:
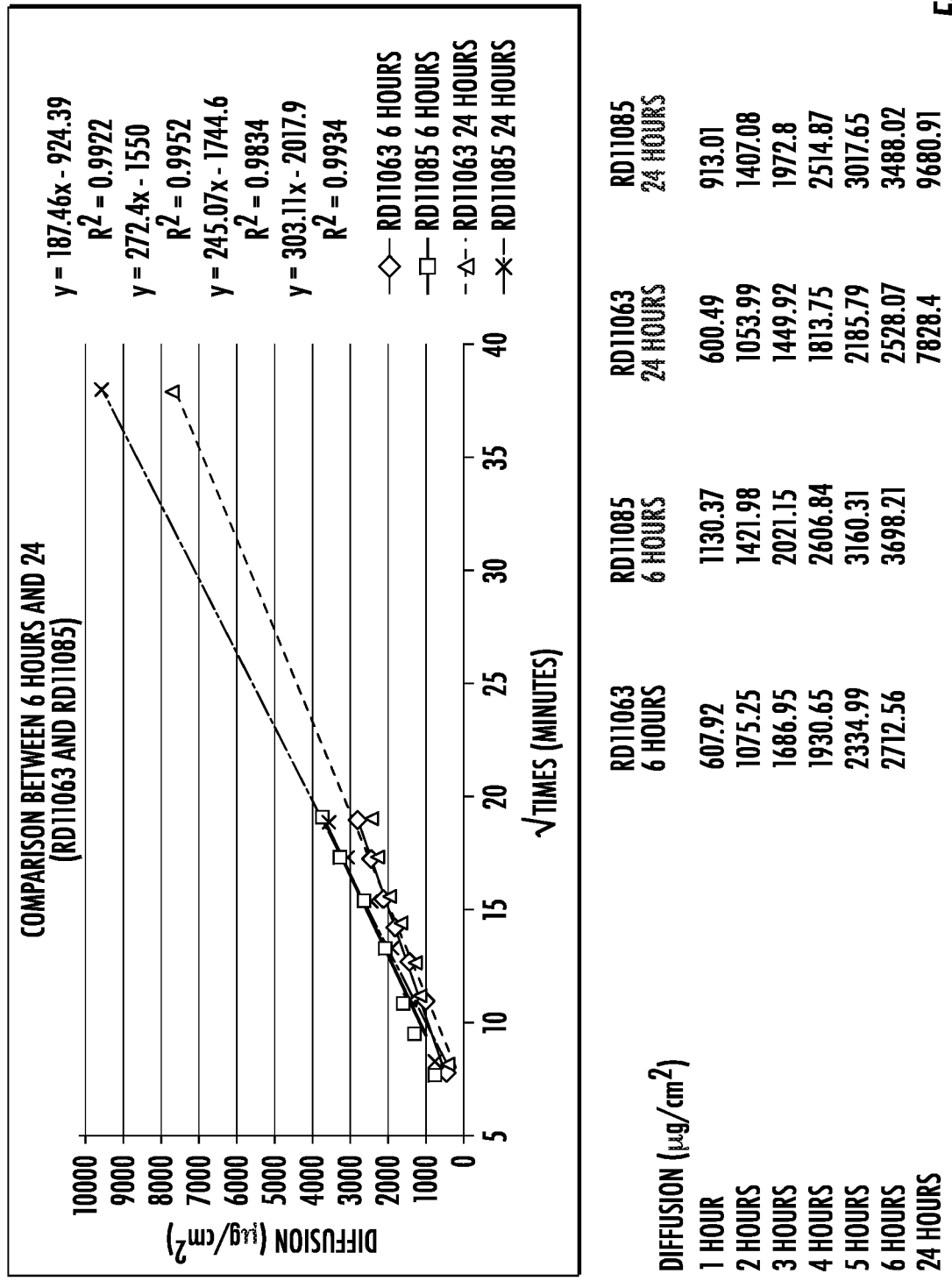
FIG. 21 depicts a comparison between 6 hours and 24 hours run (RD11063 and RD11085)
Figure 22:
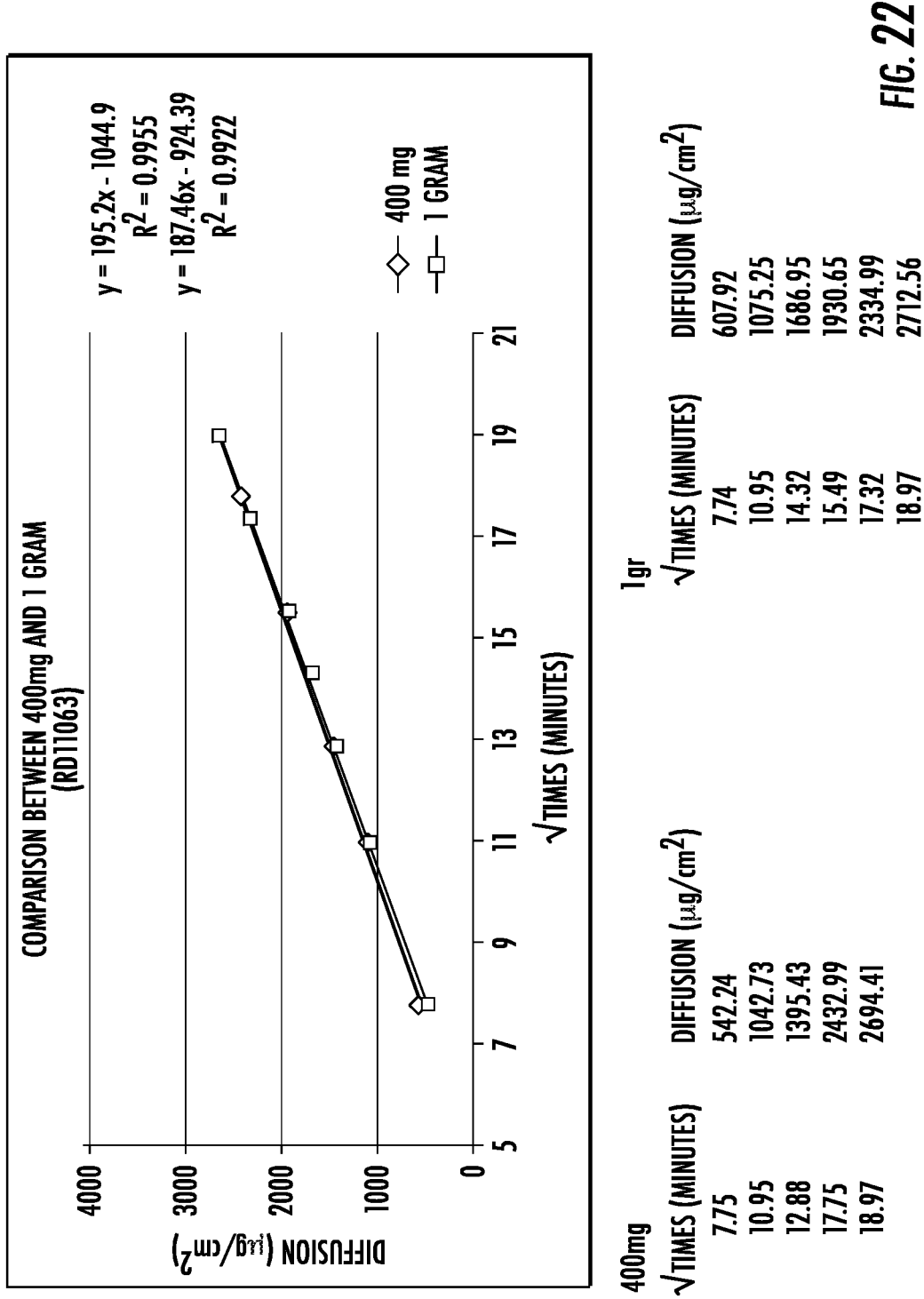
FIG. 22 depicts a comparison between 400 mg and 1 gram of gel (RD11063)

When plotting probability density of the log ratio of testosterone levels that are reached with the multiple dose dispenser over levels that are reached with the syringe as shown in FIG. 17, no significant difference is demonstrated for either $AUC_{0-12}$ or $C_{max}$ within 95% confidence intervals. There is a trend toward a difference for $C_{max}$. However, this data does not confirm bioequivalence at a confidence interval level of 90% for either $AUC_{0-12}$ or $C_{max}$, as the study is not powered for 2-one-sided tests.

TABLE 11

Testosterone TBS-1 log ratios with different confidence intervals

| Parameter | Mean | CI (%) | LLCI | ULCI |
|---|---|---|---|---|
| logRatio $AUC_{0-12\_drug}$ | 0.01398 | 95 | −0.27400 | 0.3019 |
|  |  | 90 | −0.2209574 | 0.24892 |
|  |  | 80 | −0.16438 | 0.19234 |
| logRatio $C_{max\_drug}$ | 0.45520 | 95 | −0.09145 | 1.0020 |
|  |  | 90 | 0.00917 | 0.90127 |
|  |  | 80 | 0.11658 | 0.79386 |

CI = confidence interval; log(0.8) = −0.22314; log(1.25) = 0.22314

Handling of Dropouts or Missing Data

No subjects drop out of the study. Blinded data review did not lead to removal of any data points.

Extent of Exposure

The pharmacokinetic results show that exposure to testosterone is only higher than the upper level of the normal range very briefly shortly after TBS-1 administration.

Adverse Events (AEs)

Treatment is well tolerated. There are 12 adverse event reports in total. Three events had their onset before the first administration of study medication and are therefore unrelated. Four reports of mild complaints such as sore throat are considered unlikely to be caused by study medication when considering the nature of the complaints and the time lapse after administration. One subject reschedules one occasion because of gastro-intestinal complaints that are unlikely to be related to study medication, onset of symptoms is days after study drug administration. Symptoms resolve without treatment.

Reports of bad smell and taste are the only complaints that are considered clearly related to administration of medication. These complaints are mild in intensity and could be considered a product characteristic rather than a medical condition. Bad smell and taste complaints do not lead to discontinuation of the study medication and diminishes with repeated dosing.

Display of Adverse Events

A listing of adverse events is included in Table 12.

TABLE 12

Listing of Adverse Events

| Treatment Treatment action SAE related | Subject | Visit | Start Symptoms | Diagnosis Chronicity | Duration | Severity |
|---|---|---|---|---|---|---|
| TBS-1 mdd Irritated throat. | 2 | 3 | 6 APR. 2011 8:30 single occasion | OROPHARYNGEAL PAIN 0D01H20M mild | None No | unlikely |
|  | 3 | 2 | 30 MAR. 2011 12:00 single occasion | HEADACHE 0D09H00M mild | None No | unrelated |
| Smells nasty, bad taste. |  |  | 30 MAR. 2011 21:04 single occasion | APPLICATION SITE ODOUR 0D02H55M mild | None No | definitely |
| It smells nasty. | 5 | 2 | 30 MAR. 2011 20:40 single occasion | APPLICATION SITE ODOUR 0D00H30M mild | None No | definitely |
| Bad taste. |  |  | 30 MAR. 2011 21:15 single occasion | DYSGEUSIA 0D00H45M mild | None No | definitely |
| plastic Red rash in left armpit, where cannula is placed. | 8 | 2 | 13 APR. 2011 20:45 single occasion | CATHETER SITE RASH 1D18H15M mild | Removed No | unrelated tape patch. |

TABLE 12-continued

Listing of Adverse Events

| Treatment Treatment action SAE related | Subject | Visit | Start Symptoms | Diagnosis Chronicity | Duration | Severity |
|---|---|---|---|---|---|---|
| TBS-1 syringe Sore throat, | 1 | 3 | 6 APR. 2011 8:30 single occasion | OROPHARYNGEAL PAIN 0D00H40M mild | No unlikely | None |
| Feeling agitated. | 2 single occasion | 2 | 31 MAR. 2011 13:00 | AGITATION 0D20H00M mild | No unlikely | None |
| It smells nasty. | 4 single occasion | 2 | 30 MAR. 2011 20:45 | APPLICATION SITE ODOUR 0D00H20M mild | No definitely | None |
| It smells nasty. | 6 single occasion | 2 | 30 MAR. 2011 20:33 | APPLICATION SITE ODOUR 0D00H27M mild | No definitely | None |
| Nausea, diarrhoea. | 10 single occasion | 2 | 18 APR. 2011 23:00 | DIARRHOEA 1D21H00M mild | No unlikely | None |
| No Treatment Paracetamol, unrelated | 11 Headache | 1 | 13 APR. 2011 9:19 single occasion | HEADACHE 0D06H41M mild | | No sleep. |

Note:
mdd = multiple dose dispnenser
M = Missing
U = Unknown

Analysis of Adverse Events

All adverse events are considered mild and are transient. Nasal tolerance is good. Initial complaints of bad smell or taste did not lead to discontinuation of the study.

Deaths, Other Serious Adverse Events, and Other Significant Adverse Events

There are no deaths, serious adverse events or other significant adverse events.

Evaluation of Each Laboratory Parameter

There are no abnormal hematology, blood chemistry or urine laboratory findings that are considered clinically significant in the opinion of the investigator.

Vital Signs, Physical Findings and Other Observations Related to Safety

There are no abnormal findings in vital signs, on physical examinations or other observations that are considered clinically significant in the opinion of the investigator.

Safety Conclusions

Treatment is well tolerated, nasal tolerance is good. All adverse events are considered mild and are transient. Initial complaints of bad smell or taste did not lead to study discontinuation.

Discussion and Overall Conclusions

This study compares the pharmacokinetic profile of TBS-1 testosterone nasal gel administered using a multiple dose dispenser to the profile of TBS-1 delivery using a syringe. In order to avoid carry-over effects that are caused by repeated dosing, the order of administration is randomized. Prior to first administration, subjects are admitted to the unit for blood sampling in order to determine a baseline testosterone profile.

All 12 subjects, age range 18 to 28 years, complete the study successfully. Although not assessed at screening, all subjects have baseline testosterone levels within the normal range. Treatment is well tolerated and all reported adverse events are transient and considered mild. Complaints of bad smell and taste are reported, although this did not lead to discontinuation and decreased with repeated dosing.

As expected, the total exposure to testosterone (as estimated by the mean area under the serum concentration-time curve ($AUC_{0-12}$)) after TBS-1 administration using the dispenser or syringe exceed endogenous levels. The difference in mean $AUC_{0-12}$ between the two modes of administration is small.

Unexpectedly, mean $C_{max}$ is considerably higher after administration with the dispenser than when administering using a syringe. $T_{max}$ is also earlier after administration using the dispenser than after the using the syringe. Thus, testosterone absorption seems to be faster with the multiple dose dispenser than with a syringe, but the total absorbed amount is similar.

Two subjects reach $t_{max}$ of testosterone only 10 and 12 hours after administration with the dispenser. In three subjects, $t_{max}$ is 10 and 12 hours after the syringe, and $t_{max}$ is 5 and 6 hours in two others. Most likely, the endogenous testosterone peak fluctuation exceed levels that are caused by exogenous testosterone administration. Thus, the calculated mean $t_{max}$ may be faster when testosterone is dosed high enough that the peak caused by exogenous administration exceeds the endogenous peak.

When plotting probability density of the log ratio of testosterone levels that are reached with the multiple dose dispenser over levels that are reached with the syringe, no significant difference is demonstrated for either $AUC_{0-12}$ or $C_{max}$ within 95% confidence intervals. There is a trend toward a difference for $C_{max}$. However, this data does not confirm bioequivalence at a confidence interval level of 90% for either $AUC_{0-12}$ or $C_{max}$. This finding may be due to the fact that the ideal positioning of the delivering tip is easier to find with the multiple dose device than the syringe.

Figure 23:
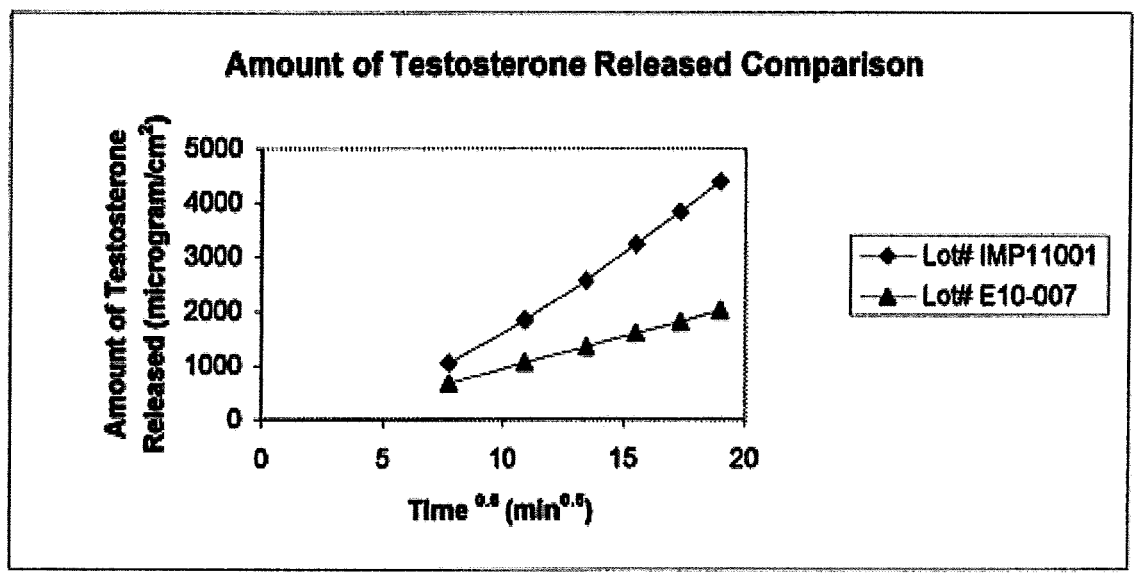
FIG. 23 depicts individual amount of testosterone released from the compositions in accordance with Example 12.

Also, in accordance with this Example 6, see FIGS. 23 and 24.

The following formulations are in Table 13 used in Examples 5-7 and in FIGS. 23 and 24.

TABLE 13

| Material | TBS1 | TBS1V (vs. H20) | TBS-1A 4% (A) | TBS-1A 4% alternate (B) | TBS-1A 8% |
|---|---|---|---|---|---|
| Dimethyl isosorbide | 0 | 0 | 25.0 | 15.0 | 25.0 |
| Diethyleneglycol ethyl ether | 0 | 0 | 10.0 | 5.0 | 10.0 |
| Povidone | 0 | 0 | 3.0 | 3.0 | 3.0 |
| Copovidone | 0 | 0 | 2.0 | 2.0 | 2.0 |
| Hydroxypropyl cellulose | 0 | 0 | 0.5 | 0.5 | 0.5 |
| Testosterone micronized | 4.0 | 4.0 | 4.0 | 4.0 | 8.0 |
| Castor oil | 88.0 | 87.95 | 50.5 | 65.5 | 46.5 |
| Labrafil M1944CS | 4.0 | 4.0 | 0 | 0 | 0 |
| Colloidal silicon dioxide | 4.0 | 4.0 | 5.0 | 5.0 | 5.0 |
| Water | 0 | 0.05 | 0 | 0 | 0 |
| Total | 100.0 | 100.0 | 100.0 | 100.0 | 100.0 |

Example 13

A Phase 3, 90-Day, Randomized, Dose-Ranging Study, Including Potential Dose Titration, Evaluating the Efficacy and Safety of Intranasal TBS-1 in the Treatment of Male Hypogonadism with Sequential Safety Extension Periods of 90 and 180 Days Investigational Product: 4.5% TBS-1 Intranasal Testosterone Gel Protocol Number: TBS-1-2011-03

Synopsis

TITLE: A 90-Day, Randomized, Dose-Ranging Study, Including Potential Dose Titration, Evaluating the Efficacy and Safety of Intranasal TBS-1 in the Treatment of Male Hypogonadism With Sequential Safety Extension Periods of 90 and 180 Days
PROTOCOL NUMBER: TBS-1-2011-03
INVESTIGATIONAL PRODUCT: TBS-1 intranasal 4.5% testosterone gel
PHASE: 3
INDICATION: Adult male hypogonadism (primary and secondary)
OBJECTIVES:

The primary objective of the study is to determine the efficacy of 4.5% TBS-1 gel, administered as 2 or 3 daily intranasal doses of 5.5 mg per nostril, as demonstrated by an increase in the 24-hour average concentration ($C_{avg}$) of serum total testosterone to the normal range (≥300 ng/dL and ≤1050 ng/dL) in ≥75% of male subjects treated for hypogonadism. See also Exhibit C (the contents of which are incorporated herein by reference).

The secondary objectives of this study are the following:
To determine the efficacy of 4.5% TBS-1 gel, administered 2 or 3 times daily at a dose of 5.5 mg per nostril, in achieving the following for serum total testosterone maximum concentration ($C_{max}$):
$C_{max}$≤1500 ng/dL in ≥85% of subjects,
$C_{max}$ 1800 to 2500 in <5% of subjects, and
$C_{max}$>2500 ng/dL in no subjects;
To determine the safety and tolerability of TBS-1 after 90, 180, and 360 days of treatment;
To determine the effect of TBS-1 treatment on body composition (total body mass, lean body mass, fat mass, and percent fat);
To determine the effect of TBS-1 treatment on bone mineral density (lumbar spine and hip);
To determine the effect of TBS-1 treatment on mood;
To determine the effect of TBS-1 treatment on erectile function; and
To determine the serum concentration and pharmacokinetics (PK) of total testosterone, dihydrotestosterone (DHT), and estradiol after TBS-1 administration.

Population:

The population for this study is adult men 18 to 80 years of age, inclusive with fasting morning (0900 h±30 min) total serum testosterone <300 ng/dL. Subjects currently treated with testosterone must undergo 2 to 4 weeks of washout depending on the route of administration.

Study Design and Duration:

This is a Phase 3, 2-group, multicenter study consisting of 4 study periods including 2 safety extension periods as follows:
A 3- to 7-week Screening Period that includes medication washout for subjects currently receiving testosterone treatment;
A 90-day randomized, open-label Treatment Period during which subjects will receive 5.5 mg per nostril of 4.5% TBS-1 twice daily (BID) or three times daily (TID) with potential daily dose adjustment on Day 45 for subjects in the BID treatment group as determined by the serum total testosterone PK profile;
A 90-day open-label Safety Extension Period (Safety Extension Period 1) for all study subjects; and
An additional 180-day open-label Safety Extension Period (Safety Extension Period 2) for a subset of 75 subjects.

The approximate total duration of study participation for subjects completing all 4 periods will be up to 406 days (~58 weeks).

Screening Period

The Screening Period will take place over 3 to 7 weeks and will consist of up to 3 study visits. The duration of screening will depend on whether subjects are naïve to testosterone treatment or if they are currently being treated with a testosterone product. Subjects currently being treated with a testosterone product will require a washout. The duration of washout will depend on the type of testosterone therapy and the date of their last dose. For subjects taking testosterone injections, there must be at least 4 weeks between their last testosterone injection and the first measurement of morning serum total testosterone for qualification. For subjects taking oral, topical, or buccal testosterone, there must be at least 2 weeks between the last administration of testosterone and the first measurement of morning serum total testosterone for qualification.

Visit 1 will occur up to 7 weeks (Week—7) prior to randomization for subjects currently receiving testosterone injections, up to 5 weeks (Week—5) prior to randomization for subjects currently receiving oral, topical, or buccal testosterone, and up to 3 weeks (Week—3) prior to randomization for naïve subjects. During Visit 1, informed consent will be obtained and the subject's inclusion and exclusion criteria will be assessed based on medical interview, concomitant medications, physical examination, digital rectal examination (DRE) of the prostate, vital sign measurements, and screening laboratory evaluations. For naïve subjects, a fasting morning (0900 h±30 min) serum total testosterone level and baseline laboratory measurements will be assessed at Visit 1.

Non-naïve subjects will be instructed to discontinue all testosterone therapies at Visit 1. After Visit 1, if it is determined that a subject does not qualify for the study, the subject will be notified and instructed to restart prior testosterone therapy.

Subjects undergoing washout from testosterone therapy will return for Visit 1.1 and will have fasting morning (0900 h±30 min) serum total testosterone levels and baseline laboratory measurements obtained. For subjects undergoing washout of testosterone injections, Visit 1.1 will occur 4 weeks after the last testosterone injection (up to Week—3). For subjects undergoing washout of oral, topical, or buccal testosterone, Visit 1.1 will occur 2 weeks after the last administration of testosterone (up to Week—3). Visit 1.1 is not required for naïve subjects.

At Visit 2 (up to Week—2), all subjects will have a fasting morning (0900 h±30 min) serum total testosterone level and 12-lead electrocardiogram (ECG) assessed. At the screening visits (Visits 1, 1.1, and 2), serum total testosterone levels will be measured using a validated assay developed by Medpace Reference Laboratories. The results will be used for determination of a subject's inclusion or exclusion from the study. To be included in the study, subjects must have 2 fasting morning (0900 h±30 min) serum total testosterone levels <300 ng/dL. In subjects with a known history of male hypogonadism, if 1 of the 2 serum total testosterone levels is 300 ng/dL, the serum total testosterone level may be retested once. After retesting, if 2 of the 3 levels are <300 ng/dL, then the subject will be eligible to participate in the study.

Subjects who qualify for the study based on screening assessments at Visits 1, 1.1, and 2 will be scheduled for an otorhinolaryngological (ENT) examination with nasal endoscopy performed by an ENT specialist. All qualified subjects will also have dual-energy x-ray absorptiometry scans scheduled in the interval between Visit 2 and randomization (Visit 3) for the assessment of body composition and bone mineral density.

Treatment Period

The randomized, open-label Treatment Period will consist of 4 study visits: Visit 3 (Day 1), Visit 4 (Day 30), Visit 5 (Day 60), and Visit 6 (Day 90).

Visit 3 (Day 1) will take place in the evening. At Visit 3, subjects will be randomized in a 3:1 ratio to 1 of the following 2 treatment groups:

5.5 mg per nostril of 4.5% TBS-1 BID or
5.5 mg per nostril of 4.5% TBS-1 TID.

Baseline levels of fasting serum total testosterone, DHT, and estradiol will be measured. Study drug (TBS-1) will be administered at 2100 h and 0700 h in the BID treatment group (total daily dose of 22 mg/day) and at 2100 h, 0700 h, and 1300 h in the TID treatment group (total daily dose of 33 mg/day). The first dose of study drug will be administered at Visit 3 (Day 1) at 2100 h and training on drug administration will be provided to subjects. Subjects will be asked to maintain a daily diary documenting administration of study drug doses throughout the Treatment Period, Safety Extension Period 1, and Safety Extension Period 2.

At Visit 4 (Day 30 to Day 31), study drug will be administered at the site, beginning with the 2100 h dose of TBS-1. Subjects will be required to remain at the site for 24 hours after the 2100 h drug administration and complete post-dose PK profiles for serum total testosterone, DHT, and estradiol will be obtained. The 24-hour $C_{avg}$ of serum total testosterone for subjects in the BID group will be estimated based on the sum of serum total testosterone levels collected at 2 sampling points during the 24-hour PK profile: the sample collected at 9.0 hours (at 1 hour before the morning 0700 h dose) and the sample collected at 10.33 hours (20 minutes after the morning 0700 h dose). The following titration criteria will be used:

If the sum of the serum total testosterone level values for PK samples collected at 9.0 hours and 10.33 hours is <755 ng/dL, then the estimated 24-hour $C_{avg}$ is <300 ng/dL and If the sum of the serum total testosterone level values for PK samples collected at 9.0 hours and 10.33 hours is ≥755 ng/dL, then the estimated 24-hour $C_{avg}$ is ≥300 ng/dL.

Subjects randomized to the BID group with an estimated serum total testosterone $C_{avg}$<300 ng/dL, will be contacted by phone and instructed to increase the daily dose of TBS-1 to TID on Day 45. The decision to increase the subject's daily dose to TID will be made by the investigator based on the criteria specified above. This daily dose will be continued throughout the remainder of the Treatment Period and, as applicable, both Safety Extension Periods.

At Visit 6 (Day 90 to Day 91), study drug will be administered at the site, beginning with the 2100 h dose of TBS-1. Subjects will be required to remain at the site for 24 hours after the 2100 h drug administration and complete post-dose PK profiles for serum total testosterone, DHT, and estradiol will be obtained.

At Visits 3, 4, and 6, serum total testosterone, DHT, and estradiol levels will be measured using a sensitive and specific assay developed and validated by Analytisch Biochemisch Laboratorium BV. The results will be used for PK analyses.

Safety Extension Period 1

All subjects will continue into Safety Extension Period 1 and will be instructed to continue their current daily dose of TBS-1 for the 90-day Safety Extension Period (Day 90 to Day 180). Subjects will return to the site for monthly visits.

Safety Extension Period 2

A subset of approximately 75 subjects will continue in the study for an additional 180-day Safety Extension Period (Day 180 to Day 360). The subset of subjects who continue into Safety Extension Period 2 will consist of the first subjects to complete Safety Extension Period 1. For the duration of Safety Extension Period 2, subjects will remain on the same daily dose of TBS-1 administered on Day 90 of the Treatment Period and throughout Safety Extension Period 1. Subjects will return to the site for monthly visits.

Dosage Forms and Route of Administration:

| | |
|---|---|
| Study Drug: | 4.5% TBS-1 |
| Pharmaceutical form: | Gel for intranasal administration |

-continued

| Content: | Active ingredient: testosterone<br>Excipients: silicon dioxide, castor oil, and oleoyl polyoxylglycerides |
|---|---|
| Mode of administration: | Intranasal |
| Batch number: | To be determined |
| Storage conditions: | Between 15-25° C. |

TBS-1 is administered intranasally by the subject. A multiple-dose dispenser will be used for gel deposition into the nasal cavity. The dispenser is a finger-actuated dispensing system designed to deliver 5.5 mg of 4.5% TBS-1 gel per actuation from a non-pressurized container into the nasal cavity. The dispenser is designed to administer 45 doses (90 actuations) of TBS-1. The key components of the multiple-dose dispenser include a barrel, base, pump, and actuator, which are composed of polypropylene, and a piston, which is composed of polyethylene.

Efficacy Variables:

The primary efficacy variable is the number and percentage of subjects with a serum total testosterone $C_{avg}$ value within the normal range (≥300 ng/dL and ≤1050 ng/dL) on Day 90.

Secondary efficacy variables include the following:
The number and percentage of subjects with a serum total testosterone maximum concentration ($C_{max}$) value in the following ranges on Day 90:
≤1500 ng/dL,
>1500 and <2500 ng/dL, and
≥2500 ng/dL;
The number and percentage of subjects with a serum total testosterone $C_{avg}$ value in the normal range (≥300 ng/dL and ≤1050 ng/dL) on Day 30;
The number and percentage of subjects with a serum total testosterone $C_{max}$ value in the following ranges on Day 30:
≤1500 ng/dL,
>1500 and <2500 ng/dL, and
≥2500 ng/dL;
The complete PK profile (including $C_{avg}$, the minimum concentration, $C_{max}$, and time to maximum concentration) of serum total testosterone on Day 30 and Day 90;
The time within the normal range for serum total testosterone based on the PK profile on Day 30 and Day 90;
The PK profile of serum estradiol on Day 30 and Day 90;
The PK profile of serum DHT on Day 30 and Day 90;
The ratio of DHT $C_{avg}$ to total testosterone $C_{avg}$ on Day 30 and Day 90;
The Positive and Negative Affect Schedule scores at baseline, Day 30, Day 60, and Day 90;
The International Index of Erectile Function scores at baseline, Day 30, Day 60, and Day 90;
Change in bone mineral density from baseline to Day 180; and
Change in body composition (total body mass, lean body mass, fat mass, and percent fat) from baseline to Day 180.

Safety Variables:

Safety assessments will include adverse events, clinical laboratory measurements (chemistry profile, liver function tests, fasting lipid profile, hematology, urinalysis, glycosylated hemoglobin, prostate specific antigen, and endocrine profile), 12-lead ECG parameters, vital signs (blood pressure, heart rate, temperature, and respiratory rate), physical examination parameters, DREs of the prostate, and ENT examinations.

Statistical Analyses:

The intent-to-treat (ITT) population will consist of all subjects who receive randomized study drug and have at least 1 valid post-baseline efficacy measurement. The safety population will consist of all subjects who receive randomized study drug and have safety measurements during the treated periods. The efficacy analyses will be based on the ITT population and the safety analyses will be based on the safety population. The primary efficacy parameter, the $C_{avg}$ of serum total testosterone at Day 90, will be calculated from the area under the curve (AUC) using the following formula:

$$C_{avg} = AUC_{0-24h}/24$$

The AUC curve for both BID and TID dosing regimens will be determined for the 0 to 24-hour time interval by using the linear trapezoidal rule.

The number and percentage of subjects who reach the treatment goal (ie, serum total testosterone $C_{avg}$ value in the normal range) at Day 90 or Early Termination will be summarized descriptively. The analysis and calculation for the frequency of attaining the secondary study objectives will be performed using similar methods.

The concentrations of serum total testosterone, DHT, and estradiol will be provided for baseline, Day 90 or Early Termination, and the change from baseline to Day 90 or Early Termination.

The same summary will be performed at Day 30 for the purpose of comparing the treatment difference between BID and TID after 30 days of treatment.

For other efficacy measurements, descriptive statistics will be provided at each visit. If appropriate, the change from baseline to post-baseline visits will be determined. The descriptive summary will also be provided for the safety extension periods.

In addition, the Day 30 24-hour $C_{avg}$ serum total testosterone values for all subjects in the BID treatment group will be compared to the estimated value determined by the titration criteria. The acceptability of the titration criteria will be assessed.

Adverse events will be coded using the latest version of the Medical Dictionary for Regulatory Activities. A general summary of the adverse events and serious adverse events for each treatment group will be presented by the overall number of adverse events, the severity, and the relationship to study drug. The incidence of adverse events will be summarized by system organ class, preferred term, and treatment group. The safety laboratory data will be summarized by visit and by treatment group along with the change or percent change from baseline. Vital signs will also be summarized by visit and by treatment group along with the change from baseline. The clinical findings in the physical examination and 12-lead ECG results will be summarized at each scheduled visit. Other safety measurements will be summarized and listed if deemed necessary.

Sample Size Determination:

A sample size of approximately 280 subjects (210 subjects randomized to the BID treatment group and 70 subjects randomized to the TID treatment group) was selected to provide a sufficient number of subjects to determine the efficacy, safety, and tolerability of intranasal 4.5% TBS-1 gel. Since this is an observational study, no formal sample size calculation was performed.

Preliminary data on 139 hypogonadal men who have completed 30 days of BID or TID treatment of the Phase 3 Study exhibit the following results, established by in accordance with the titration methods set forth in Example 15 below and as described herein:

107 males were treated with the BID dosing regimen, 4.5% TBS-1, and 32 males on the TID regimen Approximately 80% of the males treated with 4.5% TBS-1 achieved an average testosterone level above 300 ng/dl Both the BID and TID treatment groups had more than 75% of the patients above the average testosterone level 300 ng/dl cut-off.

In accordance with the present invention, an exemplary label is provided in Exhibit E (the contents of which are incorporated herein by reference).

Example 14

Statistical Analysis Plan

A 90-Day, Randomized, Dose-Ranging Study, Including Potential Dose Titration, Evaluating the Efficacy and Safety of Intranasal TBS-1 in the Treatment of Male Hypogonadism with Sequential Safety Extension Periods of 90 and 180 Days Investigational Product: 4.5% TBS-1 Intranasal Testosterone Gel Protocol Number: TBS-1-2011-03

Introduction

This example provides a description of the statistical methods and procedures to be implemented for the analyses of data from the study with protocol number TBS-1-2011-03. See also Exhibit C (the contents of which are incorporated herein by reference).

Study Design and Objectives
Study Objectives
Primary Objective

The primary objective of the study is to determine the efficacy of 4.5% TBS-1 gel, administered as 2 or 3 daily intranasal doses of 5.5 mg per nostril, as demonstrated by an increase in the 24-hour average concentration ($C_{avg}$) of serum total testosterone to the normal range ($\geq$300 ng/dL and $\leq$1050 ng/dL) in 75% of male subjects treated for hypogonadism.

Secondary Objective

The secondary objectives of this study are the following:
To determine the efficacy of 4.5% TBS-1 gel, administered 2 or 3 times daily at a dose of 5.5 mg per nostril, in achieving the following for serum total testosterone maximum concentration ($C_{max}$):
  $C_{max} \leq$1500 ng/dL in $\geq$85% of subjects,
  $C_{max}$ 1800 to 2500 in <5% of subjects, and
  $C_{max}$>2500 ng/dL in no subjects;
To determine the safety and tolerability of TBS-1 after 90, 180, and 360 days of treatment;
To determine the effect of TBS-1 treatment on body composition (total body mass, lean body mass, fat mass, and percent fat);
To determine the effect of TBS-1 treatment on bone mineral density (lumbar spine and hip);
To determine the effect of TBS-1 treatment on mood;
To determine the effect of TBS-1 treatment on erectile function; and
To determine the serum concentration and pharmacokinetics (PK) of total testosterone, dihydrotestosterone (DHT), and estradiol after TBS-1 administration.

Study Design and Duration

This is a Phase 3, 2-group, multicenter study consisting of 4 study periods including 2 safety extension periods as follows:
  A 3- to 7-week Screening Period that includes medication washout for subjects currently receiving testosterone treatment;
  A 90-day randomized, open-label Treatment Period during which subjects will receive 5.5 mg per nostril of 4.5% TBS-1 twice daily (BID) or three times daily (TID) with potential daily dose adjustment on Day 45 for subjects in the BID treatment group as determined by the serum total testosterone PK profile;
  A 90-day open-label Safety Extension Period (Safety Extension Period 1) for all study subjects; and
  An additional 180-day open-label Safety Extension Period (Safety Extension Period 2) for a subset of 75 subjects.

The approximate total duration of study participation for subjects completing all 4 periods will be up to 406 days (~58 weeks).

Screening Period

The Screening Period will take place over 3 to 7 weeks and will consist of up to 3 study visits. The duration of screening will depend on whether subjects are naïve to testosterone treatment or if they are currently being treated with a testosterone product. Subjects currently being treated with a testosterone product will require a washout. The duration of washout will depend on the type of testosterone therapy and the date of their last dose. For subjects taking testosterone injections, there must be at least 4 weeks between their last testosterone injection and the first measurement of morning serum total testosterone for qualification. For subjects taking oral, topical, or buccal testosterone, there must be at least 2 weeks between the last administration of testosterone and the first measurement of morning serum total testosterone for qualification.

Visit 1 will occur up to 7 weeks (Week—7) prior to randomization for subjects currently receiving testosterone injections, up to 5 weeks (Week—5) prior to randomization for subjects currently receiving oral, topical, or buccal testosterone, and up to 3 weeks (Week—3) prior to randomization for naïve subjects. During Visit 1, informed consent will be obtained and the subject's inclusion and exclusion criteria will be assessed based on medical interview, concomitant medications, physical examination, digital rectal examination (DRE) of the prostate, vital sign measurements, and screening laboratory evaluations. For naïve subjects, a fasting morning (0900 h±30 min) serum total testosterone level and baseline laboratory measurements will be assessed at Visit 1.

Non-naïve subjects will be instructed to discontinue all testosterone therapies at Visit 1. After Visit 1, if it is determined that a subject does not qualify for the study, the subject will be notified and instructed to restart prior testosterone therapy.

Subjects undergoing washout from testosterone therapy will return for Visit 1.1 and will have fasting morning (0900 h±30 min) serum total testosterone levels and baseline laboratory measurements obtained. For subjects undergoing washout of testosterone injections, Visit 1.1 will occur 4 weeks after the last testosterone injection (up to Week—3). For subjects undergoing washout of oral, topical, or buccal testosterone, Visit 1.1 will occur 2 weeks after the last administration of testosterone (up to Week—3). Visit 1.1 is not required for naïve subjects.

At Visit 2 (up to Week—2), all subjects will have a fasting morning (0900 h±30 min) serum total testosterone level and 12-lead electrocardiogram (ECG) assessed.

At the screening visits (Visits 1, 1.1, and 2), serum total testosterone levels will be measured using a validated assay developed by Medpace Reference Laboratories. The results will be used for determination of a subject's inclusion or exclusion from the study. To be included in the study, subjects must have 2 fasting morning (0900 h±30 min) serum total testosterone levels <300 ng/dL.

Subjects who qualify for the study based on screening assessments at Visits 1, 1.1, and 2 will be scheduled for an otorhinolaryngological (ENT) examination with nasal endoscopy performed by an ENT specialist. All qualified subjects will also have dual-energy x-ray absorptiometry scans scheduled in the interval between Visit 2 and randomization (Visit 3) for the assessment of body composition and bone mineral density.

Treatment Period

The randomized, open-label Treatment Period will consist of 4 study visits: Visit 3 (Day 1), Visit 4 (Day 30), Visit 5 (Day 60), and Visit 6 (Day 90).

Visit 3 (Day 1) will take place in the evening. At Visit 3, subjects will be randomized in a 3:1 ratio to 1 of the following 2 treatment groups:
  5.5 mg per nostril of 4.5% TBS-1 BID or
  5.5 mg per nostril of 4.5% TBS-1 TID.

Baseline levels of fasting serum total testosterone, DHT, and estradiol will be measured. Study drug (TBS-1) will be administered at 2100 h and 0700 h in the BID treatment group (total daily dose of 22 mg/day) and at 2100 h, 0700 h, and 1300 h in the TID treatment group (total daily dose of 33 mg/day). The first dose of study drug will be administered at Visit 3 (Day 1) at 2100 h and training on drug administration will be provided to subjects. Subjects will be asked to maintain a daily diary documenting administration of study drug doses throughout the Treatment Period, Safety Extension Period 1, and Safety Extension Period 2.

At Visit 4 (Day 30 to Day 31), study drug will be administered at the site, beginning with the 2100 h dose of TBS-1. Subjects will be required to remain at the site for 24 hours after the 2100 h drug administration and complete post-dose PK profiles for serum total testosterone, DHT, and estradiol will be obtained. The 24-hour $C_{avg}$ of serum total testosterone for subjects in the BID group will be estimated based on the sum of serum total testosterone levels collected at 2 sampling points during the 24-hour PK profile: the sample collected at 9.0 hours (at 1 hour before the morning 0700 h dose) and the sample collected at 10.33 hours (20 minutes after the morning 0700 h dose). The following titration criteria will be used:
  If the sum of the serum total testosterone level values for PK samples collected at 9.0 hours and 10.33 hours is <755 ng/dL, then the estimated 24-hour $C_{avg}$ is <300 ng/dL and
  If the sum of the serum total testosterone level values for PK samples collected at 9.0 hours and 10.33 hours is ≥755 ng/dL, then the estimated 24-hour $C_{avg}$ is ≥300 ng/dL.

Subjects randomized to the BID group with an estimated serum total testosterone $C_{avg}$<300 ng/dL, will be contacted by phone and instructed to increase the daily dose of TBS-1 to TID on Day 45. The decision to increase the subject's daily dose to TID will be made by the investigator based on the criteria specified above. This daily dose will be continued throughout the remainder of the Treatment Period and, as applicable, both Safety Extension Periods.

At Visit 6 (Day 90 to Day 91), study drug will be administered at the site, beginning with the 2100 h dose of TBS-1. Subjects will be required to remain at the site for 24 hours after the 2100 h drug administration and complete post-dose PK profiles for serum total testosterone, DHT, and estradiol will be obtained.

At Visits 3, 4, and 6, serum total testosterone, DHT, and estradiol levels will be measured using a sensitive and specific assay developed and validated by Analytisch Biochemisch Laboratorium BV. The results will be used for PK analyses.

Safety Extension Period 1

All subjects will continue into Safety Extension Period 1 and will be instructed to continue their current daily dose of TBS-1 for the 90-day Safety Extension Period (Day 90 to Day 180). Subjects will return to the site for monthly visits.

Safety Extension Period 2

A subset of approximately 75 subjects will continue in the study for an additional 180-day Safety Extension Period (Day 180 to Day 360). The subset of subjects who continue into Safety Extension Period 2 will consist of the first subjects to complete Safety Extension Period 1. For the duration of Safety Extension Period 2, subjects will remain on the same daily dose of TBS-1 administered on Day 90 of the Treatment Period and throughout Safety Extension Period 1. Subjects will return to the site for monthly visits.

A table of the schedule of procedures can be found below:
Schedule of Procedures

| | Study Phase | | | | | | | | | | | | | | | |
|---|---|---|---|---|---|---|---|---|---|---|---|---|---|---|---|---|
| | Screening | | | | | Randomization | Treatment Period | | | Safety Extension | | | | | | |
| | Prior Testosterone Treatment | | | Testosterone Treatment Naive | | | | Efficacy Analysis | | Period 1 Safety Analysis | | Period 2 Subset Safety Analysis | | | | |
| | | | | | | | | | | | | | | | | |
| | | | | | | | Day 30-Day 31[p] | Day 60 | Day 90-Day 91[q] | Day 120 and Day 150 | Day 180 | Day 210 and Day 240 | Day 270 | Day 300 and Day 330 | Day 360 | |
| | Week-7 or -5a | Week-3 | Week-2 | Week-3 | Week-2 | Day 1 | | | | | | | | | | Early Termination |
| | | | | | | | | | | | | | | | | |
| Study Procedures | 1 | 2 | 1.1[b] | 1 | 2 | 3 | 4[c] | 5 | 6 | 7-8[e] | 9 | 10-11[e] | 12 | 13-14 | 15 | |
| Inclusion/exclusion criteria | x | x | | x | | | | | | | | | | | | |
| Informed consent | x | | | x | | | | | | | | | | | | |
| Medical interview | x | | | x | | | | | | | | | | | | |
| Physical examination | x | | | x | | | | | x | | | | | | | x |
| Height and weight | x | | | x | | | | | | | | | | | | |
| Vital signs (HR, BP, RR, and temperature) | x | | | x | | x[r] | x[r] | x | x[r] | x | x | x | x | x | x | x |
| Concomitant medications | x | x | | x | x | x | x | x | x | x | x | x | x | x | x | x |
| DRE of the prostate | | | | | | | | | x | | x | | | | x | x |
| Chemistry profile and hematology[f] | x | | | x | | | x | | x | | x | | x | | x | x |
| Fasting lipid profile[g] | x | | | x | | | x | | x | | x | | x | | x | x |
| Liver function tests[h] | x | | | x | | | x | | x | | x | | x | | x | x |
| HbA$_{1c}$ and endocrine profile[i] | x | | | x | | | | | x | | x | | x | | x | x |
| Urinalysis[j] | x | | | x | | | | | x | | x | | x | | x | x |
| Urine drug and alcohol screen | x | | | x | | | | | | | | | | | | |
| PSA | x | | | x | | | | | x | | x | | x | | x | x |
| Estradiol and DHT[k] | x | x | | x | x | x | x | x | x | x | x | x | x | x | x | x |
| Free testosterone | x | x | | x | x | | | | x | | x | | x | | x | x |
| 12-lead electrocardiogram | | x | | | x | | | | | | | | | | | |
| Fasting serum total testosterone[k] | x | x | | x | x | x | | x | | x | x | x | x | x | x | |
| ENT exam with nasal endoscopy[l] | | x | | | x | | | | | | | | | | | |
| DEXA[m] | | x | | | x | | | | | | | | | | x | |
| IIEF and PANAS questionnaires | | | | | | x | x | x | x | | x | | | | x | x[o] |
| Administer study drug at the site | | | | | | x | x | | x | | | | | | | |
| 24-h PK profile for serum total testosterone, DHT, and estradiol | | | | | | | | | | | x[s] | | | | | |
| Basic ENT examination (non-endoscopic) | | | | | | x | x | x | x | x | x | x | x | x | x | x |
| Potential study drug daily dose titration | | | | | | | x | | | | | | | | | |
| Distribute and/or review daily diary[n] | | | | | | x | x | x | x | x | x | x | x | x | x | x |
| Weigh study drug dispensers | | | | | | x | x | x | x | x | x | x | x | x | x | x |

-continued

| | Study Phase | | | | | | | | | | | | | | |
|---|---|---|---|---|---|---|---|---|---|---|---|---|---|---|---|
| | Screening | | | | Treatment Period | | | | | | Safety Extension | | Safety Extension | | |
| | Prior Testosterone Treatment | | | Testosterone Treatment Naïve | | Randomization | | | | Efficacy Analysis | | Period 1 Safety Analysis | | Period 2[d] Subset Safety Analysis | | Early Termination |
| | Week-7 or -5a | Week-3 | Week-2 | Week-3 | Week-2 | Day 1 | Day 30-Day 31[p] | Day 60 | Day 90-Day 91[q] | | Day 120 and Day 150 | Day 180 | Day 210 and Day 240 | Day 270 | Day 300 and Day 330 | Day 360 | |
| | | | | | | | | | | | | | | | | |
| | 1 | 1.1[b] | 2 | 1 | 2 | 3 | 4[c] | 5 | 6 | | 7-8[e] | 9 | 10-11[e] | 12 | 13-14 | 15 | |
| Study Procedures | | | | | | | | | | | | | | | | | |
| Prime study drug dispensers and distribute to subjects | | | | | | x | x | x | x | | x | x[s] | x | x | x | x | |
| Assess adverse events | x | | x | x | x | x | x | x | x | | x | x | x | x | x | x | x |

[a]Visit 1 for subjects receiving intramuscular testosterone injections at the time of screening will occur up to Week-7. Visit 1 for subjects receiving buccal, oral, or topical testosterone will occur at up to Week-5.
[b]Visit 1.1 is only required for subjects who have undergone washout of testosterone therapy and will take place 4 weeks after the last administration of testosterone for subjects taking testosterone injections and 2 weeks after the last testosterone administration for subjects taking buccal, oral, or topical testosterone.
[c]Based on the PK profile for serum total testosterone performed at Visit 4, some subjects in the BID treatment group will have their daily dose increased to TID. Subjects that require a daily dose increase will be contacted by phone and instructed to increase their daily dose on Day 45.
[d]A subset of approximately 75 subjects will be enrolled in Safety Extension Period 2.
[e]During Safety Extension Period 1 and Safety Extension Period 2, study visits will be conducted once per month.
[f]Chemistry profile includes: creatine kinase, sodium, potassium, glucose, blood urea nitrogen, creatinine, calcium, phosphorus, and uric acid. Hematology includes: hemoglobin, hematocrit, red blood cell count, white blood cell count and differential, platelets, reticulocyte count, mean corpuscular volume, mean corpuscular hemoglobin, , and mean corpuscular hemoglobin concentration.
[g]Fasting lipid profile includes: total cholesterol, low-density lipoprotein cholesterol (direct), high-density lipoprotein cholesterol, and triglycerides.
[h]Liver function tests include: total bilirubin, albumin, aspartate aminotransferase, alanine aminotransferase, alkaline phosphatase, and gamma glutamyl transferase.
[i]Endocrine profile includes: thyroid-stimulating hormone, morning cortisol, sex hormone-binding globulin, luteinizing hormone, follicle-stimulating hormone, and prolactin.
[j]Urinalysis includes: specific gravity, glucose, protein, ketones, pH, blood, bilirubin, urobilinogen, nitrite, and leukocyte esterase.
[k]Fasting serum total testosterone, DHT, and estradiol should be collected at 0900 h ± 30 min at Visits 1, 1.1, 2, 9, 12, 15, and Early Termination and at 2045 h at Visit 3. In subjects with a known history of male hypogonadism, if 1 of the 2 serum total testosterone levels collected at screening is ≥300 ng/dL, the serum total testosterone level may be retested once. After retesting, if 2 of the 3 levels are <300 ng/dL, then the subject will be eligible to participate in the study.
[l]ENT examination with nasal endoscopy performed by an ENT specialist will be scheduled for the interval between Visit 2 and Visit 3 (Day 1 [randomization]) on qualified subjects.
[m]DEXA scans to evaluate body composition (total body mass, lean body mass, fat mass, and percent fat) and bone density (lumbar spine and hip) will be performed in the interval between Visit 2 and Visit 3 on qualified subjects. Follow-up DEXA will be obtained at Visit 9 (Day 180) and Visit 15 (Day 360), if scheduling is available, or within ±2 weeks of Visit 9 and Visit 15.
[n]Daily diary will be distributed to subjects to record date and time of study drug administration.
[o]IIEF and PANAS questionnaires will be administered to subjects at Early Termination if subjects terminate on or before Visit 6 (Day 90).
[p]On Day 31 of Visit 4, the following procedures will be performed: vital sign measurements, basic ENT examination, administer questionnaires (may be performed on Day 30 or Day 31), and dispense daily diary.
[q]On Day 91 of Visit 6, the following procedures will be performed: vital sign measurements, basic ENT examination, dispense daily diary, administer questionnaires (may be performed on Day 90 or Day 91), perform DRE (may be performed on Day 90 or Day 91), and perform physical examination (may be performed on Day 90 or Day 91).
[r]At Visit 3 (Day 1), vital sign measurements will be obtained prior to first dose of study drug and at approximately 1 hour after the first dose of study drug (at 2200 h). On Day 30 of Visit 4 and Day 90 of Visit 6, vital sign measurements will be obtained once prior to administration of study drug. On Day 31 of Visit 4 and Day 91 of Visit 6, vital sign measurements will be obtained at the following approximate times after administration of study drug: 6 hours (at 0300 h), 12 hours (at 0900 h), 18 hours (at 1500 h), and 24 hours (at 2100 h).
[s]At Visit 9, study drug dispensers and daily diaries will only be distributed to subjects entering Safety Extension Period 2.
BID = twice daily; BP = blood pressure; DEXA = dual-energy x-ray absorptiometry; DRE = digital rectal examination; DHT = dihydrotestosterone; ENT = otorhinolaryngological; HbA$_{1c}$ = glycosylated hemoglobin; HR = heart rate; IIEF = International Index of Erectile Function; PANAS = Positive and Negative Affect Schedule; PK = pharmacokinetic; PSA = prostate specific antigen; RR = respiratory rate; TID = three times daily.

Efficacy Variables
Primary Efficacy Variable

The primary efficacy variable is the number and percentage of subjects with a serum total testosterone $C_{avg}$ value within the normal range ($\geq$300 ng/dL and $\leq$1050 ng/dL) on Day 90.

Secondary Efficacy Variables

Secondary efficacy variables include the following:
- The number and percentage of subjects with a serum total testosterone maximum concentration ($C_{max}$) value in the following ranges on Day 90:
  - $\leq$1500 ng/dL,
  - $\geq$1800 and $\leq$2500 ng/dL, and
  - >2500 ng/dL;
- The number and percentage of subjects with a serum total testosterone $C_{avg}$ value in the normal range ($\geq$300 ng/dL and $\leq$1050 ng/dL) on Day 30;
- The number and percentage of subjects with a serum total testosterone $C_{max}$ value in the following ranges on Day 30:
  - $\leq$1500 ng/dL,
  - $\geq$1800 and $\leq$2500 ng/dL, and
  - >2500 ng/dL;
- The complete PK profile (including $C_{avg}$, the minimum concentration, $C_{max}$, and time to maximum concentration) of serum total testosterone on Day 30 and Day 90;
- The time within the normal range for serum total testosterone based on the PK profile on Day 30 and Day 90;
- The PK profile of serum estradiol on Day 30 and Day 90;
- The PK profile of serum DHT on Day 30 and Day 90;
- The ratio of DHT $C_{avg}$ to total testosterone $C_{avg}$ on Day 30 and Day 90;
- The Positive and Negative Affect Schedule scores at baseline, Day 30, Day 60, and Day 90;
- The International Index of Erectile Function scores at baseline, Day 30, Day 60, and Day 90;
- Change in bone mineral density from baseline to Day 180 and from baseline to Day 360; and
- Change in body composition (total body mass, lean body mass, fat mass, and percent fat) from baseline to Day 180 and from baseline to Day 360.

Safety Variables

Safety assessments will include adverse events, clinical laboratory measurements (chemistry profile, liver function tests, fasting lipid profile, hematology, urinalysis, glycosylated hemoglobin, prostate specific antigen, and endocrine profile), 12-lead ECG parameters, vital signs (blood pressure, heart rate, temperature, and respiratory rate), physical examination parameters, DREs of the prostate, and ENT examinations.

Statistical Methodology
Baseline, Endpoint, and Other Statistical Considerations Results will be summarized by the following treatment groups:
- TBS-1 BID,
- TBS-1 BID/TID (for subjects who up-titrated at Day 45), and
- TBS-1 TID.

For time points prior to Day 45, TBS-1 BID, TBS-1 BID/TID, and TBS-1 TID treatment groups will be presented even though no titration has occurred. Additionally, a Total TBS-1 BID treatment group (combining the TBS-1 BID and TBS-1 BID/TID groups) will be presented.

Baseline for results from the IIEF and PANAS questionnaires, vital signs, estradiol, DHT, and fasting serum total cholesterol will be the Day 1 value.

Baseline for body composition, bone mineral density, and 12-lead electrocardiogram will be the Week—2 value.

Baseline for safety laboratory results will be the Week—3 value.

If the baseline value is missing, the last value prior to the first dose of study medication will be used as baseline.

Day 90 LOCF will be the Day 90 value. If missing, the last value during the Treatment Period will be used.

Day 180 LOCF will be the Day 180 value. If missing, the last value during Safety Extension Period 1 will be used.

Day 360 LOCF will be the Day 360 value. If missing, the last value during Safety Extension Period 2 will be used.

Descriptive statistics (n, mean, standard deviation, minimum, median, maximum) will be used to summarize the continuous efficacy and safety variables. For lipids and other measurements that might violate the normal assumption, non-parametric statistics (Q1, Q3, and inter-quartile range) will be provided in addition to the conventional parametric statistics. The count and frequency will be used to tabulate the categorical measurements.

Analysis Populations
Randomized Population

The randomized population will consist of all subjects who signed the informed consent form and are assigned a randomization number at Visit 3 (Day 1).

Intent-to-Treat Populations

The intent-to-treat (ITT) population for each period will consist of all subjects who receive randomized study drug and have at least one valid post-baseline efficacy measurement in the period.

Per-Protocol Population

The per-protocol population will consist of all ITT subjects who complete the 90-day Treatment Period without any major protocol deviations.

Subjects may be excluded from the per-protocol population for the following reasons:
- Major violations of eligibility criteria for randomization,
- Withdrawal Prior to Day 90 or missing Day 90 PK profile,
- Restricted concomitant medications taken during the treatment period, or
- Any other major protocol deviation that may interfere with the assessment of drug efficacy.

Safety Populations

The safety population for each period will consist of all subjects who receive randomized study drug and have safety measurements in the respective period.

Patient Disposition

Patient disposition will be summarized by counts and percentages for each treatment group and in total. The following categories of patient disposition will be included:
- Subjects who are randomized,
- Subjects who complete the Treatment Period,
- Subjects who complete the Treatment Period and Safety Extension Period 1,
- Subjects who enter Safety Extension Period 2, and
- Subjects who complete Safety Extension Period 2.

For randomized subjects who discontinue from the study, the primary reason for discontinuation will be summarized according to the period in which the withdrawal occurred. Reasons for discontinuation will be listed.

The total number of subjects who are screened and the total number of screen failures with reasons for screen failure will be tabulated.

The number and percentage of subjects in the ITT populations, PP population, and safety populations will be presented by treatment group and in total.

Demographic and Baseline Characteristics

Demographic and baseline characteristics will be summarized for all subjects in the randomized population by treatment group and in total.

Gender, race, testosterone therapy history, smoking status, and alcohol use will be summarized with counts and percentages. Age, height, weight, body mass index (BMI), and duration of hypogonadism will be summarized with descriptive statistics.

Baseline values for fasting serum total testosterone will be described with descriptive statistics.

Baseline is defined in Section 0

Baseline, Endpoint, and Other Statistical Considerations.

Medical history will be listed for all randomized subjects.

Prior/Concomitant Medications

Medication start and stop dates that are recorded on the Prior and Concomitant Medications Case Report Form (CRF) will be used to determine whether the medications are prior or concomitant to the treatment and safety extension periods. Prior medications are defined as those used prior to and stopped before the first dose of study medication.

Concomitant medications are those that are used during the treatment period or safety extension periods (i.e., start date is on or after the first dose date of study medication, or start prior to the date of first dose and the stop date is either after the first dose date or marked as "continuing").

Concomitant medication/therapy verbatim terms will be coded with Anatomical Therapeutic Chemical (ATC) class and preferred term by the World Health Organization Drug Dictionary. The numbers and percentages of subjects in each treatment group taking concomitant medications will be summarized by ATC class and preferred term for the safety population for the Treatment Period. Concomitant medications taken during Safety Extension Period 1 and Safety Extension Period 2 will be summarized in a similar manner.

Prior and concomitant medications will be listed.

Study Exposure, Dispensation, and Accountability

Days of exposure to study medication during the Treatment Period, Safety Extension Period 1, and Safety Extension Period 2 will be summarized with descriptive statistics for the safety populations for each treatment group and overall. Contingency tables will be provided to display the number and percentage of subjects with exposure by visit for each treatment group for the safety populations.

Days of exposure is defined as the date of the last dose of study medication (in the respective period)—the date of the first dose of study medication+1.

Drug dispensation and accountability data will be listed.

Analysis of Efficacy

Efficacy evaluations will be performed for the ITT populations. The primary efficacy analysis will be repeated for the PP population.

Analysis of the Primary Efficacy Parameter

The primary objective of this study is to determine the efficacy of 4.5% TBS-1 gel, administered intranasally BID and/or TID, in increasing the $C_{avg}$ of serum total testosterone to the normal range (≥300 ng/dL and ≤1050 ng/dL) in male subjects with hypogonadism after 90 days of treatment. The primary efficacy parameter, $C_{avg}$, will be calculated from the AUC using the following formula:

$$C_{avg} = AUC_{0-24h}/24.$$

The AUC curve for both the BID and TID dosing regimens will be determined for the 0-24 hour time interval by using linear trapezoidal and linear interpolation methods. Actual collection times will be used in the calculation.

The number and percentage of subjects who reach the treatment goal (ie, serum total testosterone $C_{avg}$ value in the normal range) at Day 90 or Early Termination (Day 90 LOCF) will be summarized by treatment group. 95% confidence intervals for the frequency will be approximated by a binomial distribution within each treatment group.

Analysis of the Secondary Efficacy Parameters

The primary efficacy analysis will be repeated for the serum total testosterone $C_{avg}$ values on Day 30. Additionally, for $C_{avg}$ on Day 30, the Total BID treatment group and the TID treatment group will be compared using the chi-square test to evaluate the number of subjects with $C_{avg}$ within the normal range (≥300 ng/dL and ≤1050 ng/dL).

The odds ratio, 95% confidence interval, and p-value will be presented.

The serum total testosterone $C_{max}$ values on Day 30 and Day 90 will be summarized by counts and percentages for each treatment group for the following categories:

$C_{max}$≤1500 ng/dL, 1800 ng/dL≤$C_{max}$≤2500 ng/dL, and $C_{max}$>2500 ng/dL.

The PK profile, including $AUC_{0-24h}$, $C_{avg}$, $C_{min}$, $C_{max}$, and $T_{max}$, for serum total testosterone, serum estradiol, and serum DHT will be summarized with descriptive statistics, including the arithmetic mean, standard deviation, coefficient of variation (CV %), geometric mean, median, minimum, and maximum by treatment at Day 30 and Day 90. Geometric mean and CV % will not be presented for T. The same descriptive statistics will be calculated for serum concentrations at each sampling time by treatment and visit.

Data will be listed individually for all subjects. A figure displaying the distribution of the $C_{avg}$ values at Day 30 and Day 90 will be provided.

All concentrations below the lower limit of quantification (LLOQ) or missing data will be labeled as such in the concentration data listings. Concentrations below the LLOQ prior to the first measurable concentration will be treated as zero in the summary statistics and for the calculation of PK profile parameters. Concentrations below LLOQ after the time point of the first measurable concentration will be set to missing and not included in the calculation of AUC.

The time within normal range (≥300 ng/dL and ≤1050 ng/dL) for serum total testosterone and the ratio of DHT $C_{avg}$ to total testosterone $C_{avg}$ on Day 30 and Day 90 will be summarized with descriptive statistics for each treatment group.

The concentrations of fasting serum total testosterone, DHT, and estradiol will be summarized with descriptive statistics at baseline, Day 30, Day 90, Day 90 LOCF, Day 180, Day 180 LOCF, Day 270, Day 360, and Day 360 LOCF. The change from baseline will also be summarized.

The change in bone mineral density, total body mass, lean body mass, fat mass, and percent fat will be summarized with descriptive statistics at baseline, Day 180, and Day 360, as well as the change from baseline to Day 180 and the change from baseline to Day 360 for each treatment group.

The Day 30 24-hour $C_{avg}$ serum total testosterone values for all subjects in the BID treatment group will be assessed for appropriate dose titration (from BID to TID) at Day 45.

The IIEF questionnaire will be broken up into five domains: erectile function, intercourse satisfaction, orgasmic function, sexual desire, and overall satisfaction. Point values will be assigned to each answer in the questionnaire according to Appendix 1. (See Appendix 1 in the Appendix to the Specification.) Domain scores will be the sum of the points of each question making up the domain. The breakdown can be found in the table below.

| Domain | Questions | Maximum Score |
| --- | --- | --- |
| Erectile Function | 1, 2, 3, 4, 5, 15 | 30 |
| Intercourse Satisfaction | 6, 7, 8 | 15 |
| Orgasmic Function | 9, 10 | 10 |
| Sexual Desire | 11, 12 | 10 |
| Overall Satisfaction | 13, 14 | 10 |

The scores for each domain will be summarized with descriptive statistics at baseline, Day 30, Day 60, Day 90, Day 90 LOCF, and the change from baseline at each visit.

PANAS scores will be summarized with descriptive statistics for each emotion/feeling as well as the Positive and Negative Affect Score by treatment at baseline, Day 30, Day 60, Day 90, and Day 90 LOCF. Change from baseline to each visit will be provided for the Positive and Negative Affect Scores. Positive Affect Score is found by adding the scores from items 1, 3, 5, 9, 10, 12, 14, 16, 17, and 19. Negative Affect Score is found by adding the scores from items 2, 4, 6, 7, 8, 11, 13, 15, 18, and 20. A separate summary will be performed to summarized the PANAS scores based on how the subject 'felt over the past week', not including those scores based on how the subject 'feels right now'.

Analysis of Safety

All analyses of safety will be conducted on the safety populations and will be summarized by treatment group and in total. The safety assessments include adverse events, clinical laboratory measurements, DRE of the prostate, 12-lead ECGs, vital sign measurements, basic ENT examination, and physical examination.

Adverse Events

An adverse event (AE) is defined as any untoward medical occurrence associated with the use of a drug in humans, whether or not considered drug related. An adverse event can therefore be any unfavorable and/or unintended sign (including an abnormal laboratory finding), symptom, or disease temporally associated with the use of an investigational medication product, whether or not related to the investigational medication product. All adverse events, including observed or volunteered problems, complaints, or symptoms, are to be recorded on the appropriate eCRF. AEs will be coded using the latest version of MedDRA.

Treatment-emergent adverse events (TEAEs) are defined as those AEs that have a start date on or after the first dose of randomized study medication, or occur prior to the first dose and worsen in severity during the treatment period. Drug-related AEs are defined as those AEs with relationship to study drug as "Probable" or "Definitely Related".

TEAEs will be summarized in which period the AE began. For example, TEAEs during Safety Extension Period 1 will be any TEAEs that occur on or after the first day of Safety Extension Period 1 through the end of the study or the start of Extension Period 2.

A table overview of adverse events will be provided summarizing the counts and percentages of subjects with the following adverse events during the Treatment Period:
TEAEs,
Maximum severity of TEAEs,
Drug-related TEAEs,
Maximum severity of drug-related TEAEs,
All serious adverse events (SAEs),
All treatment-emergent SAEs,
Drug-related SAEs,
Death due to AEs,
Withdrawals due to AEs, and
Withdrawals due to drug-related AEs.

A similar overview for TEAEs with onset date during Safety Extension Period 1 and Safety Extension Period 2 will be provided.

The counts and percentages of subjects with TEAEs during the Treatment Period will be summarized for each treatment group by system organ class and preferred term. Drug-related TEAEs, SAEs, and TEAEs leading to discontinuation of study medication during the Treatment Period will be summarized in the same manner. Summaries of maximum severity for TEAEs and drug-related TEAEs will be provided.

The counts and percentages of subjects with TEAEs during Safety Extension Period 1 and Safety Extension Period 2 will be summarized for each treatment group by system organ class and preferred term. Drug-related TEAEs will be summarized in the same manner.

All SAEs and TEAEs leading to discontinuation of study medication will be listed with detailed information.

Clinical Laboratory Assessments

Continuous laboratory results for selected laboratory parameters (including hematology, chemistry, urinalysis, lipid profile, liver function tests, $HbA_{1c}$ and endocrine profile) will be presented by treatment group and summarized with descriptive statistics for each scheduled visit and for the end of each period. The change from baseline will also be presented.

Categorical laboratory results will be presented with the frequency and percentage in each category by treatment group for each scheduled visit and for the end of each period.

The number and percentage of subjects with laboratory abnormalities will be summarized by treatment group and overall for each period. The worst value for each subject in each period will be summarized.

Listings will be provided for all laboratory parameters.

Physical Examination, Digital Rectal Exam, ENT Exam, and Nasal Endoscopy

Physical examination findings will be summarized by treatment group with counts and percentages for each body system for each scheduled visit and for the end of each period. Digital rectal exam, ENT examination, and nasal endoscopy results will be summarized in a similar manner.

Physical examination, digital rectal exam, ENT exam, and nasal endoscopy findings will be listed by subject.

Weight, BMI, Vital Signs, and 12-Lead Electrocardiogram

Weight, BMI, vital signs, and quantitative ECG parameters (Heart Rate, PR Interval, QRS Interval, and QT Interval) will be summarized with descriptive statistics at baseline, each post-baseline visit, and the end of each period. The change from baseline will also be presented. Counts and percentages of subjects with abnormal ECG results will be tabulated.

Vital signs recorded during the PK sampling and overall interpretations from ECG will be listed.

Report Analyses

Two report analyses will be generated for this study.

The first analysis will be conducted after all subjects complete the Treatment Period.

The analysis will include all primary and secondary efficacy endpoints. Safety data collected through Safety Extension Period 1 will also be summarized.

After all subjects complete the study, including Safety Extension Period 2, a second analysis will be generated including all safety and efficacy data.

Sample Size Determination

A sample size of approximately 280 subjects (210 subjects randomized to the BID treatment group and 70 subjects randomized to the TID treatment group) was selected to provide a sufficient number of subjects to determine the efficacy, safety, and tolerability of 4.5% TBS-1 gel. Since this is an observational study, no formal sample size calculation was performed.

Programming Specifications

The programming specifications, including the mock-up validity listings, analysis tables, figures, and data listings, as well as the derived database specifications, will be prepared in stand-alone documents. The programming specification documents will be finalized prior to database lock.

LIST OF ABBREVIATIONS AND DEFINITION OF TERMS

ALT Alanine transaminase
AST Aspartate transaminase
AUC Area under the curve
BID Twice daily
$C_{avg}$ Average concentration
$C_{max}$ Maximum concentration
$C_{min}$ Minimum concentration
CRA Clinical research associate
CTIVRS ClinTrak™ Interactive Voice Response System
DEXA Dual-energy x-ray absorptiometry
DHEA Dehydroepiandrosterone
DHT Dihydrotestosterone
DRE Digital rectal examination
ECG Electrocardiogram
eCRF Electronic case report form
EDC Electronic data capture
ENT Otorhinolaryngological
FSH Follicle-stimulating hormone
GnRH Gonadotropin-releasing hormone
H2 Histamine 2
$HbA_{1c}$ Glycosylated hemoglobin
IIEF International Index of Erectile Function
IRB Institutional Review Board
ITT Intent-to-treat
LH Luteinizing hormone
MedDRA Medical Dictionary for Regulatory Activities
PANAS Positive and Negative Affect Schedule
PDE5 Phosphodiesterase 5
PK Pharmacokinetic
PSA Prostate specific antigen
SAE Serious adverse event
SHBG Sex hormone-binding globulin
TID Three times daily
TWNR Time within the normal range
$t_{1/2}$ Half-life
$T_{max}$ Time to maximum concentration
TSH Thyroid-stimulating hormone
TU Testosterone undecanoate
ULN Upper limit of normal
See Appendix 1 in the Appendix to the Specification Example 15

Titration Method for Dosing BID or TID Intranasal Testosterone Gels

The present invention is also concerned with a novel titration method to determine the appropriate daily treatment regimen, i.e., a BID or TID treatment regimen, to administer the intranasal gels of the present invention to treat hypogonadism or TRT. While the preferred treatment regimen in accordance with the present invention for administering the intranasal testosterone gels, such as 4.0% or 4.5% TBS-1 as described in Examples 1, 2, 3, 5, 7, 8, 9 and 10 above, to treat hypogonadism or TRT is twice-daily (BID) treatment regimen, the present invention contemplates that certain subjects may be more effectively treated with a three-times-a-day (TID) treatment regimen. Thus, the novel titration method of the present invention has been developed to determine which subject will require a BID or TID treatment regimen to more effectively treat hypogonadism or TRT when treated with the intranasal testosterone gels of the present invention. See also Exhibit C (the contents of which are incorporated herein by reference).

In carrying out the novel titration method in accordance with the present invention, subjects will have 2 blood draws, preferably at 7 am and at 8:20 am on the test day. The day before the first blood draw, the subject will take at 10 pm, his evening intranasal dose of TBS-1. On test day, the subject will take at about 8 am, his morning intranasal dose of TBS-1.

The 24-hour $C_{avg}$ of serum total testosterone will be estimated based on the sum of serum total testosterone levels collected at the 2 sampling points: the sample collected at about 9.0 hours (at 7 am, which is 1 hour before the morning 0800 h intranasal dose) and the sample collected at about 10.33 hours following the last evening's intranasal dose (20 minutes after the morning 0800 h dose+/−20 minutes). Note that, the blood draw times may be changed (+/−1 hour) but the delay between the last dose and the first blood draw is preferably 9 hours+/−20 minutes and the delay between the next dose administered at about 10 hours+/−20 minutes after the last dose and the second blood draw is preferably +/−20 minutes.

Testosterone serum concentrations are preferably measured by a validated method at a clinical laboratory and reported in ng/dL units.

The following titration criteria is preferably used:
If the sum of the serum total testosterone level values for PK samples collected at 9.0 hours and 10.33 hours is <755 ng/dL, then the estimated 24-hour $C_{avg}$ for the male patient is <300 ng/dL
If the sum of the serum total testosterone level values for PK samples collected at 9.0 hours and 10.33 hours is ≥755 ng/dL, then the estimated 24-hour $C_{avg}$ for the male patient is ≥300 ng/dL.

With respect to those subjects with an estimated serum total testosterone $C_{avg}$<300 ng/dL, i.e., those subjects who sum of the serum total testosterone level values for PK samples collected at 9.0 hours and 10.33 hours is <755 ng/dL, their BID treatment regimen should be titrated to a TID treatment regimen of TBS-1 to achieve a 24-hour $C_{avg}$ of ≥300 ng/dL. The decision to titrate the subject's daily dose to TID, however, will be made by the doctor based on the criteria specified above.

With respect to those subjects with an estimated serum total testosterone $C_{avg}$≥300 ng/dL, i.e., those subjects who sum of the serum total testosterone level values for pK samples collected at 9.0 hours and 10.33 hours is ≥755 ng/dL, their BID treatment regimen should remain unchanged at a BID treatment regimen of TBS-1 since their 24-hour $C_{avg}$ is ≥300 ng/dL. The decision to titrate the subject's daily dose to TID or remain at BID, however, will be made by the doctor based on the criteria specified above.

It should be understood that, while it is preferred to draw blood from a subject to test the subject's serum total testosterone level values for pK samples at 9 hours and at 10.33 hours after the last evening's BID dose, the difference in the total draw time, i.e., 10.33 hours, may vary by as much as about +/−60 minutes and preferably no more than about +/−20 minutes between one another. It should also be understood that while, serum total testosterone level values for PK samples is 755 ng/dL is the preferred level to use to determine if titration to TID is necessary, the serum total testosterone level values for PK samples may vary as much as +/−50 and preferably no more than +/−25.

As an alternative, it should be understood that, while the titration method is described above with starting the titration method based upon the last evening's BID dose, the titration method could also be used by starting the titration method based upon the first morning dose. For example, under this alternative embodiment, the first blood draw would be taken at about 9 hours and the second blood draw would be taken at about 10.33 hours after the morning dose, so long as the second blood draw is taken at about 20 minutes after the last BID dose of the day.

Phase III Study—Rationale for the Titration Protocol for Compleo (4.5% TBS-1 Gel)

1. Introduction

At the Mar. 14, 2011 End of Phase II Meeting, the Compleo (4.5% TBS-1 Gel) Phase III study includes the modifications suggested by the Agency ("FDA") and a rationale for the choice of secondary endpoints, the titration scheme and the ENT examination protocol. See Example _____ for the final Phase 3 protocol.

The primary endpoint of this study is the percentage of subjects with a serum total testosterone $C_{avg}$ value within the normal range on Day 90. This endpoint is consistent with Agency standards used for approval of other testosterone replacement therapy formulations. Although there are no generally accepted lower limits of normal for serum total testosterone, guidelines recommend using the range of 280-300 ng/dL. The sponsor has defined the normal range for Testosterone as 300 ng/dL to 1050 ng/dL for this study. This range is consistent with Agency standards and is in agreement with the AACF Hypogonadism and Endocrine Society Clinical Practice Guidelines.

Secondary Endpoints

The secondary endpoints in the Compleo (4.5% TBS-1 Gel) Phase III study and the rationale are listed below and included in the final protocol. All of the secondary endpoints proposed are well established for testosterone replacement therapies.

DHT—

In previous trials with Compleo, following the administration of Compleo, the DHT levels of responders were increased from below normal to within the normal range. These levels remained stable within the normal range during the treatment and returned to basal levels after discontinuation of Compleo. The upper limit of the physiological reference range of DHT was not achieved or exceeded by any subjects for any treatment. As DHT is the major metabolite of Testosterone, an increase in DHT to within the normal range is evidence of Testosterone replacement. A full DHT pharmacokinetic profile will be collected at Day 30 and 90 for comparison against the baseline levels.

Body Composition and Lean Body Mass—

The effect of testosterone replacement therapy on body composition and lean body mass has been included as an additional objective measurement of efficacy. The sponsor will use DEXA to evaluate the subjects for this criteria at baseline and Day 90.

Bone Mineral Density—

This parameter will be measured by DEXA at baseline and Day

Erectile Function—

Erectile function was included in the proposed protocol but based on the recommendations from the Division, erectile function will now be assessed using the IIEF (International Index of Erectile Function Questionnaire), Mood Scales—

The sponsor intends to collect data on changes in subject mood compared to baseline using the PANAS scale for information purposes only. The PANAS scale was chosen as it is a validated instrument that measures the balance between positive and negative mood. Data will be collected for each subject at baseline, Day 30 and Day 90.

Study Design

The study includes a fixed dose arm for the t.i.d. administration and the previously proposed b.i.d. titration arm. The subjects in the b.i.d. group will be evaluated at Day 30 in accordance with the established titration scheme and those subjects that require titration will be titrated to t.i.d. dosing. The subjects in the b.i.d. group that are not titrated will constitute a second fixed dose arm for b.i.d. dosing.

The sample size has been modified accordingly to ensure that sufficient subjects are available for the safety evaluation. The new sample size of 280 subjects will be split into two groups, with 210 subjects randomized to the b.i.d. titration treatment group and 70 subjects randomized to the t.i.d. treatment group. The sample size (see Table 1) incorporates a 50% titration rate from b.i.d. to t.i.d., a 75% responder rate for all t.i.d. patients and a 20% drop out rate.

TABLE 1

Sample Size Estimation

| | Randomization Arm | | |
|---|---|---|---|
| | b.i.d. | b.i.d/t.i.d. | t.i.d. |
| Number of Subjects | 210 | — | 70 |
| Number Post-titration (50% titration rate) | 105 | 105 | 70 |
| Responder Rate at Day 90 | 100% | 75% | 75% |
| Drop Outs | 20% | 20% | 20% |
| Total Subjects for Safety Evaluation | 84 | 63 | 42 |

Titration Scheme

Titration Model Development

Following the discussion with the Division the recommendation to prospectively develop a titration scheme and include this in the Phase III study has been adopted. The titration scheme, based on two individual blood levels, has been designed to consistently titrate subjects from the b.i.d. treatment group to the t.i.d. treatment group, when testosterone replacement is not being achieved with b.i.d. dosing. Two hundred and ten (210) subjects will be randomized to the b.i.d. treatment group. Subjects will receive Compleo at 2100 h and 0700 h. On Day 30, all subjects will be required to remain at the site for 24 hours after drug administration to obtain a 24 hour pharmacokinetic profile, actual $C_{avg}$. Although a 24 hour profile will be taken, the full profile will not be used for titration decisions. A titration scheme has been developed to allow for a simple and consistent assessment of each subject.

A number of different models were examined in the development of the titration scheme for Compleo that included both single and multiple analysis points. The model fit development and subsequent analysis was completed based on the data from the TBS-1-2010-01 study.

The model selected uses two testosterone measurements, one taken one hour prior to the morning dose (sample A, 9.00 h post $1^{st}$ dose) and one taken 20 minutes after the morning dose (sample B, 10.33 h (10 h20 min) post $1^{st}$ dose). The $C_{avg}$ for a given subject was predicted using a ratio of the two testosterone measurements triangulated to predict the area under the curve for the morning peak. This morning peak area was used to predict the total area under the curve for a 24 hour dosing interval which was converted to the 24 hour $C_{avg}$ for testosterone. This is referred to as the 'model predicted $C_{avg}$' or 'calculated $C_{avg}$' in this text. The calculated $C_{avg}$ was then compared against the lower limit of normal of 300 ng/dL as the decision level for titration. If the $C_{avg}$ is calculated to be greater than 300 ng/dL then the b.i.d. regimen is maintained. If the $C_{avg}$ is calculated to be less than 300 ng/dL then the patient is titrated to the t.i.d. regimen. The individual data comparing the predicted $C_{avg}$ with the actual $C_{avg}$ $C_{avg}$ is provided in Appendix 2.

The model was further challenged on simulated pharmacokinetic profile data from 200 patients based on the 11 mg b.i.d. treatment group from the TBS-1-2010-01 study. Using the sampling points from the model and the individual subject profiles from these 200 subjects, a model predicted $C_{avg}$ was calculated and compared to the actual $C_{avg}$. The individual data from this analysis is provided in Appendix 3. The model was designed to have a high degree of precision, (successful prediction rate of greater than 80%) around the decision level of 300 ng/dL, and the data from both datasets shows a good correlation between the predicted $C_{avg}$ and the actual $C_{avg}$ around this key decision level.

The titration model was used to create a titration scheme that will be utilized and challenged in the Phase III study. This scheme uses the two sampling points from the model; one sample taken one hour prior to the morning dose (Sample A) and one sample taken 20 minutes after the morning dose (Sample B). If the sum of Sample A and Sample B is 755 ng/dL or greater, the 24 hour testosterone $C_{avg}$ is predicted to be greater than 300 ng/dL and titration is not required. If the sum of Sample A and Sample B is less than 755 ng/dL, the 24 hour testosterone $C_{avg}$ is predicted to be lower than 300 ng/dL and titration is required.

Titration Model Robustness

The robustness of the model and the resulting titration scheme was evaluated using the data from the TBS-1-2010-01 study and the 200 patient simulated subject profiles. In addition to the two sampling points in the model, analysis was performed on three other sampling timepoints after the morning dose, 30 minutes, 60 minutes and 90 minutes. In each case the titration scheme was used to predict the requirement for titration following which each subject was sorted into one of two groups, Titration Required or Titration Not Required. The actual $C_{avg}$ for each subject was used to assess the accuracy of the titration scheme with the total number of correct and incorrect titration predictions determined. The incorrect predictions were further separated into two groups in which:

(1) Titration was not predicted but required—The titration scheme indicated that titration was not required, whereas the actual $C_{avg}$ was less than 300 ng/dL. The subjects would not be titrated.

(2) Titration was predicted but not required—The titration scheme indicated that titration was required, whereas the actual $C_{avg}$ was greater than 300 ng/dL. The subjects would be titrated.

The data for this analysis is shown in Table 2. The individual model data for each of the different sample timepoints can be found in Appendix 4, 5 and 6.

TABLE 2

Success Ratio for the Titration Model Analysis based on a Comparison of Predicted and Actual 24 hour Average Concentration Values ($C_{avg}$)

| | Model Dataset and Sampling Time | | | | |
|---|---|---|---|---|---|
| Success Criteria | TBS-1-2010-01 Sample A)-1 hr before AM dosing Sample B) + 20 min after AM dose | TBS-1-2010-1 Simulated Data Sample A)-1 hr before AM dosing Sample B) + 20 min after AM dose | TBS-1-2010-1 Simulated Data Sample A)-1 hr before AM dosing Sample B) + 40 min after AM dose | TBS-1-2010-1 Simulated Data Sample A)-1 hr before AM dosing Sample B) + 60 mm after AM dose | TBS-1-2010-1 Simulated Data Sample A)-1 hr before AM dosing Sample B) + 90 min after AM dose |
| Number of Subjects Evaluated | 22 | 200 | 200 | 200 | 200 |
| Total Correct (%) | 18 (81.8%) | 169 (84.5%) | 165 (82.5%) | 144 (72.5%) | 147 (73.5%) |
| Titration Required | 3 | 36 | 37 | 38 | 43 |
| Not Titrated | 15 | 133 | 128 | 106 | 104 |
| Titration predicted but not required (%) | 4 (18.2%) | 23 (11.5%) | 26 (13.0%) | 44 (22.0%) | 50 (25.0%) |
| Titration not predicted but required (%) | 0 (0.0%) | 8 (4%) | 9 (4.5%) | 7 (3.5%) | 3 (1.5%) |

As the data indicates the model is capable of predicting the need for titration on a consistent basis with an over 80% success ratio for correct predictions at the proposed sampling points. This holds true for the sampling point at 40 minutes after the morning dose as well. At sampling points 60 minutes and 90 minutes after the morning dose the prediction success falls below 80%, which is likely explained by the variability of the values in testosterone concentration at these timepoints and the added variability introduced by the simulation analysis. The model performs slightly better using the 90 minute sampling point than the 60 minute sampling point.

accurately identify those subjects that would benefit from titration from the b.i.d. to the t.i.d. dosing regimen and, in doing so, kept the number of subjects for which titration was not predicted but required to a minimum. The titration scheme achieved this with very low numbers of subjects from the TBS-1-2010-01 study data and TBS-1-2010-01 simulation data across all post dose timepoints.

The remaining subjects that were not correctly predicted by the titration scheme were titrated when it was not necessarily required. Based on the safety and pharmacokinetic profile data from the TBS-1-2010-01 study, none of the subjects that were on a t.i.d. regimen of 4.5% gel (33.75 mg/day) showed any supra-physiologic levels for testosterone or high Cmax values, meaning there is no safety concern with subjects who are titrated to t.i.d. when they were achieving acceptable testosterone levels on b.i.d. treatment.

Titration Scheme Validation

By including the titration scheme in the Phase III study and correlating the titration decision made with the actual measured $C_{avg}$ on Day 30 for each subject in the b.i.d. group at the end of the study, the exercise performed above on the simulation data will be repeated to evaluate and assess the accuracy of the titration. This internal validation will serve to support the validation scheme as proposed or provide the necessary information required to make any modifications for the product label.

ENT Evaluation During Safety Assessment

The detailed synopsis has been updated to clarify the procedure and criteria for the ENT evaluation that will be included in the safety extension for the Phase III study. As previously agreed, a long-term safety assessment will be performed; 200 subjects will be exposed for an addition 3 months and 50 subjects will be exposed for an additional 6 months.

The purpose of the ENT examination is to determine if there have been any adverse reactions related to the nasal cavity that were caused by either the study drug or the multiple dose dispenser. A trained physician will perform the ENT examination as described.

1. History:

The examining physician will inquire about the following symptoms:
 Excessive nasal dryness,
 Excessive nasal crusting,
 Unexpected nasal bleeding,
 Progressive nasal pain,
 Progressive nasal obstruction, and
 Alternation to sense of smell.

2. Physical exam:

Using an anterior rhinoscope with a headlight or other light source, the trained physician will look for the following:
 Large amounts of nasal crusting,
 Scar tissue blocking the nose,
 Dried or fresh nasal blood, and
 Fissuring of the nasal skin.

The safety evaluation measures (Day 90 to 180) will consist of monthly ENT examinations, vital signs and adverse events assessments. On Day 180 (or early termination), subjects will also undergo a physical examination, 12-lead ECG, DRE of the prostate, and laboratory assessments (CBC, PSA, chemistry profile, liver function tests, lipid profile, urinalysis, fasting morning serum total testosterone, DHT, and estradiol).

A subset of subjects will be asked to continue in the study for a safety extension period (Day 180 to 360). In this period, safety evaluations will consist of monthly ENT examinations, vital signs, and adverse events. On Day 270 and Day 360 (or early termination), subjects will also undergo a physical examination, 12-lead ECG, DRE of the prostate, and laboratory assessments (CBC, PSA, chemistry profile, liver function tests, lipid profile, urinalysis, fasting morning serum total testosterone, DHT, and estradiol).

| Titration Model Results-TBS-1-2010-01 Data | | | |
|---|---|---|---|
| | Testosterone Concentration (ng/dL) Time From Morning Dose | | Model Predicted 24 h Cavg | Actual 24 h Cavg |
| Subject Number | −1 hr | +20 min | (ng/dL) | (ng/dL) |
| C1 | 399 | 600 | 428 | 518 |
| C2 | 251 | 327 | 248 | 360 |
| C3 | 344 | 604 | 406 | 387 |
| C4 | 463 | 648 | 476 | 429 |
| C5 | 292 | 558 | 364 | 410 |
| C6 | 161 | 304 | 199 | 179 |
| C7 | 316 | 1140 | 624 | 489 |
| A1 | 284 | 482 | 328 | 372 |
| A2 | 249 | 363 | 262 | 308 |
| A3 | 303 | 611 | 392 | 337 |
| A4 | 216 | 549 | 328 | 325 |
| A5 | 552 | 872 | 610 | 523 |
| A6 | 320 | 671 | 425 | 603 |
| A7 | 347 | 979 | 568 | 582 |
| A8 | 185 | 424 | 261 | 248 |
| B1 | 308 | 847 | 495 | 369 |
| B2 | 333 | 1100 | 614 | 446 |
| B3 | 226 | 492 | 308 | 311 |
| B4 | 249 | 658 | 389 | 351 |
| B5 | 195 | 472 | 286 | 295 |
| B6 | 446 | 959 | 602 | 723 |
| B7 | 355 | 370 | 311 | 359 |

| Titration Model Results TBS-1-2010 Patient Simulation Data Testosterone Sample A taken 1 hour before the morning dose Testosterone Sample B taken 20 minutes after the morning dose | | | |
|---|---|---|---|
| | Testosterone Concentration (ng/dL) Time From Morning Dose | | Model Predicted 24 h Cavg | Actual 24 h Cavg |
| Subject Number | −1 hr | +20 min | (ng/dL) | (ng/dL) |
| 1 | 217 | 879 | 433 | 501 |
| 2 | 286 | 724 | 399 | 393 |
| 3 | 406 | 296 | 278 | 358 |
| 4 | 449 | 665 | 440 | 392 |
| 5 | 367 | 561 | 367 | 514 |
| 6 | 254 | 566 | 324 | 334 |
| 7 | 406 | 832 | 489 | 584 |
| 8 | 483 | 639 | 444 | 450 |
| 9 | 108 | 339 | 177 | 175 |
| 10 | 260 | 827 | 430 | 366 |
| 11 | 327 | 550 | 347 | 322 |
| 12 | 522 | 1430 | 772 | 757 |
| 13 | 240 | 995 | 488 | 442 |

Titration Model Results TBS-1-2010 Patient Simulation Data
Testosterone Sample A taken 1 hour before the morning dose
Testosterone Sample B taken 20 minutes after the morning dose

| Subject Number | Testosterone Concentration (ng/dL) Time From Morning Dose −1 hr | Testosterone Concentration (ng/dL) Time From Morning Dose +20 min | Model Predicted 24 h Cavg (ng/dL) | Actual 24 h Cavg (ng/dL) |
|---|---|---|---|---|
| 14 | 278 | 852 | 447 | 288 |
| 15 | 249 | 448 | 276 | 330 |
| 16 | 523 | 930 | 574 | 506 |
| 17 | 497 | 726 | 483 | 423 |
| 18 | 375 | 945 | 522 | 412 |
| 19 | 132 | 278 | 162 | 291 |
| 20 | 231 | 439 | 265 | 306 |
| 21 | 363 | 844 | 477 | 505 |
| 22 | 535 | 770 | 516 | 505 |
| 23 | 340 | 680 | 403 | 673 |
| 24 | 252 | 630 | 349 | 346 |
| 25 | 231 | 583 | 322 | 322 |
| 26 | 156 | 430 | 232 | 362 |
| 27 | 226 | 719 | 374 | 375 |
| 28 | 197 | 485 | 270 | 339 |
| 29 | 466 | 635 | 435 | 459 |
| 30 | 232 | 920 | 455 | 316 |
| 31 | 263 | 897 | 459 | 431 |
| 32 | 183 | 1260 | 570 | 352 |
| 33 | 491 | 655 | 453 | 436 |
| 34 | 277 | 497 | 306 | 475 |
| 35 | 362 | 403 | 302 | 441 |
| 36 | 140 | 395 | 212 | 233 |
| 37 | 164 | 410 | 227 | 301 |
| 38 | 195 | 374 | 225 | 209 |
| 39 | 381 | 904 | 508 | 527 |
| 40 | 206 | 464 | 265 | 316 |
| 41 | 176 | 809 | 389 | 397 |
| 42 | 200 | 485 | 271 | 282 |
| 43 | 479 | 2640 | 1233 | 877 |
| 44 | 280 | 511 | 313 | 332 |
| 45 | 212 | 705 | 363 | 315 |
| 46 | 246 | 436 | 270 | 300 |
| 47 | 117 | 358 | 188 | 203 |
| 48 | 420 | 679 | 434 | 308 |
| 49 | 262 | 781 | 412 | 406 |
| 50 | 191 | 688 | 347 | 359 |
| 51 | 381 | 447 | 327 | 439 |
| 52 | 321 | 553 | 346 | 422 |
| 53 | 195 | 424 | 245 | 397 |
| 54 | 325 | 425 | 296 | 301 |
| 55 | 413 | 895 | 517 | 472 |
| 56 | 179 | 952 | 447 | 328 |
| 57 | 180 | 472 | 258 | 249 |
| 58 | 206 | 689 | 354 | 359 |
| 59 | 255 | 563 | 323 | 318 |
| 60 | 380 | 683 | 420 | 437 |
| 61 | 226 | 358 | 231 | 317 |
| 62 | 370 | 628 | 395 | 388 |
| 63 | 265 | 885 | 455 | 388 |
| 64 | 163 | 475 | 252 | 245 |
| 65 | 302 | 756 | 418 | 595 |
| 66 | 274 | 597 | 344 | 377 |
| 67 | 250 | 666 | 362 | 456 |
| 68 | 383 | 789 | 463 | 456 |
| 69 | 291 | 662 | 377 | 411 |
| 70 | 430 | 1060 | 589 | 417 |
| 71 | 236 | 514 | 296 | 307 |
| 72 | 248 | 550 | 315 | 248 |
| 73 | 244 | 692 | 370 | 374 |
| 74 | 362 | 711 | 424 | 572 |
| 75 | 310 | 1370 | 664 | 589 |
| 76 | 467 | 475 | 372 | 367 |
| 77 | 256 | 465 | 285 | 236 |
| 78 | 222 | 557 | 308 | 267 |
| 79 | 198 | 727 | 366 | 333 |
| 80 | 371 | 397 | 304 | 346 |
| 81 | 213 | 993 | 477 | 549 |
| 82 | 288 | 646 | 369 | 386 |
| 83 | 221 | 538 | 300 | 314 |
| 84 | 226 | 574 | 316 | 355 |
| 85 | 168 | 679 | 335 | 286 |
| 86 | 139 | 507 | 255 | 334 |
| 87 | 211 | 611 | 325 | 363 |
| 88 | 225 | 686 | 360 | 412 |
| 89 | 265 | 456 | 285 | 313 |
| 90 | 520 | 1140 | 656 | 510 |
| 91 | 207 | 1120 | 525 | 365 |
| 92 | 191 | 515 | 279 | 304 |
| 93 | 242 | 689 | 368 | 399 |
| 94 | 121 | 916 | 410 | 331 |
| 95 | 105 | 398 | 199 | 294 |
| 96 | 299 | 686 | 389 | 348 |
| 97 | 153 | 466 | 245 | 441 |
| 98 | 242 | 417 | 261 | 260 |
| 99 | 288 | 697 | 389 | 448 |
| 100 | 530 | 720 | 494 | 494 |
| 101 | 178 | 685 | 341 | 211 |
| 102 | 410 | 424 | 330 | 343 |
| 103 | 491 | 646 | 449 | 401 |
| 104 | 443 | 830 | 503 | 408 |
| 105 | 218 | 489 | 279 | 314 |
| 106 | 322 | 526 | 335 | 347 |
| 107 | 404 | 660 | 421 | 420 |
| 108 | 217 | 491 | 280 | 281 |
| 109 | 277 | 454 | 289 | 294 |
| 110 | 200 | 281 | 190 | 229 |
| 111 | 258 | 425 | 270 | 276 |
| 112 | 523 | 642 | 461 | 440 |
| 113 | 283 | 568 | 336 | 408 |
| 114 | 260 | 596 | 338 | 242 |
| 115 | 231 | 600 | 329 | 389 |
| 116 | 481 | 757 | 489 | 405 |
| 117 | 293 | 543 | 330 | 370 |
| 118 | 261 | 375 | 251 | 311 |
| 119 | 152 | 226 | 149 | 227 |
| 120 | 291 | 412 | 278 | 282 |
| 121 | 383 | 547 | 368 | 440 |
| 122 | 295 | 352 | 256 | 295 |
| 123 | 276 | 527 | 317 | 304 |
| 124 | 113 | 1100 | 480 | 311 |
| 125 | 245 | 421 | 263 | 307 |
| 126 | 421 | 666 | 430 | 499 |
| 127 | 313 | 514 | 327 | 371 |
| 128 | 238 | 787 | 405 | 432 |
| 129 | 256 | 493 | 296 | 380 |
| 130 | 175 | 278 | 179 | 278 |
| 131 | 199 | 394 | 234 | 303 |
| 132 | 296 | 491 | 311 | 363 |
| 133 | 319 | 879 | 474 | 342 |
| 134 | 274 | 812 | 429 | 346 |
| 135 | 140 | 412 | 218 | 220 |
| 136 | 466 | 441 | 359 | 434 |
| 137 | 449 | 2330 | 1099 | 739 |
| 138 | 252 | 347 | 237 | 282 |
| 139 | 330 | 698 | 406 | 440 |
| 140 | 165 | 513 | 268 | 215 |
| 141 | 292 | 667 | 379 | 389 |
| 142 | 306 | 574 | 348 | 473 |
| 143 | 345 | 319 | 263 | 292 |
| 144 | 359 | 880 | 490 | 492 |
| 145 | 399 | 561 | 380 | 449 |
| 146 | 593 | 932 | 603 | 696 |
| 147 | 581 | 712 | 511 | 426 |
| 148 | 222 | 356 | 229 | 229 |
| 149 | 231 | 640 | 344 | 301 |
| 150 | 274 | 1160 | 567 | 460 |
| 151 | 178 | 764 | 372 | 411 |

Titration Model Results TBS-1-2010 Patient Simulation Data
Testosterone Sample A taken 1 hour before the morning dose
Testosterone Sample B taken 20 minutes after the morning dose

| Subject Number | Testosterone Concentration (ng/dL) Time From Morning Dose | | Model Predicted 24 h Cavg (ng/dL) | Actual 24 h Cavg (ng/dL) |
|---|---|---|---|---|
| | −1 hr | +20 min | | |
| 152 | 176 | 1030 | 477 | 312 |
| 153 | 346 | 542 | 351 | 491 |
| 154 | 221 | 378 | 237 | 259 |
| 155 | 236 | 527 | 302 | 361 |
| 156 | 257 | 456 | 282 | 358 |
| 157 | 146 | 609 | 298 | 295 |
| 158 | 241 | 358 | 237 | 304 |
| 159 | 199 | 636 | 330 | 434 |
| 160 | 280 | 1220 | 593 | 506 |
| 161 | 370 | 500 | 344 | 417 |
| 162 | 148 | 710 | 339 | 250 |
| 163 | 246 | 402 | 256 | 284 |
| 164 | 263 | 930 | 472 | 349 |
| 165 | 178 | 537 | 283 | 275 |
| 166 | 393 | 715 | 438 | 432 |
| 167 | 193 | 426 | 245 | 246 |
| 168 | 148 | 449 | 236 | 214 |
| 169 | 120 | 596 | 283 | 217 |
| 170 | 262 | 593 | 338 | 307 |
| 171 | 369 | 652 | 404 | 366 |
| 172 | 394 | 666 | 419 | 415 |
| 173 | 289 | 543 | 329 | 396 |
| 174 | 282 | 548 | 328 | 329 |
| 175 | 225 | 654 | 347 | 336 |
| 176 | 255 | 970 | 484 | 544 |
| 177 | 212 | 548 | 300 | 344 |
| 178 | 203 | 251 | 179 | 201 |
| 179 | 488 | 612 | 435 | 560 |
| 180 | 247 | 809 | 417 | 425 |
| 181 | 206 | 565 | 305 | 280 |
| 182 | 134 | 497 | 249 | 252 |
| 183 | 401 | 442 | 333 | 368 |
| 184 | 253 | 550 | 317 | 329 |
| 185 | 252 | 843 | 433 | 352 |
| 186 | 314 | 677 | 392 | 494 |
| 187 | 370 | 532 | 357 | 378 |
| 188 | 368 | 551 | 363 | 342 |
| 189 | 241 | 511 | 297 | 251 |
| 190 | 229 | 794 | 404 | 379 |
| 191 | 333 | 636 | 383 | 526 |
| 192 | 217 | 834 | 415 | 360 |
| 193 | 264 | 411 | 267 | 263 |
| 194 | 382 | 1180 | 618 | 479 |
| 195 | 283 | 380 | 262 | 344 |
| 196 | 332 | 1360 | 669 | 442 |
| 197 | 310 | 911 | 483 | 321 |
| 198 | 194 | 610 | 318 | 327 |
| 199 | 172 | 465 | 252 | 192 |
| 200 | 335 | 894 | 486 | 473 |

Figure 40:
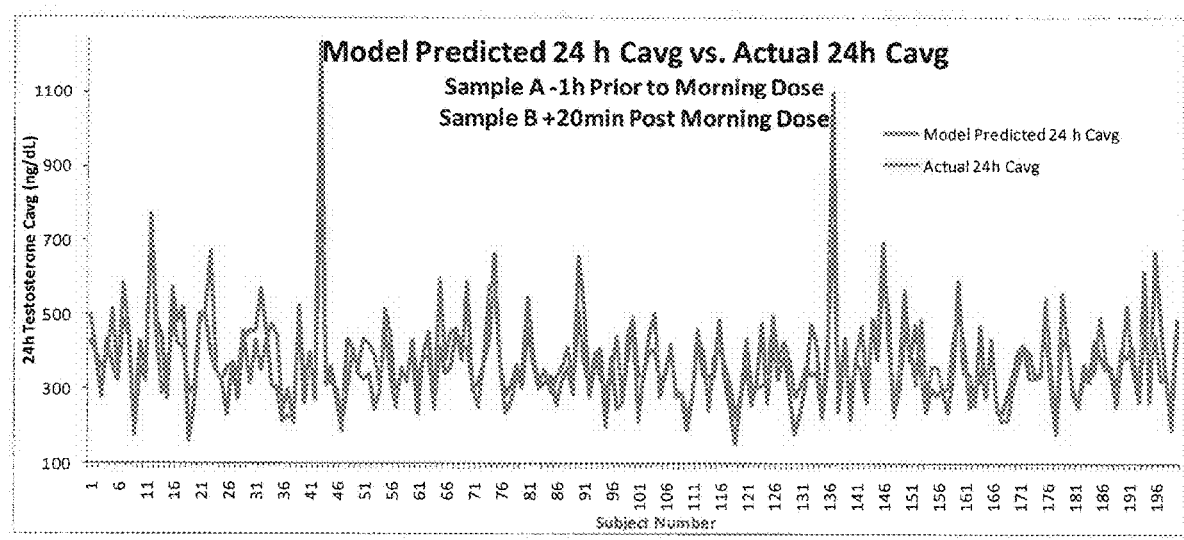
FIG. 40 depicts titration model results with testosterone Sample A taken 1 hour before morning dose and testosterone Sample B taken 20 minutes after morning dose.

See FIG. 40,

Titration Model Results TBS-1-2010 Patient Simulation Data
Testosterone Sample A taken 1 hour before the morning dose
Testosterone Sample B taken 40 minutes after the morning dose

| Subject Number | Testosterone Concentration (ng/dL) Time From Morning Dose | | Model Predicted 24 h Cavg (ng/dL) | Actual 24 h Cavg (ng/dL) |
|---|---|---|---|---|
| | −1 hr | +40 min | | |
| 1 | 217 | 1070 | 509 | 501 |
| 2 | 286 | 962 | 493 | 393 |
| 3 | 406 | 399 | 318 | 358 |
| 4 | 449 | 676 | 445 | 392 |
| 5 | 367 | 1420 | 706 | 514 |
| 6 | 254 | 863 | 441 | 334 |
| 7 | 406 | 991 | 552 | 584 |
| 8 | 483 | 758 | 490 | 450 |
| 9 | 108 | 229 | 133 | 175 |
| 10 | 260 | 441 | 277 | 366 |
| 11 | 327 | 432 | 300 | 322 |
| 12 | 522 | 1160 | 665 | 757 |
| 13 | 240 | 565 | 318 | 442 |
| 14 | 278 | 417 | 275 | 288 |
| 15 | 249 | 474 | 286 | 330 |
| 16 | 523 | 1020 | 610 | 506 |
| 17 | 497 | 992 | 588 | 423 |
| 18 | 375 | 1130 | 595 | 412 |
| 19 | 132 | 379 | 202 | 291 |
| 20 | 231 | 439 | 256 | 306 |
| 21 | 363 | 858 | 483 | 505 |
| 22 | 535 | 770 | 476 | 505 |
| 23 | 340 | 630 | 383 | 673 |
| 24 | 252 | 630 | 366 | 346 |
| 25 | 231 | 1130 | 538 | 322 |
| 26 | 156 | 736 | 353 | 362 |
| 27 | 226 | 456 | 270 | 375 |
| 28 | 197 | 324 | 206 | 339 |
| 29 | 466 | 467 | 369 | 459 |
| 30 | 232 | 348 | 229 | 316 |
| 31 | 263 | 1170 | 566 | 431 |
| 32 | 183 | 603 | 311 | 352 |
| 33 | 491 | 660 | 455 | 436 |
| 34 | 277 | 426 | 278 | 475 |
| 35 | 362 | 334 | 275 | 441 |
| 36 | 140 | 485 | 247 | 233 |
| 37 | 164 | 568 | 289 | 301 |
| 38 | 195 | 374 | 225 | 209 |
| 39 | 381 | 1020 | 554 | 527 |
| 40 | 206 | 410 | 243 | 316 |
| 41 | 176 | 588 | 302 | 397 |
| 42 | 200 | 651 | 336 | 282 |
| 43 | 479 | 1750 | 881 | 877 |
| 44 | 280 | 686 | 382 | 332 |
| 45 | 212 | 524 | 291 | 315 |
| 46 | 246 | 353 | 237 | 300 |
| 47 | 117 | 532 | 256 | 203 |
| 48 | 420 | 437 | 339 | 308 |
| 49 | 262 | 988 | 494 | 406 |
| 50 | 191 | 536 | 287 | 359 |
| 51 | 381 | 770 | 455 | 439 |
| 52 | 321 | 591 | 360 | 422 |
| 53 | 195 | 789 | 389 | 397 |
| 54 | 325 | 499 | 326 | 301 |
| 55 | 413 | 702 | 441 | 472 |
| 56 | 179 | 786 | 381 | 328 |
| 57 | 180 | 357 | 212 | 249 |
| 58 | 206 | 662 | 343 | 359 |
| 59 | 255 | 414 | 264 | 318 |
| 60 | 380 | 698 | 426 | 437 |
| 61 | 226 | 465 | 273 | 317 |
| 62 | 370 | 462 | 329 | 388 |
| 63 | 265 | 874 | 450 | 388 |
| 64 | 163 | 279 | 175 | 245 |
| 65 | 302 | 1140 | 570 | 595 |
| 66 | 274 | 615 | 351 | 377 |
| 67 | 250 | 830 | 427 | 456 |
| 68 | 383 | 842 | 484 | 456 |
| 69 | 291 | 848 | 450 | 411 |
| 70 | 430 | 579 | 399 | 417 |
| 71 | 236 | 874 | 439 | 307 |
| 72 | 248 | 400 | 256 | 248 |
| 73 | 244 | 460 | 278 | 374 |
| 74 | 362 | 481 | 333 | 572 |

Titration Model Results TBS-1-2010 Patient Simulation Data
Testosterone Sample A taken 1 hour before the morning dose
Testosterone Sample B taken 40 minutes after the morning dose

| Subject Number | Testosterone Concentration (ng/dL) Time From Morning Dose | | Model Predicted 24 h Cavg (ng/dL) | Actual 24 h Cavg (ng/dL) |
|---|---|---|---|---|
| | −1 hr | +40 min | | |
| 75 | 310 | 676 | 390 | 589 |
| 76 | 467 | 589 | 417 | 367 |
| 77 | 256 | 462 | 284 | 236 |
| 78 | 222 | 462 | 270 | 267 |
| 79 | 198 | 663 | 340 | 333 |
| 80 | 371 | 442 | 321 | 346 |
| 81 | 213 | 740 | 377 | 549 |
| 82 | 288 | 548 | 330 | 386 |
| 83 | 221 | 454 | 267 | 314 |
| 84 | 226 | 742 | 383 | 355 |
| 85 | 168 | 626 | 314 | 286 |
| 86 | 139 | 670 | 320 | 334 |
| 87 | 211 | 811 | 404 | 363 |
| 88 | 225 | 662 | 351 | 412 |
| 89 | 265 | 679 | 373 | 313 |
| 90 | 520 | 681 | 475 | 510 |
| 91 | 207 | 723 | 368 | 365 |
| 92 | 191 | 691 | 349 | 304 |
| 93 | 242 | 431 | 266 | 399 |
| 94 | 121 | 861 | 388 | 331 |
| 95 | 105 | 647 | 297 | 294 |
| 96 | 299 | 663 | 380 | 348 |
| 97 | 153 | 1040 | 471 | 441 |
| 98 | 242 | 336 | 228 | 260 |
| 99 | 288 | 396 | 270 | 448 |
| 100 | 530 | 798 | 525 | 494 |
| 101 | 178 | 494 | 266 | 211 |
| 102 | 410 | 758 | 462 | 343 |
| 103 | 491 | 646 | 387 | 401 |
| 104 | 443 | 603 | 413 | 408 |
| 105 | 218 | 742 | 379 | 314 |
| 106 | 322 | 496 | 323 | 347 |
| 107 | 404 | 897 | 514 | 420 |
| 108 | 217 | 659 | 346 | 281 |
| 109 | 277 | 563 | 332 | 294 |
| 110 | 200 | 438 | 252 | 229 |
| 111 | 258 | 495 | 298 | 276 |
| 112 | 523 | 829 | 534 | 440 |
| 113 | 283 | 486 | 304 | 408 |
| 114 | 260 | 444 | 278 | 242 |
| 115 | 231 | 750 | 388 | 389 |
| 116 | 481 | 609 | 431 | 405 |
| 117 | 293 | 969 | 499 | 370 |
| 118 | 261 | 375 | 282 | 311 |
| 119 | 152 | 335 | 192 | 227 |
| 120 | 291 | 302 | 234 | 282 |
| 121 | 383 | 629 | 400 | 440 |
| 122 | 295 | 640 | 370 | 295 |
| 123 | 276 | 440 | 283 | 304 |
| 124 | 113 | 1050 | 460 | 311 |
| 125 | 245 | 659 | 357 | 307 |
| 126 | 421 | 629 | 415 | 499 |
| 127 | 313 | 533 | 334 | 371 |
| 128 | 238 | 513 | 297 | 432 |
| 129 | 256 | 488 | 294 | 380 |
| 130 | 175 | 617 | 313 | 278 |
| 131 | 199 | 390 | 233 | 303 |
| 132 | 296 | 458 | 298 | 363 |
| 133 | 319 | 675 | 393 | 342 |
| 134 | 274 | 812 | 440 | 346 |
| 135 | 140 | 286 | 168 | 220 |
| 136 | 466 | 862 | 525 | 434 |
| 137 | 449 | 1530 | 782 | 739 |
| 138 | 252 | 489 | 293 | 282 |
| 139 | 330 | 421 | 297 | 440 |
| 140 | 165 | 313 | 189 | 215 |
| 141 | 292 | 609 | 356 | 389 |
| 142 | 306 | 688 | 393 | 473 |
| 143 | 345 | 403 | 296 | 292 |
| 144 | 359 | 880 | 466 | 492 |
| 145 | 399 | 506 | 358 | 449 |
| 146 | 593 | 1040 | 645 | 696 |
| 147 | 581 | 619 | 474 | 426 |
| 148 | 222 | 273 | 196 | 229 |
| 149 | 231 | 814 | 413 | 301 |
| 150 | 274 | 1360 | 646 | 460 |
| 151 | 178 | 1300 | 584 | 411 |
| 152 | 176 | 750 | 366 | 312 |
| 153 | 346 | 904 | 494 | 491 |
| 154 | 221 | 488 | 280 | 259 |
| 155 | 236 | 772 | 398 | 361 |
| 156 | 257 | 538 | 314 | 358 |
| 157 | 146 | 428 | 227 | 295 |
| 158 | 241 | 437 | 268 | 304 |
| 159 | 199 | 568 | 303 | 434 |
| 160 | 280 | 1530 | 715 | 506 |
| 161 | 370 | 476 | 334 | 417 |
| 162 | 148 | 628 | 307 | 250 |
| 163 | 246 | 700 | 374 | 284 |
| 164 | 263 | 602 | 342 | 349 |
| 165 | 178 | 674 | 337 | 275 |
| 166 | 393 | 712 | 437 | 432 |
| 167 | 193 | 437 | 249 | 246 |
| 168 | 148 | 397 | 215 | 214 |
| 169 | 120 | 596 | 290 | 217 |
| 170 | 262 | 573 | 330 | 307 |
| 171 | 369 | 647 | 402 | 366 |
| 172 | 394 | 431 | 326 | 415 |
| 173 | 289 | 949 | 489 | 396 |
| 174 | 282 | 461 | 294 | 329 |
| 175 | 225 | 785 | 399 | 336 |
| 176 | 255 | 1010 | 500 | 544 |
| 177 | 212 | 646 | 339 | 344 |
| 178 | 203 | 386 | 233 | 201 |
| 179 | 488 | 853 | 530 | 560 |
| 180 | 247 | 680 | 366 | 425 |
| 181 | 206 | 532 | 292 | 280 |
| 182 | 134 | 497 | 427 | 252 |
| 183 | 401 | 607 | 398 | 368 |
| 184 | 253 | 640 | 353 | 329 |
| 185 | 252 | 716 | 383 | 352 |
| 186 | 314 | 846 | 458 | 494 |
| 187 | 370 | 552 | 364 | 378 |
| 188 | 368 | 616 | 389 | 342 |
| 189 | 241 | 465 | 279 | 251 |
| 190 | 229 | 645 | 345 | 379 |
| 191 | 333 | 636 | 387 | 526 |
| 192 | 217 | 834 | 258 | 360 |
| 193 | 264 | 231 | 196 | 263 |
| 194 | 382 | 649 | 407 | 479 |
| 195 | 283 | 608 | 352 | 344 |
| 196 | 332 | 730 | 420 | 442 |
| 197 | 310 | 536 | 334 | 321 |

| Titration Model Results TBS-1-2010 Patient Simulation Data Testosterone Sample A taken 1 hour before the morning dose Testosterone Sample B taken 40 minutes after the morning dose | | | |
|---|---|---|---|
| Subject Number | Testosterone Concentration (ng/dL) Time From Morning Dose | Model Predicted 24 h Cavg (ng/dL) | Actual 24 h Cavg (ng/dL) |
| | −1 hr    +40 min | | |
| 198 | 194    684 | 347 | 327 |
| 199 | 172    285 | 181 | 192 |
| 200 | 335    655 | 391 | 473 |

Figure 41:
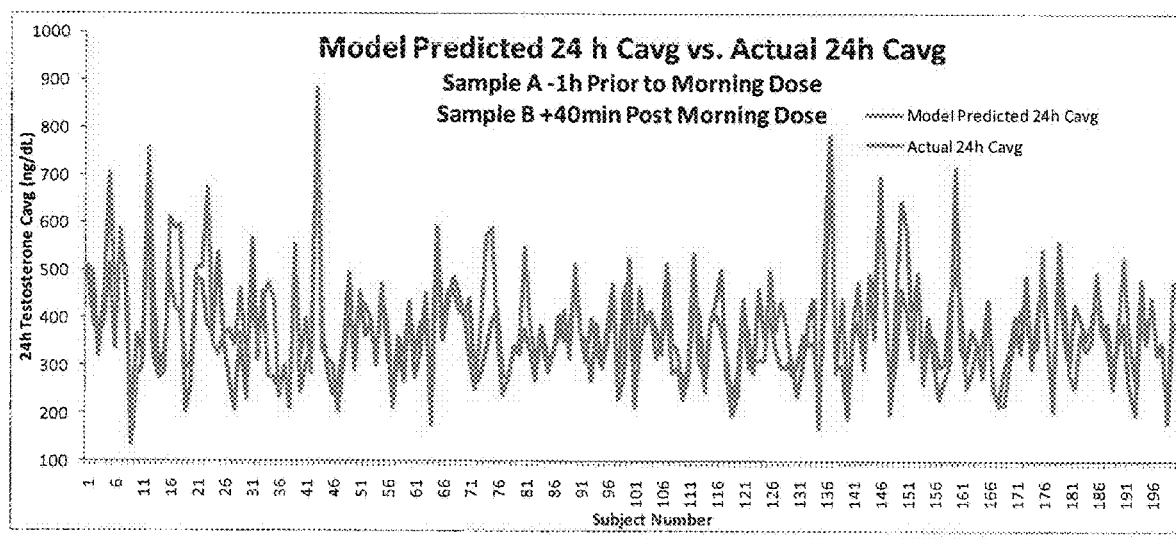
FIG. 41 depicts titration model results with testosterone Sample A taken 1 hour before morning dose and testosterone Sample B taken 40 minutes after morning dose.

See FIG. 41.

| Titration Model Results TBS-1-2010 Patient Simulation Data Testosterone Sample A taken 1 hour before the morning dose Testosterone Sample B taken 60 minutes after the morning dose | | | |
|---|---|---|---|
| Subject Number | Testosterone Concentration (ng/dL) Time From Morning Dose | Model Predicted 24 h Cavg (ng/dL) | Actual 24 h Cavg (ng/dL) |
| | −1 hr    +60 min | | |
| 1 | 217    1400 | 225 | 501 |
| 2 | 286    896 | 238 | 393 |
| 3 | 406    372 | 315 | 358 |
| 4 | 449    822 | 324 | 392 |
| 5 | 367    970 | 262 | 514 |
| 6 | 254    554 | 178 | 334 |
| 7 | 406    846 | 312 | 584 |
| 8 | 483    684 | 395 | 450 |
| 9 | 108    212 | 103 | 175 |
| 10 | 260    739 | 212 | 366 |
| 11 | 327    373 | 287 | 322 |
| 12 | 522    1030 | 546 | 757 |
| 13 | 240    862 | 201 | 442 |
| 14 | 278    444 | 379 | 294 |
| 15 | 249    298 | 200 | 330 |
| 16 | 523    367 | 461 | 506 |
| 17 | 497    615 | 352 | 423 |
| 18 | 375    907 | 307 | 412 |
| 19 | 132    491 | 140 | 291 |
| 20 | 231    415 | 176 | 306 |
| 21 | 363    822 | 258 | 505 |
| 22 | 535    917 | 370 | 505 |
| 23 | 340    859 | 392 | 673 |
| 24 | 252    735 | 199 | 346 |
| 25 | 231    486 | 210 | 322 |
| 26 | 156    856 | 163 | 362 |
| 27 | 226    611 | 186 | 375 |
| 28 | 197    505 | 269 | 339 |
| 29 | 466    450 | 384 | 459 |
| 30 | 232    377 | 220 | 316 |
| 31 | 263    693 | 368 | 431 |
| 32 | 183    791 | 216 | 352 |
| 33 | 491    1020 | 339 | 436 |
| 34 | 277    762 | 199 | 475 |
| 35 | 362    371 | 320 | 441 |
| 36 | 140    543 | 117 | 233 |
| 37 | 164    502 | 174 | 301 |
| 38 | 195    303 | 184 | 209 |
| 39 | 381    1000 | 334 | 527 |
| 40 | 206    557 | 209 | 316 |
| 41 | 176    570 | 183 | 397 |
| 42 | 200    631 | 128 | 282 |
| 43 | 479    1040 | 385 | 877 |
| 44 | 280    466 | 260 | 332 |
| 45 | 212    229 | 220 | 315 |
| 46 | 246    482 | 188 | 300 |
| 47 | 117    286 | 116 | 203 |
| 48 | 420    386 | 255 | 308 |
| 49 | 262    830 | 220 | 406 |
| 50 | 191    601 | 233 | 359 |
| 51 | 381    405 | 337 | 439 |
| 52 | 321    420 | 263 | 422 |
| 53 | 195    677 | 129 | 397 |
| 54 | 325    364 | 282 | 301 |
| 55 | 413    697 | 315 | 472 |
| 56 | 179    1390 | 123 | 328 |
| 57 | 180    307 | 156 | 249 |
| 58 | 206    482 | 191 | 359 |
| 59 | 255    491 | 195 | 318 |
| 60 | 380    680 | 341 | 437 |
| 61 | 226    463 | 239 | 317 |
| 62 | 370    573 | 299 | 388 |
| 63 | 265    819 | 265 | 388 |
| 64 | 163    413 | 134 | 245 |
| 65 | 302    1110 | 246 | 595 |
| 66 | 274    409 | 236 | 377 |
| 67 | 250    609 | 191 | 456 |
| 68 | 383    643 | 314 | 456 |
| 69 | 291    548 | 227 | 411 |
| 70 | 430    966 | 298 | 417 |
| 71 | 236    497 | 185 | 307 |
| 72 | 248    486 | 169 | 248 |
| 73 | 244    665 | 183 | 374 |
| 74 | 362    605 | 318 | 572 |
| 75 | 310    571 | 313 | 589 |
| 76 | 467    488 | 308 | 367 |
| 77 | 256    462 | 190 | 236 |
| 78 | 222    277 | 176 | 267 |
| 79 | 198    459 | 168 | 333 |
| 80 | 371    424 | 229 | 346 |
| 81 | 213    1020 | 233 | 549 |
| 82 | 288    662 | 247 | 386 |
| 83 | 221    373 | 168 | 314 |
| 84 | 226    522 | 243 | 355 |
| 85 | 168    768 | 143 | 286 |
| 86 | 139    842 | 187 | 334 |
| 87 | 211    491 | 235 | 363 |
| 88 | 225    777 | 200 | 412 |
| 89 | 265    480 | 184 | 313 |
| 90 | 520    757 | 488 | 510 |
| 91 | 207    642 | 193 | 365 |
| 92 | 191    673 | 164 | 304 |
| 93 | 242    661 | 211 | 399 |
| 94 | 121    491 | 168 | 331 |
| 95 | 105    541 | 111 | 294 |
| 96 | 299    718 | 235 | 348 |
| 97 | 153    894 | 179 | 441 |
| 98 | 242    509 | 184 | 260 |
| 99 | 288    541 | 263 | 448 |
| 100 | 530    921 | 362 | 494 |
| 101 | 178    258 | 153 | 211 |
| 102 | 410    538 | 270 | 343 |
| 103 | 491    499 | 304 | 401 |
| 104 | 443    665 | 382 | 408 |
| 105 | 218    483 | 198 | 314 |
| 106 | 322    534 | 285 | 347 |
| 107 | 404    521 | 307 | 420 |
| 108 | 217    402 | 198 | 281 |
| 109 | 277    372 | 209 | 294 |
| 110 | 200    392 | 173 | 229 |
| 111 | 258    523 | 193 | 276 |
| 112 | 523    804 | 438 | 440 |
| 113 | 283    899 | 247 | 408 |
| 114 | 260    476 | 176 | 242 |
| 115 | 231    486 | 178 | 389 |
| 116 | 481    903 | 361 | 405 |
| 117 | 293    453 | 295 | 370 |
| 118 | 261    416 | 201 | 311 |
| 119 | 152    276 | 140 | 227 |
| 120 | 291    409 | 240 | 282 |

Titration Model Results TBS-1-2010 Patient Simulation Data
Testosterone Sample A taken 1 hour before the morning dose
Testosterone Sample B taken 60 minutes after the morning dose

| Subject Number | Testosterone Concentration (ng/dL) Time From Morning Dose −1 hr | Testosterone Concentration (ng/dL) Time From Morning Dose +60 min | Model Predicted 24 h Cavg (ng/dL) | Actual 24 h Cavg (ng/dL) |
|---|---|---|---|---|
| 121 | 383 | 547 | 284 | 440 |
| 122 | 295 | 536 | 173 | 295 |
| 123 | 276 | 312 | 259 | 304 |
| 124 | 113 | 865 | 146 | 311 |
| 125 | 245 | 578 | 191 | 307 |
| 126 | 421 | 476 | 313 | 499 |
| 127 | 313 | 545 | 220 | 371 |
| 128 | 238 | 772 | 190 | 432 |
| 129 | 256 | 393 | 200 | 380 |
| 130 | 175 | 437 | 216 | 278 |
| 131 | 199 | 404 | 170 | 303 |
| 132 | 296 | 545 | 303 | 363 |
| 133 | 319 | 465 | 204 | 342 |
| 134 | 274 | 917 | 200 | 346 |
| 135 | 140 | 287 | 124 | 220 |
| 136 | 466 | 794 | 333 | 434 |
| 137 | 449 | 1030 | 292 | 739 |
| 138 | 252 | 347 | 176 | 282 |
| 139 | 330 | 445 | 321 | 440 |
| 140 | 165 | 271 | 144 | 215 |
| 141 | 292 | 460 | 268 | 389 |
| 142 | 306 | 637 | 217 | 473 |
| 143 | 345 | 419 | 253 | 292 |
| 144 | 359 | 852 | 327 | 492 |
| 145 | 399 | 690 | 292 | 449 |
| 146 | 593 | 1770 | 450 | 696 |
| 147 | 581 | 601 | 380 | 426 |
| 148 | 222 | 262 | 213 | 229 |
| 149 | 231 | 290 | 186 | 301 |
| 150 | 274 | 580 | 195 | 460 |
| 151 | 178 | 871 | 116 | 411 |
| 152 | 176 | 643 | 158 | 312 |
| 153 | 346 | 815 | 268 | 491 |
| 154 | 221 | 815 | 209 | 259 |
| 155 | 236 | 500 | 203 | 361 |
| 156 | 257 | 498 | 296 | 358 |
| 157 | 146 | 385 | 162 | 295 |
| 158 | 241 | 344 | 240 | 304 |
| 159 | 199 | 609 | 221 | 434 |
| 160 | 280 | 976 | 223 | 506 |
| 161 | 370 | 306 | 386 | 417 |
| 162 | 148 | 425 | 181 | 250 |
| 163 | 246 | 487 | 206 | 284 |
| 164 | 263 | 699 | 222 | 349 |
| 165 | 178 | 346 | 151 | 275 |
| 166 | 393 | 645 | 354 | 432 |
| 167 | 193 | 459 | 201 | 246 |
| 168 | 148 | 359 | 124 | 214 |
| 169 | 120 | 352 | 121 | 217 |
| 170 | 262 | 398 | 180 | 307 |
| 171 | 369 | 613 | 305 | 366 |
| 172 | 394 | 518 | 271 | 415 |
| 173 | 289 | 780 | 186 | 396 |
| 174 | 282 | 481 | 181 | 329 |
| 175 | 225 | 691 | 216 | 336 |
| 176 | 255 | 1190 | 278 | 544 |
| 177 | 212 | 466 | 229 | 344 |
| 178 | 203 | 209 | 150 | 201 |
| 179 | 488 | 367 | 375 | 560 |
| 180 | 247 | 501 | 208 | 425 |
| 181 | 206 | 483 | 152 | 280 |
| 182 | 134 | 455 | 99 | 252 |
| 183 | 401 | 605 | 283 | 368 |
| 184 | 253 | 352 | 199 | 329 |
| 185 | 252 | 470 | 181 | 352 |
| 186 | 314 | 721 | 287 | 494 |
| 187 | 370 | 789 | 281 | 378 |
| 188 | 368 | 277 | 255 | 342 |
| 189 | 241 | 522 | 182 | 251 |
| 190 | 229 | 711 | 175 | 379 |
| 191 | 333 | 645 | 326 | 526 |
| 192 | 217 | 387 | 181 | 360 |
| 193 | 264 | 472 | 198 | 263 |
| 194 | 382 | 401 | 421 | 479 |
| 195 | 283 | 726 | 191 | 344 |
| 196 | 332 | 582 | 305 | 442 |
| 197 | 310 | 534 | 252 | 321 |
| 198 | 194 | 726 | 200 | 327 |
| 199 | 172 | 286 | 184 | 192 |
| 200 | 335 | 322 | 363 | 473 |

Figure 42:
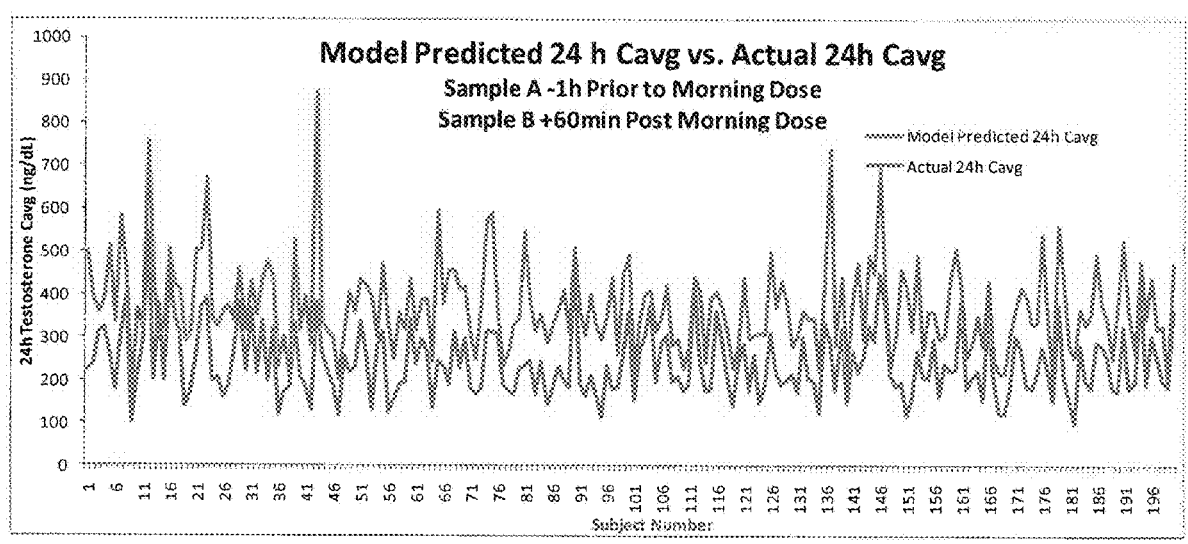
FIG. 42 depicts titration model results with testosterone Sample A taken 1 hour before morning dose and testosterone Sample B taken 60 minutes after morning dose.

See FIG. 42.

Titration Model Results TBS-1-2010 Patient Simulation Data
Testosterone Sample A taken 1 hour before the morning dose
Testosterone Sample B taken 90 minutes after the morning dose

| Subject Number | Testosterone Concentration (ng/dL) Time From Morning Dose −1 hr | Testosterone Concentration (ng/dL) Time From Morning Dose +90 min | Model Predicted 24 h Cavg (ng/dL) | Actual 24 h Cavg (ng/dL) |
|---|---|---|---|---|
| 1 | 217 | 860 | 726 | 501 |
| 2 | 286 | 633 | 531 | 393 |
| 3 | 406 | 407 | 349 | 358 |
| 4 | 449 | 276 | 571 | 392 |
| 5 | 367 | 949 | 600 | 514 |
| 6 | 254 | 846 | 363 | 334 |
| 7 | 406 | 1360 | 562 | 584 |
| 8 | 483 | 668 | 524 | 450 |
| 9 | 108 | 274 | 144 | 175 |
| 10 | 260 | 565 | 449 | 366 |
| 11 | 327 | 259 | 314 | 322 |
| 12 | 522 | 602 | 697 | 757 |
| 13 | 240 | 651 | 495 | 442 |
| 14 | 278 | 361 | 324 | 288 |
| 15 | 249 | 363 | 246 | 330 |
| 16 | 523 | 614 | 400 | 506 |
| 17 | 497 | 660 | 499 | 423 |
| 18 | 375 | 638 | 576 | 412 |
| 19 | 132 | 672 | 280 | 291 |
| 20 | 231 | 384 | 290 | 306 |
| 21 | 363 | 796 | 532 | 505 |
| 22 | 535 | 869 | 652 | 505 |
| 23 | 340 | 763 | 538 | 673 |
| 24 | 252 | 462 | 443 | 346 |
| 25 | 231 | 250 | 322 | 322 |
| 26 | 156 | 624 | 454 | 362 |
| 27 | 226 | 745 | 376 | 375 |
| 28 | 197 | 237 | 315 | 339 |
| 29 | 466 | 910 | 411 | 459 |
| 30 | 232 | 343 | 273 | 316 |
| 31 | 263 | 704 | 429 | 431 |
| 32 | 183 | 420 | 437 | 352 |
| 33 | 491 | 775 | 678 | 436 |
| 34 | 277 | 1610 | 466 | 475 |
| 35 | 362 | 714 | 329 | 441 |
| 36 | 140 | 212 | 307 | 233 |
| 37 | 164 | 322 | 299 | 301 |
| 38 | 195 | 325 | 224 | 209 |
| 39 | 381 | 1030 | 620 | 527 |
| 40 | 206 | 387 | 343 | 316 |
| 41 | 176 | 766 | 335 | 397 |
| 42 | 200 | 271 | 373 | 282 |
| 43 | 479 | 1500 | 682 | 877 |

Titration Model Results TBS-1-2010 Patient Simulation Data
Testosterone Sample A taken 1 hour before the morning dose
Testosterone Sample B taken 90 minutes after the morning dose

| Subject Number | Testosterone Concentration (ng/dL) Time From Morning Dose −1 hr | +90 min | Model Predicted 24 h Cavg (ng/dL) | Actual 24 h Cavg (ng/dL) |
|---|---|---|---|---|
| 44 | 280 | 537 | 335 | 332 |
| 45 | 212 | 361 | 198 | 315 |
| 46 | 246 | 342 | 327 | 300 |
| 47 | 117 | 246 | 181 | 203 |
| 48 | 420 | 416 | 362 | 308 |
| 49 | 262 | 812 | 490 | 406 |
| 50 | 191 | 415 | 356 | 359 |
| 51 | 381 | 880 | 353 | 439 |
| 52 | 321 | 755 | 333 | 422 |
| 53 | 195 | 917 | 392 | 397 |
| 54 | 325 | 375 | 309 | 301 |
| 55 | 413 | 472 | 498 | 472 |
| 56 | 179 | 907 | 704 | 328 |
| 57 | 180 | 269 | 219 | 249 |
| 58 | 206 | 490 | 309 | 359 |
| 59 | 255 | 413 | 335 | 318 |
| 60 | 380 | 555 | 476 | 437 |
| 61 | 226 | 494 | 309 | 317 |
| 62 | 370 | 385 | 423 | 388 |
| 63 | 265 | 627 | 409 | 388 |
| 64 | 163 | 228 | 259 | 245 |
| 65 | 302 | 709 | 634 | 595 |
| 66 | 274 | 550 | 307 | 377 |
| 67 | 250 | 477 | 386 | 456 |
| 68 | 383 | 635 | 461 | 456 |
| 69 | 291 | 666 | 377 | 411 |
| 70 | 430 | 636 | 627 | 417 |
| 71 | 236 | 561 | 329 | 307 |
| 72 | 248 | 345 | 330 | 248 |
| 73 | 244 | 554 | 408 | 374 |
| 74 | 362 | 443 | 434 | 572 |
| 75 | 310 | 762 | 396 | 589 |
| 76 | 467 | 317 | 429 | 367 |
| 77 | 256 | 368 | 322 | 236 |
| 78 | 222 | 417 | 224 | 267 |
| 79 | 198 | 585 | 295 | 333 |
| 80 | 371 | 402 | 357 | 346 |
| 81 | 213 | 917 | 554 | 549 |
| 82 | 288 | 426 | 427 | 386 |
| 83 | 221 | 702 | 267 | 314 |
| 84 | 226 | 747 | 336 | 355 |
| 85 | 168 | 455 | 420 | 286 |
| 86 | 139 | 622 | 440 | 334 |
| 87 | 211 | 401 | 315 | 363 |
| 88 | 225 | 658 | 450 | 412 |
| 89 | 265 | 378 | 334 | 313 |
| 90 | 520 | 653 | 573 | 510 |
| 91 | 207 | 525 | 381 | 365 |
| 92 | 191 | 472 | 388 | 304 |
| 93 | 242 | 694 | 405 | 399 |
| 94 | 121 | 605 | 275 | 331 |
| 95 | 105 | 437 | 290 | 294 |
| 96 | 299 | 359 | 457 | 348 |
| 97 | 153 | 504 | 470 | 441 |
| 98 | 242 | 363 | 337 | 260 |
| 99 | 288 | 281 | 372 | 448 |
| 100 | 530 | 593 | 651 | 494 |
| 101 | 178 | 378 | 196 | 211 |
| 102 | 410 | 286 | 426 | 343 |
| 103 | 491 | 530 | 444 | 401 |
| 104 | 443 | 634 | 497 | 408 |
| 105 | 218 | 454 | 315 | 314 |
| 106 | 322 | 390 | 384 | 347 |
| 107 | 404 | 680 | 415 | 420 |
| 108 | 217 | 309 | 278 | 281 |
| 109 | 277 | 319 | 291 | 294 |
| 110 | 200 | 538 | 266 | 229 |
| 111 | 258 | 342 | 351 | 276 |
| 112 | 523 | 774 | 596 | 440 |
| 113 | 283 | 715 | 531 | 408 |
| 114 | 260 | 612 | 330 | 242 |
| 115 | 231 | 468 | 322 | 389 |
| 116 | 481 | 394 | 621 | 405 |
| 117 | 293 | 431 | 335 | 370 |
| 118 | 261 | 358 | 304 | 311 |
| 119 | 152 | 355 | 192 | 227 |
| 120 | 291 | 448 | 314 | 282 |
| 121 | 383 | 673 | 418 | 440 |
| 122 | 295 | 310 | 373 | 295 |
| 123 | 276 | 368 | 264 | 304 |
| 124 | 113 | 494 | 439 | 311 |
| 125 | 245 | 444 | 370 | 307 |
| 126 | 421 | 524 | 403 | 499 |
| 127 | 313 | 626 | 385 | 371 |
| 128 | 238 | 952 | 453 | 432 |
| 129 | 256 | 499 | 291 | 380 |
| 130 | 175 | 344 | 275 | 278 |
| 131 | 199 | 472 | 271 | 303 |
| 132 | 296 | 301 | 378 | 363 |
| 133 | 319 | 522 | 352 | 342 |
| 134 | 274 | 464 | 535 | 346 |
| 135 | 140 | 626 | 192 | 220 |
| 136 | 466 | 531 | 566 | 434 |
| 137 | 449 | 1200 | 664 | 739 |
| 138 | 252 | 424 | 337 | 282 |
| 139 | 330 | 304 | 348 | 440 |
| 140 | 165 | 252 | 196 | 215 |
| 141 | 292 | 362 | 338 | 389 |
| 142 | 306 | 909 | 423 | 473 |
| 143 | 345 | 269 | 343 | 292 |
| 144 | 359 | 527 | 544 | 492 |
| 145 | 399 | 743 | 489 | 449 |
| 146 | 593 | 1080 | 1061 | 696 |
| 147 | 581 | 448 | 531 | 426 |
| 148 | 222 | 416 | 217 | 229 |
| 149 | 231 | 523 | 234 | 301 |
| 150 | 274 | 551 | 383 | 460 |
| 151 | 178 | 1150 | 471 | 411 |
| 152 | 176 | 775 | 368 | 312 |
| 153 | 346 | 667 | 521 | 491 |
| 154 | 221 | 265 | 340 | 259 |
| 155 | 236 | 771 | 330 | 361 |
| 156 | 257 | 558 | 339 | 358 |
| 157 | 146 | 309 | 238 | 295 |
| 158 | 241 | 341 | 263 | 304 |
| 159 | 199 | 528 | 363 | 434 |
| 160 | 280 | 916 | 564 | 506 |
| 161 | 370 | 487 | 304 | 417 |
| 162 | 148 | 380 | 257 | 250 |
| 163 | 246 | 413 | 329 | 284 |
| 164 | 263 | 510 | 432 | 349 |
| 165 | 178 | 421 | 235 | 275 |
| 166 | 393 | 770 | 466 | 432 |
| 167 | 193 | 475 | 293 | 246 |
| 168 | 148 | 262 | 228 | 214 |
| 169 | 120 | 368 | 212 | 217 |
| 170 | 262 | 616 | 296 | 307 |
| 171 | 369 | 606 | 441 | 366 |
| 172 | 394 | 598 | 409 | 415 |
| 173 | 289 | 475 | 480 | 396 |
| 174 | 282 | 427 | 343 | 329 |
| 175 | 225 | 524 | 411 | 336 |
| 176 | 255 | 864 | 649 | 544 |
| 177 | 212 | 531 | 304 | 344 |
| 178 | 203 | 253 | 185 | 201 |
| 179 | 488 | 516 | 384 | 560 |
| 180 | 247 | 546 | 336 | 425 |
| 181 | 206 | 396 | 309 | 280 |

-continued

Titration Model Results TBS-1-2010 Patient Simulation Data
Testosterone Sample A taken 1 hour before the morning dose
Testosterone Sample B taken 90 minutes after the morning dose

| Subject Number | Testosterone Concentration (ng/dL) Time From Morning Dose | | Model Predicted 24 h Cavg (ng/dL) | Actual 24 h Cavg (ng/dL) |
|---|---|---|---|---|
| | −1 hr | +90 min | | |
| 182 | 134 | 468 | 264 | 252 |
| 183 | 401 | 663 | 452 | 368 |
| 184 | 253 | 282 | 272 | 329 |
| 185 | 252 | 584 | 324 | 352 |
| 186 | 314 | 750 | 465 | 494 |
| 187 | 370 | 425 | 520 | 378 |
| 188 | 368 | 392 | 290 | 342 |
| 189 | 241 | 234 | 343 | 251 |
| 190 | 229 | 390 | 422 | 379 |
| 191 | 333 | 695 | 439 | 526 |
| 192 | 217 | 695 | 271 | 360 |
| 193 | 264 | 321 | 330 | 263 |
| 194 | 382 | 564 | 352 | 479 |
| 195 | 283 | 630 | 453 | 344 |
| 196 | 332 | 531 | 410 | 442 |
| 197 | 310 | 323 | 379 | 321 |
| 198 | 194 | 454 | 413 | 327 |
| 199 | 172 | 290 | 206 | 192 |
| 200 | 335 | 533 | 295 | 473 |

Figure 43:
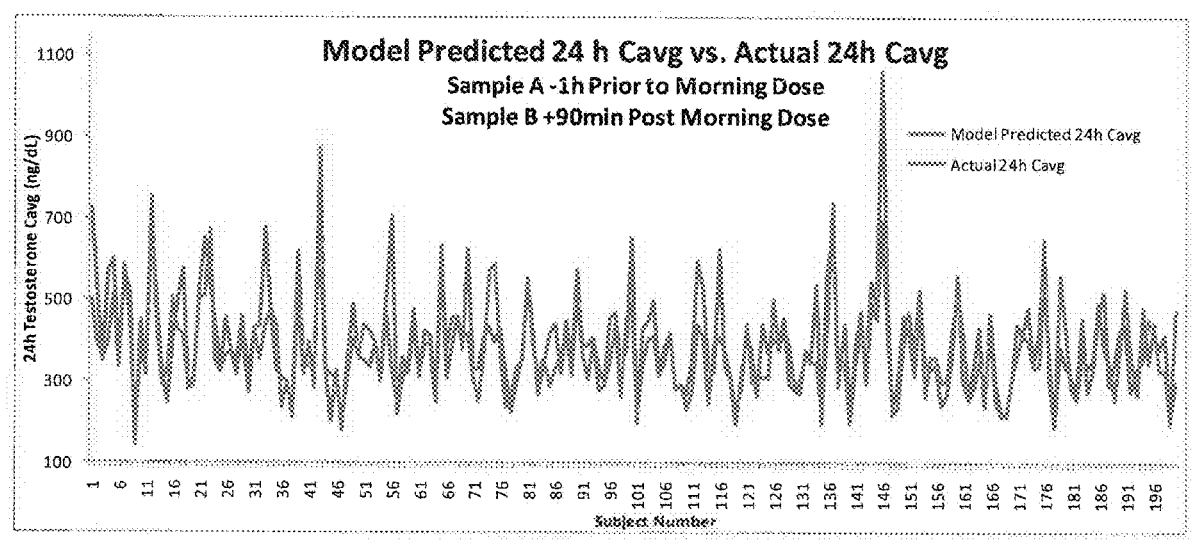
FIG. 43 depicts titration model results with testosterone Sample A taken 1 hour before morning dose and testosterone Sample B taken 90 minutes after morning dose.

See FIG. 43.

Example 15

A Randomized 3-Way Cross Over Study to Assess the Relative Bioavailability, Safety and Tolerability of TBS-1 (4.5%) when Administered to Male Subjects with Seasonal Allergic Rhinitis in Symptomatic, Symptomatic but Treated (Oxymetazoline) and Asymptomatic States Using an Environmental Challenge Chamber (ECC) Model Study Title: A randomized 3-way cross over study to assess the relative bioavailability, safety and tolerability of TBS-1 (4.5%) when administered to male subjects with seasonal allergic rhinitis in symptomatic, symptomatic but treated (oxymetazoline) and asymptomatic states using an environmental challenge chamber (ECC) model
Investigational Intranasal Testosterone Gel (TBS-1)
Products: Oxmetazoline Nasal Spray (0.05%) Dactylus gemerata pollen (challenge substance)
EudraCT No.: 2011-006098-24
Development Phase: I (Extrinsic Factor Study)
Synopsis
Study Title:
Objectives:
Primary:
The primary objective of this study was to determine and compare the pharmacokinetic (PK) profile of 11 mg TBS-1 (4.5%) administered intranasally 3 times a day in subjects who suffered from seasonal allergic rhinitis, whilst they were in the symptomatic, symptomatic but treated (with oxymetazoline) and asymptomatic states.
Secondary:
The secondary objective of this study was to determine and compare the local and systemic safety and tolerability, following 3 administrations of TBS-1 in subjects with seasonal allergic rhinitis, whilst they were in the above states.

Methodology:
This study was an open-label, balanced, randomized 3-way crossover, three-group, three-treatment, three-period pharmacokinetic study. Otherwise healthy male human subjects within the age range of 18 to 45 years with seasonal allergic rhinitis in an asymptomatic state were randomized to 1 of 3 sequence groups (A, B and C). Subjects in sequence group A received treatment 1 in period I, treatment 2 in period II and treatment 3 in period III. Subjects in sequence group B received treatment 2 in period I and treatment 3 in period II and treatment 1 in period III. Subjects in sequence group C received treatment 3 in period I, treatment 1 in period II and treatment 2 in period III. Subjects randomized to Treatment 1 (asymptomatic state) entered the ECC and were exposed to Dactylis glomerate pollen prior to each administration of TBS-1. Treatment 2 was administered to subjects who were in the symptomatic state of their diagnosed seasonal allergic rhinitis and were treated with oxymetazoline 30 min prior to the 07:00 h dose of TBS-1 and 12 hours ater the first administration. Subjects were exposed to Dactylis glomerate pollen in the ECC prior to each TBS-1 administration. Subjects receiving Treatment 3 were to be in the asymptomatic state (<3 for TNSS and <2 for the congestion score) and received three doses of TBS-1.

| NUMBER OF SUBJECTS: | |
|---|---|
| Planned Sample Size: | 18 |
| Actual Sample Size: | |
| Safety Set: | 18 |
| Full PK population: | 18 |
| PK population for bioequivalence: | 14 |

Name of Finished Product:
  TBS-1
Name of Active Ingredient:
  Testosterone 4.5% (TBS-1)
Diagnosis and Main Inclusion Criteria:
  Diagnosis: otherwise healthy male human subjects with seasonal allergic rhinitis in asymptomatic state
Main Inclusion Criteria:
  1. Otherwise healthy male human subjects within the age range of 18 to 45 years inclusive with seasonal allergic rhinitis in asymptomatic state, which was defined by a positive case history and a positive skin prick and/or intradermal test for Dactylis glomerata pollen allergen within 12 months of screening.
  1. Total Nasal Symptom Score (TNSS) of ≥6/12 and a congestion score of ≥⅔ on at least one card during the 2-hour screening challenge.
  2. Willingness to provide written informed consent to participate in the study.
  3. Body-mass index of 30 kg/m².
  4. Absence of significant disease or clinically significant (cs) abnormal laboratory values on laboratory evaluations, medical history or physical examination during screening.
  5. Otorhinolaryngological examination without clinically significant abnormal findings within 4 weeks of screening.
  6. Non-smokers or ex-smokers for at least six months.
  Comprehension of the nature and purpose of the study and compliance with the requirement of the protocol.

| STUDY DRUGS, DOSE AND MODE OF ADMINISTRATION, BATCH NUMBER: | |
| --- | --- |
| Study drug: | Intranasal testosterone gel (TBS-1) |
| Form and description: | Multiple-dose dispenser |
| Unit strength: | 5.5 mg of 4.5% testosterone gel |
| Daily dose: | 33.0 mg of 4.5% testosterone gel |
| Route of administration: | intranasal |
| Posology: | t.i.d. |
| Batch number: | 2372 |
| Study drug: | Oxymetazoline (Nasivin ® ohne Konservierungsstoffe) |
| Form and description: | Multiple-dose dispenser |
| Unit strength: | 0.05% oxymetazoline hydrochloride |
| Daily dose: | 4 puffs (2 per nostril) of 5.05% oxymetazoline hydrochloride |
| Route of administration: | Intranasal |
| Posology: | 30 min prior to the 07:00 h dose of TBS-1 and 12 h after the first dose (during Treatment Sequence 3) |
| Study drug: | *Dactylis glomerata* (pollen) |
| Form and description: | Challenge substance for pollen chamber |
| Unit strength: | 6 g |
| Daily dose: | 4000 ± 500 of *Dactylis glomerate* pollen |
| Route of administration: | Inhalation |
| STUDY PERIOD: | 5 weeks |

Criteria for Evaluation:
Primary Endpoint (Pharmakokinetics):

The following pharmacokinetic (PK) parameters were determined for all subjects in all treatments: Area under the serum concentration time plot up to 24 h ($AUC_{0-24}$), the average of the observed concentration of testosterone and DHT in the 24 h interval ($C_{avg}$), minimum observed concentration of testosterone and DHT ($C_{min}$), maximum observed concentration of testosterone and DHT ($C_{max}$), and time of maximum observed concentration testosterone and DHT ($t_{max}$) for 3 treatment phases (Treatments 1-3). The relative PK profiles of the 3 treatments were determined using $AUC_{0-24}$ and $C_{max}$ corrected for the serum testosterone concentration.

Secondary Endpoint (Safety):
Safety and tolerability were assessed by monitoring:
Adverse events
Otolaryngological examination
Vital signs
Complete blood count to evaluate changes in white blood cell (WBC) count, hemoglobin and hematocrit
Clinical chemistry profile
Urinalysis (urine specific gravity, glucose, protein, ketone, pH, blood, bilirubin, urobilinogen, nitrite, leukocytes)

Statistical Methods:

Continuous measurements were summarized by means of descriptive statistics (i.e., number of observations, arithmetic mean, standard deviation [SD], minimum, median, maximum). Categorical variables were summarized by means of frequency tables (i.e. count and percentages). All baseline corrected PK parameters were tested regarding bioequivalence (ANOVA).

Summary—Conclusions

The 18 treated subjects were aged between 27 and 44. All 6 subjects in sequence group A completed the study as scheduled. In sequence group B, 4 out of 6 subjects and sequence group C, 5 out of 6 subjects completed the study as scheduled.

Pharmacokinetic Conclusion:

Administration of TBS-1 under asymptomatic, symptomatic and symptomatic but treated conditions of allergic rhinitis demonstrated a reliable increase in testosterone serum concentrations in all three treatment groups. The drug induced exposure to testosterone and DHT, determined as $AUC_{0-24,bc}$ was higher in the asymptomatic state compared to symptomatic and symptomatic but treated state. ANOVA analysis failed to demonstrate bioequivalence between the asymptomatic state and either symptomatic or symptomatic but treated state.

A comparison of the $AUC_{bc}$ over 0-24 h between symptomatic and symptomatic but treated state revealed no bioequivalence between these two treatment conditions.

However, given that the point estimates were close to 1 (1.0903 for testosterone and 0.9944 for DHT) the failure to show bioequivalence may be due to large inter-individual variations. These large variations led to wide confidence intervals, which exceed the threshold values for bioequivalence of 0.8 to 1.25.

While TBS-1 bioavailability during the symptomatic state of allergic rhinitis is lower than during the asymptomatic state, the post-dose concentrations of testosterone still demonstrate a reliable increase in levels as compared to baseline. The relative decrease in bioavailability of TBS-1 under symptomatic seasonal rhinitis is not either ameliorated or aggravated by the administration of oxymetazoline.

Safety Conclusion:

TBS-1 was well tolerated. All reported AEs were of mild or moderate intensity and all were transient. All reported AEs were deemed treatment emergent with no causality to TBS-1. Physical examination, vital signs and clinical laboratory results did not reveal any clinically significant finding.

Example 16

An Open Label, Randomized, Balanced, Three Treatments, Parallel Design, Pharmacokinetic Study of Intra-Nasal TBS-1 Administration to Hypogonadal Men Pharmacokinetic Simulation Report See Exhibit D (the contents of which are incorporated herein by reference).

It should be understood that the present invention contemplates any effective pharmacokinetic parameter for the intra-nasal TBS-1 gels of the present invention, including those that may vary as much as about ±25% of the pharmacokinetic parameters set forth in Exhibit D. Preferably, the present invention contemplates pharmacokinetic parameters for the intra-nasal TBS-1 gels that are about 25% greater and/or about 20% lesser than those pharmacokinetic parameters set forth in Exhibit D.

Example 17

Stability Intra Nasal Testosterone Gels and Diffusion Rates

The present invention also contemplates stable intranasal TBS-1 testosterone gels as set forth in Exhibits F, G, H, I, J, K1, K2, L, M1, M2 and M3 (the contents of which are incorporated herein by reference) and intranasal TBS-1 testosterone gels having diffusion rates as set forth in Exhibit N (the contents of which are incorporated herein by reference).

Example 18

A Randomized 3-Way Cross Over Study to Assess the Relative Bioavailability, Safety and Tolerability of 4.5% TBS-1 when Administered to Male Subjects with Seasonal Allergic Rhinitis

| Component | Amount (% w/w) 4.5% TBS-1 |
|---|---|
| Testosterone | 4.5% |
| Castor Oil, USP | 87.5% |
| Oleoyl polyoxylglycerides, Ph Eur/NF | 4.0% |
| Colloidal silicon dioxide, NF | 4.0% |

Composition of TBS-1

This study assessed the relative bioavailability, safety and tolerability of 4.5% TBS-1 when administered to patients with symptomatic untreated and treated (oxymetazoline) seasonal allergic rhinitis as well as asymptomatic subjects using an environmental challenge chamber (ECC) model.

The purpose of this study was to determine effect of allergic rhinitis and the treatment of allergic rhinitis, oxymetazoline, on the absorption of TBS-1. This was achieved by determining the testosterone pharmacokinetic profile following administration of 11 mg TBS-1 (4.5%) three times a day in subjects that suffer from seasonal allergic rhinitis, while in the symptomatic, symptomatic but treated (with Oxymetazoline) and asymptomatic states. The secondary objective of the study was to determine the local and systemic safety and tolerability, following three administrations of TBS-1 in subjects with seasonal allergic rhinitis and while taking oxymetazoline.

Symptoms of allergic rhinitis were induced in 18 male patients using allergen challenge with Dactylis glomerate pollen in and Environmental Challenge Chamber. The study was a 3-period cross over design in which all subjects received each of the following treatments:
A: TBS-1 (Symptomatic State)
Symptoms of allergic rhinitis were induced in men with seasonal allergic rhinitis by exposing them to pollen of Dactylis glomerate in an environmental challenge chamber (ECC) prior to each administration of TBS-1.
B: TBS-1 and Oxymetazoline (Symptomatic and Treated)
Oxymetazoline nasal spray was administered 30 minutes prior to the 0700 hr dose of TBS-1 and again 12 hrs after the first dose. Symptoms of allergic rhinitis were induced in men with seasonal allergic rhinitis by exposing them to pollen in an Environmental Challenge Chamber.
C: TBS-1 (Asymptomatic State)
TBS-1 was administered 3 times a day to men in the asymptomatic state.

This is a single site study with a planned enrolment of 18 healthy men. A 24 hour pharmacokinetic profile of testosterone and DHT will be performed on all subjects in all treatments.

Safety Results
Eighteen (18) healthy men with allergic rhinitis were exposed to TBS-1. TBS-1 was well tolerated by subjects. There were no deaths in the study and none of the subjects experienced any SAEs. Fifteen (15) adverse events were encountered in the study: 2 in asymptomatic state; 6 in the symptomatic state; and 7 in the symptomatic but treated state. None of the adverse events were considered related to the study drug. All events were of mild to moderate severity. None of the subjects were discontinued from the treatment because of an AE (see results in the following table).

TABLE

Adverse Events Unrelated to TBS-1

| Event | Asymptomatic State (n = 18) | Symptomatic state (n = 15) | Symptomatic but treated state (n = 17) |
|---|---|---|---|
| Musculoskeletal and connective tissue disorder | | | |
| Muscuosketal stiffness | 1 (5.6%) | | |
| Respiratory, thoracic and mediastinal disorder | | | |
| Epistaxis | | 1 (6.7%) | |
| Dysphonia | | 1 (6.7%) | 2 (11.8%) |
| Oropharyngeal pain | | 1 (6.7%) | |
| Rhinitis allergic Invesigations | | 1 (6.7%) | |
| Forced expiry volume decreased | | 1 (6.7%) | 1 (5.9%) |
| General disorders and administration site condition | | | |
| Injection site phlebitis | | 2 (13.3%) | 1 (5.9%) |
| Infections and infestations | | | |
| Nasopharyngitis | | | 2 (11.8%) |
| Nervous system disorders | | | |
| Dizziness | | | 1 (5.9%) |

Test results are also presented in Exhibit M (the contents of which are incorporated herein by reference).

Example 19

A Randomized 3 Way Cross Over Study to Assess Relative Bioavailability, Safety and Tolerability of 4.5% TBS 1TBS-1 (4.5%) when Administered to Male Subjects with Seasonal Allergic Rhinitis in Symptomatic, Symptomatic but Treated (Oxymetazoline) and Asymptomatic States An environmental challenge chamber (ECC) model was used in this study.
Objectives:
The primary objective of this study was to determine and compare the pharmacokinetic (PK) profile of 11 mg TBS-1 (4.5%) administered intranasally 3 times a day in subjects who suffered from seasonal allergic rhinitis, whilst they were in the symptomatic, symptomatic but treated (with oxymetazoline) and asymptomatic states.

The secondary objective of this study was to determine and compare the local and systemic safety and tolerability, following 3 administrations of TBS-1 in subjects with seasonal allergic rhinitis, whilst they were in the above states.

General Study Design:

The chosen cross over design allows to control for non-treatment effects such as period and sequence. Intra-individual measurements allow to detect treatment effects with a higher sensitivity as compared to inter-individual measurements based on smaller intra-individual variation.

This was an open-label study, as the physical differences in the intranasal dosing devices prevent blinding. Since pharmacokinetic parameters are objective measures, they were likely not affected by the open-label design of the study.

Methodology:

This study was an open-label, balanced, randomized 3-way crossover, three-group, three-treatment, three-period pharmacokinetic study. Otherwise healthy male human subjects within the age range of 18 to 45 years with seasonal allergic rhinitis in an asymptomatic state were randomized to 1 of 3 sequence groups (A, B and C).

Subjects in sequence group A received treatment 1 in period I, treatment 2 in period II and treatment 3 in period III. Subjects in sequence group B received treatment 2 in period I and treatment 3 in period II and treatment 1 in period III. Subjects in sequence group C received treatment 3 in period I, treatment 1 in period II and treatment 2 in period III (as shown in the following table).

Treatments in the Three Dose Sequences

|  | PERIOD I Visit 3 | PERIOD II Visit 4 | PERIOD III Visit 5 |
| --- | --- | --- | --- |
| Time | 04:00-07:00 (+1 day) | 04:00-07:00 (+1 day) | 04:00-07:00 (+1 Day) |
| Sequence group A | Treatment 1 | Treatment 2 | Treatment 3 |
| Sequence group B | Treatment 2 | Treatment 3 | Treatment 1 |
| Sequence group C | Treatment 3 | Treatment 1 | Treatment 2 |

Subjects randomized to Treatment 1 (asymptomatic state) entered the ECC and were exposed to Dactylis glomerata pollen prior to each administration of TBS-1. Treatment 2 was administered to subjects who were in the symptomatic state of their diagnosed seasonal allergic rhinitis and were treated with oxymetazoline 30 min prior to the 07:00 h dose of TBS-1 and 12 hours after the first administration. Subjects were exposed to Dactylis glomerata pollen in the ECC prior to each TBS-1 administration. Subjects receiving Treatment 3 were to be in the asymptomatic state (<3 for TNSS and <2 for the congestion score) and received three doses of TBS-1.

Number of Subjects: 18

Safety Set:

Full PK population: 18

PK population for Bioequivalence: 14

Subject Population:

A male subject population with a history of seasonal allergic rhinitis, aged 18-45 years was chosen for this study in order to investigate the effect of allergic rhinitis on the absorption of TBS-1 in an asymptomatic, symptomatic and symptomatic but treated state.

Diagnosis criteria: otherwise healthy male human subjects with seasonal allergic rhinitis in asymptomatic state.

Main Inclusion Criteria:

1. Otherwise healthy male human subjects within the age range of 18 to 45 years inclusive with seasonal allergic rhinitis in asymptomatic state, which was defined by a positive case history and a positive skin prick and/or intradermal test for Dactylis glomerate pollen allergen within 12 months of screening.
2. Total Nasal Symptom Score (TNSS) of ≥6/12 and a congestion score of ≥⅔ on at least one card during the 2-hour screening challenge.
3. Willingness to provide written informed consent to participate in the study.
4. Body-mass index of 30 kg/m².
5. Absence of significant disease or clinically significant (cs) abnormal laboratory values on laboratory evaluations, medical history or physical examination during screening.
6. Otorhinolaryngological examination without clinically significant abnormal findings within 4 weeks of screening.
7. Non-smokers or ex-smokers for at least six months.
8. Comprehension of the nature and purpose of the study and compliance with the requirement of the protocol.

Study drug: Intranasal testosterone gel (TBS-1)

Form and description: Multiple-dose dispenser

Unit strength: 5.5 mg of 4.5% testosterone gel

Daily dose: 33.0 mg of 4.5% testosterone gel

Route of administration: intranasal

Posology: t.i.d.

Batch number: 2372

Study drug: Oxymetazoline (Nasivin® ohne Konservierungsstoffe)

Form and description: Multiple-dose dispenser

Unit strength: 0.05% oxymetazoline hydrochloride

Daily dose: 4 puffs (2 per nostril) of 5.05% oxymetazoline hydrochloride

Route of administration: Intranasal

Posology: 30 min prior to the 07:00 h dose of TBS-1 and 12 h after the first dose (during Treatment Sequence 3)

Study drug: *Dactylis glomerata* (pollen)

Form and description: Challenge substance for pollen chamber

Unit strength: 6 g

Daily dose: 4000±500 of *Dactylis glomerata* pollen

Route of administration: Inhalation

Study Period: 5 Weeks

Criteria for Evaluation:

Primary Endpoint (Pharmacokinetics):

The following pharmacokinetic (PK) parameters were determined for all subjects in all treatments: Area under the serum concentration time plot up to 24 h ($AUC_{0-24}$), the average of the observed concentration of testosterone and DHT in the 24 h interval ($C_{avg}$), minimum observed concentration of testosterone and DHT ($C_{min}$), maximum observed concentration of testosterone and DHT ($C_{max}$), and time of maximum observed concentration testosterone and DHT ($t_{max}$) for 3 treatment phases (Treatments 1-3).

The relative PK profiles of the 3 treatments were determined using $AUC_{0-24}$ and $C_{max}$ corrected for the serum testosterone concentration.

Secondary Endpoint (Safety):

Safety and tolerability were assessed by monitoring:

Adverse events

Otolaryngological examination

Vital signs

Complete blood count to evaluate changes in white blood cell (WBC) count, hemoglobin and hematocrit Clinical chemistry profile Urinalysis (urine specific gravity, glucose, protein, ketone, pH, blood, bilirubin, urobilinogen, nitrite, leukocytes)

Statistical Methods:

Continuous measurements were summarized by means of descriptive statistics (i.e., number of observations, arithmetic mean, standard deviation [SD], minimum, median, maximum). Categorical variables were summarized by means of frequency tables (i.e. count and percentages). All baseline corrected PK parameters were tested regarding bioequivalence (ANOVA).

Subjects participating in this study were at risk for the side effects common to all formulations of testosterone. In addition to risks inherent to all testosterone administration, subjects receiving TBS-1 in prior clinical studies have experienced mild nasal symptoms including dryness, inflammation, congestion, and discomfort. None of these AEs prevented subjects from continuing the medication.

The exposure to pollen in order to induce symptoms of allergic rhinitis was associated with a minimal risk of anaphylactic reactions. Allergen challenges with Dactylis glomerate pollen in the Fraunhofer ECC were designed to mimic the situation for the subject under quasi-natural conditions. Therefore, the pollen exposure in the ECC did not present a greater risk than natural exposure during the grass pollen season in summer. The experimental setting was validated and used in numerous clinical trials. Inhalation of pollen can cause bronchoconstriction in asthmatic subjects. However, asthmatic subjects were excluded from the study. For risk minimization measures with respect to pollen challenge.

Subjects receiving oxymetazoline (Nasivin©) were at risk of the described side-effects of this product. Frequent side-effects are burning and dryness of the nasal mucosa and sneezing. Uncommon side effects are agitation, fatigue, headache, hallucinations (mainly observed in children), tachycardia, hypertension, arrhythmia, nose bleeding, convulsions (mainly observed in children) and hypersensitivity reactions, such as, itching and rash. However, since each subject received only 2 doses of oxymetazoline, the risk of developing side-effects was minimal.

Testosterone replacement therapy for hypogonadal men should correct the clinical abnormalities of testosterone deficiency. Since this was a Phase I study enrolling men not suffering from hypogonadism between the ages of 18-45 years it was not anticipated that these volunteers would directly benefit by taking part in this study.

Conclusions

The 18 treated subjects were aged between 27 and 44. All 6 subjects in sequence group A completed the study as scheduled. In sequence group B, 4 out of 6 subjects and sequence group C, 5 out of 6 subjects completed the study as scheduled.

Pharmacokinetic Conclusion:

Administration of TBS-1 under asymptomatic, symptomatic and symptomatic but treated conditions of allergic rhinitis demonstrated a reliable increase in testosterone serum concentrations in all three treatment groups. The drug induced exposure to testosterone and DHT, determined as $AUC_{0-24,bc}$ was higher in the asymptomatic state compared to symptomatic and symptomatic but treated state. ANOVA analysis failed to demonstrate bioequivalence between the asymptomatic state and either symptomatic or symptomatic but treated state.

A comparison of the $AUC_{bc}$ over 0-24 h between symptomatic and symptomatic but treated state revealed no bioequivalence between these two treatment conditions. However, given that the point estimates were close to 1 (1.0903 for testosterone and 0.9944 for DHT) the failure to show bioequivalence may be due to large inter-individual variations. These large variations led to wide confidence intervals, which exceed the threshold values for bioequivalence of 0.8 to 1.25.

Administration of 4.5% TBS-1 under asymptomatic, symptomatic and symptomatic but treated conditions of allergic rhinitis demonstrated a reliable increase in testosterone serum concentrations under all three treatment conditions. 4.5% TBS 1 bioavailability during the symptomatic state of allergic rhinitis was 21% lower compared to the asymptomatic state, based on AUC0-24 values.

While TBS-1 bioavailability during the symptomatic state of allergic rhinitis is lower than during the asymptomatic state, the post-dose concentrations of testosterone still demonstrate a reliable increase in levels as compared to baseline. The relative decrease in bioavailability of 4.5% TBS 1 under symptomatic seasonal rhinitis was neither ameliorated nor aggravated by the administration of oxymetazoline.

Safety Conclusion:

TBS-1 was well tolerated. All reported AEs were of mild or moderate intensity and all were transient. All reported AEs were deemed treatment emergent with no causality to TBS-1. Physical examination, vital signs and clinical laboratory results did not reveal any clinically significant finding.

Figure 44:
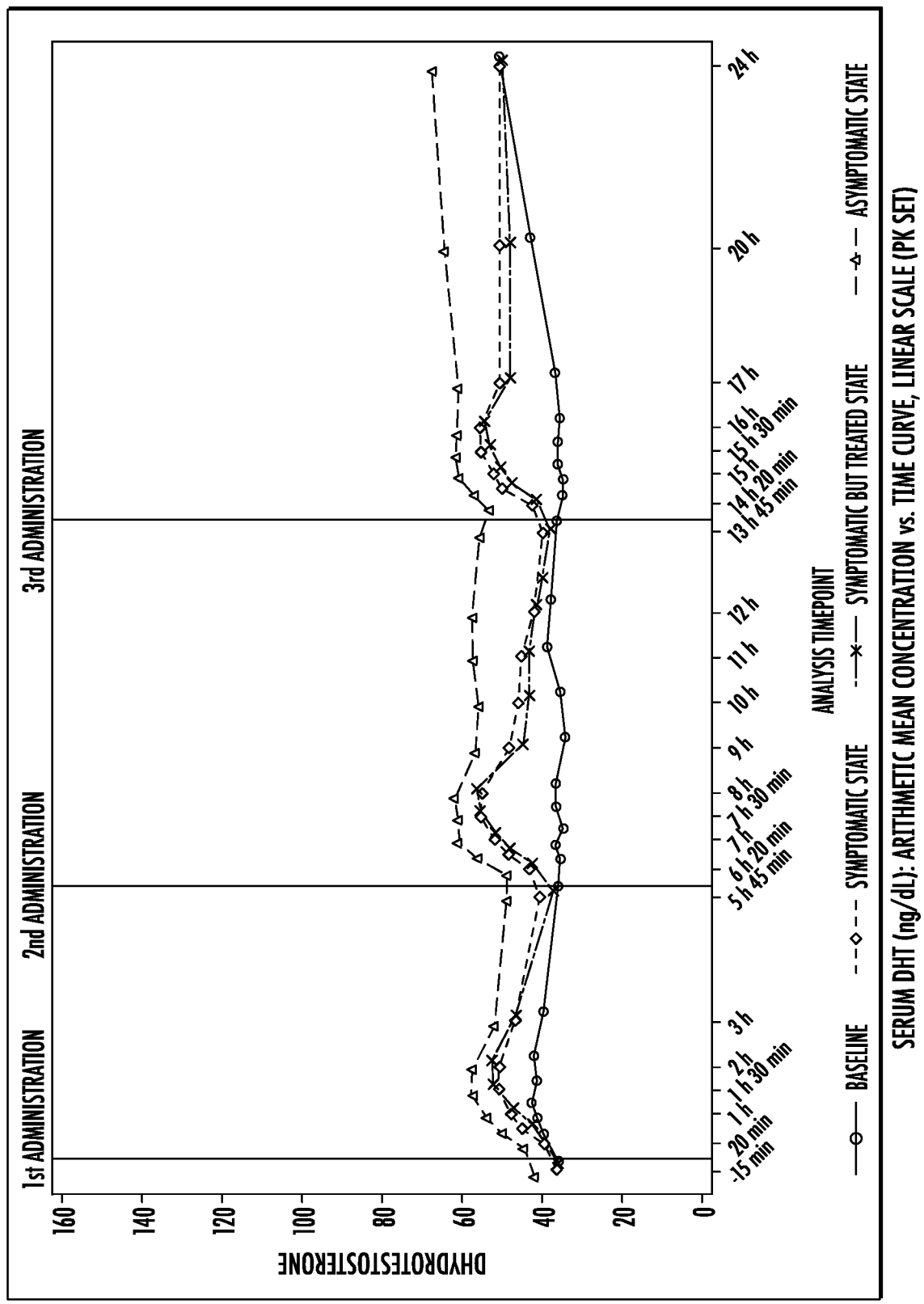
FIG. 44 depicts a linear-scale mean serum concentration time plot for testosterone.
Figure 45:
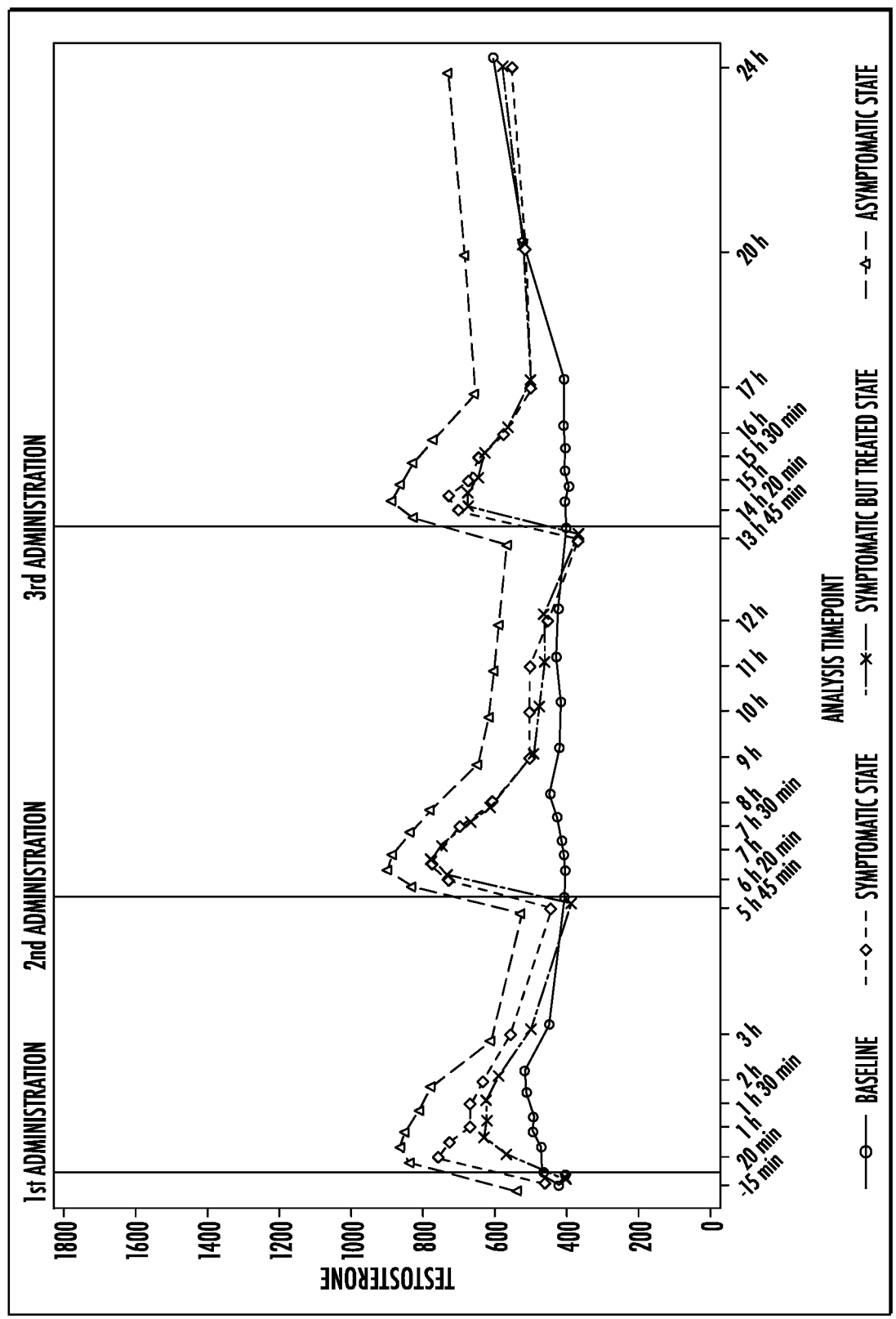
FIG. 45 depicts a linear-scale mean serum concentration time plot for testosterone.

See FIGS. 44 and 45 respectively

Example 20

Drug-Drug Interaction Study to Evaluate Administration Route of Intranasal Application of Testosterone and to Investigate Potential Interaction of Testosterone with a Nasal Decongestant Spray A drug-drug Interaction study was completed, which was an extrinsic factor study to evaluate whether intranasal application of testosterone is a reliable route of administration during naturally occurring nasal inflammation such as allergic rhinitis and to investigate the potential interaction of TBS-1 with a nasal decongestant spray, oxymetazoline. The study was conducted at one site in Germany.

Treatment Regimen.

Subjects were randomly assigned to a treatment sequence comprised of TBS-1 when they were asymptomatic, symptomatic and untreated and symptomatic and treated with oxymetazoline nasal spray. The symptomatic state was induced by exposure to Dactylis glomerata pollen in an environment exposure chamber (EEC).

The symptomatic state was defined by a positive case history, a positive skin prick and/or interdermal test for Dactylis glomerata allergen and a Total nasal Symptom Score (TNSS) of ≥6/12 and a congestion score of ≥⅔. TBS-1 administration to subjects in a symptomatic and treated arm received oxymetazoline 30 minutes prior to the 07:00 hour dose of TBS 1 and 12 hours after the first administration. All patients received 3 doses of TBS-1 at 07:00, 13:00 and 21:00 hrs.

Primary Objective

The primary objective of this study was to determine and compare the pharmacokinetic (PK) profile of 11 mg TBS-1 (4.5%) administered intranasally 3 times a day in subjects who suffered from seasonal allergic rhinitis, whilst they were in the symptomatic, symptomatic but treated (with oxymetazoline) and asymptomatic states.

Subject Disposition

The 18 treated subjects were healthy subjects with seasonal allergic rhinitis aged between 27 and 44. All 6 subjects in sequence group A completed the study as scheduled. In sequence group B, 4 out of 6 subjects and sequence group C, 5 out of 6 subjects completed the study as scheduled. In total, the number of subjects completing each of the 3 states were: asymptomatic (N=18), symptomatic but treated (N=17), and symptomatic untreated (N=15).

Analysis of Primary Endpoint

Administration of TBS-1 under asymptomatic, symptomatic and symptomatic but treated conditions of allergic rhinitis demonstrated a reliable increase in testosterone serum concentrations under all 3 treatment conditions as presented in the following table and the following figure.

TABLE

AUC Values for Serum Testosterone by Treatment Condition Including Non-Corrected Values, Corrected Values and Pre-dose Corrected Values

|  | Non-corrected Values | Corrected Values* | Pre-dose Corrected Values# |
|---|---|---|---|
| Asymptomatic | 16746 ± 3894 | 5797 ± 2643 | 3841 ± 2713 |
| Symptomatic | 13217 ± 3589 | 2267 ± 2172 | 3041 ± 1967 |
| Symptomatic but treated | 12778 ± 3379 | 1828 ± 1889 | 3138 ± 1480 |

Figure 46:
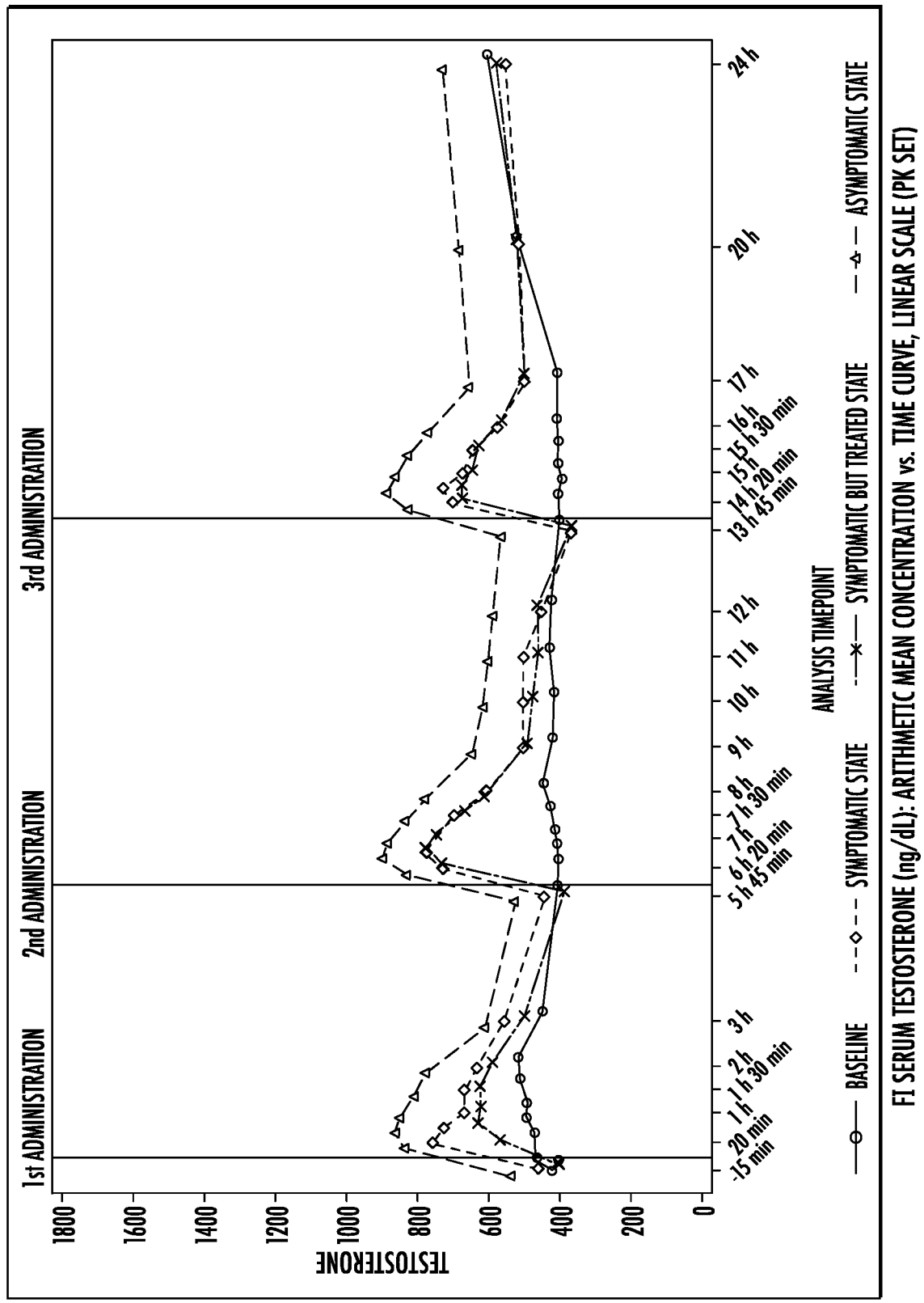
FIG. 46 depicts a scale indicating testosterone and concentration vs.

*Corrected values = uncorrected values-baseline 24 hour
Pre-dose corrected values = PK values were corrected for treatment specific pre-dose levels See FIG. 46.

FI Serum Testosterone (ng/dL): Arithmetic Mean Concentration vs. Time Curve, Linear Scale (PK set)

The testosterone exposure as estimated by the mean baseline-corrected area under the serum concentration-time curve from 0 to 24 hours post-dose $AUC_{0-24,bc}$ was higher for subjects in the asymptomatic state compared to symptomatic and symptomatic but treated state. An analysis of variance did not demonstrate bioequivalence between the asymptomatic state and either symptomatic and symptomatic but treated state.

The difference in $AUC_{0-24,bc}$ between the symptomatic untreated and the symptomatic treated states was small, indicating that administration of oxymetazoline did not relevantly affect the absorption of TBS-1; however, they were not bioequivalent. Given that the point estimates were close to 1 (1.0903) the failure to show bioequivalence may be due to large interindividual variations. These large variations led to wide confidence intervals, which exceed the threshold for bioequivalence of 0.8 to 1.25.

TBS 1 bioavailability during the symptomatic state of allergic rhinitis was 21% lower compared the asymptomatic state, based on $AUC_{0-24}$ values. However, the post-dose concentrations of testosterone still demonstrate a reliable increase in levels as compared to baseline. The relative decrease in bioavailability of TBS-1 under symptomatic seasonal rhinitis is neither ameliorated nor aggravated by the administration of oxymetazoline.

Additional exploratory analysis revealed that the different treatment conditions influenced the pre-dose value of testosterone. A student t-test showed significant differences in the pre-dose testosterone between the asymptomatic treatment condition compared to the symptomatic and the symptomatic and treated conditions. Subjects were exposed to an EEC in the symptomatic and symptomatic and treated condition but not in the asymptomatic condition. It is hypothesized that the earlier wake up time and/or stress caused by procedures associated with confinement in the EEC may have led to lower testosterone values in both symptomatic states compared to the asymptomatic state. As such, the baseline profile collected under the EEC conditions and used for correction purposes was not truly representative of the non-treated state under all study conditions. The additional analysis corrected for endogenous testosterone by pre-dose values instead of correction by 24 hour baseline profile. This analysis showed that the differences between asymptomatic and both symptomatic treatment conditions were less pronounced with respect to $AUC_{bc}$, $C_{avg,bc}$, and $C_{max,bc}$. However, bioequivalence could not be shown between treatment conditions.

REFERENCE LIST

1. Tietz Textbook of Clinical Chemistry and Molecular Diagnostics, 4th edition, 2006. Editors; Burtis C A, Ashwood E R, and Bruns D E.
2. Wang C, Swerdloff RS. Androgen replacement therapy. Ann Med 1997; 29: 365-370.
3. Matsumoto A M. Andropause: clinical implications of the decline in serum Testosterone levels with aging in men. J Gerontol A Med Sci 2002; 57: M76-M99.
4. Haren M T, Kim M J, Tariq S H, Wittert G A, Morley J E. Andropause: a quality-of-life issue in older males. Med Clin North Am 2006; 90: 1005-1023.
5. Nieschlag E. Testosterone treatment comes of age: new options for hypogonadal men. Clin Endocrinol (Oxf) 2006: 65: 275-281.
6. Tenover J L. The androgen-deficient aging male: current treatment options. Rev Urol 2003; 5 (Suppl): S22-S28.
7. Jockenhovel F. Testosterone therapy—what, when and to whom? Aging Male 2004; 7: 319-324.
8. Kunz G H, Klein K O, Clemons R D, Gottschalk M E, Jones K L. Virilization of young children after topical androgen use by their parents. Pediatrics 2004; 114: 282-284.
9. Brachet C, Vermeulen J, Heinrichs C. Children's virilisation and the use of a Testosterone gel by their fathers. Eur J Pediatr 2005; 164: 646-647.
10. Bagchus W M, Hust R, Maris F, Schnabel P G, Houwing N S. Important effect of food on the bioavailability of oral Testosterone undecanoate. Pharmacotherapy 2003; 23: 319-325.
11. Haren M, Chapman I M, Haren M T, MacKintosh S, Coates P, Morley J E. Oral Testosterone supplementation increases muscle and decreases fat mass in healthy elderly males with low normal gonadal status. J Gerontol A Biol Sci Med Sci 2003; 58: 618-625.
12. Haren M, Chapman I, Coates P, Morley J E, Wittert G. Effect of 12 month oral Testosterone on Testosterone deficiency symptoms in symptomatic elderly males with low-normal gonadal status. Age Ageing 2005; 34: 123-130.
13. Mattern C, Hoffmann C, Morley J E, Badiu C. The Aging Male 2008; 11: 171-178.

What is claimed is:

1. A method of treating a male, who is experiencing symptomatic allergic or seasonal rhinitis, with testosterone replacement therapy for a condition associated with a deficiency or absence of endogenous testosterone who is in need of such testosterone replacement treatment, the method comprising:

administering intranasally to the symptomatic male three times a day an intranasal testosterone gel to deliver intranasally to the symptomatic male a total daily dose of about 33 mg of testosterone to effectively treat said condition in the symptomatic male wherein said condition is hypogonadism; and providing a metered dose pump containing 11 grams of the intranasal testosterone gel, wherein the metered dose pump dispenses 60 metered pump actuations, wherein one pump actuation delivers 5.5 mg of the testosterone in 0.122 grams of the intranasal testosterone gel, so that, when the symptomatic male actuates the one said pump from the metered dose pump into each nostril of the symptomatic male three times a day, the total daily dose of about 33 mg of testosterone is intranasally administered to the symptomatic male.

2. An intranasal testosterone method for treating a male, who is symptomatic for allergic or seasonal rhinitis, with testosterone replacement therapy for a condition associated with a deficiency or absence of endogenous testosterone that is in need of such testosterone replacement treatment, said method comprising:

providing a metered dose pump containing 11 grams of an intranasal testosterone gel, wherein the metered dose pump dispenses 60 metered pump actuations of the intranasal testosterone gel; and instructing the symptomatic male to actuate one pump from the metered dose pump into each nostril of the symptomatic male three times a day to deliver intranasally to the symptomatic male a total daily dose of about 33 mg of testosterone to effectively treat the symptomatic male for the condition;

wherein the one pump actuation delivers 5.5 mg of the testosterone in 0.122 grams of the intranasal testosterone gel into each of the nostrils;

wherein the condition is hypogonadism; and wherein the hypogonadism is selected from a group of hypogonadisms consisting of congenital or acquired primary hypogonadism and congenital or acquired hypogonadotropic hypogonadism.

* * * * *